US009206183B2

(12) United States Patent
Bach Taña et al.

(10) Patent No.: US 9,206,183 B2
(45) Date of Patent: Dec. 8, 2015

(54) SUBSTITUTED PYRAZOLO[1,5-A]PYRIDINES AS JAK INHIBITORS

(75) Inventors: Jordi Bach Taña, Barcelona (ES); Lluis Miquel Pages Santacana, Barcelona (ES); Joan Taltavull Moll, Barcelona (ES); Paul Robert Eastwood, Barcelona (ES); Jacob Gonzalez Rodrigues, Barcelona (ES); Victor Giulio Matassa, Barcelona (ES)

(73) Assignee: ALMIRALL, S.A., Barcelona (ES)

( * ) Notice: Subject to any disclaimer, the term of this patent is extended or adjusted under 35 U.S.C. 154(b) by 0 days.

(21) Appl. No.: 13/579,344

(22) PCT Filed: Feb. 18, 2011

(86) PCT No.: PCT/EP2011/000792
§ 371 (c)(1),
(2), (4) Date: Sep. 21, 2012

(87) PCT Pub. No.: WO2011/101161
PCT Pub. Date: Aug. 25, 2011

(65) Prior Publication Data
US 2013/0209400 A1    Aug. 15, 2013
US 2014/0086870 A9    Mar. 27, 2014

Related U.S. Application Data

(60) Provisional application No. 61/306,051, filed on Feb. 19, 2010, provisional application No. 61/371,081, filed on Aug. 5, 2010.

(30) Foreign Application Priority Data

Feb. 18, 2010   (EP) .................................... 10382039
Aug. 5, 2010    (EP) .................................... 10382217

(51) Int. Cl.
| | |
|---|---|
| A61K 31/437 | (2006.01) |
| C07D 221/04 | (2006.01) |
| C07D 487/04 | (2006.01) |
| A61K 31/497 | (2006.01) |
| A61K 31/4985 | (2006.01) |
| A61K 31/506 | (2006.01) |
| A61K 45/06 | (2006.01) |
| C07D 471/04 | (2006.01) |

(52) U.S. Cl.
CPC ............ C07D 487/04 (2013.01); A61K 31/437 (2013.01); A61K 31/497 (2013.01); A61K 31/4985 (2013.01); A61K 31/506 (2013.01); A61K 45/06 (2013.01); C07D 471/04 (2013.01)

(58) Field of Classification Search
CPC ............................. A61K 31/437; C07D 221/04
USPC ........... 514/300; 544/333, 405; 546/121, 199; 548/266.4
See application file for complete search history.

(56) References Cited

U.S. PATENT DOCUMENTS

| | | |
|---|---|---|
| 7,074,801 B1 | 7/2006 | Yoshida et al. |
| 8,501,735 B2 | 8/2013 | Rosales et al. |
| 2013/0089512 A1 | 4/2013 | Eastwood et al. |
| 2013/0216498 A1 | 8/2013 | Eastwood et al. |
| 2013/0309200 A1 | 11/2013 | Almirall |
| 2014/0170110 A1 | 6/2014 | Eastwood et al. |
| 2014/0271543 A1 | 9/2014 | Eastwood et al. |

FOREIGN PATENT DOCUMENTS

| | | |
|---|---|---|
| EP | 1382603 A1 | 1/2004 |
| WO | WO 01/14375 A1 | 3/2001 |
| WO | WO 02/16359 A1 | 2/2002 |
| WO | WO 03/000682 A1 | 1/2003 |
| WO | WO 03/092595 A2 | 11/2003 |
| WO | WO 2005/095400 | 10/2005 |
| WO | WO 2006/038001 A1 | 4/2006 |
| WO | WO 2006/068826 A2 | 6/2006 |
| WO | WO 2007/146087 A2 | 12/2007 |

(Continued)

OTHER PUBLICATIONS

Dörwald, F. Zaragoza. Side Reactions in Organic Synthesis: A Guide to Successful Synthesis Design, Weinheim: WILEY-VCH Verlag GmbH & Co. KGaA, 2005, Preface.*
Vippagunta, et al. Advanced Drug Delivery Reviews, 48, 2001, 18.*
Jordan, V. C. Nature Reviews: Drug Discovery, 2, 2003, 205.*
Hackam, et al. JAMA, 296(14), 2006, 1731-1732.*
U.S. Appl. No. 13/704,302, filed Dec. 14, 2012, Eastwood et al.
International Search Report, PCT/EP2011/002917, mailed Sep. 6, 2011.
English Language Abstract for WO 2008/081914 A1 (2008).
International Search Report for PCT International Application No. PCT/EP2011/000792, mailed Jul. 21, 2011.
U.S. Appl. No. 13/518,863, filed Jun. 22, 2012, Eastwood et al.
Atreya R., et al., "Blockade of Interleukin 6 trans Signaling Suppresses T-cell Resistance Against Apoptosis in Chronic Intestinal Inflammation: Evidence in Crohn Disease and Experimental Colitis in vivo," Nature Medicine, 6(5):583-588 (2000).

(Continued)

Primary Examiner — Douglas M Willis
(74) Attorney, Agent, or Firm — Finnegan, Henderson, Farabow, Garrett & Dunner, L.L.P.

(57) ABSTRACT

New pyrazole derivatives having the chemical structure of formula (I) are disclosed; as well as process for their preparation, pharmaceutical compositions comprising them and their use in therapy as inhibitors of Janus Kinases (JAK).

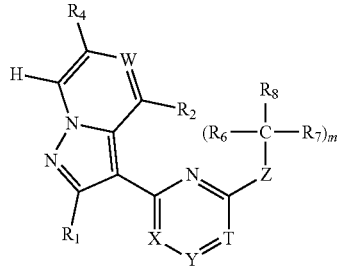

Formula (I)

28 Claims, No Drawings

(56) References Cited

FOREIGN PATENT DOCUMENTS

| WO | WO 2008/043031 | | 4/2008 |
|----|----|----|----|
| WO | WO 2008/045393 | A2 | 4/2008 |
| WO | WO 2008/078100 | A2 | 7/2008 |
| WO | WO 2008/081914 | A1 | 7/2008 |
| WO | WO 2009/021990 | A1 | 7/2008 |
| WO | WO 2008/118823 | | 10/2008 |
| WO | WO 2009/026254 | A1 | 2/2009 |
| WO | WO 2009/050183 | A2 | 2/2009 |
| WO | WO 2009/054941 | | 4/2009 |
| WO | WO 2009/085913 | A1 | 7/2009 |
| WO | WO 2009/086123 | A1 | 7/2009 |
| WO | WO 2009/106442 | | 9/2009 |
| WO | WO 2010/016005 | A1 | 2/2010 |
| WO | WO 2010/072823 | * | 7/2010 |
| WO | WO 2011/076419 | A1 | 6/2011 |
| WO | WO 2011/101161 | | 8/2011 |
| WO | WO 2011/157397 | A1 | 12/2011 |
| WO | WO 2012/069202 | | 5/2012 |
| WO | WO 2012/160030 | | 11/2012 |
| WO | WO 2013/017461 | | 2/2013 |

OTHER PUBLICATIONS

Baird A. M., et al., "T Cell Development and Activation in Jak3-deficient Mice," J. Leukocyte Biol., 63:669-677 (1998).
Bright J. J., et al., "Tyrphostin B42 Inhibits IL-12-Induced Tyrosine Phosphorylation and Activation of Janus Kinase-2 and Prevents Experimental Allergic Encephalomyelitis," J. Immunol., 162:6255-6262(1999).
Briscoe J., et al., "Kinase-negative Mutants of JAK1 Can Sustain Interferon-γ-Inducible Gene Expression But Not an Antiviral State," EMBO Journal, 15(4):799-809 (1996).
Buckley G. M., et al., "IRAK-4 Inhibitors. Part II: A Structure-Based Assessment of Imidazo[1,2-a]Pyridine Binding," Bioorganic & Medicinal Chemistry Letters, 18:3291-3295 (2008).
Buckley G. M., et al., "IRAK-4 Inhibitors. Part III: A Series of Imidazo[1,2-a]Pyridines," Bioorganic & Medicinal Chemistry Letters, 18:3656-3660 (2008).
Chang B. Y., et al., "JAK3 Inhibition Significantly Attenuates Psoriasiform Skin Inflammation in CD18 Mutant PL/J Mice," J. Immunol., 183:2183-2192 (2009).
Chang B. Y., et al., "JAK3 Inhibition Significantly Attenuates Psoriasiform Skin Inflammation in CD18 Mutant PL/J Mice," J. Immunol., 183:Supplemental Data (3 pages) (2009).
Disanto J. P., et al., "Lymphoid Development in Mice With a Targeted Deletion of the Interleukin 2 Receptor γ Chain," PNAS, 92:377-381(1995).
Flex E., et al., "Somatically Acquired JAK1 Mutations in Adult Acute Lymphoblastic Leukemia," J. Exper. Med., 295(4):751-758 (2008).
Grossman W. J., et al., "Dysregulated Myelopoiesis in Mice Lacking JAK3," Blood, 94:932-939 (1999).
Guschin D., et al., "A Major Role for the Protein Tyrosine Kinase JAK1 in the JAK/STAT Signal Transduction Pathway in Response to Interleukin-6," EMBO Journal, 14(7):1421-1429 (1995).
Heinrich P. C., et al., "Principles of Interleukin (IL)-6-type Cytokine Signaling and Its Regulation," Biochem. J., 374:1-20 (2003).
Hexner E. O., et al., "Lestaurtinib (CEP701) is a JAK2 Inhibitor That Suppresses JAK2/STAT5 Signaling and the Proliferation of Primary Erythroid Cells Form Patients With Myeloproliferative Disorders," Blood, 111(12):5663-5671 (2008).
International Search Report, PCT/EP2010/007913, mailed Jun. 1, 2011.
Ivashkiv L. B., et al., "The JAK/STAT Pathway in Rheumatoid Arthritis: Pathogenic or Protective?" Arthritis & Rheumatism, 48(8):2092-2096 (2003).
Karaghiosoff M., et al., "Partial Impairment of Cytokine Responses in Tyk2-Deficient Mice," Immunity, 13:549-560 (2000).
Kudlacz E., et al., "The JAK-3 Inhibitor CP-690550 is a Potent Anti-Inflammatory Agent in a Murine Model of Pulmonary Eosinophilia," European J. Pharmacol., 582:154-161(2008).
Lim L. L., et al., "Biologic Therapies for Inflammatory Eye Disease," Clin. Exper. Opthalmology, 34:365-374 (2006).
Lovato P., et al., "Constitutive STAT3 Activation in Intestinal T Cells From Patients with Crohn's Disease," J. Biol. Chem., 278(19):16777-16781 (2003).
Malaviya R., et al., "Targeting Janus Kinase 3 in Mast Cells Prevents Immediate Hypersensitivity Reactions and Anaphylaxis," J. Biol. Chem., 274(38):27028-27038 (1999).
Malaviya R., et al., "Treatment of Allergic Asthma by Targeting Janus Kinase 3-Dependent Leukotriene Synthesis in Mast Cells with 4-(3', 5'-Dibromo-4'-hydroxyphenyl)amino-6,7-dimethoxyquinazoline (WHI-P97)," J. Pharmacol. Expt. Ther., 295(3):912-926 (2000).
Manshouri T., et al., "The JAK Kinase Inhibitor CCP-690,550 Suppresses the Growth of Human Polycythemia Vera Cells Carrying the $JAK2^{V617F}$ Mutation," Cancer Sci., 99(6):1265-1273 (2008).
McInnes I. B., et al., "Cytokines in the Pathogenesis of Rheumatoid Arthritis," Nature, 7:429-442 (2007).
Meydan N., et al., "Inhibition of Acute Lymphoblastic Leukaemia by a JAK-2 Inhibitor," Nature, 379:645-648 (1996).
Migone Thi-Sau, et al., "Constitutively Activated Jak-STAT Pathway in T Cells Transformed with HTLV-I," Science, 269:79-81 (1995).
Milici A. J., et al., "Cartilage Preservation by Inhibition of Janus Kinase 3 in Two Rodent Models of Rheumatoid Arthritis", Arthritis Research & Therapy, 10(1):1-9 (2008).
Minegishi Y., et al., "Human Tyrosine Kinase 2 Deficiency Reveals Its Requisite Roles in Multiple Cytokine Signals Involved in Innate and Acquired Immunity," Immunity, 25:745-755 (2006).
Murray P. J., "The JAK-STAT Signaling Pathway: Input and Output Integration," J. Immunol.,178:2623-2629 (2007).
Nickoloff B. J., "Cracking the Cytokine Code in Psoriasis," Nature Medicine, 13(3):242-244 (2007).
O'Shea J. J., et al., "Jak3 and the Pathogenesis of Severe Combined Immunodeficiency," Mol. Immunol., 41:727-737 (2004).
Ozaki A., et al., "The Control of Allergic Conjunctivitis by Suppressor of Cytokine Signaling (SOCS)3 and SOCS5 in a Murine Model," J. Immunol., 175:5489-5497 (2005).
Pardanani, A., et al., "CYT387, A Selective JAK1/JAK2 Inhibitor: in vitro Assessment of Kinase Selectivity and Preclinical Studies Using Cell Lines and Primary Cells from Polycythema Vera Patients," Leukemia, 23:1441-1445 (2009).
Pardanani A., et al., "TG101209, A Small Molecule JAK2-Selective Kinase Inhibitor Potently Inhibits Myeloproliferative Disorder-Associated JAK2V617F and MPLW515L/K Mutations," Leukemia, 21:1658-1668 (2007).
Parganas E., et al., "Jak2 Is Essential for Signaling Through a Variety of Cytokine Receptors," Cell, 93:385-395 (1998).
Park S. Y., et al., "Developmental Defects of Lymphoid Cells in JAK3 Kinase-Deficient Mice," Immunity, 3:771-782 (1995).
Peschon J. J., et al., "Early Lymphocyte Expansion Is Severely Impaired in Interleukin 7 Receptor-Deficient Mice," J. Exp. Med., 180:1955-1960 (1994).
Rodig S. J., et al., "Disruption of the Jak1 Gene Demonstrates Obligatory and Nonredundant Roles of the Jaks in Cytokine-Induced Biologic Responses," Cell, 93:373-383 (1998).
Russell S. M., et al., "Mutation of Jak3 in a Patient with SCID: Essential Role of Jak3 in Lymphoid Development," Science, 270:797-800 (1995).
Shimoda K., et al., "Tyk2 Plays a Restricted Role in IFNα Signaling, Although it is Required for IL-12-Mediated T Cell Function," Immunity, 13:561-571 (2000).
Siddiquee K. A. Z., et al., "STAT3 As a Target for Inducing Apoptosis in Solid and Hematological Tumors," Cell Res., 18(2):254-267 (2008).
Skarica M., et al., "Signal Transduction Inhibition of APCs Diminishes Th17 and Th1 Responses in Experimental Autoimmune Encephalomyelitis," J. Immunol., 182:4192-4199 (2009).
Steinman L., "Nuanced Roles of Cytokines in Three Major Human Brain Disorders," J. Clin. Invest., 118:3557-3663 (2008).
Strober W., et al., "The Immunology of Mucosal Models of Inflammation," Annu. Rev. Immunol., 20:495-549 (2002).
Thomis D. C., et al., "Defects in B Lymphocyte Maturation and T Lymphocyte Activation in Mice Lacking Jak3," Science, 270:794-797 (1994).

(56) References Cited

OTHER PUBLICATIONS

Tomita M., et al., "Inhibition of Constitutively Active Jak-Stat Pathway Suppresses Cell Growth of Human T-cell Leukemia Virus Type I-infected T-cell lines and Primary Adult T-cell Leukemia Cells," Retrovirology, 3(22):1-10 (2006).
Vallochi A. L., et al., "The Role of Cytokines in the Regulation of Ocular Autoimmune Inflammation," Cytokine & Growth Factor Reviews, 18:135-141 (2007).
Von Freeden-Jeffry U., et al., "Lymphopenia in Interleukin (IL)-7 Gene-Deleted Mice Identifies IL-7 as a Nonredundant Cytokine," J. Exp. Med.,181:1519-1526 (1995).
Wernig G., et al., "Efficacy of TG101348, A Selective JAK2 Inhibitor, in Treatment of a Murine Model of JAK2V617F-Induced Polycythemia Vera," Cancer Cell, 13(4):311-320 (2008).
Wernig G., et al., "Efficacy of TG101348, A Selective JAK2 Inhibitor, in Treatment of a Murine Model of JAK2V617F-Induced Polycythemia Vera," Cancer Cell, 13:Supplemental Data (2008).
West, K., "CP-690550, A JAK3 Inhibitor as an Immunosuppressant for the Treatment of Rheumatoid Arthritis, Transplant Rejection, Psoriasis and Other Immune-Mediated Disorders," Current Opinion in Investigational Drugs, 10(5):491-504 (2009).
Wu Z., et at, "Design and synthesis of 3,7-diarylimidazopyridines as inhibitors of the VEGF-receptor KDR," Bioorganic & Medicinal Chemistry Letters, 14:909-912 (2004).
Office Action (Restriction Requirement) dated Oct. 10, 2012, in U.S. Appl. No. 13/518,863, Examiner J. Kenyon.
International Search Report of International Application No. PCT/EP2012/059394, dated Jul. 6, 2012.
U.S. Appl. No. 14/119,920, filed Nov. 25, 2013.
U.S. Appl. No. 13/988,798, filed May 22, 2013.
Office Action (Restriction Requirement) dated Mar. 11, 2014, in U.S. Appl. No. 13/704,302, Examiner L. Daniel.
Office Action dated May 22, 2014, in U.S. Appl. No. 13/518,863, Examiner J. Kenyon.
Lucet, Isabel, et al. "The structural basis of Janus kinase 2 inhibition by a potent and specific pan-Janus kinase inhibitor." Blood. (2006), vol. 1 07, No. 1, pp. 176-183.
Clark, James, D., et al. "Discovery and Development of Janus Kinase (JAK) Inhibitors for Inflammatory Diseases." (miniperspective) J. Med. Chem., Article ASAP: Publication Date (Web): Jan. 13, 2014.
Parks, Deborah L. "Tofacitinib and Other Kinase Inhibitors Offer New Approach to Treating Rheumatoid Arthritis." The Rheumatologist. Jun. 2013, pp. 1-12. Available from: <http://www.therheumatologist.org/details/article/4871 781 IT ofacitin lb and_Other_Kinase Inhibitors_Offer_New_Approach_to_Treating_Rheumatol.html>.

Madal, A. "Cancer Classification." ©2014. Available from: < http://www.news-medical.net/health/Cancer-Classification.aspx.
MD Anderson Cancer Center. "Myeloproliferative Disease Prevention and Screening." (c) 2014.
MD Anderson Cancer Center. "Leukemia Prevention and Screening." (c) 2014.
Oxford Dictionary of Biochemistry and Molecular Biology, 1997, Oxford University Press, pp. 314-315.
International Search Report for International Application No. PCT/EP2012/064426, dated Sep. 25, 2012.
International Search Report of International Application No. PCT/EP2011/005929, dated Feb. 17, 2012.
Office Action (Restriction Requirement) dated Sep. 29, 2014, in U.S. Appl. No. 14/119,920, Examiner V Balasurbramanian.
Office Action (Restriction Requirement) dated Nov. 11, 2014, in U.S. Appl. No. 13/988,798, Examiner J. Gonzalez Rodriguez.
Wang, Z. at al, IRAK-4 Inhibitors for Inflammation, Current Topics in Medicinal Chemistry, 2009, 9, 724-737.
Clinical Trials "A Study Evaluating the Efficacy and Safety of CP-690,550 in Patients with Moderate to Severe Ulcerative Colitis (OCTAVE)," Clinicaltrials.gov (NCT01465763) retrieved Sep. 17, 2014.
Clinical Trials "A Open-Label Study of CP-690,550 as Long-Term Therapy (48 Weeks) in Subjects with Crohn's Disease." (NCT01470599) retrieved Sep. 17, 2014.
Clinical Trials "Tofacitnib Ointment for Atopic Dermatitis (Atopic Eczema)," (NCT02001181) retrieved Sep. 17, 2014.
Clinical Trials "Effectiveness and Safety of 3 Dosing Regimens of CP-690,550 to Placebo in Subjects with Moderate to Severe Chronic Plaque Psoriasis," (NCT00878210) retrieved Sep. 17, 2014.
Clinical Trials "A Phase 3, Multi Site, Randomized, Double Bind, Placebo Controlled Study of the Efficacy and Safety Comparing CP-690,550 and Etanercept in Subjects with Moderate to Severe Chronic Plaque Psoriasis," (NCT01241591) retrieved Sep. 17, 2014.
Clinical Trials Immunomodulatory effect of the topical ophthalmic Janus kinase inhibitor tofacitinib (CP-690,550) in patients with dry eye disease, Opthalmology. Jul. 2012;119(7):e43-50.
U.S. Appl. No. 14/236,340, filed Jan. 31, 2014.
Office Action dated Jan. 21, 2015, in U.S. Appl. No. 13/988,798, Examiner Paul V. Ward.
Office Action dated Feb. 10, 2015, in U.S. Appl. No. 14/119,920, Examiner Venkataraman Balasubramanian.
Notice of Aliowance dated Mar. 3, 2015, in U.S. Appl. No. 14/236,340, Examiner Valerie Rodriguez-Garcia.

* cited by examiner

SUBSTITUTED PYRAZOLO[1,5-A]PYRIDINES AS JAK INHIBITORS

CROSS-REFERENCE TO RELATED APPLICATIONS

This is a national stage filing under 35 U.S.C. 371 of International Application No. PCT/EP2011/000792, filed on Feb. 18, 2011, which claims priority to European Patent Application No. 10382039.5, filed Feb. 18, 2010, U.S. Provisional Application No. 61/306,051, filed Feb. 19, 2010, U.S. Provisional Application No. 61/371,081, filed Aug. 5, 2010, and European Patent Application No. 10382217.7, filed Aug. 5, 2010. The contents of all five applications are incorporated herein by reference.

BACKGROUND OF THE INVENTION

Cytokines have critical functions in regulating many aspects of immunity and inflammation, ranging from the development and differentiation of immune cells to the suppression of immune responses. Type I and type II cytokine receptors lack intrinsic enzymatic activity capable of mediating signal transduction, and thus require association with tyrosine kinases for this purpose. The JAK family of kinases comprises four different members, namely JAK1, JAK2, JAK3 and TYK2, which bind to type I and type II cytokine receptors for controlling signal transduction (Murray P J, (2007). The JAK-STAT signalling pathway: input and output Integration. J Immunol, 178: 2623). Each of the JAK kinases is selective for the receptors of certain cytokines. In this regard, JAK-deficient cell lines and mice have validated the essential role of each JAK protein in receptor signalling: JAK1 In class II cytokine receptors (IFN and IL-10 family), those sharing the gp130 chain (IL-6 family) and the common gamma chain (IL-2, IL-4, IL-7, IL-9, IL-15 and IL-21) (Rodig et at. (1998). Disruption of the JAK1 gene demonstrates obligatory and nonredundant roles of the Jaks in cytokine-induced biological response. Cell, 93:373; Guschin et at. (1995). A major role for the protein tyrosine kinase JAK1 in the JAK/STAT signal transduction pathway in response to interleukin-6. EMBO J. 14: 1421; Briscoe et at. (1996). Kinase-negative mutants of JAK1 can sustain intereferon-gamma-inducible gene expression but not an antiviral state. EMBO J. 15:799); JAK2 in hematopoietic factors (Epo, Tpo, GM-CSF, IL-3, IL-5) and type II IFNs (Parganas et al., (1998). JAK2 Is essential for signalling through a variety of cytokine receptors. Cell, 93:385); JAK3 in receptors sharing the common gamma chain (IL-2 family) (Park et al., (1995). Developmental defects of lymphoid cells in JAK3 kinase-deficient mice. Immunity, 3:771; Thomis et al., (1995). Defects in B lymphocyte maturation and T lymphocyte activation in mice lacking JAK3. Science, 270:794; Russell et al, (1995). Mutation of JAK3 in a partient with SCID: Essential role of JAK3 in lymphoid development. Science, 270:797); and Tyk2 in the receptors of IL-12, IL-23, IL-13 and type I IFNs (Karaghiosoff et al., (2000). Partial impairment of cytokine responses in Tyk2-deficient mice. Immunity, 13:549; Shimoda et al., (2000). Tyk2 plays a restricted role in IFNg signaling, although it is required for IL-12-mediated T cell function. Immunity, 13:561; Minegishi et al., (2006). Human Tyrosine kinase 2 deficiency reveals its requisite roles in multiple cytokine signals involved in innate and acquired immunity. Immunity, 25:745).

Receptor stimulation leads sequentially to JAK activation by phosphorylation, receptor phosphorylation, STAT protein recruitment and STAT activation and dimerization. The STAT dimer then functions as a transcription factor, translocating to the nucleus and activating the transcription of multiple response genes. There are seven STAT proteins identified: STAT1, STAT2, STAT3, STAT4, STAT5a, STAT5b and STAT6. Each particular cytokine receptor associates preferentially with a particular STAT protein. Some associations are independent of cell type (ex: IFNg-STAT1) while others may be cell type dependent (Murray P J, (2007). The JAK-STAT signaling pathway: input and output integration. J Immunol, 178: 2623).

The phenotype of deficient mice has provided insights on the function of each JAK and the cytokine receptors signaling through them. JAK3 associates exclusively with the common gamma chain of the receptors for IL-2, IL-4, IL-7, IL-9, IL-15 and IL-21 cytokines. By virtue of this exclusive association, JAK3 knock out mice and common gamma chain deficient mice have an identical phenotype (Thomis et al., (1995). Defects in B lymphocyte maturation and T lymphocyte activation in mice lacking JAK3. Science, 270:794; DiSanto et at., (1995). Lymphoid development in mice with a targeted deletion of the interleukin 2 receptor gamma chain. PNAS, 92:377). Moreover, this phenotype is shared to a great extent with SCID patients that hold mutations/defects in the common gamma chain or JAK3 genes (O'Shea et al, (2004). JAK3 and the pathogenesis of severe combined immunodeficiency. Mol Immunol, 41: 727). JAK3-deficient mice are viable but display abnormal lymphopoiesis which leads to a reduced thymus size (10-100 fold smaller than wild type). JAK3-deficient peripheral T cells are unresponsive and have an activated/memory cell phenotype (Baird et al, (1998). T cell development and activation in JAK3-deficient mice. J. Leuk. Biol. 63: 669). The thymic defect in these mice strongly resembles that seen in IL-7 and IL-7 receptor knockout mice, suggesting that the absence of IL-7 signaling accounts for this defect in JAK3−/−mice (von Freeden-Jeffry et al, (1995). Lymphopenia in Interleukin (IL)-7 Gene-deleted Mice Identifies IL-7 as a non-redundant Cytokine. J Exp Med, 181: 1519; Peschon et al, (1994). Early lymphocyte expansion is severely impaired in interleukin 7 receptor-deficient mice. J Exp Med, 180: 1955). These mice, like SCID humans, have no NK cells, probably due to the absence of IL-15 signaling, a survival factor for these cells. JAK3 knockout mice, unlike SCID patients, show deficient B cell lymphopoiesis while in human patients, B cells are present in circulation but are not responsive leading to hypoglobulinemia (O'Shea et al, (2004). JAK3 and the pathogenesis of severe combined immunodeficiency. Mol Immunol, 41: 727). This is explained by species-specific differences in IL-7 function in B and T cell development in mice and humans. On the other hand, Grossman et al. (1999. Dysregulated myelopoiesis in mice lacking JAK3. Blood, 94:932:939) have shown that the loss of JAK3 in the T-cell compartment drives the expansion of the myeloid lineages leading to dysregulated myelopoiesis.

JAK2-deficient mice are embrionically lethal, due to the absence of definitive erythropoiesis. Myeloid progenitors fail to respond to Epo, Tpo, IL-3 or GM-CSF, while G-CSF and IL-6 signaling are not affected. JAK2 is not required for the generation, amplification or functional differentiation of lymphoid progenitors (Parganas et al., (1998). JAK2 is essential for signaling through a variety of cytokine receptors. Cell, 93:385).

JAK1-deficient mice die perinatally due to a nursing defect. JAK1 binds exclusively to the gp130 chain shared by the IL-6 cytokine family (i.e. LIF, CNTF, OSM, CT-1) and along with JAK3, is an essential component of the receptors sharing the common gamma chain, by binding to the nonshared receptor subunit. In this regard, JAK1-deficient mice show similar hematopoiesis defects as JAK3-deficient mice. In addition, they show defective responses to neurotrophic factors and to all interferons (class II cytokine receptors) (Rodig et al, (1998). Disruption of the JAK1 gene demonstrates obligatory and non-redundant roles of the Jaks in cytokine-induced biological response. *Cell,* 93:373).

Finally, Tyk2-deficient mice show an impaired response to IL-12 and IL-23 and only partially impaired to IFN-alpha (Karaghiosoff et al., (2000). Partial impairment of cytokine responses in Tyk2-deficient mice. *Immunity,* 13:549; Shimoda et al., (2000). Tyk2 plays a restricted role in IFNg signaling, although it is required for IL-12-mediated T cell function. *Immunity,* 13:561). However, human Tyk2 deficiency demonstrates that Tyk2 is involved in the signaling from IFN-α, IL-6, IL-10, IL-12 and IL-23 (Minegishi et al., (2006). Human Tyrosine kinase 2 deficiency reveals its requisite roles in multiple cytokine signals involved in innate and acquired immunity. *Immunity,* 25:745).

The role of JAK kinases in transducing the signal from a myriad of cytokines makes them potential targets for the treatment of diseases in which cytokines have a pathogenic role, such as inflammatory diseases, including but not limited to allergies and asthma, chronic obstructive pulmonary disease (COPD), psoriasis, autoimmune diseases such as rheumatoid arthritis, amyotrophic lateral sclerosis and multiple sclerosis, uveitis, transplant rejection, as well as in solid and hematologic malignancies such as myeloproliferative disorders, leukemia and lymphomas.

Inhibition of JAK kinases, especially JAK1 and JAK3, could give rise to potent immunosuppression which could be used therapeutically to prevent transplant rejection. In this regard, the JAK inhibitor CP-690,550 (tasocitinib) has shown efficacy in several animal models of transplantation (heretopic heart transplantation in mice, cardiac allografts implanted in the ear of mice, renal allotransplantation in cynomolgous monkeys, aorta and tracheal transplantation in rats) by prolonging the mean survival time of grafts (West K (2009). CP-690,550, a JAK3 inhibitor as an immunosuppressant for the treatment of rheumatoid arthritis, transplant rejection, psoriasis and other immune-mediated disorders. *Curr. Op. Invest. Drugs* 10: 491).

In rheumatoid joints, an imbalance between pro and antiinflammatory cytokine activities favours the induction of autoimmunity, followed by chronic inflammation and tissue destruction. In this regard, the pathogenic role of IL-6 in rheumatoid arthritis (RA) has been validated clinically by the use of the anti-IL-6R antibody tocilizumab. IL-6 activates the transcription factor STAT3, through the use of JAK1 binding to the gp130 receptor chain (Heinrich et al., (2003). Principles of interleukin (IL)-6-type cytokine signaling and its regulation. *Biochem J.* 374: 1). Constitutive STAT3 mediates the abnormal growth and survival properties of RA synoviocytes (Ivashkiv and Hu (2003). The JAK/STAT pathway in rheumatoid arthritis: pathogenic or protective? *Arth & Rheum.* 48:2092). Other cytokines that have been implicated in the pathogenesis of arthritis include IL-12 and IL-23, implicated in Th1 and Th17 cell proliferation, respectively; IL-15, and GM-CSF (McInnes and Schett, (2007). Cytokines in the pathogenesis of rheumatoid arthritis. *Nature Rew Immunol.* 7:429.). The receptors for these cytokines also utilize JAK proteins for signal transduction, making JAK inhibitors potential pleiotropic drugs in this pathology. Consequently, administration of several JAK inhibitors in animal models of murine collagen-induced arthritis and rat adjuvant-induced arthritis has shown to reduce inflammation, and tissue destruction (Milici et al., (2008). Cartilage preservation by inhibition of Janus kinase 3 in two rodent models of rheumatoid arthritis. *Arth. Res.* 10:R14).

Inflammatory bowel disease (IBD) encloses two major forms of intestinal inflammation: ulcerative colitis and Crohn's disease. Growing evidence has shown that multiple cytokines, including interleukins and interferons, are involved in the pathogenesis of IBD (Strober et al, (2002). The immunology of mucosal models of inflammation. *Annu Rev Immunol.* 20: 495). Activation of the IL-6/STAT3 cascade in lamina propia T cells has been shown to induce prolonged survival of pathogenic T cells (Atreya et al, (2000). Blockade of interleukin 6 trans signaling suppresses T-cell resistance against apoptosis in chronic intestinal inflammation: Evidence in Crohn's disease and experimental colitis in vivo. *Nature Med.* 6:583). Specifically, STAT3 has been shown to be constitutively active in intestinal T cells of Crohn's disease patients and a JAK inhibitor has been shown to block the constitutive activation of STAT3 in these cells (Lovato et al, (2003). Constitutive STAT3 activation in intestinal T cells from patients with Crohn's disease. *J Biol Chem.* 278:16777). These observations indicate that the JAK-STAT pathway plays a pathogenic role in IBD and that a JAK inhibitor could be therapeutic in this setting.

Multiple sclerosis is an autoimmune demyelinating disease characterized by the formation of plaques in the white matter. The role of cytokines in the generation of multiple sclerosis has long been known. Potential therapies include blockade of IFN-g, IL-6, IL-12 and IL-23 (Steinman L. (2008). Nuanced roles of cytokines in three major human brain disorders. *J Clin Invest.* 118:3557), cytokines that signal through the JAK-STAT pathways. Use of tyrphostin, a JAK inhibitor, has been shown to inhibit IL-12-induced phosphorylation of STAT3, and to reduce the incidence and severity of active and passive experimental autoimmune encephalitis (EAE) (Bright et al., (1999) Tyrphostin B42 inhibits IL-12-induced tyrosine phosphorylation and activation of Janus kinase-2 and prevents experimental allergic encephalomyelitis. *J Immunol.* 162:6255). Another multikinase inhibitor, CEP701, has been shown to reduce secretion of TNF-alpha, IL-6 and IL-23 as well as the levels of phospho-STAT1, STAT3, and STAT5 in peripheral DCs of mice with EAE, significantly improving the clinical course of EAE in mice (Skarica et al, (2009). Signal transduction inhibition of APCs diminishes Th17 and Th1 responses in experimental autoimmune encephalyelitis. *J. Immunol.* 182:4192.).

Psoriasis is a skin inflammatory disease which involves a process of immune cell infiltration and activation that culminates in epithelial remodeling. The current theory behind the cause of psoriasis states the existence of a cytokine network that governs the interaction between immune and epithelial cells (Nickoloff B J. (2007). Cracking the cytokine code in psoriasis, *Nat Med,* 13:242). In this regard, IL-23 produced by dendritic cells is found elevated in psoriatic skin, along with IL-12. IL-23 induces the formation of Th17 cells which in turn produce IL-17 and IL-22, the last one being responsible for epidermis thickening. IL-23 and IL-22 induce the phosphorylation of STAT-3, which is found abundantly in psoriatic skin. JAK inhibitors may thus be therapeutic in this setting. In accordance, a JAK1/3 inhibitor, R348, has been found to attenuate psoriasiform skin inflammation in a spontaneous T cell-dependent mouse model of psoriasis (Chang et al., (2009). JAK3 inhibition significantly attenuates psoriasiform skin inflammation on CD18 mutant PUJ mice. *J Immunol.* 183:2183).

Th2 cytokine-driven diseases such as allergy and asthma could also be a target of JAK inhibitors. IL-4 promotes Th2 differentiation, regulates B-cell function and immunoglobulin class switching, regulates eotaxin production, induces expression of IgE receptor and MHC II on B cells, and stimulates mast cells. Other Th2 cytokines like IL-5 and IL-13 can also contribute to eosinophil recruitment in bronchoalveolar lavage by stimulating eotaxin production. Pharmacological inhibition of JAK has been shown to reduce the expression of IgE receptor and MHCII induced by IL-4 stimulation on B cells (Kudlacz et al., (2008). The JAK3 inhibitor CP-690,550 is a potent anti-inflammatory agent in a murine model of pulmonary eosinophilia. *European J. Pharm.* 582: 154). Furthermore, JAK3-deficient mice display poor eosinophil recruitment and mucus secretion to the airway lumen upon OVA challenge, as compared to wild type mice (Malaviya et al, (2000). Treatment of allergic asthma by targeting Janus kinase 3-dependent leukotriene synthesis in mast cells with 4-(3',5'-dibromo-4'-hydroxyphenyl)amino-6,7-dimethoxyquinazoline (WHI-P97). JPET 295:912.). In this regard, systemic administration of the CP-690,550 JAK inhibitor in mice has been shown to reduce the eosinophil count as well as the levels of eotaxin and IL13 in BAL in a murine model of pulmonary eosinophilia (Kudlacz et al., (2008). The JAK3 inhibitor CP-690,550 is a potent anti-inflammatory agent in a murine model of pulmonary eosinophilia. *European J. Pharm.* 582:154).

There is increasing evidence that cytokines play a pathogenetic role in ocular inflammatory disease such as uveitis or dry eye syndrome. Some cytokines implicated in experimental autoimmune uveitis, such as IL-2, IL-6, IL-12 and IFNg, would be amenable to JAK inhibition (Vallochi et al, (2007). The role of cytokines in the regulation of ocular autoimmune inflammation. *Cytok Growth Factors Rev.* 18:135). In this regard, drugs or biologicals that interfere with IL-2 signaling such as cyclosporine or anti-IL-2 receptor antibody (daclizumab) have shown efficacy in the treatment of keratoconjuctivitis sicca and refractory uveitis, respectively (Lim et al, (2006). Biologic therapies for inflammatory eye disease. *Clin Exp Opht* 34:365). Similarly, allergic conjunctivitis, a common allergic eye disease characterized by conjuctival congestion, mast cell activation and eosinophil infiltration, could benefit from JAK inhibition. STAT6-deficient mice, showing decreased TH2-mediated immune responses which are normally triggered by IL-4, do not develop the classical early and late phase responses, suggesting that IL-4 pathway abrogation through JAK inhibition may be therapeutic in this setting (Ozaki et al, (2005). The control of allergic conjunctivitis by suppression of cytokine signaling (SOCS)$_3$ and SOCS5 in a murine model. *J Immunol,* 175:5489).

There is growing evidence of the critical role of STAT3 activity in processes involved in tumorigenesis like cell cycle dysregulation, promotion of uncontrolled growth, induction of survival factors and inhibition of apoptosis (Siddiquee et al., (2008). STAT3 as a target for inducing apoptosis in solid and haematological tumors. *Cell Res.* 18: 254). Antagonism of STAT3 by means of dominant-negative mutants or antisense oligonucleotides has shown to promote apoptosis of cancer cells, inhibition of angiogenesis and up-regulation of host immunocompetence. Inhibition of constitutively active STAT3 in human tumors by means of JAK inhibitors may provide a therapeutic option to the treatment of this disease. In this regard, the use of the JAK inhibitor tyrphostin has been shown to induce apoptosis of malignant cells and inhibit cell proliferation in vitro and in vivo (Meydan et al., (1996). Inhibition of acute lymphoblastic leukemia by a JAK-2 inhibitor. *Nature,* 379:645).

Hematological malignancies with dysregulated JAK-STAT pathways may benefit from JAK inhibition. Recent studies have implicated dysregulation of JAK2 kinase activity by chromosomal translocations and mutations within the pseudokinase domain (such as the JAK2V617F mutation) in a spectrum of myeloproliferative diseases (Ihle and Gililand, 2007), including polycythemia vera, myelofibrosis and essential thrombocythemia. In this regard, several JAK inhibitors that tackle JAK2 potently, such as TG-101209 (Pardanani et al., (2007). TG101209, a small molecular JAK2-selective inhibitor potently inhibits myeloproliferative disorder-associated JAK2V617F and MPLW515L/K mutations *Leukemia.* 21:1658-68), TG101348 (Wernig et al, (2008). Efficacy of TG101348, a selective JAK2 inhibitor, in treatment of a murine model of JAK2V617F-induced polycythemia vera. *Cancer Cell,* 13: 311), CEP701, (Hexner et al, (2008). Lestaurtinib (CEP701) is a JAK2 inhibitor that suppresses JAK2/STAT5 signaling and the proliferation of primary erythroid cells from patients with myeloproliferative disorders. *Blood,* 111: 5663), CP-690,550 (Manshouri et al, (2008). The JAK kinase inhibitor CP-690,550 suppresses the growth of human polycythemia vera cells carrying the JAK2V617F mutation. *Cancer Sci,* 99:1265), and CYT387 (Pardanani et al., (2009). CYT387, a selective JAK1/JAK2 inhibitor: invitro assessment of kinase selectivity and preclinical studies using cell lines and primary cells from polycythemia vera patients. *Leukemia,* 23:1441) have been proposed for treating myeloproliferative diseases on the basis of their antiproliferative activity on cells carrying the JAK2V617F mutation. Similarly, T-cell leukemia due to human T-cell leukemia virus (HTLV-1) transformation is associated with JAK3 and STAT5 constitutive activation (Migone et al, (1995). Constitutively activated JAK-STAT pathway in T cells transformed with HTLV-I. *Science,* 269: 79) and JAK inhibitors may be therapeutic in this setting (Tomita et al, (2006). Inhibition of constitutively active JAK-STAT pathway suppresses cell growth of human T-cell leukemia virus type I-infected T cell lines and primary adult T-cell leukemia cells. *Retrovirology,* 3:22). JAK1-activating mutations have also been identified in adult acute lymphoblastic leukemia of T cell origin (Flex et al, (2008). Somatically acquired JAK1 mutations in adult acute lymphoblastic leukemia. *J. Exp. Med.* 205:751-8) pointing to this kinase as a target for the development of novel antileukemic drugs.

Conditions in which targeting of the JAK pathway or modulation of the JAK kinases, particularly JAK1, JAK2 and JAK3 kinases, are contemplated to be therapeutically useful for the treatment or prevention of diseases include: neoplastic diseases (e.g. leukemia, lymphomas, solid tumors); transplant rejection, bone marrow transplant applications (e.g., graft-versus-host disease); autoimmune diseases (e.g. diabetes, multiple sclerosis, rheumatoid arthritis, inflammatory bowel disease); respiratory inflammation diseases (e.g. asthma, chronic obstructive pulmonary disease), inflammation-linked ocular diseases or allergic eye diseases (e.g. dry eye, glaucoma, uveitis, diabetic retinopathy, allergic conjunctivitis or age-related macular degeneration) and skin inflammatory diseases (e.g., atopic dermatitis or psoriasis).

In view of the numerous conditions that are contemplated to benefit by treatment involving modulation of the JAK pathway or of the JAK kinases it is immediately apparent that new compounds that modulate JAK pathways and use of these compounds should provide substantial therapeutic benefits to a wide variety of patients.

Provided herein are novel heteroaryl imidazolone derivatives for use in the treatment of conditions in which targeting of the JAK pathway or inhibition of JAK kinases can be therapeutically useful.

BRIEF SUMMARY OF THE INVENTION

The compounds described in the present invention are simultaneously potent JAK1, JAK2 and JAK3 inhibitors, i.e. pan-JAK inhibitors. This property makes them useful for the treatment or prevention of pathological conditions or diseases such as myeloproliferative disorders (such as polycythemia vera, essential thrombocythemia or myelofibrosis), leukemia, lymphomas and solid tumors; bone marrow and organ transplant rejection; or immune-mediated diseases such as autoimmune and inflammation diseases, including rheumatoid arthritis, multiple sclerosis, inflammatory bowel disease (such as ulcerative colitis or Crohn's disease), inflammation-linked ocular diseases or allergic eye diseases (such as dry eye, uveitis, or allergic conjunctivitis), allergic rhinitis, asthma, chronic obstructive pulmonary disease (COPD), and skin inflammatory diseases (such as atopic dermatitis or psoriasis).

It has now been found that certain pyrazole derivatives are novel and potent JAK inhibitors and can therefore be used in the treatment or prevention of these diseases.

DETAILED DESCRIPTION OF THE INVENTION

Thus the present invention is directed to compounds which are pyrazole derivatives of formula (I), or a pharmaceutically acceptable salt, or solvate, or N-oxide, or stereoisomer or deuterated derivative thereof:

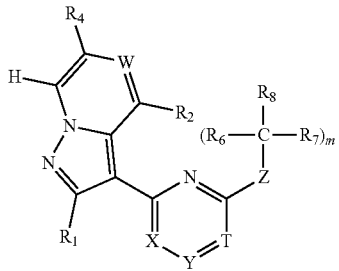

Formula (I)

wherein
m is 0 or an integer from 1 to 3;
Z represents an oxygen atom or a group $NR_5$;
W represents a nitrogen atom or a —$CR_3$ group;
X, Y and T independently represent a nitrogen atom or a —$CR_9$ group, wherein when one of X, Y or T represents a nitrogen atom the remaining represent a —$CR_9$ group;
$R_1$, $R_2$, $R_3$, $R_4$ and $R_9$ each independently represent a hydrogen atom, a halogen atom, a cyano group, a linear or branched $C_1$-$C_6$ alkyl group, a $C_2$-$C_4$ alkenyl group, a $C_2$-$C_4$ alkynyl group, a $C_1$-$C_4$ haloalkyl group, a $C_1$-$C_4$ hydroxyalkyl group, a $C_3$-$C_{10}$ cycloalkyl group, a $C_3$-$C_{10}$ cycloalkenyl group, a monocyclic or polycyclic $C_5$-$C_{14}$ aryl group, a 5- to 14-membered heteroaryl group containing at least one heteroatom selected from O, S and N, a 5- to 14-membered heterocyclyl group containing at least one heteroatom selected from O, S and N, a bicyclyl group containing a monocyclic $C_5$-$C_9$ aryl or heteroaryl group bonded directly to a 5- to 9-membered cycloalkyl or heterocyclyl group, said heteroaryl or heterocyclyl group containing at least one heteroatom selected from O, S and N, an aza-bicycloalkyl group having up to 12 carbon atoms or an aza-bicycloalkenyl group having up to 12 carbon atoms, wherein the alkenyl, alkynyl, haloalkyl, hydroxyalkyl, cycloalkyl, cycloalkenyl, aryl, heteroaryl, heterocyclyl, bicyclyl, aza-bicycloalkyl and aza-bicycloalkenyl groups are unsubstituted or substituted by one or more substituents selected from substituents Ra, and the alkyl groups are unsubstituted or substituted by one or more substituents selected from Rb;

or $R_1$, $R_2$, $R_3$, $R_4$ and $R_9$ independently represent a —$SR_{13}$ group, a —$SOR_{13}$ group, a —$S(O)_2R_{13}$ group, a —$S(O)_2NR_{13}R_{14}$ group, a —$NR_{13}S(O)_2R_{14}$ group, a —$NR_{13}S(O)_2NR_{14}$ group, a —$(CH_2)_nOR_{13}$ group, a —$C(O)OR_{13}$ group, a —O—$C(O)R_{13}$ group, a —$C(O)$—$(CH_2)_n$—$R_{15}$ group, a —$NR_{13}R_{14}$ group, a —$C(O)$—$(CH_2)_n$—$NR_{13}R_{14}$ group, a —$NR_{13}C(O)$—$(CH_2)$—$R_{14}$ group or a —$NR_{13}C(O)$—$(CH_2)_n$—$NR_{14}R_{15}$ group, wherein each n is 0, 1 or 2;

or in the case when two adjacent —$CR_9$ groups are present, two adjacent —$CR_9$ groups and the carbon atoms to which they are bonded optionally form a $C_5$-$C_{12}$ aryl group or a 4- to 12-membered heteroaryl, cycloalkyl or heterocyclyl group, said heteroaryl and heterocyclyl groups containing at least one heteroatom selected from O, S and N, the aryl, heteroaryl, cycloalkyl and heterocyclyl groups being unsubstituted or substituted by one or more substituents selected from a halogen atom, a linear or branched $C_1$-$C_6$ alkyl group, a monocyclic or polycyclic $C_5$-$C_{14}$ aryl group, a 5- to 14-membered heteroaryl group containing at least one heteroatom selected from O, S and N, or a 5-to 14-membered heterocyclyl group containing at least one heteroatom selected from O, S and N, wherein the alkyl, the aryl, the heteroaryl and the heterocyclyl substituents are unsubstituted or substituted by one or more substituents selected from a halogen atom, a hydroxyl group, a cyano group, a linear or branched $C_1$-$C_6$ alkyl group or a $C_1$-$C_4$ haloalkyl group;

$R_5$ represents a hydrogen atom, a linear or branched $C_1$-$C_6$ alkyl group optionally substituted by one or more substituents selected from a hydroxyl group, a cyano group, a $C_1$-$C_4$ haloalkyl group, a $C_1$-$C_4$ hydroxyalkyl group, a $C_3$-$C_{10}$ cycloalkyl group, a phenyl group or a 6 membered, saturated N-containing heterocyclyl ring, or $R_5$ represents a —$S(O)_2R_{10}$ group, a —$S(O)_2NR_{10}R_{11}$ group, a —$C(O)OR_{10}$ group, a —$C(O)$—$(CH_2)_n$—$R_{10}$ group, or a —$C(O)$—$(CH_2)_n$—$NR_{10}R_{11}$ group;

$R_6$ and $R_7$ each independently represent a hydrogen atom or a linear or branched $C_1$-$C_6$ alkyl group optionally substituted by one or more substituents selected from a hydroxyl group, a cyano group, a $C_1$-$C_4$ haloalkyl group, a $C_1$-$C_4$ hydroxyalkyl group, a $C_1$-$C_4$ alkoxycarbonyl group, a $C_3$-$C_7$ cycloalkyl group, a phenyl group or a 6 membered, saturated N-containing heterocyclyl ring;

$R_8$ represents a hydrogen atom, a halogen atom, a cyano group, a linear or branched $C_1$-$C_6$ alkyl group, a $C_2$-$C_4$ alkenyl group, a $C_2$-$C_4$ alkynyl group, a $C_1$-$C_4$ haloalkyl group, a $C_1$-$C_4$ hydroxyalkyl group, a $C_3$-$C_{10}$ cycloalkyl group, a $C_3$-$C_{10}$ cycloalkenyl group, a monocyclic or polycyclic $C_5$-$C_{14}$ aryl group, a 5- to 14-membered heteroaryl group containing at least one heteroatom selected from O, S and N, a 5- to 14-membered heterocyclyl group containing at least one heteroatom selected from O, S and N, a bicyclyl group containing a monocyclic $C_5$-$C_9$ aryl or heteroaryl group bonded directly to a 5- to 9-membered cycloalkyl or heterocyclyl group, said heteroaryl or heterocyclyl group containing at least one heteroatom selected from O, S and N, an aza-bicycloalkyl group having up to 12 carbon atoms or a aza-bicycloalkenyl group having up to 12 carbon atoms, wherein the alkenyl, alkynyl, haloalkyl, hydroxyalkyl, cycloalkyl, cycloalkenyl, aryl, heteroaryl, heterocyclyl, bicyclyl, aza-bicycloalkyl and aza-bicycloalkenyl groups are unsubstituted or substituted by one or more substituents selected from Ra, —($C_1$-$C_4$ alkyl)-CN groups, or —($C_1$-$C_4$ alkyl)-C(O)NR'R" groups wherein R' and R" are the same or different and are selected from hydrogen atoms and linear or branched $C_1$-$C_4$ alkyl groups; and the alkyl groups are unsubstituted or substituted by one or more substituents selected from Rb;

or $R_8$ represents a —$SR_{13}$ group, a —$SOR_{13}$ group, a —$S(O)_2R_{13}$ group, a —$S(O)_2NR_{13}R_{14}$ group, a —$NR_{13}S(O)_2R_{14}$ group, a —$NR_{13}S(O)_2NR_{14}$ group, a —$(CH_2)_nOR_{13}$ group, a —$C(O)OR_{13}$ group, a —O—$C(O)R_{13}$ group, a —C(O)—$(CH_2)_n$—$R_{13}$ group, a —$NR_{13}R_{14}$ group, a —C(O)—$(CH_2)$—$NR_{15}R_{14}$ group, a —$NR_{13}C(O)$—$(CH_2)_n$—$R_{14}$ group, or a —$NR_{13}C(O)$—$(CH_2)_n$—$NR_{14}R_{15}$ group, wherein each n is 0, 1 or 2, or $R_8$ together with $R_5$ and the nitrogen atom to which $R_5$ is bonded form a 4- to 10-membered, saturated heterocyclyl group, which contains, as heteroatoms, one or two nitrogen atoms and which is substituted by a linear or branched $C_1$-$C_6$ alkyl group, a monocyclic or polycyclic $C_5$-$C_{14}$ aryl group, a 5- to 14-membered heteroaryl group containing at least one heteroatom selected from O, S and N, a 5- to 14-membered heterocyclyl group containing at least one heteroatom selected from O, S and N, a —$SO_2R_{10}$ group, a —C(O)—$(CH_2)_n$—$R_{10}$ group, or a —C(O)—$(CH_2)_n$—$NR_{10}R_{11}$ group, wherein each n is 0, 1 or 2, wherein the alkyl, aryl, heteroaryl and heterocyclyl groups are unsubstituted or substituted by one or more substituents selected from a halogen atom, a hydroxyl group, a cyano group, a linear or branched $C_1$-$C_6$ alkyl group or a $C_1$-$C_4$ haloalkyl group, and wherein the alkyl groups are unsubstituted or substituted by one or more substituents selected from a halogen atom, a hydroxyl group, a cyano group or a $C_1$-$C_4$ haloalkyl group;

provided that when m is zero, $R_8$ is other than a —$SR_{13}$ group, a —$SOR_{13}$ group, a —$S(O)_2R_{13}$ group, a —$S(O)_2NR_{13}R_{14}$ group, a —$NR_{13}S(O)_2R_{14}$ group, a —$NR_{13}S(O)_2NR_{14}$ group, a —$(CH_2)_nOR_{13}$ group, a —O—$C(O)R_{13}$ group, a —$NR_{13}R_{14}$ group, a —$NR_{13}C(O)$—$(CH_2)_n$—$R_{14}$ group, or a —$NR_{13}C(O)$—$(CH_2)_n$—$NR_{14}R_{15}$ group, wherein Ra is a halogen atom, a cyano group, a hydroxyl group, a linear or branched $C_1$-$C_6$ alkyl group, a $C_1$-$C_4$ haloalkyl group, $C_1$-$C_4$ alkoxy group, a $C_1$-$C_4$ hydroxyalkyl group, a $C_3$-$C_7$ cycloalkyl or a $C_3$-$C_7$ cycloalkenyl group unsubstituted or substituted by one or more substituents selected from substituents Re, a monocyclic or polycyclic $C_5$-$C_{14}$ aryl group unsubstituted or substituted by one or more substituents selected from substituents Re, a 5- to 14-membered heteroaryl group containing at least one heteroatom selected from O, S and N unsubstituted or substituted by one or more substituents selected from substituents Re, a 5- to 14-membered heterocyclyl group containing at least one heteroatom selected from O, S and N unsubstituted or substituted by one or more substituents selected from substituents Re, a —$SR_{10}$ group, a —$SOR_{10}$ group, a —$S(O)_2R_{10}$ group, a —$S(O)_2NR_{10}R_{11}$ group, a —$NR_{10}S(O)_2R_{11}$ group, a —$NR_{10}S(O)_2NR_{11}$ group, a —$(CH_2)_nOR_{10}$ group, a —C(O)$OR_{10}$ group, a —O—$C(O)R_{10}$ group, a —C(O)—$(CH_2)_n$—$R_{10}$ group, a —$NR_{10}R_{11}$ group, a —C(O)—$(CH_2)_n$—$NR_{10}R_{11}$ group, a —$NR_{10}C(O)$—$(CH_2)_n$—$R_{11}$ group or a —$NR_{10}C(O)$—$(CH_2)_n$—$NR_{11}R_{12}$ group, wherein each n is 0, 1 or 2;

Rb is a cyano group, a $C_1$-$C_4$ haloalkyl group, $C_1$-$C_4$ alkoxy group, a $C_1$-$C_4$ hydroxyalkyl group, a $C_3$-$C_7$ cycloalkyl or a $C_3$-$C_7$ cycloalkenyl group unsubstituted or substituted by one or more substituents selected from substituents Re, a monocyclic or polycyclic $C_5$-$C_{14}$ aryl group unsubstituted or substituted by one or more substituents selected from substituents Re, a 5- to 14-membered heteroaryl group containing at least one heteroatom selected from O, S and N unsubstituted or substituted by one or more substituents selected from substituents Re, a 5- to 14-membered heterocyclyl group containing at least one heteroatom selected from O, S and N unsubstituted or substituted by one or more substituents selected from substituents Re, a —$SR_{10}$ group, a —$SOR_{10}$ group, a —$S(O)_2R_{10}$ group, a —$S(O)_2NR_{10}R_{11}$ group, a —$NR_{10}S(O)_2R_{11}$ group, a —$NR_{10}S(O)_2NR_{11}$ group, a —$(CH_2)_nOR_{10}$ group, a —$C(O)OR_{10}$ group, a —O—$C(O)R_{10}$ group, a —C(O)—$(CH_2)_n$—$R_{10}$ group, a —$NR_{10}R_{11}$ group, a —C(O)—$(CH_2)_n$—$NR_{10}R_{11}$ group, a —$NR_{10}C(O)$—$(CH_2)_n$—$R_{11}$ group or a —$NR_{10}C(O)$—$(CH_2)$—$NR_{11}R_{12}$ group, wherein each n is 0, 1 or 2;

$R_{10}$, $R_{11}$ and $R_{12}$ each independently represents a hydrogen atom, a cyano group, a linear or branched $C_1$-$C_6$ alkyl group, a $C_1$-$C_4$ haloalkyl group, a $C_1$-$C_4$ hydroxyalkyl group, a $C_1$-$C_4$ alkoxycarbonyl group, a $C_3$-$C_7$ cycloalkyl group, a phenyl group, a 5- to 6-membered monocyclic heteroaryl group containing 1, 2 or 3 heteroatoms selected from N, O and S, a 5- to 6-membered, heterocyclyl group containing 1, 2 or 3 nitrogen atoms, a bicyclyl group containing a monocyclic $C_5$-$C_6$ aryl or heteroaryl group bonded directly to a 5- to 6-membered cycloalkyl or heterocyclyl group which heteroaryl or heterocyclyl group contains 1, 2 or 3 nitrogen atoms, the haloalkyl, hydroxyalkyl, alkoxycarbonyl, cycloalkyl, phenyl, heteroaryl, heterocyclyl and bicyclyl group being unsubstituted or substituted by one or more substituents selected from substituents Rc, and the alkyl groups being unsubstituted or substituted by one or more substituents selected from substituents Rd;

Rc is a halogen atom, a hydroxyl group, a cyano group, a linear or branched $C_1$-$C_6$ alkyl group, a $C_1$-$C_4$ haloalkyl group, a $C_1$-$C_4$ alkoxy group, a $C_1$-$C_4$ hydroxyalkyl group, a $C_3$-$C_7$ cycloalkyl group, a phenyl group, a 5- to 6-membered monocyclic heteroaryl group containing 1, 2 or 3 nitrogen atoms, a 5- to 6-membered heterocyclyl group containing 1, 2 or 3 nitrogen atoms, or a $C_3$-$C_7$ heterocycloalkyl ketone group containing 1, 2 or 3 nitrogen atoms, said phenyl group being unsubstituted or substituted by one or more halogen atoms, and said heteroaryl, heterocyclyl and heterocycloalkyl ketone groups being unsubstituted or substituted by one or more linear or branched $C_1$-$C_3$ alkyl groups;

Rd is a cyano group, a $C_1$-$C_4$ haloalkyl group, a $C_1$-$C_4$ alkoxy group, a $C_1$-$C_4$ hydroxyalkyl group, a $C_3$-$C_7$ cycloalkyl group, a phenyl group, a 5- to 6-membered monocyclic heteroaryl group containing 1, 2 or 3 nitrogen atoms, a 5- to 6-membered heterocyclyl group containing 1, 2 or 3 nitrogen atoms, or a $C_3$-$C_7$ heterocycloalkyl ketone group containing 1, 2 or 3 nitrogen atoms, said phenyl group being unsubstituted or substituted by one or more halogen atoms, and said heteroaryl, heterocyclyl and heterocycloalkyl ketone groups being unsubstituted or substituted by one or more linear or branched $C_1$-$C_3$ alkyl groups;

Re is a halogen atom, a hydroxyl group, a cyano group, a linear or branched $C_1$-$C_6$ alkyl group or a $C_1$-$C_4$ haloalkyl group;

$R_{13}$, $R_{14}$, and $R_{15}$ each independently represents a hydrogen atom, a cyano group, a linear or branched $C_1$-$C_6$ alkyl group, a $C_1$-$C_4$ haloalkyl group, a $C_1$-$C_4$ hydroxyalkyl group, a $C_1$-$C_4$ alkoxycarbonyl group, a $C_3$-$C_7$ cycloalkyl group, a monocyclic or polycyclic $C_5$-$C_{14}$ aryl group, a 5- to 14-membered heteroaryl group containing at least one heteroatom selected from O, S and N, or a 5- to 14-membered heterocyclyl group containing at least one heteroatom selected from O, S and N, wherein the haloalkyl, hydroxyalkyl, alkoxycarbonyl, cycloalkyl, aryl, heteroaryl and heterocyclyl groups are unsubstituted or substituted by one or more substituents selected from the substituents Ra, and the alkyl groups are optionally substituted by one or more substitutents selected from Rb, for use in the treatment of a pathological condition or disease susceptible to amelioration by inhibition of Janus kinases (JAK).

The invention further provides new pyrazole derivatives of formula (I), or a pharmaceutically acceptable salt, or solvate, or N-oxide, or stereoisomer or deuterated derivative thereof, wherein T represents a $CR_9$ group and m, Z, W, X, Y and $R_1$ to $R_9$ are as defined above.

In one embodiment, in the compound of formula (I) both Y and T represent a —$CR_9$ group and m, Z, W, X and $R_1$ to $R_9$ are as defined above.

In another embodiment, in the compound of formula (I) Y represents N, X and T represent a —$CR_9$ group and m, Z, W and $R_1$ to $R_9$ are as defined above, provided that when $R_8$ represents a 5- to 7-membered heterocyclyl group containing one nitrogen atom, said heterocyclyl group is substituted by one or more substituents, wherein said substitution is at least on the ring nitrogen of the heterocyclyl group, and provided that this substituent on the ring nitrogen of the heterocyclyl group is other than a tert-butoxycarbonyl group.

The invention further provides synthetic processes and intermediates described herein, which are useful for preparing said compounds.

The invention also provides a pharmaceutical composition comprising the compounds of the invention and a pharmaceutically-acceptable diluent or carrier.

The pathological condition or disease susceptible to amelioration by inhibition of Janus Kinases (JAK) is, in particular, selected from myeloproliferative disorders, leukemia, lymphoid malignancies and solid tumors; bone marrow and organ transplant rejection; immune-mediated diseases and inflammatory diseases, for example from myeloproliferative disorders, leukemia, lymphoid malignancies and solid tumors; bone marrow and organ transplant rejection; and immune-mediated diseases. More particularly the pathological condition or disease is selected from rheumatoid arthritis, multiple sclerosis, inflammatory bowel disease, dry eye, uveitis, allergic conjunctivitis, allergic rhinitis, asthma, chronic obstructive pulmonary disease (COPD), atopic dermatitis and psoriasis.

In one aspect, the compounds of formula (I) may be used in the treatment of myeloproliferative disorders, leukemia, lymphoid malignancies and solid tumors. In this aspect, the treatment is typically effected by inhibition of Janus Kinases in the subject. In another aspect, the compounds of formula (I) may be used in the treatment of bone marrow and organ transplant rejection; immune-mediated diseases and inflammatory diseases, for example from bone marrow and organ transplant rejection; and immune-mediated diseases, e.g. bone marrow and organ transplant rejection.

The invention also provides a pyrazole derivative of formula (I) as defined herein, or a pharmaceutically acceptable salt, or solvate, or N-oxide, or stereoisomer or deuterated derivative thereof for use in inhibiting Janus Kinases. In particular, the invention provides a pyrazole derivative of formula (I) as defined herein, or a pharmaceutically acceptable salt, or solvate, or N-oxide, or stereoisomer or deuterated derivative thereof for treating a pathological condition or disease as described above, wherein the treatment is by inhibition of Janus Kinases.

The invention also provides a method of treatment of a pathological condition or disease susceptible to amelioration by inhibition of Janus Kinases (JAK), in particular wherein the pathological condition or disease is selected from myeloproliferative disorders, leukemia, lymphoid malignancies and solid tumors; bone marrow and organ transplant rejection; immune-mediated diseases and inflammatory diseases, for example from myeloproliferative disorders, leukemia, lymphoid malignancies and solid tumors; bone marrow and organ transplant rejection; and immune-mediated diseases, more particularly wherein the pathological condition or disease is selected from rheumatoid arthritis, multiple sclerosis, inflammatory bowel disease, dry eye, uveitis, allergic conjunctivitis, allergic rhinitis, asthma, chronic obstructive pulmonary disease (COPD), atopic dermatitis and psoriasis; comprising administering a therapeutically effective amount of the compounds defined herein or a pharmaceutical composition comprising a compound as defined herein in association with a pharmaceutically acceptable diluent or carrier. to a subject in need of such treatment. In particular, the treatment is effected by inhibition of Janus Kinases in the subject.

The invention also provides a method of inhibiting Janus kinases in a subject in need thereof, which comprises administering to said subject a therapeutically effective amount of a compound as defined herein, or a pharmaceutical composition comprising a compound as defined herein in association with a pharmaceutically acceptable diluent or carrier to a subject in need of such treatment.

The invention also provides a combination product comprising (i) a compound as described herein; and (ii) one or more additional active substances which are known to be useful in the treatment of myeloproliferative disorders (such as polycythemia vera, essential thrombocythemia or mielofibrosis), leukemia, lymphoid malignancies and solid tumors; bone marrow and organ transplant rejection; immune-mediated diseases and inflammatory diseases, for example from myeloproliferative disorders, leukemia, lymphoid malignancies and solid tumors; bone marrow and organ transplant rejection; and immune-mediated diseases, more particularly wherein the pathological condition or disease is selected from rheumatoid arthritis, multiple sclerosis, inflammatory bowel disease (such as ulcerative colitis or Crohn's disease), dry eye, uveitis, allergic conjunctivitis, allergic rhinitis, asthma, chronic obstructive pulmonary disease (COPD), atopic dermatitis and psoriasis.

As used herein the term $C_1$-$C_6$ alkyl embraces optionally substituted, linear or branched radicals having 1 to 6 carbon atoms, preferably 1 to 4 carbon atoms. Examples include methyl, ethyl, n-propyl, i-propyl, n-butyl, sec-butyl, t-butyl, n-pentyl, 1-methylbutyl, 2-methylbutyl, isopentyl; 1-ethylpropyl, 1,1-dimethylpropyl, 1,2-dimethylpropyl, n-hexyl, 1-ethylbutyl, 2-ethylbutyl, 1,1-dimethylbutyl, 1,2-dimethylbutyl, 1,3-dimethylbutyl, 2,2-dimethylbutyl, 2,3-dimethylbutyl, 2-methylpentyl, 3-methylpentyl and iso-hexyl radicals.

As used herein, the term $C_2$-$C_4$ alkenyl embraces optionally substituted, linear or branched, mono or polyunsaturated radicals having 2 to 4 carbon atoms. Examples include vinyl, allyl, 1-propenyl, isopropenyl, 1-butenyl, 2-butenyl and 3-butenyl radicals.

As used herein, the term $C_2$-$C_4$ alkynyl embraces optionally substituted, linear or branched, mono or polyunsaturated radicals having 2 to 4 carbon atoms. Examples include 1-propynyl, 2-propynyl, 1-butynyl, 2-butynyl and 3-butynyl radicals.

When it is mentioned that alkyl, alkenyl or alkynyl radicals may be optionally substituted it is meant to include linear or branched alkyl, alkenyl or alkynyl radicals as defined above, which may be unsubstituted or substituted in any position by one or more substituents, for example by 1, 2 or 3 substituents. When two or more substituents are present, each substituent may be the same or different.

A said optionally substituted alkenyl group is typically unsubstituted or substituted by 1, 2 or 3 substituents which may be the same or different. Typically, substituents on an alkenyl group are themselves unsubstituted. Preferred substituents on the alkenyl groups are halogen atoms and hydroxy groups, and are more preferably halogen atoms.

A said optionally substituted alkynyl group is typically unsubstituted or substituted by 1, 2 or 3 substituents which may be the same or different. Typically, substituents on an alkynyl group are themselves unsubstituted. Preferred substituents on the alkynyl groups are halogen atoms and hydroxy groups, and are more preferably halogen atoms.

As used herein, the term $C_1$-$C_4$ haloalkyl group is an alkyl group, for example a $C_{1-4}$ or $C_{1-2}$ alkyl group, which is bonded to one or more, preferably 1, 2 or 3 halogen atoms. Preferably, said haloakyl group is chosen from —$CCl_3$ and —$CF_3$.

As used herein, the term $C_1$-$C_4$ hydroxyalkyl embraces linear or branched alkyl radicals having 1 to 4 carbon atoms, any one of which may be substituted by one or more, preferably 1 or 2, more preferably 1 hydroxyl radicals. Examples of such radicals include hydroxymethyl, hydroxyethyl, hydroxypropyl, and hydroxybutyl.

As used herein, the term $C_1$-$C_4$ alkoxy (or alkyloxy) embraces optionally substituted, linear or branched oxy-containing radicals each having alkyl portions of 1 to 4 carbon atoms. An alkoxy group is typically unsubstituted or substituted by 1, 2 or 3 substituents which may be the same or different. Typically, the substituents on an alkoxy group are themselves unsubstituted. Preferred alkoxy radicals include methoxy, ethoxy, n-propoxy, i-propoxy, n-butoxy, sec-butoxy, t-butoxy, trifluoromethoxy, difluoromethoxy, hydroxymethoxy, 2-hydroxyethoxy and 2-hydroxypropoxy.

As used herein, the term $C_1$-$C_4$ alkoxycarbonyl group embraces radicals of formula —C(O)O($C_1$-$C_4$ alkyl), wherein said $C_1$-$C_4$ alkyl is a linear or branched hydrocarbon radical having 1 to 4 carbon atoms. Examples include methoxycarbonyl, ethoxycarbonyl, n-propyloxycarbonyl, i-propyloxycarbonyl, n-butyloxycarbonyl, sec-butyloxycarbonyl and tert-butyloxycarbonyl radicals.

As used herein, the term $C_3$-$C_{10}$ cycloalkyl embraces saturated monocyclic or polycyclic carbocyclic radicals having from 3 to 10 carbon atoms, preferably from 3 to 7 carbon atoms. A $C_3$-$C_{10}$ cycloalkyl radical is typically unsubstituted or substituted by 1, 2 or 3 substituents which may be the same or different. When a $C_3$-$C_{10}$ cycloalkyl radical carries 2 or more substituents, the substituents may be the same or different. Typically the substituents on a $C_3$-$C_{10}$ cycloalkyl group are themselves unsubstituted. Polycyclic cycloalkyl radicals contains two or more fused cycloalkyl groups, preferably two cycloalkyl groups. Typically, polycyclic cycloalkyl radicals are selected from decahydronaphthyl (decalyl), bicyclo[2.2.2]octyl, adamantly, camphyl or bornyl groups. Examples of monocyclic cycloalkyl groups include cyclopropyl, cyclobutyl, cyclopentyl, cyclohexyl, cycloheptyl, cyclooctyl, cyclononyl and cyclodecyl.

As used herein, the term $C_3$-$C_{10}$ cycloalkenyl embraces partially unsaturated carbocyclic radicals having from 3 to 10 carbon atoms, preferably from 3 to 7 carbon atoms. A $C_3$-$C_{10}$ cycloalkenyl radical is typically unsubstituted or substituted by 1, 2 or 3 substituents which may be the same or different. When a $C_3$-$C_{10}$ cycloalkenyl radical carries 2 or more substituents, the substituents may be the same or different. Typically, the substituents on a cycloalkenyl group are themselves unsubstituted. Examples include cyclobutenyl, cyclopentenyl, cyclohexenyl, cycloheptenyl, cyclooctenyl, cyclononenyl and cyclodecenyl.

As used herein, the term $C_5$-$C_{14}$ aryl radical embraces typically a $C_5$-$C_{14}$, preferably $C_6$-$C_{14}$, more preferably $C_6$-$C_{10}$ monocyclic or polycyclic aryl radical such as phenyl, naphthyl, anthranyl and phenanthryl. Phenyl is preferred. A said optionally substituted $C_5$-$C_{14}$ aryl radical is typically unsubstituted or substituted by 1, 2 or 3 substituents which may be the same or different. When a $C_5$-$C_{14}$ aryl radical carries 2 or more substituents, the substituents may be the same or different. Unless otherwise specified, the substituents on a $C_5$-$C_{14}$ aryl group are typically themselves unsubstituted.

As used herein, the term 5- to 14-membered heteroaryl radical embraces typically a 5- to 14-membered ring system, preferably a 5- to 10-membered ring system, more-preferably a 5- to 6-membered ring system, comprising at least one heteroaromatic ring and containing at least one heteroatom selected from O, S and N. A 5- to 14-membered heteroaryl radical may be a single ring or two or more fused rings wherein at least one ring contains a heteroatom.

A said optionally substituted 5- to 14-membered heteroaryl radical is typically unsubstituted or substituted by 1, 2 or 3 substituents which may be the same or different. When a 5- to 14-membered heteroaryl radical carries 2 or more substituents, the substituents may be the same or different. Unless otherwise specified, the substituents on a 5- to 14-membered heteroaryl radical are typically themselves unsubstituted.

Examples include pyridyl, pyrazinyl, pyrimidinyl, pyridazinyl, furyl, benzofuranyl, oxadiazolyl, oxazolyl, isoxazolyl, benzoxazolyl, imidazolyl, benzimidazolyl, thiazolyl, thiadiazolyl, thienyl, pyrrolyl, pyridinyl, benzothiazolyl, indolyl, indazolyl, purinyl, quinolyl, isoquinolyl, phthalazinyl, naphthyridinyl, quinoxalinyl, quinazolinyl, quinolizinyl, cinnolinyl, triazolyl, indolizinyl, indolinyl, isoindolinyl, isoindolyl, imidazolidinyl, pteridinyl, thianthrenyl, pyrazolyl, 2H-pyrazolo[3,4-d]pyrimidinyl, 1H-pyrazolo[3,4-d]pyrimidinyl, thieno[2,3-d]pyrimidnyl and the various pyrrolopyridyl radicals.

As used herein, the term 5- to 14-membered heterocyclyl radical embraces typically a non-aromatic, saturated or unsaturated $C_5$-$C_{14}$ carbocyclic ring system, preferably $C_5$-$C_{10}$ carbocyclic ring system, more preferably $C_5$-$C_6$ carbocyclic ring system, in which one or more, for example 1, 2, 3 or 4 of the carbon atoms preferably 1 or 2 of the carbon atoms are replaced by a heteroatom selected from N, O and S. A heterocyclyl radical may be a single ring or two or more fused rings wherein at least one ring contains a heteroatom. When a 5 to 14-membered heterocyclyl radical carries 2 or more substituents, the substituents may be the same or different.

A said optionally substituted 5- to 14-membered heterocyclyl radical is typically unsubstituted or substituted by 1, 2 or 3 substituents which may be the same or different. Typically, the substituents on a 5 to 14-membered heterocyclyl radical are themselves unsubstituted.

Examples of 5- to 14-membered heterocyclyl radicals include piperidyl, pyrrolidyl, pyrrolinyl, piperazinyl, morpholinyl, thiomorpholinyl, pyrrolyl, pyrazolinyl, pirazolidinyl, quinuclidinyl, triazolyl, pyrazolyl, tetrazolyl, imidazolidinyl, imidazolyl, oxiranyl, 4,5-dihydro-oxazolyl, 2-benzofuran-1(3H)-one, 1,3-dioxol-2-one, 3-aza-tetrahydrofuranyl and tetrahydropyranyl, for example piperidyl, pyrrolidyl, pyrrolinyl, piperazinyl, morpholinyl, thiomorpholinyl, pyrrolyl, pyrazolinyl, pirazolidinyl, quinuclidinyl, triazolyl, pyrazolyl, tetrazolyl, imidazolidinyl, imidazolyl, oxiranyl, 4,5-dihydro-oxazolyl, 2-benzofuran-1(3H)-one, 1,3-dioxol-2-one and 3-aza-tetrahydrofuranyl.

Where a 5- to 14-membered heterocyclyl radical carries 2 or more substituents, the substituents may be the same or different.

As used herein, the term 6-membered saturated N-containing heterocyclic group is a $C_6$ saturated carbocyclic ring system in which one of the carbon atoms is replaced by N and optionally in which 1, 2, or 3, preferably 1 or 2, further carbon atoms are replaced by heteroatoms selected from N and O.

A said 6-membered saturated N-containing heterocyclic group is typically unsubstituted or substituted by 1, 2 or 3 substituents which may be the same or different. Typically, the substituents on a 6-membered saturated N-containing heterocyclic group are themselves unsubstituted, unless otherwise specified.

Examples of 6-membered saturated N-containing heterocyclic group include piperidyl and piperazinyl.

As used herein, the term $C_3$-$C_7$ heterocycloalkyl ketone group embraces typically a non-aromatic, saturated or unsaturated $C_3$-$C_7$ carbocyclic ring system, in which one of the carbon atoms is replaced by a C=O group and 1, 2 or 3, preferably 1 or 2, more preferably 1, further carbon atoms preferably are replaced by N. Examples include pyridone groups.

As used herein, the term aza-bicycloalkyl group having up to 12 carbon atoms denotes a fused ring system consisting of a cycloalkyl group and a N-containing heterocyclyl group, as defined herein.

As used herein, the term aza-bicycloalkenyl group having up to 12 carbon atoms embraces an aza-bicycloalkyl group, as defined herein, containing at least one unsaturated carbon-carbon bond.

As used herein, a bicyclyl group containing a monocyclic $C_5$-$C_9$ aryl or heteroaryl group bonded directly to a 5- to 9-membered cycloalkyl or heterocyclyl group typically refers to groups where a monocyclic $C_5$-$C_9$ aryl or heteroaryl group is bonded to a 5- to 9-membered cycloalkyl or heterocyclyl group by a single bond. Examples include biphenyl groups or chromanyl groups.

As used herein, some of the atoms, radicals, moieties, chains and cycles present in the general structures of the invention are "optionally substituted". This means that these atoms, radicals, moieties, chains and cycles can be either unsubstituted or substituted in any position by one or more, for example 1, 2, 3 or 4, substituents, whereby the hydrogen atoms bound to the unsubstituted atoms, radicals, moieties, chains and cycles are replaced by chemically acceptable atoms, radicals, moieties, chains and cycles. When two or more substituents are present, each substituent may be the same or different. The substituents are typically themselves unsubstituted.

Typically when a cyclic radical is bridged by an alkylene or alkylenedioxy radical, the bridging alkylene radical is bonded to the ring at non-adjacent atoms.

As used herein, the term halogen atom embraces chlorine, fluorine, bromine and iodine atoms. A halogen atom is typically a fluorine, chlorine or bromine atom, most preferably chlorine or fluorine. The term halo when used as a prefix has the same meaning.

As used herein, the term pharmaceutically acceptable salt embraces salts with a pharmaceutically acceptable acid or base. Pharmaceutically acceptable acids include both inorganic acids, for example hydrochloric, sulphuric, phosphoric, diphosphoric, hydrobromic, hydroiodic and nitric acid and organic acids, for example citric, fumaric, maleic, malic, mandelic, ascorbic, oxalic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases, for example alkyl amines, arylalkyl amines and heterocyclyl amines.

Other preferred salts according to the invention are quaternary ammonium compounds wherein an equivalent of an anion (X–) is associated with the positive charge of the N atom. X– may be an anion of various mineral acids such as, for example, chloride, bromide, iodide, sulphate, nitrate, phosphate, or an anion of an organic acid such as, for example, acetate, maleate, fumarate, citrate, oxalate, succinate, tartrate, malate, mandelate, trifluoroacetate, methanesulphonate and p-toluenesulphonate. X– is preferably an anion selected from chloride, bromide, iodide, sulphate, nitrate, acetate, maleate, oxalate, succinate or trifluoroacetate. More preferably X– is chloride, bromide, trifluoroacetate or methanesulphonate.

As used herein, an N-oxide is formed from the tertiary basic amines or imines present in the molecule, using a convenient oxidising agent.

As used herein, the term solvate means a compound which further includes a stoichiometric or non-stoichiometric amount of solvent such as water, acetone, ethanol, methanol, dichloromethane, 2-propanol, or the like, bound by non-covalent intermolecular forces. When the solvent is water, the term hydrate is used instead of solvate.

As used herein, the term deuterated derivative embraces compounds of the invention where in a particular position at least one hydrogen atom is replaced by deuterium. Deuterium (D or $^2H$) is a stable isotope of hydrogen which is present at a natural abundance of 0.015 molar %.

Hydrogen deuterium exchange (deuterium incorporation) is a chemical reaction in which a covalently bonded hydrogen atom is replaced by a deuterium atom. Said exchange (incorporation) reaction can be total or partial.

Typically, a deuterated derivative of a compound of the invention has an isotopic enrichment factor (ratio between the isotopic abundance and the natural abundance of that isotope, i.e. the percentage of incorporation of deuterium at a given position in a molecule in the place of hydrogen) for each deuterium present at a site designated as a potential site of deuteration on the compound of at least 3500 (52.5% deuterium incorporation).

In a preferred embodiment, the isotopic enrichment factor is at least 5000 (75% deuterium). In a more preferred embodiment, the isotopic enrichment factor is at least 6333.3 (95% deuterium incorporation). In a most preferred embodiment, the isotopic enrichment factor is at least 6633.3 (99.5%-deuterium incorporation). It is understood that the isotopic enrichment factor of each deuterium present at a site designated as a site of deuteration is independent from the other deuteration sites.

The isotopic enrichment factor can be determined using conventional analytical methods known too en ordinary skilled in the art, including mass spectrometry (MS) and nuclear magnetic resonance (NMR).

Typically, the compounds of formula (I) are other than
trans-5-cyano-3-[6-(4-hydroxycyclohexylamino)pyridin-2-yl]pyrazolo[1,5-a]pyridine,
trans-5-cyano-3-[6-(4-hydroxycyclohexyl-N-methylamino)pyridin-2-yl]pyrazolo[1,5-a]pyridine,
trans-5-cyano-3-[6-(N-ethyl-N-(4-hydroxycyclohexyl)amino)pyridin-2-yl]pyrazolo[1,5-a]pyridine,
5-cyano-3-[6-(piperidin-4-ylamino)pyridin-2-yl]pyrazolo[1,5-a]pyridine,
5-cyano-3-[6-(methyl(piperidin-4-yl)amino)pyridin-2-yl]pyrazolo[1,5-a]pyridine,
5-cyano-3-[6-(1-(2-cyanoacetyl)piperidin-3-ylamino)pyridin-2-yl]pyrazolo[1,5-a]pyridine,
(R)-5-cyano-3-[6-(1-(2-cyanoacetyl)piperidin-3-ylamino)pyridin-2-yl]pyrazolo[1,5-a]pyridine, and
(R)-5-cyano-3-[6-(N-methyl-1-(2-cyanoacetyl)piperidin-3-ylamino)pyridin-2-yl]pyrazolo[1,5-a]pyridine,
and salts of the above compounds; and
3-[6-(1-Hydroxymethylcyclopentylamino)pyridin-2-yl]pyrazolo[1,5-a]pyridine
3-[6-(4-hyroxymethylpiperidin-1-yl)pyridin-2-yl]pyrazolo[1,5-a]pyridine,
3-[6-(3-hyroxycyclohexylamino)pyridin-2-yl]pyrazolo[1,5-a]pyridine,
trans-3-[6-(4-hydroxycyclohexyl-N-methylamino)pyridin-2-yl]pyrazolo[1,5-a]pyridine,
3-[6-(1-ethoxycarbonylpiperidin-4-ylamino)pyridin-2-yl]pyrazolo[1,5-a]pyridine,
trans-3-[6-(4-aminocyclohexylamino)pyridin-2-yl]pyrazolo[1,5-a]pyridine,
trans-3-[6-(4-hydroxycyclohexylamino)pyridin-2-yl]pyrazolo[1,5-a]pyridine,
3-[6-(tetrahydro-4H-piran-4-ylamino)pyridin-2-yl]pyrazolo[1,5-a]pyridine,
3-[6-(N-methylcyclohexylamino)pyridin-2-yl]pyrazolo[1,5-a]pyridine,
3-[6-(3-hydroxymethylpiperidin-1-yl)pyridin-2-yl]pyrazolo[1,5-a]pyridine,
3-[6-(1-methylpiperidin-4-ylamino)pyridin-2-yl]pyrazolo[1,5-a]pyridine,
3-[6-(2,2,6,6-tetramethylpiperidin-4-ylamino)pyridin-2-yl]pyrazolo[1,5-a]pyridine,
3-[6-(2-phenylpropan-2-amino)pyridin-2-yl]pyrazolo[1,5-a]pyridine,
(S)-3-[6-(1-phenylethylamino)pyridin-2-yl]pyrazolo[1,5-a]pyridine,
3-[6-(1-benzylamino)pyridin-2-yl]pyrazolo[1,5-a]pyridine,
(S)-3-[6-(1-cyclohexylethylamino)pyridin-2-yl]pyrazolo[1,5-a]pyridine,
(S)-3-[6-(1-methoxypropan-2-ylamino)pyridin-2-yl]pyrazolo[1,5-a]pyridine,
3-[6-(methylamino)pyridin-2-yl]pyrazolo[1,5-a]pyridine,
3-[6-(phenylamino)pyridin-2-yl]pyrazolo[1,5-a]pyridine,
3-[6-(pyridin-3-ylamino)pyridin-2-yl]pyrazolo[1,5-a]pyridine,
3-[6-(pyridin-4-ylamino)pyridin-2-yl]pyrazolo[1,5-a]pyridine,
trans-3-[6-(4-aminocyclohexylamino)pyridin-2-yl]-5-cyanopyrazolo[1,5-a]pyridine,
5-cyano-(S)-3-[6-(1-phenylethylamino)pyridin-2-yl]pyrazolo[1,5-a]pyridine,
5-cyano-3-[6-(4-hydroxybutylamino)pyridin-2-yl]pyrazolo[1,5-a]pyridine
5-cyano-3-[6-(N-methyl-(3-hydroxypropyl)amino)pyridin-2-yl]pyrazolo[1,5-a]pyridine,
3-[6-(3-aminocyclohexylamino)pyridin-2-yl]-5-cyanopyrazolo[1,5-a]pyridine,
5-cyano-3-[6-(N-methyl-N-(2-methylamino)ethylamino)pyridin-2-yl]pyrazolo[1,5-a]pyridine,
5-cyano-3-[6-(1-ethoxycarbonyl)piperidin-3-ylamino)pyridin-2-yl]pyrazolo[1,5-a]pyridine,
3-[6-(2-aminoethylamino)pyridin-2-yl]-5-cyanopyrazolo[1,5-a]pyridine,
(S)-5-cyano-3-[6-(2-hydroxymethylpyrrolidin-1-yl)pyridin-2-yl]pyrazolo[1,5-a]pyridine,
(R)-5-cyano-3-[6-(2-hydroxymethylpyrrolidin-1-yl)pyridin-2-yl]pyrazolo[1,5-a]pyridine,
5-cyano-3-[6-(N-ethyl-N-(4-hydroxybutyl)amino)pyridin-2-yl]pyrazolo[1,5-a]pyridine,
5-cyano-3-[6-(3-hydroxypropylamino)pyridin-2-yl]pyrazolo[1,5-a]pyridine,
(S)-5-cyano-3-[6-(1-(ethoxycarbonyl)piperidin-3-ylamino)pyridin-2-yl]pyrazolo[1,5-a]pyridine
trans-3-[6-(4-acetylaminocyclohexylamino)pyridin-2-yl]pyrazolo[1,5-a]pyridine
trans-3-[6-(4-methanosulfonylaminocyclohexylamino)pyridin-2-yl]pyrazolo[1,5-a]pyridine
3-[6-(3-(2-oxopyrrolidin-1-yl)phenylamino)pyridin-2-yl]pyrazolo[1,5-a]pyridine
3-[6-(N-cyclohexylamino)pyridin-2-yl]pyrazolo[1,5-a]pyridine,
3-[6-(N-(2-methylcyclohexyl)amino)pyridin-2-yl]pyrazolo[1,5-a]pyridine,
3-[6-(4-acetylaminophenylamino)pyridin-2-yl]pyrazolo[1,5-a]pyridine,
3-[6-(3-acetylaminophenylamino)pyridin-2-yl]pyrazolo[1,5-a]pyridine,
3-[6-((3-methylaminocarbonyl)phenylamino)pyridin-2-yl]pyrazolo[1,5-a]pyridine,
3-[6-(3-hydroxyphenyl-N-methylamino)pyridin-2-yl]pyrazolo[1,5-a]pyridine
3-[6-(N-cyclopropylcarbonylamino)pyridin-2-yl]pyrazolo[1,5-a]pyridine
(S)-3-[6-(1-phenylethylamino)pyridin-2-yl]-5-hydroxymethylpyrazolo[1,5-a]pyridine
3-[6-(piperidin-4-ylamino)pyridin-2-yl]pyrazolo[1,5-a]pyridine
3-[6-(piperidin-4-ylamino)pyridin-2-yl]-5-carboxypyrazolo[1,5-a]pyridine,
3-[6-(1-acetylpiperidin-4-ylamino)pyridin-2-yl]pyrazolo[1,5-a]pyridine
5-cyano-3-[6-((1-acetyl)piperidin-3-ylamino)pyridin-2-yl]pyrazolo[1,5-a]pyridine
(S)-5-cyano-3-[6-(piperidin-3-ylamino)pyridin-2-yl]pyrazolo[1,5-a]pyridine. The salts and solvates of these compounds may also be excluded from the compounds of formula (I).

The above compounds are disclosed in WO 2010/072823. Typically, the compounds of formula (I) exclude the compounds disclosed in WO 2010/072823, including the salts, solvates and stereoisomers disclosed therein.

For example, the compounds defined herein may exclude compounds of formula (I) wherein
$R_1$, $R_2$ and $R_4$ each represent a hydrogen atom;
W represents a —$CR_3$ group;
Z represents a group —$NR_5$;
X, Y and T each represent a group —$CR_9$, wherein $R_9$ represents a hydrogen atom;
$R_3$ represents hydrogen, halogen, $C_{1-4}$alkyl, halo$C_{1-4}$alkyl, hydroxy$C_{1-4}$alkyl, $R_{27}$—$C_{1-4}$alkyl halogen, cyano, —C(O)—$NR_{24}R_{24}$, —C(O)$R_{25}$, —C(O)O$R_{25}$, —O$R_{24}$, —S(O)$_2R_{25}$, —S(O)$_2NR_{24}R_{24}$, —$NR_{24}R_{24}$, —NHCO$R_{24}$, —N($C_{1-4}$alkyl)CO$R_{24}$, —NHCON$R_{24}R_{24}$, —N($C_{1-4}$alkyl)CON$R_{24}R_{24}$, —NHC(O)O$R_{35}$, —N($C_{1-4}$alkyl)C(O)O$R_{35}$, —NHS(O)$_2$R$_{25}$, N(C$_{1-4}$alkyl)S(O)$_2$R$_{25}$, or Cy$_1$, wherein Cy$_1$ is optionally substituted with one or more substituents selected from R$_{28}$;

R$_5$ represents a hydrogen atom, C$_{1-4}$alkyl, haloC$_{1-4}$alkyl, hydroxyC$_{1-4}$alkyl or C$_{1-4}$alkyl substituted with a group selected from cyano, hydroxyl or Cy$_1$, wherein Cy$_1$ is optionally substituted with one or more R$_{26}$, for example R$_5$ may represent a hydrogen atom, C$_{1-4}$alkyl, haloC$_{1-4}$alkyl, hydroxyC$_{1-4}$alkyl or R$_{27}$—C$_{1-4}$alkyl or Cy$_2$, wherein Cy$_2$ is optionally substituted with one or more R$_{28}$;

the group —(CR$_6$R$_7$)$_m$—R$_8$ represents C$_{1-4}$alkyl, C$_{1-4}$haloalkyl, hydroxyC$_{1-4}$alkyl, R$_{211}$—C$_{1-4}$alkyl, —CONR$_{209}$R$_{209}$, —COR$_{210}$, —C(O)OR$_{210}$, —S(O)$_2$R$_{210}$, —SO$_2$NR$_{209}$R$_{209}$ or Cy$_3$, wherein Cy$_3$ is optionally substituted with one or more R$_{212}$;

or R$_5$ together with R$_8$ and the nitrogen atom to which they are bonded form a Cy$_4$ group, wherein Cy$_4$ is optionally substituted with one or more R$_{212}$;

each R$_{24}$ independently represents hydrogen or R$_{25}$;

each R$_{25}$ independently represents C$_{1-4}$alkyl, haloC$_{1-4}$alkyl, C$_{1-4}$alkoxyC$_{1-4}$alkyl, hydroxyC$_{1-4}$alkyl, cyanoC$_{1-4}$alkyl, Cy$_1$-C$_{1-4}$alkyl, or Cy$_1$, wherein Cy$_1$ is optionally substituted with one or more R$_{28}$;

each R$_{35}$ independently represents C$_{1-4}$alkyl, C$_{1-4}$alkoxy C$_{1-4}$alkyl, hydroxyC$_{1-4}$alkyl, cyanoC$_{1-4}$alkyl or Cy$_1$-C$_{1-4}$alkyl, wherein Cy$_1$ is optionally substituted with one or more R$_{28}$; for example each R$_{35}$ may independently represent C$_{1-4}$alkyl, haloC$_{1-4}$alkyl, hydroxyC$_{1-4}$alkyl, cyanoC$_{1-4}$alkyl, C$_{1-4}$alkyl, or Cy$_1$ wherein Cy$_1$ is optionally substituted with one or more R$_{28}$;

each R$_{28}$ independently represents C$_{1-4}$alkyl, haloC$_{1-4}$alkyl, C$_{1-4}$alkoxyC$_{1-4}$alkyl, hydroxyC$_{1-4}$alkyl, cyanoC$_{1-4}$alkyl, halogen or hydroxyl;

R$_{27}$ represents a cyano group, —C(O)—NR$_{24}$R$_{24}$, —C(O)R$_{25}$, —C(O)OR$_{25}$, —OR$_{24}$, —S(O)$_2$R$_{25}$, —S(O)$_2$NR$_{24}$R$_{24}$, —NR$_{24}$R$_{24}$, —NHCOR$_{24}$, —N(C$_{1-4}$alkyl)COR$_{24}$, —NHCONR$_{24}$R$_{24}$, —N(C$_{1-4}$alkyl)CONR$_{24}$R$_{24}$, —NHC(O)OR$_{25}$, —N(C$_{1-4}$alkyl)C(O)OR$_{25}$, —NHS(O)$_2$R$_{25}$, N(C$_{1-4}$alkyl)S(O)$_2$R$_{25}$, or Cy$_1$, wherein Cy$_1$ is optionally substituted with one or more substituents selected from R$_{28}$;

each R$_{209}$ independently represents hydrogen or R$_{210}$;

each R$_{210}$ independently represents C$_{1-4}$alkyl, haloC$_{1-4}$alkyl, hydroxyC$_{1-4}$alkyl, R$_{211}$—C$_{1-4}$alkyl or Cy$_5$, wherein Cy$_5$ is optionally substituted with one or more substituents selected from R$_{213}$;

R$_{211}$ represents halogen, cyano, —CONR$_{214}$R$_{214}$, —COR$_{215}$, —C(O)OR$_{215}$, —OR$_{214}$, —SO$_2$R$_{215}$, —SO$_2$NR$_{214}$R$_{214}$, —NR$_{214}$R$_{214}$, —NHCOR$_{214}$, —N(C$_{1-4}$alkyl)COR$_{214}$, —NHCONR$_{214}$R$_{214}$, —N(C$_{1-4}$alkyl)CONR$_{214}$R$_{214}$, —NHC(O)OR$_{215}$, —N(C$_{1-4}$alkyl)C(O)OR$_{215}$, —NHS(O)$_2$R$_{215}$, N(C$_{1-4}$alkyl)S(O)$_2$R$_{215}$, or Cy$_5$, wherein Cy$_5$ is optionally substituted with one or more substituents selected from R$_{213}$; for example R$_{211}$ may represent halogen, cyano, —CONR$_{214}$R$_{214}$, —COR$_{215}$, —C(O)OR$_{215}$, —OR$_{214}$, —SO$_2$R$_{215}$, —OCONR$_{214}$R$_{214}$, —SO$_2$NR$_{214}$R$_{214}$, —NR$_{214}$R$_{214}$, —NHCOR$_{214}$, —N(C$_{1-4}$alkyl)COR$_{214}$, —NHCONR$_{214}$R$_{214}$, —N(C$_{1-4}$alkyl)CONR$_{214}$R$_{214}$, —NHC(O)OR$_{215}$, —N(C$_{1-4}$alkyl)C(O)OR$_{215}$, —NHS(O)$_2$R$_{215}$, N(C$_{1-4}$alkyl)S(O)$_2$R$_{215}$, or Cy$_5$, wherein Cy$_5$ is optionally substituted with one or more substituents selected from R$_{213}$;

each R$_{212}$ independently represents C$_{1-4}$alkyl, haloC$_{1-4}$alkyl, hydroxyC$_{1-4}$alkyl, R$_{211}$—C$_{1-4}$alkyl or R$_{212}$ represents any of the meanings described for R$_{211}$;

each R$_{213}$ independently represents C$_{1-4}$alkyl, C$_{1-4}$haloalkyl, C$_{1-4}$alkoxyC$_{1-4}$alkyl, hydroxyC$_{1-4}$alkyl, cyanoC$_{1-4}$alkyl, halogen, cyano, —CONR$_{216}$R$_{216}$, —COR$_{217}$, —C(O)OR$_{217}$, —OR$_{216}$, —OCONR$_{216}$R$_{216}$, —S(O)$_2$R$_{217}$, —SO$_2$NR$_{216}$R$_{216}$, —NR$_{216}$R$_{216}$, —NHCOR$_{216}$, —N(C$_{1-4}$alkyl)COR$_{216}$, —NHCONR$_{216}$R$_{216}$, —N(C$_{1-4}$alkyl)CONR$_{216}$R$_{216}$, —NHC(O)OR$_{217}$, —N(C$_{1-4}$alkyl)C(O)OR$_{217}$, —NHS(O)$_2$R$_{217}$, N(C$_{1-4}$alkyl)S(O)$_2$R$_{217}$;

each R$_{214}$ independently represents hydrogen or R$_{215}$;

each R$_{215}$ independently represents C$_{1-4}$alkyl, haloC$_{1-4}$alkyl, C$_{1-4}$alkoxyC$_{1-4}$alkyl, hydroxyC$_{1-4}$alkyl, cyanoC$_{1-4}$alkyl, Cy$_5$-C$_{1-4}$alkyl or Cy$_5$, wherein Cy$_5$ is optionally substituted with one or more R$_{213}$;

each R$_{216}$ independently represents hydrogen or R$_{217}$;

each R$_{217}$ independently represents C$_{1-4}$alkyl, haloC$_{1-4}$alkyl, C$_{1-4}$alkoxyC$_{1-4}$alkyl, hydroxyC$_{1-4}$alkyl or cyanoC$_{1-4}$alkyl;

Cy1 represents a 3- to 7-membered monocyclic carbocyclic ring that is saturated, partially unsaturated or aromatic, and which optionally contains from 1 to 3 heteroatoms independently selected from N, S and O, wherein said ring is bonded to the rest of the molecule through any available C or N atom, and wherein one or more C or S ring atoms are optionally oxidized forming CO, SO or SO2 groups;

Cy2 represents a 3- to 7-membered monocyclic carbocyclic ring that is saturated, partially unsaturated or aromatic, and which optionally contains from 1 to 3 heteroatoms independently selected from N, S and O, wherein said ring is bonded to the rest of the molecule through any available C atom, and wherein one or more C or S ring atoms are optionally oxidized forming CO, SO or SO2 groups;

Cy3 represents a 3- to 7-membered monocyclic or 8- to 12-membered bicyclic carbocyclic ring that is saturated, partially unsaturated or aromatic, and which optionally contains from 1 to 4 heteroatoms independently selected from N, S and O, wherein said ring is bonded to the rest of the molecule through any available C atom, and wherein one or more C or S ring atoms are optionally oxidized forming CO, SO or SO2 groups;

Cy4 represents a 3- to 7-membered monocyclic heterocyclic ring that is saturated or partially unsaturated, which is optionally fused to a 5- or 6-membered carbocyclic or heterocyclic ring that is saturated, partially unsaturated or aromatic, wherein Cy4 optionally contains from 1 to 4 heteroatoms in total independently selected from N, S and O; and wherein one or more C or S atoms of Cy4 are optionally oxidized forming CO, SO or SO2 groups; and Cy5 represents a 3- to 7-membered monocyclic or 8- to 12-membered bicyclic carbocyclic ring that is saturated, partially unsaturated or aromatic, and which optionally contains from 1 to 4 heteroatoms independently selected from N, S and O, wherein said ring is bonded to the rest of the molecule through any available C or N atom, and wherein one or more C or S ring atoms are optionally oxidized forming CO, SO or SO2 groups, as well as the salts and solvates of these compounds, in particular the salts, solvates and stereoisomers of these compounds.

Typically, the compounds of formula (I) are other than

1-[4-[4-[(5-chloro-4-pyrazolo[1,5-a]pyridin-3-yl-pyrimidin-2-yl)amino]-3-methoxy-phenyl]piperazin-1-yl]ethanone;

5-chloro-N-(2-methoxy-4-(piperazin-1-yl)phenyl)-4-(pyrazolo[1,5-a]pyridin-3-yl)pyrimidin-2-amine;

1-[4-[4-[(5-chloro-4-pyrazolo[1,5-a]pyridin-3-yl-pyrimidin-2-yl)amino]-3-methoxy-phenyl]piperazin-1-yl]-2-hydroxy-ethanone;

(2R)-1-[4-[4-[(5-chloro-4-pyrazolo[1,5-a]pyridin-3-yl-pyrimidin-2-yl)amino]-3-methoxy-phenyl]piperazin-1-yl]-2-hydroxy-propan-1-one;

(2S)-1-[4-[4-[(5-chloro-4-pyrazolo[1,5-a]pyridin-3-yl-pyrimidin-2-yl)amino]-3-methoxy-phenyl]piperazin-1-yl]-2-hydroxy-propan-1-one;
1-[4-[4-[(5-chloro-4-pyrazolo[1,5-a]pyridin-3-yl-pyrimidin-2-yl)amino]-3-methoxy-phenyl]piperazin-1-yl]-2-methylamino-ethanone;
2-[4-[4-[(5-chloro-4-pyrazolo[1,5-a]pyridin-3-yl-pyrimidin-2-yl)amino]-3-methoxy-phenyl]piperazin-1-yl]ethanol;
(2S)-1-(3-(4-(5-chloro-4-(pyrazolo[1,5-a]pyridin-3-yl)pyrimidin-2-ylamino)-3-methoxyphenyl)azetidin-1-yl)-2-hydroxypropan-1-one;
(2R)-1-(3-(4-(5-chloro-4-(pyrazolo[1,5-a]pyridin-3-yl)pyrimidin-2-ylamino)-3-methoxyphenyl)azetidin-1-yl)-2-hydroxypropan-1-one;
5-chloro-N-[2-methoxy-4-(4-piperidyl)phenyl]-4-pyrazolo[1,5-a]pyridin-3-yl-pyrimidin-2-amine;
1-[4-[4-[(5-chloro-4-pyrazolo[1,5-a]pyridin-3-yl-pyrimidin-2-yl)amino]-3-methoxy-phenyl]-1-piperidyl]-2-hydroxy-ethanone;
(2R)-1-[4-[4-[5-chloro-4-pyrazolo[1,5-a]pyridin-3-yl-pyrimidin-2-yl)amino]-3-methoxy-phenyl]-1-piperidyl]-2-hydroxy-propan-1-one;
(2S)-1-[4-[4-[(5-chloro-4-pyrazolo[1,5-a]pyridin-3-yl-pyrimidin-2-yl)amino]-3-methoxy-phenyl]-1-piperidyl]-2-hydroxy-propan-1-one;
5-chloro-N-(2-methoxy-5-piperazin-1-yl-phenyl)-4-pyrazolo[1,5-a]pyridin-3-yl-pyrimidin-2-amine;
2-[4-[(5-chloro-4-pyrazolo[1,5-a]pyridin-3-yl-pyrimidin-2-yl)amino]-3-methoxy-phenyl]propane-1,3-diol;
5-chloro-N-[2-methoxy-4-(9-oxa-3,7-diazabicyclo[3.3.1]nonan-7-yl)phenyl]-4-pyrazolo[1,5-a]pyridin-3-yl-pyrimidin-2-amine;
1-[4-[3-[(5-chloro-4-pyrazolo[1,5-a]pyridin-3-yl-pyrimidin-2-yl)amino]-4-methoxy-phenyl]piperazin-1-yl]-2-(methylamino)ethanone;
1-[4-[3-[(5-chloro-4-pyrazolo[1,5-a]pyridin-3-yl-pyrimidin-2-yl)amino]-4-methoxy-phenyl]piperazin-1-yl]-2-(dimethylamino)ethanone;
N-[3-[(5-chloro-4-pyrazolo[1,5-a]pyridin-3-yl-pyrimidin-2-yl)amino]-4-methoxy-phenyl]-2-(dimethylamino)acetamide;
1-[6-[(5-chloro-4-pyrazolo[1,5-a]pyridin-3-yl-pyrimidin-2-yl)amino]-5-methoxy-indolin-1-yl]ethanone;
N-(5-chloro-4-pyrazolo[1,5-a]pyridin-3-yl-pyrimidin-2-yl)-5-methoxy-indolin-6-amine;
1-[6-[(5-chloro-4-pyrazolo[1,5-a]pyridin-3-yl-pyrimidin-2-yl)amino]-5-methoxy-indolin-1-yl]-2-(methylamino)ethanone;
1-[6-[(5-chloro-4-pyrazolo[1,5-a]pyridin-3-yl-pyrimidin-2-yl)amino]-5-methoxy-indolin-1-yl]-2-(dimethylamino)ethanone;
1-[4-[3-methoxy-4-[(5-methyl-4-pyrazolo[1,5-a]pyridin-3-yl-pyrimidin-2-yl)amino]phenyl]piperazin-1-yl]ethanone;
N-(2-methoxy-4-piperazin-1-yl-phenyl)-5-methyl-4-pyrazolo[1,5-a]pyridin-3-yl-pyrimidin-2-amine;
1-[4-[3-methoxy-4-[5-methyl-4-pyrazolo[1,5-a]pyridin-3-yl-pyrimidin-2-yl)amino]phenyl]piperazin-1-yl]-2-(methylamino)ethanone;
2-[4-[3-methoxy-4-[(5-methyl-4-pyrazolo[1,5-a]pyridin-3-yl-pyrimidin-2-yl)amino]phenyl]piperazin-1-yl]ethanol;
N-[2-methoxy-4-(4-piperidyl)phenyl]-5-methyl-4-pyrazolo[1,5-a]pyridin-3-yl-pyrimidin-2-amine;
2-hydroxy-1-[4-[3-methoxy-4-[(5-methyl-4-pyrazolo[1,5-a]pyridin-3-yl-pyrimidin-2-yl)amino]phenyl]-1-piperidyl]ethanone;
(2R)-2-hydroxy-1-[4-[3-methoxy-4-[(5-methyl-4-pyrazolo[1,5-a]pyridine-3-yl-pyrimidin-2-yl)amino]phenyl]-1-piperidyl]propan-1-one;
(2S)-2-hydroxy-1-[4-[3-methoxy-4-[(5-methyl-4-pyrazolo[1,5-a]pyridine-3-yl-pyrimidin-2-yl)amino]phenyl]-1-piperidyl]propan-1-one;
N-(2-methoxy-5-piperazin-1-yl-phenyl)-5-methyl-4-pyrazolo[1,5-a]pyridin-3-yl-pyrimidin-2-amine;
1-[4-[4-methoxy-3-[(5-methyl-4-pyrazolo[1,5-a]pyridin-3-yl-pyrimidin-2-yl)amino]phenyl]piperazin-1-yl]-2-(methylamino)ethanone;
1-[5-methoxy-6-[(5-methyl-4-pyrazolo[1,5-a]pyridin-3-yl-pyrimidin-2-yl)amino]indolin-1-yl]ethanone;
2-(dimethylamino)-1-[5-methoxy-6-[(5-methyl-4-pyrazolo[1,5-a]pyridin-3-yl-pyrimidin-2-yl)amino]indolin-1-yl]ethanone;
1-[4-[4-[(5-fluoro-4-pyrazolo[1,5-a]pyridin-3-yl-pyrimidin-2-yl)amino]-3-methoxy-phenyl]piperzain-1-yl]ethanone;
5-fluoro-N-(2-methoxy-4-piperazin-1-yl-phenyl)-4-pyrazolo[1,5-a]pyridin-3-yl-pyrimidin-2-amine;
1-[4-[4-[(5-fluoro-4-pyrazolo[1,5-a]pyridin-3-yl-pyrimidin-2-yl)amino]-3-methoxy-phenyl]piperazin-1-yl]-2-(methylamino)ethanone;
5-fluoro-N-[2-methoxy-4-(4-piperidyl)phenyl]-4-pyrazolo[1,5-a]pyridin-3-yl-pyrimidin-2-amine;
5-fluoro-N-(2-methoxy-5-piperazin-1-yl-phenyl)-4-pyrazolo[1,5-a]pyridin-3-yl-pyrimidin-2-amine;
2-(dimethylamino)-1-[6-[5-fluoro-4-pyrazolo[1,5-a]pyridin-3-yl-pyrimidin-2-yl)amino]-5-methoxy-indolin-1-yl]ethanone;
5-chloro-N-[2-methoxy-5-(9-oxa-3,7-diazabicyclo[3.3.1]nonan-7-yl)phenyl]-4-pyrazolo[1,5-a]pyridin-3-yl-pyrimidin-2-amine;
2-[[4-[(5-chloro-4-pyrazolo[1,5-a]pyridin-3-yl-pyrimidin-2-yl)amino]-3-methoxy-phenyl]methyl]propane-1,3-diol;
2-[4-[4-[(5-chloro-4-pyrazolo[1,5-a]pyridin-3-yl-pyrimidin-2-yl)amino]-3-methoxy-phenyl]piperazin-1-yl]-2-methyl-propan-1-ol;
2-[4-[3-methoxy-4-[(5-methyl-4-pyrazolo[1,5-a]pyridin-3-yl-pyrimidin-2-yl)amino]phenyl]piperazin-1-yl]-2-methyl-propan-1-ol;
1-[4-[3-methoxy-4-[(5-methyl-4-pyrazolo[1,5-a]pyridin-3-yl-pyrimidin-2-yl)amino]phenyl]-1-piperidyl]ethanone;
1-[4-[4-[(5-cyclopropyl-4-pyrazolo[1,5-a]pyridin-3-yl-pyrimidin-2-yl)amino]-3-methoxy-phenyl]piperazin-1-yl]ethanone;
2-(dimethylamino)-1-[4-[4-methoxy-3-[(5-methyl-4-pyrazolo[1,5-a]pyridin-3-yl-pyrimidin-2-yl)amino]phenyl]piperazin-1-yl]ethanone;
1-[4-[3-methoxy-4-[(5-methyl-4-pyrazolo[1,5-a]pyridin-3-yl-pyrimidin-2-yl)amino]phenyl]-1-piperidyl]-2-(methylamino)ethanone;
1-[4-[4-[(5-fluoro-4-pyrazolo[1,5-a]pyridin-3-yl-pyrimidin-2-yl)amino]-3-methoxy-phenyl]-1-piperidyl]-2-(methylamino)ethanone;
2-[4-(1-acetyl-4-piperidyl)-2-methoxy-anilino]-4-pyrazolo[1,5-a]pyridin-3-yl-pyrimidine-5-carbonitrile;
2-[4-[1-(2-hydroxyacetyl)-4-piperidyl]-2-methoxy-anilino]-4-pyrazolo[1,5-a]pyridin-3-yl-pyrimidine-5-carbonitrile;
and pharmaceutically acceptable salts thereof. These compounds are typically excluded from the scope of the invention for use in the production of an anti-proliferative effect in a human or animal, for example for use in the treatment of a disease or medical condition mediated alone or in part by insulin-like growth factor receptor (IGF-1R) tyrosine kinase, for example for use in the prevention or treatment of those tumours which are sensitive to inhibition of insulin-like growth factor-1 receptor (IGF-1R) tyrosine kinase, involved in the signal transduction steps which lead to the proliferation and/or survival of tumour cells, for example for use in the treatment of cancer. These compounds are typically excluded from the scope of the invention when used in combination with methotrexate.

The above compounds are disclosed in WO 2010/049731. Typically, the compounds of formula (I) exclude the compounds disclosed in WO 2010/049731, including the salts disclosed therein.

Typically, the compounds defined herein are other than compounds of formula (I) and pharmaceutically acceptable salts thereof in which:
  m is 0;
  Z is NH;
  W is $CR^{1b'}$
  X is $CR^{2'}$, wherein $R^{2'}$ represents a halogen atom, a cyano group, a trifluoromethyl group, a cyclopropyl group or an unsubstituted $C_1$-$C_3$ alkyl group;
  Y is CH;
  T is a nitrogen atom;
  $R_1$ and $R_2$ are both H;
  $R_4$ is $R^{1a'}$;
  $R_8$ represents a moiety

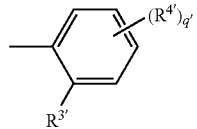

wherein
  $R^{3'}$ represents hydroxy, cyano, halogeno, $(C_1$-$C_6)$alkyl, $(C_1$-$C_4)$alkoxy, $(C_1$-$C_4)$haloalkyl or $(C_1$-$C_4)$hydroxyalkyl;
  each $R^{4'}$, which may be the same or different, is selected from hydroxy, cyano, halogeno, formyl, carboxy, $(C_1$-$C_6)$alkyl, $(C_1$-$C_4)$alkoxy, $(C_2$-$C_6)$alkanoyl, $(C_1$-$C_6)$alkoxycarbonyl, $(C_3$-$C_7)$cycloalkyl, $(C_3$-$C_7)$cycloalkylcarbonyl, amino, $(C_1$-$C_6)$alkylamino, di-[$(C_1$-$C_6)$alkyl]amino, carbamoyl, $(C_1$-$C_6)$alkylcarbamoyl, di-[$(C_1$-$C_6)$alkyl]carbamoyl, sulfamoyl, $(C_1$-$C_6)$alkylsulfamoyl, di-[$(C_1$-$C_6)$alkyl]sulfamoyl, —$S(O)_m$R' wherein R' is selected from hydrogen and $(C_1$-$C_6)$alkyl and m' represents 0, 1 or 2, —N(R")C(O)R' wherein R' is as defined above and R" is selected from hydrogen and $(C_1$-$C_6)$alkyl and —X-Q wherein X is a direct bond and Q represents a saturated 5-, 6-, 7-, 8-, 9- or 10-membered heterocyclic ring comprising at least one ring heteroatom selected from nitrogen, oxygen and sulfur,
  or two $R^{4'}$ groups on adjacent carbon atoms of the phenyl ring, together with the carbon atoms to which they are attached, form a saturated or unsaturated monocyclic 5- or 6-membered heterocyclic ring comprising at least one ring heteroatom selected from nitrogen, oxygen and sulfur, each of which groups or rings within $R^4$ may be optionally substituted by one or more substituents independently selected from hydroxy, halogeno, cyano, formyl, carboxy, $(C_1$-$C_6)$alkyl, $(C_3$-$C_7)$cycloalkyl, $(C_3$-$C_7)$cycloalkylcarbonyl, $(C_1$-$C_6)$alkoxy, amino, $(C_1$-$C_6)$alkylamino, di-[$(C_1$-$C_6)$alkyl]amino, $(C_2$-$C_6)$alkanoyl, $(C_1$-$C_6)$alkoxycarbonyl, carbamoyl, $(C_1$-$C_6)$alkylcarbamoyl, di-[$(C_1$-$C_6)$alkyl]carbamoyl, sulfamoyl, $(C_1$-$C_6)$alkylsulfamoyl, di-[$(C_1$-$C_6)$alkyl]sulfamoyl, —$S(O)_m$R' wherein R' and m' are each as defined above, —N(R")C(O)R' wherein R' and R" are each as defined above, and —X-Q wherein X and Q are each as defined above, any of which substituents may be optionally substituted by one or more further substituents independently selected from $(C_1$-$C_4)$alkyl, $(C_1$-$C_4)$alkoxy, hydroxy, halogeno, cyano, hydroxy $(C_1$-$C_4)$alkyl, and —X-Q' wherein X as defined above and Q' represents a saturated 5- or 6-membered heterocyclic ring comprising at least one ring nitrogen atom; and
  each $R^{1a'}$ and $R^{1b'}$, which may be the same or different, is selected from hydrogen, halogeno, cyano, $(C_1$-$C_6)$ alkyl, amino, $(C_1$-$C_6)$alkylamino and di-[$(C_1$-$C_6)$ alkyl]amino, each of which groups within $R^{1a'}$ and $R^{1b'}$ may be optionally substituted by one or more substituents independently selected from hydroxy, halogeno, cyano, $(C_1$-$C_6)$alkyl, $(C_1$-$C_4)$alkoxy, amino, $(C_1$-$C_6)$alkylamino, di-[$(C_1$-$C_6)$alkyl]amino, —N(R")C(O)R' wherein R' and R" are as defined above, and a saturated monocyclic 5-, 6-, 7- or 8-membered ring optionally comprising one or more heteroatoms independently selected from nitrogen, oxygen and sulfur.

These compounds are typically excluded from the scope of the invention for use in the production of an anti-proliferative effect in a human or animal, for example for use in the treatment of a disease or medical condition mediated alone or in part by insulin-like growth factor receptor (IGF-1R) tyrosine kinase, for example for use in the prevention or treatment of those tumours which are sensitive to inhibition of insulin-like growth factor-1 receptor (IGF-1R) tyrosine kinase, involved in the signal transduction steps which lead to the proliferation and/or survival of tumour cells, for example for use in the treatment of cancer. These compounds are typically excluded from the scope of the invention when used in combination with methotrexate.

Typically, in the compound of formula (I) $R_1$ represents a hydrogen atom, a halogen atom, a hydroxyl group, a cyano group, a linear or branched $C_1$-$C_6$ alkyl group, a $C_1$-$C_4$ haloalkyl group, a $C_1$-$C_4$ hydroxyalkyl group, a $C_3$-$C_{10}$ cycloalkyl group or a —NR'R" group; wherein R' and R" are the same or different and each represents a hydrogen atom, a linear or branched $C_1$-$C_6$ alkyl group, a $C_1$-$C_4$ haloalkyl group or $C_1$-$C_4$ hydroxyalkyl group;

$R_2$, $R_3$ and $R_4$ are the same or different and each represent a hydrogen atom, a halogen atom, a hydroxyl group, a cyano group, a linear or branched $C_1$-$C_6$ alkyl group, a $C_1$-$C_4$ haloalkyl group, a $C_1$-$C_4$ hydroxyalkyl group, or a $C_3$-$C_{10}$ cycloalkyl group;

$R_5$ represents a hydrogen atom, a linear or branched $C_1$-$C_6$ alkyl group optionally substituted by one or more substituents selected from a hydroxyl group, a cyano group, a $C_1$-$C_4$ haloalkyl group, a $C_1$-$C_4$ hydroxyalkyl group or a $C_3$-$C_{10}$ cycloalkyl group; or $R_5$ together with $R_8$ and the nitrogen atom to which $R_5$ is bonded form a 5- to 9-membered, saturated heterocyclyl group, which contains, as heteroatoms, one or two nitrogen atoms and which heterocyclyl ring is unsubstituted or substituted by a —C(O)—(CH$_2$)$_n$—R group or a —C(O)—(CH$_2$)—NR'R" group, wherein n is 0, 1 or 2, R represents a hydrogen atom, or a linear or branched $C_1$-$C_6$ alkyl group, a $C_1$-$C_4$ haloalkyl group, a $C_1$-$C_4$ hydroxyalkyl group, or a cyano group and R' and R" are the same or different and each represents a hydrogen atom, a linear or branched $C_1$-$C_6$ alkyl group, a $C_1$-$C_4$ haloalkyl group, or $C_1$-$C_4$ hydroxyalkyl group;

$R_6$ and $R_7$ are the same or different and each represent a hydrogen atom, a linear or branched $C_1$-$C_6$ alkyl group, a $C_1$-$C_4$ haloalkyl group or a $C_1$-$C_4$ hydroxyalkyl group;

$R_9$ represents a hydrogen atom, a halogen atom, a hydroxyl group, a cyano group, a linear or branched $C_1$-$C_6$ alkyl group, a $C_1$-$C_4$ haloalkyl group, a $C_1$-$C_4$ hydroxyalkyl group, a 5- to 10-membered heterocyclyl group, or a 5- to 10-membered heteroaryl group, wherein said heterocyclyl and heteroaryl groups are unsubstituted or substituted by one or more substituents selected from a halogen atom, a linear or branched $C_1$-$C_6$ alkyl group, a cyano group, a hydroxyl group or a $C_1$-$C_4$ alkoxy group; or $R_9$ represents a —C(O)—O—R' group or a —C(O)—(CH$_2$)$_n$—NR'R" group, wherein n is 0, 1 or 2, and R' and R" are the same or different and each represents a hydrogen atom, a linear or branched $C_1$-$C_6$ alkyl group, a $C_1$-$C_4$ haloalkyl group, or $C_1$-$C_4$ hydroxyalkyl group; or in the case when two adjacent —CR$_9$ groups are present, the two adjacent —CR$_9$ groups and the carbon atoms to which they are bonded optionally form a $C_6$-$C_{10}$ aryl group which is unsubstituted or substituted by one or more substituents selected from a halogen atom, a linear or branched $C_1$-$C_6$ alkyl group, a hydroxy group or a $C_1$-$C_4$ alkoxy group;

$R_8$ represents a hydrogen atom, a linear or branched $C_1$-$C_6$ alkyl group, a $C_1$-$C_4$ haloalkyl group, a $C_1$-$C_4$ hydroxyalkyl group, a $C_3$-$C_{10}$, cycloalkyl group, a $C_6$-$C_{10}$ aryl group, a 5- to 10-membered heteroaryl group containing 1, 2 or 3 heteroatoms selected from N, O and S, a 5- to 10-membered heterocyclyl group containing 1, 2 or 3 heteroatoms selected from N, O and S, -L-Het-R''', -L-A, -A-SO$_2$—R', -A-SO—R''', -A-A', -A-L-C(O)NR'R", -A-L-CN, -A-C(O)-Het'-L-CN, -A-C(O)—NR'R", -A-C(O)$_z$-A", -A-C(O)—R''', -A-CO$_2$—R', -A-C(O)$_z$-L-A", -A-C(O)$_z$-L-R''', -A-C(O)$_z$-L-CN, or -A-C(O)$_z$-L-Het-R' group, wherein z is 1 or 2, R' and R" are the same or different and each represents a hydrogen atom or linear or a branched $C_1$-$C_6$ alkyl group, a $C_1$-$C_4$ haloalkyl group or a $C_1$-$C_4$ hydroxyalkyl group, and R''' represents a linear or branched $C_1$-$C_6$ alkyl group, a $C_1$-$C_4$ haloalkyl group or a $C_1$-$C_4$ hydroxyalkyl group, the heterocyclyl and heteroaryl groups being optionally fused to a phenyl group, and wherein the cycloalkyl, heterocyclyl, aryl and heteroaryl groups being unsubstituted or substituted by one or more substituents selected from a halogen atom, a hydroxyl group, a cyano group, a linear or branched $C_1$-$C_6$ alkyl group, or a $C_1$-$C_4$ alkoxy group, and wherein L is a linear or branched $C_1$-$C_6$ alkylene group, Het represents O or NR$^{IV}$, and Het' represents NR$^{IV}$, wherein R$^{IV}$ is a hydrogen atom, a linear or branched $C_1$-$C_4$ alkyl group, a $C_1$-$C_4$ haloalkyl group, or $C_1$-$C_4$ hydroxyalkyl group, A, A', A" and A''' are the same or different and each represent a $C_3$-$C_{10}$ cycloalkyl group, a 5- to 10-membered heterocyclyl group, a $C_6$-$C_{10}$ aryl group, or a 5- to 10-membered heteroaryl group, the cycloalkyl, heterocyclyl, aryl and heteroaryl groups being unsubstituted or substituted by one or more substituents selected from a halogen atom, a hydroxyl group, a cyano group, a linear or branched $C_1$-$C_6$ alkyl group, or a $C_1$-$C_4$ alkoxy group.

Alternatively, in the compounds of formula (I), $R_9$ represents a hydrogen atom, a halogen atom, a hydroxyl group, a cyano group, a linear or branched $C_1$-$C_6$ alkyl group, a $C_1$-$C_4$ haloalkyl group, a $C_1$-$C_4$ hydroxyalkyl group or a —NR'R" group; wherein R' and R" are the same or different and each represents a hydrogen atom, a linear or branched $C_1$-$C_6$ alkyl group, a $C_1$-$C_4$ haloalkyl group or $C_1$-$C_4$ hydroxyalkyl group, and $R_1$, $R_2$, $R_3$, $R_4$, $R_5$, $R_6$, $R_7$, $R_9$, L, Het, A, A', A" and A''' are as defined above.

Preferably, in the compound of formula (I) Z is a NR$_5$ group, wherein R$_5$ represents a hydrogen atom, a linear or branched $C_1$-$C_6$ alkyl group optionally substituted by one or more substituents selected from a hydroxyl group, a cyano group, a $C_1$-$C_4$ haloalkyl group, a $C_1$-$C_4$ hydroxyalkyl group, a $C_3$-$C_{10}$ cycloalkyl group, a phenyl group or a 6 membered, saturated N-containing heterocyclyl ring, or R$_5$ represents a —S(O)$_2$R$_{10}$ group, a —S(O)$_2$NR$_{10}$R$_{11}$ group, a —C(O)OR$_{10}$ group, a —C(O)—(CH$_2$)$_n$—R$_{10}$ group, or a —C(O)—(CH$_2$)$_n$—NR$_{10}$R$_{11}$ group, wherein n is 0, 1 or 2 and R$_{10}$ and R$_{11}$ are as defined before.

Typically, in the compound of formula (I), Y represents a —CR$_9$ group. Typically, in the compound of formula (I), T represents a —CR$_9$ group. Preferably, both Y and T represent a —CR$_9$ group.

Typically, in the compound of formula (I), at least one of X, Y and T, preferably at least one of X and Y, represents N.

In the compound of formula (I), Y may represent N, in which case X and T each represent a —CR$_9$ group.

When Y represents N and R$_8$ represents a 5- to 7-membered heterocyclyl group containing one nitrogen atom, typically said heterocyclyl group is substituted by one or more substituents, wherein said substitution is at least on the ring nitrogen atom of the heterocyclyl group, and wherein this substituent is other than a tert-butoxycarbonyl group. Preferred substituents for an R$_8$ heterocyclyl group are defined herein. Preferably, when Y represents N and R$_8$ represents a 5- to 7-membered heterocyclyl group containing one nitrogen atom, said heterocyclyl group is a piperidinyl group which is substituted by one or more substituents, wherein said substitution is at least on the ring nitrogen of the piperidinyl group, the substituents being selected from a linear or branched $C_1$-$C_3$ alkyl group;

a halogen atom;

a pyridyl group, which pyridyl group is unsubstituted or substituted by one or more cyano groups;

a 1,2,4-triazolyl group; and a —C(O)—(CH$_2$)$_n$—R" group, wherein n is 0 or 1 and R" is a cyano group, a linear or branched $C_1$-$C_6$ alkyl group, a $C_1$-$C_4$ haloalkyl group or a $C_3$-$C_7$ cycloalkyl group.

Typically, in the compound of formula (I) $R_1$ represents a hydrogen atom, a halogen atom, a cyano group, a linear or branched $C_1$-$C_6$ alkyl group, a $C_3$-$C_7$ cycloalkyl group or a —NR'R" group, wherein R' and R" are the same or different and each represents a hydrogen atom, a linear or branched $C_1$-$C_6$ alkyl group, a $C_1$-$C_4$ haloalkyl group; preferably $R_1$ represents a hydrogen atom or a —NH$_2$ group; more preferably $R_1$ represents a hydrogen atom.

Typically, in the compound of formula (I) $R_2$ represents a hydrogen atom, a halogen atom, a cyano group, a linear or branched $C_1$-$C_6$ alkyl group or a $C_3$-$C_7$ cycloalkyl group; preferably $R_2$ represents a hydrogen atom or a linear or branched $C_1$-$C_3$ alkyl group; more preferably $R_2$ represents a hydrogen atom.

Typically, in the compound of formula (I) $R_3$ represents a hydrogen atom, a halogen atom, a cyano group, a linear or branched $C_1$-$C_6$ alkyl group or a $C_3$-$C_7$ cycloalkyl group; preferably $R_3$ represents a hydrogen atom, a cyano group or a linear or branched $C_1$-$C_3$ alkyl group; more preferably $R_3$ represents a hydrogen atom or a cyano group.

Typically, in the compound of formula (I) $R_4$ represents a hydrogen atom, a halogen atom, a cyano group, a linear or branched $C_1$-$C_6$ alkyl group or a $C_3$-$C_7$ cycloalkyl group; preferably $R_4$ represents a hydrogen atom or a linear or branched $C_1$-$C_3$ alkyl group; more preferably $R_4$ represents a hydrogen atom.

Typically, in the compound of formula (I) Z is $NR_5$ and $R_5$ represents a hydrogen atom, a linear or branched $C_1$-$C_4$ alkyl group optionally substituted by one or more substituents selected from a hydroxyl group, a $C_1$-$C_4$ haloalkyl group, a $C_1$-$C_4$ hydroxyalkyl group or a $C_3$-$C_7$ cycloalkyl group; preferably $R_5$ represents a hydrogen atom or a linear or branched $C_1$-$C_3$ alkyl group; more preferably $R_5$ represents a hydrogen atom.

Typically, in the compound of formula (I) $R_6$ and $R_7$ independently represent a hydrogen atom or a linear or branched $C_1$-$C_6$ alkyl group; preferably $R_6$ and $R_7$ independently represent a hydrogen atom or a linear or branched $C_1$-$C_3$ alkyl group.

Typically, in the compound of formula (I) $R_8$ represents a linear or branched $C_1$-$C_6$-alkyl group, a $C_1$-$C_4$ haloalkyl group, a $C_1$-$C_4$ hydroxyalkyl group, a $C_3$-$C_{10}$ cycloalkyl group, a $C_6$-$C_{10}$ aryl group, a 5- to 10-membered heteroaryl group containing 1, 2 or 3 heteroatoms selected from N, O and S, a 5- to 10-membered heterocyclyl group containing 1, 2 or 3 heteroatoms selected from N, O and S, -L-Het-R''', -L-A, -A-A', -A-L-C(O)NR'R'', -A-L-CN, -A-C(O)-Het'-L-CN, -A-C(O)—NR'R'', -A-C(O)$_z$-A'', -A-C(O)—R''', -A-CO$_2$—R', -A-C(O)$_z$-L-A''', -A-C(O)$_z$-L-R''', -A-C(O)$_z$-L-CN, or -A-C(O)$_z$-L-Het-R' group, wherein z is 1 or 2, R' and R'' are the same or different and each represents a hydrogen atom or linear or a branched $C_1$-$C_6$ alkyl group, a $C_1$-$C_4$ haloalkyl group or a $C_1$-$C_4$ hydroxyalkyl group, and R''' represents a linear or branched $C_1$-$C_6$ alkyl group, a $C_1$-$C_4$ haloalkyl group or a $C_1$-$C_4$ hydroxyalkyl group, the heterocyclyl and heteroaryl groups being optionally fused to a phenyl group, and wherein the cycloalkyl, heterocyclyl, aryl and heteroaryl groups being unsubstituted or substituted by one or more substituents selected from a halogen atom, a hydroxyl group, a cyano group, a linear or branched $C_1$-$C_4$ alkyl group, or a $C_1$-$C_4$ alkoxy group.

Typically, L is a linear or branched $C_1$-$C_6$ alkylene group. Preferably, L is a linear or branched $C_1$-$C_5$ alkylene group; more preferably, L is a linear or branched $C_1$-$C_3$ alkylene group.

Typically, Het represents O or $NR^{IV}$ and Het' represents $NR^{IV}$, wherein $R^{IV}$ is a hydrogen atom or a linear or branched $C_1$-$C_4$ alkyl group, preferably a hydrogen atom or a straight or branched $C_1$-$C_2$ alkyl group. Preferably, Het represents O.

Typically, A, A', A'' and A''' are the same or different and each represent a $C_3$-$C_6$ cycloalkyl, 5- to 6-membered heterocyclyl, phenyl, 5- to 6-membered heteroaryl group, the cycloalkyl, heterocyclyl, phenyl and heteroaryl groups being unsubstituted or substituted by 1, 2 or 3 halogen atoms, or hydroxyl, cyano, linear or branched $C_1$-$C_2$ alkyl, or $C_1$-$C_2$ alkoxy groups.

Typically, A is a 5- to 6-membered heterocyclyl group, phenyl or $C_3$-$C_6$ cycloalkyl group, said heterocyclyl, phenyl and cycloalkyl groups being unsubstituted or substituted by 1, 2 or 3, preferably 1 or 2, halogen atoms or hydroxyl or $C_1$-$C_2$ alkyl groups. Preferably, A is a piperidinyl, phenyl or cyclohexyl group, which piperidinyl, phenyl and cyclohexyl groups are unsubstituted or substituted by one halogen atom, or hydroxyl group or $C_1$-$C_2$ alkyl group, Typically, A' is phenyl group or a 5- or 6-membered heteroaryl group, which phenyl and heteroaryl groups are unsubstituted or substituted by 1, 2 or 3 halogen atoms, or cyano, hydroxy or $C_1$-$C_2$ alkyl groups. Preferably, A' is a phenyl, pyridinyl or triazolyl group, for example a phenyl or pyridinyl group, which is unsubstituted or substituted by 1 or 2 halogen atoms or cyano groups.

Typically, A'' is a 5- to 6-membered heterocyclyl, $C_3$-$C_6$ cycloalkyl or 5- or 6-membered heteroaryl group, which heterocyclyl, cycloalkyl and heteroaryl groups are unsubstituted or substituted by 1, 2 or 3, halogen atoms, or cyano, hydroxy or $C_1$-$C_2$ alkyl groups. Preferably, A'' is a pyrrolidinyl, cyclopropyl or pyridinyl group, which pyrrolidinyl, cyclopropyl and pyridinyl groups are unsubstituted or substituted by 1 or 2 halogen atoms or cyano groups.

Typically, A''' is a 5- to 6-membered heteroaryl group, which heteroaryl group is unsubstituted or substituted by 1, 2 or 3, preferably 1 or 2 halogen atoms or hydroxy or $C_1$-$C_2$ alkyl groups. Preferably, A' is an imidazolyl group.

Preferably in the compounds of formula (I), $R_8$ represents a hydrogen atom, a linear or branched $C_1$-$C_6$ alkyl group, a $C_1$-$C_4$ haloalkyl group, a $C_1$-$C_4$ hydroxyalkyl group, a $C_3$-$C_{10}$ cycloalkyl group, a $C_6$-$C_{10}$ aryl group, a 5- to 10-membered heteroaryl group containing 1, 2 or 3 heteroatoms selected from N, O and S, a 5- to 10-membered heterocyclyl group containing 1, 2 or 3 heteroatoms selected from N, O and S, -L-Het-R''', -L-A, -A-A', -A-L-CN, -A-C(O)—R''', -A-C(O)$_z$-L-R''', -A-C(O)$_z$-L-CN, or -A-C(O)$_z$-L-Het-R' group, wherein z is 1 or 2 and R''' represents a linear or branched $C_1$-$C_3$ alkyl group, a $C_1$-$C_3$ haloalkyl group or a $C_1$-$C_3$ hydroxyalkyl group, and wherein the cycloalkyl, heterocyclyl, aryl and heteroaryl groups are unsubstituted or substituted by one or more substituents selected from a halogen atom, a hydroxyl group, a cyano group, a linear or branched $C_1$-$C_6$ alkyl group, or a $C_1$-$C_4$ alkoxy group, and wherein L is a linear or branched $C_1$-$C_3$ alkylene group, Het represents O or $NR^{IV}$, wherein $R^{IV}$ is a hydrogen atom, a linear or branched $C_1$-$C_4$ alkyl group, a $C_1$-$C_4$ haloalkyl group, or $C_1$-$C_4$ hydroxyalkyl group, A and A' are the same or different and each represents a $C_3$-$C_{10}$ cycloalkyl group, a 5- to 10-membered heterocyclyl group, a $C_6$-$C_{10}$ aryl group, or a 5- to 10-membered heteroaryl group, the cycloalkyl, heterocyclyl, aryl and heteroaryl groups being unsubstituted or substituted by one or more substituents selected from a halogen atom, a hydroxyl group, a cyano group, a linear or branched $C_1$-$C_6$ alkyl group, or a $C_1$-$C_4$ alkoxy group.

Preferably, in the compound of formula (I) $R_8$ represents a linear or branched $C_1$-$C_6$ alkyl group, a $C_1$-$C_4$ haloalkyl group, a $C_3$-$C_7$ cycloalkyl group, a phenyl group, a 5- to 6-membered monocyclic heteroaryl group containing 1, 2 or 3 heteroatoms selected from N, O and S, a 5- to 7-membered heterocyclyl group containing 1, 2 or 3 heteroatoms selected from N, O and S, or a —(CH$_2$)OR group wherein n is 0 or 1 and R represents a linear or branched $C_1$-$C_6$ alkyl group or a $C_1$-$C_4$ haloalkyl group;

wherein the haloalkyl, cycloalkyl, phenyl, heteroaryl and heterocyclyl groups are unsubstituted or substituted by one or more substituents selected from Ra; and the alkyl group is unsubstituted or substituted by one or more substituents selected from Rb;

Ra is a halogen atom; a cyano group; a hydroxyl group; a linear or branched $C_1$-$C_6$ alkyl group; a $C_1$-$C_4$ haloalkyl group; a $C_1$-$C_4$ alkoxy group; a $C_3$-$C_7$ cycloalkyl group unsubstituted or substituted by one or more substituents selected from substituents Re; a phenyl group unsubstituted or substituted by one or more substituents selected from substituents Re; a 5- to 6-membered monocyclic heteroaryl group containing 1, 2 or 3 heteroatoms selected from N, O and S unsubstituted or substituted by one or more substituents selected from substituents Re; a 6 membered, saturated N-containing heterocyclyl ring, unsubstituted or substituted by one or more substituents selected from substituents Re; a —C(O)OR' group or a —C(O)—(CH$_2$)$_n$—R'' group wherein n is 0 or 1, Rb is a cyano group; a $C_1$-$C_4$ haloalkyl group; a $C_1$-$C_4$ alkoxy group; a $C_3$-$C_7$ cycloalkyl group unsubstituted or substituted by one or more substituents selected from substituents Re; a phenyl group unsubstituted or substituted by one or more substituents selected from substituents Re; a 5- to 6-membered monocyclic heteroaryl group containing 1, 2 or 3 heteroatoms selected from N, O and S unsubstituted or substituted by one or more substituents selected from substituents Re; a 6 membered, saturated N-containing heterocyclyl ring, unsubstituted or substituted by one or more substituents selected from substituents Re; a —C(O)OR' group or a —C(O)—(CH$_2$)$_n$—R'' group wherein n is 0 or 1, Re is a halogen atom, a hydroxyl group, a cyano group, a linear or branched $C_1$-$C_6$ alkyl group or a $C_1$-$C_4$ haloalkyl group;

R' is a hydrogen atom, a linear or branched $C_1$-$C_6$ alkyl group, a $C_1$-$C_4$ haloalkyl group, a $C_3$-$C_7$ cycloalkyl group, a phenyl group, a 5- to 6-membered monocyclic heteroaryl group containing 1, 2 or 3 heteroatoms selected from N, O and S or a 5- to 6-membered, saturated N-containing heterocyclyl ring; and R'' is a cyano group, a linear or branched $C_1$-$C_6$ alkyl group, a $C_1$-$C_4$ haloalkyl group, a $C_3$-$C_7$ cycloalkyl group, a phenyl group, a 5- to 6-membered monocyclic heteroaryl group containing 1, 2 or 3 heteroatoms selected from N, O and S or a 5- to 6-membered, saturated N-containing heterocyclyl ring; wherein the cycloalkyl, phenyl, heteroaryl and heterocyclyl groups are unsubstituted or substituted by one or more substituents selected from a hydroxyl group, a cyano group, a linear or branched $C_1$-$C_6$ alkyl group or a $C_1$-$C_4$ haloalkyl group.

More preferably, in the compound of formula (I) $R_8$ represents a linear or branched $C_1$-$C_6$ alkyl group, a $C_1$-$C_4$ haloalkyl group, a $C_3$-$C_7$ cycloalkyl group, a phenyl group, a 5- to 6-membered monocyclic heteroaryl group containing 1, 2 or 3 heteroatoms selected form N, O and S, a 5- to 7-membered heterocyclyl group containing 1, 2 or 3 heteroatoms selected from N, O and S, or a —(CH$_2$)OR group wherein n is 0 or 1 and R represents a linear or branched $C_1$-$C_6$ alkyl group or a $C_1$-$C_4$ haloalkyl group, for example $R_8$ represents a linear or branched $C_1$-$C_6$ alkyl group, a $C_1$-$C_4$ haloalkyl group, a $C_3$-$C_7$ cycloalkyl group, a phenyl group, a 5- to 7-membered heterocyclyl group containing 1, 2 or 3 heteroatoms selected from N, O and S, or a —(CH$_2$)$_n$OR group wherein n is 0 or 1 and R represents a linear or branched $C_1$-$C_6$ alkyl group or a $C_1$-$C_4$ haloalkyl group;

wherein the haloalkyl, cycloalkyl, phenyl, heteroaryl and heterocyclyl groups are unsubstituted or substituted by one or more substituents selected from Ra; and the alkyl group is unsubstituted or substituted by one or more substituents selected from Rb;

Ra is a halogen atom; a cyano group; a hydroxyl group; a linear or branched $C_1$-$C_6$ alkyl group; a $C_1$-$C_4$ haloalkyl group; a 5- to 6-membered monocyclic heteroaryl group containing 1, 2 or 3 heteroatoms selected from N, O and S unsubstituted or substituted by one or more substituents selected from a halogen atom, a hydroxyl group, a cyano group, a linear or branched $C_1$-$C_6$ alkyl group or a $C_1$-$C_4$ haloalkyl group; a —C(O)OR' group or a —C(O)—(CH$_2$)$_n$—R'' group wherein n is 0 or 1, Rb is a cyano group; a $C_1$-$C_4$ haloalkyl group; a $C_1$-$C_4$ alkoxy group; a $C_3$-$C_7$ cycloalkyl group unsubstituted or substituted by one or more substituents selected from a halogen atom, a hydroxyl group or a cyano group; a phenyl group unsubstituted or substituted by one or more substituents selected from a halogen atom, a hydroxyl group, a cyano group or a linear or branched $C_1$-$C_6$ alkyl group; a —C(O)OR' group or a —C(O)—(CH$_2$)$_n$—R'' group wherein n is 0 or 1, R' is a hydrogen atom, a linear or branched $C_1$-$C_6$ alkyl group, a $C_1$-$C_4$ haloalkyl group or a $C_3$-$C_7$ cycloalkyl group; and R'' is a cyano group, a linear or branched $C_1$-$C_6$ alkyl group, a $C_1$-$C_4$ haloalkyl group or a $C_3$-$C_7$ cycloalkyl group.

In one embodiment, $R_8$ represents a linear or branched $C_1$-$C_6$ alkyl group, a $C_1$-$C_4$ haloalkyl group, a $C_3$-$C_7$ cycloalkyl group, a 6-membered heterocyclyl group containing 1, 2 or 3 heteroatoms selected from N, O and S, or a —(CH$_2$)OR group wherein n is 0 or 1 and R represents a linear or branched $C_1$-$C_6$ alkyl group or a $C_1$-$C_4$ haloalkyl group; in particular, $R_8$ may represent a 6-membered heterocyclyl group containing 1, 2 or 3 heteroatoms selected from N, O and S;

wherein the haloalkyl, cycloalkyl and heterocyclyl groups are unsubstituted or substituted by one or more substituents selected from Ra; and the alkyl group is unsubstituted or substituted by one or more substituents selected from Rb, wherein Ra and Rb are as defined above.

More preferably, when $R_8$ is an alkyl or haloalkyl group, it is an unsubstituted alkyl or haloalkyl group; when $R_8$ is a cycloalkyl or phenyl group, it is unsubstituted or substituted by one or more substituents selected from a halogen atom, a cyano group, a hydroxyl group, a linear or branched $C_1$-$C_6$ alkyl group, a $C_1$-$C_4$ haloalkyl group, a —C(O)OR' group or a —C(O)—(CH$_2$), —R'' group wherein n is 0 or 1, R' is a hydrogen atom, a linear or branched $C_1$-$C_3$ alkyl group or a $C_1$-$C_3$ haloalkyl group and R'' is a cyano group, a linear or branched $C_1$-$C_3$ alkyl group or a $C_1$-$C_3$ haloalkyl group; and when $R_8$ is a heteroaryl or heterocyclyl group it is unsubstituted or substituted with one or more substituents selected from Ra, wherein Ra is as defined above.

Preferably, when $R_8$ is a heteroaryl group, it is a 5- to 6-membered heteroaryl group containing one or two nitrogen atoms. Pyridyl is preferred. Preferably, when $R_8$ is a heteroaryl group it is unsubstituted or substituted with one or more halogen atoms.

When $R_8$ is a heterocyclyl group it is preferably a 5- or 6-membered heterocyclyl group, e.g. a 6-membered heterocyclyl group, containing one or two heteroatoms selected from N and O, more preferably containing one or two nitrogen atoms. Preferred examples are piperidinyl and tetrahydropyranyl. Piperidinyl is preferred. Preferably, the heterocyclyl group is linked to the rest of the molecule via a ring carbon atom, in other words it is linked to the group —Z—(CR$_6$R$_7$)$_m$— via a ring carbon atom. Substituents on a piperidinyl group may be present on any ring atom but are preferably present on the nitrogen atom. Preferably, at least one substituent is present on the ring nitrogen atom.

Most preferably, $R_8$ represents a linear or branched $C_1$-$C_6$ alkyl group; a $C_1$-$C_4$ haloalkyl group; a $C_3$-$C_7$ cycloalkyl group, which cycloalkyl group is unsubstituted or substituted by one or more substituents selected from halogen atoms and hydroxyl groups; a phenyl group, which phenyl group is unsubstituted or substituted by one or more halogen atoms; a —(CH$_2$)$_n$—OR group wherein n is 0 or 1 and R represents a linear or branched $C_1$-$C_3$ alkyl group; a pyridyl group, which pyridyl group is unsubstituted or substituted by one or more substituents selected from halogen atoms and hydroxyl groups; a tetrahydropyranyl group, which tetrahydropyranyl group is unsubstituted or substituted by one or more substituents selected from halogen atoms and hydroxyl groups; or a piperidinyl group, which piperidinyl group is unsubstituted or substituted by one or more substituents selected from a linear or branched $C_1$-$C_3$ alkyl group;
a halogen atom;
a pyridyl group, which pyridyl group is unsubstituted or substituted by one or more cyano groups;
a 1,2,4-triazolyl group; and
a —C(O)—(CH$_2$)$_n$—R" group, wherein n is 0 or 1 and R" is a cyano group, a linear or branched $C_1$-$C_6$ alkyl group, a $C_1$-$C_4$ haloalkyl group or a $C_3$-$C_7$ cycloalkyl group.

For example, $R_8$ may represent a linear or branched $C_1$-$C_6$ alkyl group; a $C_1$-$C_4$ haloalkyl group; a $C_3$-$C_7$ cycloalkyl group, which cycloalkyl group is unsubstituted or substituted by one or more hydroxyl groups; a phenyl group, which phenyl group is unsubstituted or substituted by one or more halogen atoms; a (CH$_2$)$_n$—OR group wherein n is 0 or 1 and R represents a linear or branched $C_1$-$C_3$ alkyl group; or a piperidinyl group, which piperidinyl group is unsubstituted or substituted by one or more substituents selected from
a pyridyl group, which pyridyl group is unsubstituted or substituted by one or more cyano groups; and
a —C(O)—(CH$_2$)$_n$—R" group, wherein n is 0 or 1 and R" is a cyano group, a linear or branched $C_1$-$C_6$ alkyl group, a $C_1$-$C_4$ haloalkyl group or a $C_3$-$C_7$ cycloalkyl group.

Alternatively, $R_8$ may represent a linear or branched $C_1$-$C_6$ alkyl group; a $C_1$-$C_4$ haloalkyl group; a $C_3$-$C_7$ cycloalkyl group, which cycloalkyl group is unsubstituted or substituted by one or more substituents selected from halogen atoms and hydroxyl groups; a —(CH$_2$)$_n$—OR group wherein n is 0 or 1 and R represents a linear or branched $C_1$-$C_3$ alkyl group; a tetrahydropyranyl group, which tetrahydropyranyl group is unsubstituted or substituted by one or more substituents selected from halogen atoms and hydroxyl groups; or a piperidinyl group, which piperidinyl group is unsubstituted or substituted by one or more substituents selected from
a linear or branched $C_1$-$C_3$ alkyl group;
a halogen atom;
a pyridyl group, which pyridyl group is unsubstituted or substituted by one or more cyano groups;
a 1,2,4-triazolyl group; and
a —C(O)—(CH$_2$)—R" group, wherein n is 0 or 1 and R" is a cyano group, a linear or branched $C_1$-$C_6$ alkyl group, a $C_1$-$C_4$ haloalkyl group or a $C_3$-$C_7$ cycloalkyl group.

Particularly preferred substituents on the piperidinyl group at $R_8$ are substituents selected from
a pyridyl group, which pyridyl group is unsubstituted or substituted by one or more cyano groups;
a 1,2,4-triazolyl group, and
a —C(O)—(CH$_2$)$_n$—R" group, wherein n is 0 or 1 and R" is a cyano group or a linear or branched $C_1$-$C_3$ alkyl group.

For example, preferred substituents on the piperidinyl group at $R_8$ are substituents selected from
a pyridyl group, which pyridyl group is unsubstituted or substituted by one or more cyano groups; and
a —C(O)—(CH$_2$)—R" group, wherein n is 0 or 1 and R" is a cyano group or a linear or branched $C_1$-$C_3$ alkyl group.

In one embodiment $R_8$ represents a 6-membered heterocyclyl group, e.g. a tetrahydropyranyl group or a piperidinyl group, e.g. a piperidinyl group. Preferred substituents on these groups are defined above.

In one embodiment, when $R_8$ represents a 5- to 7-membered heterocyclyl group containing one nitrogen atom, said heterocyclyl group is substituted by one or more substituents, wherein said substitution is at least on the ring nitrogen atom of the heterocyclyl group, and wherein this substituent is other than a tert-butoxycarbonyl group. Preferably, said heterocyclyl group is a piperidinyl group which is substituted by one or more substituents, wherein said substitution is at least on the ring nitrogen of the piperidinyl group, the substituents being selected from
a linear or branched $C_1$-$C_3$ alkyl group;
a halogen atom;
a pyridyl group, which pyridyl group is unsubstituted or substituted by one or more cyano groups;
a 1,2,4-triazolyl group; and
a —C(O)—(CH$_2$)$_n$—R" group, wherein n is 0 or 1 and R" is a cyano group, a linear or branched $C_1$-$C_6$ alkyl group, a $C_1$-$C_4$ haloalkyl group or a $C_3$-$C_7$ cycloalkyl group.
Preferred substituents are selected from
a pyridyl group, which pyridyl group is unsubstituted or substituted by one or more cyano groups;
a 1,2,4-triazolyl group, and
a —C(O)—(CH$_2$)$_n$—R" group, wherein n is 0 or 1 and R" is a cyano group or a linear or branched $C_1$-$C_3$ alkyl group.

Typically, in the compound of formula (I) $R_9$ represents a hydrogen atom, a halogen atom, a hydroxyl group, a cyano group or a linear or branched $C_1$-$C_6$ alkyl group; preferably $R_9$ represents a hydrogen atom, a halogen atom or a linear or branched $C_1$-$C_3$ alkyl group.

Typically, in the compounds of formula (I), m is 0, 1 or 2, preferably 0 or 1.

In a particularly preferred embodiment, the compound of the invention is of formula (I-c)

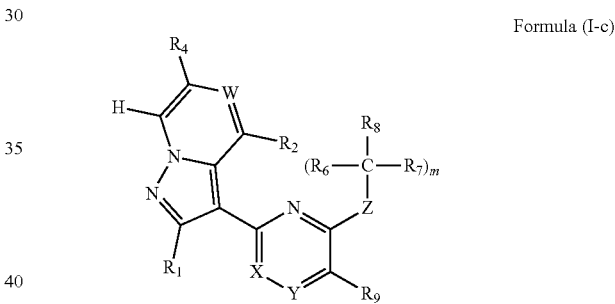

Formula (I-c)

wherein
m is 0 or an integer from 1 to 3;
Z represents an oxygen atom or a NR$_5$ group;
W represents a nitrogen atom or a —CR$_3$ group;
X and Y independently represent a nitrogen atom or a —CR$_9$ group, wherein at least one of X and Y represents a nitrogen atom, and the other represents a —CR$_9$ group;
$R_1$ represents a hydrogen atom, a halogen atom, a hydroxyl group, a cyano group, a linear or branched $C_1$-$C_6$ alkyl group, a $C_1$-$C_4$ haloalkyl group, a $C_1$-$C_4$ hydroxyalkyl group, a $C_3$-$C_{10}$ cycloalkyl group or a —NR'R" group; wherein R' and R" are the same or different and each represents a hydrogen atom, a linear or branched $C_1$-$C_6$ alkyl group, a $C_1$-$C_4$ haloalkyl group or $C_1$-$C_4$ hydroxyalkyl group;
$R_2$, $R_3$ and $R_4$ are the same or different and each represent an hydrogen atom, a halogen atom, a hydroxyl group, a cyano group, a linear or branched $C_1$-$C_6$ alkyl group, a $C_1$-$C_4$ haloalkyl group, a $C_1$-$C_4$ hydroxyalkyl group, or a $C_3$-$C_{10}$ cycloalkyl group;
$R_5$ represents a hydrogen atom, a linear or branched $C_1$-$C_6$ alkyl group unsubstituted or substituted by one or more substituents selected from a hydroxyl group, a cyano group, a $C_1$-$C_4$ haloalkyl group, a $C_1$-$C_4$ hydroxyalkyl group, a $C_3$-$C_{10}$ cycloalkyl group, a phenyl group, a piridyl group or a 6 membered, saturated N-containing heterocyclyl ring;

$R_6$ and $R_7$ are the same or different and each represent a hydrogen atom, a linear or branched $C_1$-$C_6$ alkyl group, a $C_1$-$C_4$ haloalkyl group or a $C_1$-$C_4$ hydroxyalkyl group;

$R_9$ represents a hydrogen atom, a halogen atom, a hydroxyl group, a cyano group, a linear or branched $C_1$-$C_6$ alkyl group, a $C_1$-$C_4$ haloalkyl group, a $C_1$-$C_4$ hydroxyalkyl group or a —NR'R" group; wherein R' and R" are the same or different and each represents a hydrogen atom, a linear or branched $C_1$-$C_6$ alkyl group, a $C_1$-$C_4$ haloalkyl group or $C_1$-$C_4$ hydroxyalkyl group;

$R_8$ represents a linear or branched $C_1$-$C_6$ alkyl group, a $C_1$-$C_4$ haloalkyl group, a $C_3$-$C_7$ cycloalkyl group, a phenyl group, a 5- to 6-membered monocyclic heteroaryl group containing 1, 2 or 3 heteroatoms selected from N, O and S, a 5- to 7-membered heterocyclyl group containing 1, 2 or 3 heteroatoms selected from N, O and S, or a —$(CH_2)_n$OR group wherein n is 0 or 1 and R represents a linear or branched $C_1$-$C_6$ alkyl group or a $C_1$-$C_4$ haloalkyl group;

wherein the haloalkyl, cycloalkyl, phenyl, heteroaryl and heterocyclyl groups are unsubstituted or substituted by one or more substituents selected from Ra; and the alkyl group is unsubstituted or substituted by one or more substituents selected from Rb;

Ra is a halogen atom; a cyano group; a hydroxyl group; a linear or branched $C_1$-$C_5$ alkyl group; a $C_1$-$C_4$ haloalkyl group; a $C_1$-$C_4$ alkoxy group; a $C_3$-$C_7$ cycloalkyl group unsubstituted or substituted by one or more substituents selected from substituents Re; a phenyl group unsubstituted or substituted by one or more substituents selected from substituents Re; a 5- to 6-membered monocyclic heteroaryl group containing 1, 2 or 3 heteroatoms selected from N, O and S unsubstituted or substituted by one or more substituents selected from substituents Re; a 6 membered, saturated N-containing heterocyclyl ring, unsubstituted or substituted by one or more substituents selected from substituents Re; a —C(O)OR' group or a —C(O)—$(CH_2)_n$—R" group wherein n is 0 or 1, Rb is a cyano group; a $C_1$-$C_4$ haloalkyl group; a $C_1$-$C_4$ alkoxy group; a $C_3$-$C_7$ cycloalkyl group unsubstituted or substituted by one or more substituents selected from substituents Re; a phenyl group unsubstituted or substituted by one or more substituents selected from substituents Re; a 5- to 6-membered monocyclic heteroaryl group containing 1, 2 or 3 heteroatoms selected from N, O and S unsubstituted or substituted by one or more substituents selected from substituents Re; a 6 membered, saturated N-containing heterocyclyl ring, unsubstituted or substituted by one or more substituents selected from substituents Re; a —C(O)OR' group or a —C(O)—$(CH_2)_n$—R" group wherein n is 0 or 1;

Re is a halogen atom, a hydroxyl group, a cyano group, a linear or branched $C_1$-$C_6$ alkyl group or a $C_1$-$C_4$ haloalkyl group;

R' is a hydrogen atom, a linear or branched $C_1$-$C_6$ alkyl group, a $C_1$-$C_4$ haloalkyl group, a $C_3$-$C_7$ cycloalkyl group, a phenyl group, a 5- to 6-membered monocyclic heteroaryl group containing 1, 2 or 3 heteroatoms selected from N, O and S or a 5- to 6-membered, saturated N-containing heterocyclyl ring; and R" is a cyano group, a linear or branched $C_1$-$C_6$ alkyl group, a $C_1$-$C_4$ haloalkyl group, a $C_3$-$C_7$ cycloalkyl group, a phenyl group, a 5- to 6-membered monocyclic heteroaryl group containing 1, 2 or 3 heteroatoms selected from N, O and S or a 5- to 6-membered, saturated N-containing heterocyclyl ring; wherein the cycloalkyl, phenyl, heteroaryl and heterocyclyl groups are unsubstituted or substituted by one or more substituents selected from a hydroxyl group, a cyano group, a linear or branched $C_1$-$C_6$ alkyl group or a $C_1$-$C_4$ haloalkyl group.

In the compounds of formula (I-c), when Y is N and $R_8$ represents a 5- to 7-membered heterocyclyl group containing one nitrogen atom, said heterocyclyl group is typically substituted by one or more substituents, wherein said substitution is at least on the ring nitrogen of the heterocyclyl group, and this substituent on the ring nitrogen of the heterocyclyl group is typically other than a tert-butoxycarbonyl group.

Preferred substituents for the compounds of formula (I-c) are defined above with regard to formula (I) and are further described in more detail below.

Typically, in the compound of formula (I-c), X and Y independently represent a nitrogen atom or a —$CR_9$ group, wherein at least one of X and Y represents a nitrogen atom, and the other represents a —$CR_9$ group. Typically, when X represents a nitrogen atom, Y represents a —$CR_9$ group. Typically, when X represents a —$CR_9$ group, Y represents a nitrogen atom.

Typically, in the compound of the invention of formula (I-c), Z is a $NR_5$ group, wherein $R_5$ represents a hydrogen atom or a linear or branched $C_1$-$C_6$ alkyl group unsubstituted or substituted by one or more substituents selected from a hydroxyl group, a cyano group, a $C_1$-$C_4$ haloalkyl group, a $C_1$-$C_4$ hydroxyalkyl group, a $C_3$-$C_{10}$ cycloalkyl group, a phenyl group, a piridyl group or a 6 membered, saturated N-containing heterocyclyl ring.

Typically, in the compound of the invention of formula (I-c) $R_1$ represents a hydrogen atom, a halogen atom, a cyano group, a linear or branched $C_1$-$C_6$ alkyl group, a $C_3$-$C_7$ cycloalkyl group or a —NR'R" group, wherein R' and R" are the same or different and each represents a hydrogen atom, a linear or branched $C_1$-$C_6$ alkyl group or a $C_1$-$C_4$ haloalkyl group; preferably $R_1$ represents a hydrogen atom, a linear or branched $C_1$-$C_3$ alkyl group or a —$NH_2$ group; more preferably $R_1$ represents a hydrogen atom.

Typically, in the compound of the invention of formula (I-c) $R_2$ represents a hydrogen atom, a halogen atom, a cyano group, a linear or branched $C_1$-$C_6$ alkyl group or a $C_3$-$C_7$ cycloalkyl group; preferably $R_2$ represents a hydrogen atom or a linear or branched $C_1$-$C_3$ alkyl group; more preferably $R_2$ represents a hydrogen atom.

Typically, in the compound of the invention of formula (I-c) $R_3$ represents a hydrogen atom, a halogen atom, a cyano group, a linear or branched $C_1$-$C_6$ alkyl group or a $C_3$-$C_7$ cycloalkyl group; preferably $R_3$ represents a hydrogen atom, a cyano group or a linear or branched $C_1$-$C_3$ alkyl group; more preferably $R_3$ represents a hydrogen atom or a cyano group.

Typically, in the compound of the invention of formula (I-c) $R_4$ represents a hydrogen atom, a halogen atom, a cyano group, a linear or branched $C_1$-$C_6$ alkyl group or a $C_3$-$C_7$ cycloalkyl group; preferably $R_4$ represents a hydrogen atom or a linear or branched $C_1$-$C_3$ alkyl group; more preferably $R_4$ represents a hydrogen atom.

Typically, in the compound of the invention of formula (I-c) $R_5$ represents a hydrogen atom or a linear or branched $C_1$-$C_4$ alkyl group unsubstituted or substituted by one or more substituents selected from a hydroxyl group, a $C_1$-$C_4$ haloalkyl group, a $C_1$-$C_4$ hydroxyalkyl group or a $C_3$-$C_7$ cycloalkyl group; preferably $R_5$ represents a hydrogen atom or a linear or branched $C_1$-$C_3$ alkyl group; more preferably $R_5$ represents a hydrogen atom.

Typically, in the compound of the invention of formula (I-c) $R_6$ and $R_7$ independently represent a hydrogen atom or a linear or branched $C_1$-$C_6$ alkyl group; preferably $R_6$ and $R_7$ independently represent a hydrogen atom or a linear or branched $C_1$-$C_3$ alkyl group.

Typically, in the compound of the invention of formula (I-c) $R_8$ represents a linear or branched $C_1$-$C_6$ alkyl group, a $C_1$-$C_4$ haloalkyl group, a $C_3$-$C_7$ cycloalkyl group, a phenyl group, a 5- to 6-membered monocyclic heteroaryl group containing 1, 2 or 3 heteroatoms selected from N, O and S, a 5- to 7-membered heterocyclyl group containing 1, 2 or 3 heteroatoms selected from N, O and S, or a —$(CH_2)_n$OR group wherein n is 0 or 1 and R represents a linear or branched $C_1$-$C_6$ alkyl group or a $C_1$-$C_4$ haloalkyl group;

wherein the haloalkyl, cycloalkyl, phenyl, heteroaryl and heterocyclyl groups are unsubstituted or substituted by one or more substituents selected from Ra; and the alkyl group is unsubstituted or substituted by one or more substituents selected from Rb;

Ra is a halogen atom; a cyano group; a hydroxyl group; a linear or branched $C_1$-$C_6$ alkyl group; a $C_1$-$C_4$ haloalkyl group; a $C_1$-$C_4$ alkoxy group; a $C_3$-$C_7$ cycloalkyl group unsubstituted or substituted by one or more substituents selected from substituents Re; a phenyl group unsubstituted or substituted by one or more substituents selected from substituents Re; a 5- to 6-membered monocyclic heteroaryl group containing 1, 2 or 3 heteroatoms selected from N, O and S unsubstituted or substituted by one or more substituents selected from substituents Re; a 6 membered, saturated N-containing heterocyclyl ring, unsubstituted or substituted by one or more substituents selected from substituents Re; a —C(O)OR' group or a —C(O)—$(CH_2)_n$—R" group wherein n is 0 or Rb is a cyano group; a $C_1$-$C_4$ haloalkyl group; a $C_1$-$C_4$ alkoxy group; a $C_3$-$C_7$ cycloalkyl group unsubstituted or substituted by one or more substituents selected from substituents Re; a phenyl group unsubstituted or substituted by one or more substituents selected from substituents Re; a 5- to 6-membered monocyclic heteroaryl group containing 1, 2 or 3 heteroatoms selected from N, O and S unsubstituted or substituted by one or more substituents selected from substituents Re; a 6 membered, saturated N-containing heterocyclyl ring, unsubstituted or substituted by one or more substituents selected from substituents Re; a —C(O)OR' group or a —C(O)—$(CH_2)_n$—R" group wherein n is 0 or 1;

Re is a halogen atom, a hydroxyl group, a cyano group, a linear or branched $C_1$-$C_6$ alkyl group or a $C_1$-$C_4$ haloalkyl group;

R' is a hydrogen atom, a linear or branched $C_1$-$C_6$ alkyl group, a $C_1$-$C_4$ haloalkyl group, a $C_3$-$C_7$ cycloalkyl group, a phenyl group, a 5- to 6-membered monocyclic heteroaryl group containing 1, 2 or 3 heteroatoms selected from N, O and S or a 5- to 6-membered, saturated N-containing heterocyclyl ring; and R" is a cyano group, a linear or branched $C_1$-$C_6$ alkyl group, a $C_1$-$C_4$ haloalkyl group, a $C_3$-$C_7$ cycloalkyl group, a phenyl group, a 5- to 6-membered monocyclic heteroaryl group containing 1, 2 or 3 heteroatoms selected from N, O and S or a 5- to 6-membered, saturated N-containing heterocyclyl ring; wherein the cycloalkyl, phenyl, heteroaryl and heterocyclyl groups are unsubstituted or substituted by one or more substituents selected from a hydroxyl group, a cyano group, a linear or branched $C_1$-$C_6$ alkyl group or a $C_1$-$C_4$ haloalkyl group.

When $R_8$ represents a 5- to 7-membered heterocyclyl group containing one nitrogen atom, said heterocyclyl group is typically substituted by one or more substituents, wherein said substitution is at least on the ring nitrogen of the heterocyclyl group, and this substituent on the ring nitrogen of the heterocyclyl group is typically other than a tert-butoxycarbonyl group.

Preferably, in the compound of the invention of formula (I-c) $R_8$ represents a linear or branched $C_1$-$C_6$ alkyl group, a $C_1$-$C_4$ haloalkyl group, a $C_3$-$C_7$ cycloalkyl group, a phenyl group, a 5- to 6-membered monocyclic heteroaryl group containing 1, 2 or 3 heteroatoms selected form N, O and S, a 5- to 7-membered heterocyclyl group containing 1, 2 or 3 heteroatoms selected from N, O and S, or a —$(CH_2)_n$OR group wherein n is 0 or 1 and R represents a linear or branched $C_1$-$C_6$ alkyl group or a $C_1$-$C_4$ haloalkyl group;

wherein the haloalkyl, cycloalkyl, phenyl, heteroaryl and heterocyclyl groups are unsubstituted or substituted by one or more substituents selected from Ra; and the alkyl group is unsubstituted or substituted by one or more substituents selected from Rb;

Ra is a halogen atom; a cyano group; a hydroxyl group; a linear or branched $C_1$-$C_6$ alkyl group; a $C_1$-$C_4$ haloalkyl group; a 5- to 6-membered monocyclic heteroaryl group containing 1, 2 or 3 heteroatoms selected from N, O and S unsubstituted or substituted by one or more substituents selected from a halogen atom, a hydroxyl group, a cyano group, a linear or branched $C_1$-$C_6$ alkyl group or a $C_1$-$C_4$ haloalkyl group; a —C(O)OR' group or a —C(O)—$(CH_2)_n$—R" group wherein n is 0 or 1, Rb is a cyano group; a $C_1$-$C_4$ haloalkyl group; a $C_1$-$C_4$ alkoxy group; a $C_3$-$C_7$ cycloalkyl group unsubstituted or substituted by one or more substituents selected from a halogen atom, a hydroxyl group or a cyano group; a phenyl group unsubstituted or substituted by one or more substituents selected from a halogen atom, a hydroxyl group, a cyano group or a linear or branched $C_1$-$C_6$ alkyl group; a —C(O)OR' group or a —C(O)—$(CH_2)_n$—R" group wherein n is 0 or 1, R' is a hydrogen atom, a linear or branched $C_1$-$C_6$ alkyl group, a $C_1$-$C_4$ haloalkyl group or a $C_3$-$C_7$ cycloalkyl group; and R" is a cyano group, a linear or branched $C_1$-$C_6$ alkyl group, a $C_1$-$C_4$ haloalkyl group or a $C_3$-$C_7$ cycloalkyl group.

In one embodiment, in the compounds of formula (I-c) $R_8$ represents a linear or branched $C_1$-$C_6$ alkyl group, a $C_1$-$C_4$ haloalkyl group, a $C_3$-$C_7$ cycloalkyl group, a 6-membered heterocyclyl group containing 1, 2 or 3 heteroatoms selected from N, O and S, or a —$(CH_2)_n$OR group wherein n is 0 or 1 and R represents a linear or branched $C_1$-$C_6$ alkyl group or a $C_1$-$C_4$ haloalkyl group; in particular, $R_8$ may represent a 6-membered heterocyclyl group containing 1, 2 or 3 heteroatoms selected from N, O and S;

wherein the haloalkyl, cycloalkyl and heterocyclyl groups are unsubstituted or substituted by one or more substituents selected from Ra; and the alkyl group is unsubstituted or substituted by one or more substituents selected from Rb, wherein Ra and Rb are as defined above.

More preferably, in the compound of the invention of formula (I-c) when $R_8$ is an alkyl or haloalkyl group, it is an unsubstituted alkyl or haloalkyl group; when $R_8$ is a cycloalkyl, phenyl or pyridyl group, it is unsubstituted or substituted by one or more substituents selected from a halogen atom, a cyano group, a hydroxyl group, a linear or branched $C_1$-$C_6$ alkyl group, a $C_1$-$C_4$ haloalkyl group, a —C(O)OR' group or a —C(O)—$(CH_2)$—R" group wherein n is 0 or 1, R' is a hydrogen atom, a linear or branched $C_1$-$C_3$ alkyl group or a $C_1$-$C_3$ haloalkyl group and R" is a cyano group, a linear or branched $C_1$-$C_3$ alkyl group or a $C_1$-$C_3$ haloalkyl group; and when $R_8$ is a heteroaryl or heterocyclyl group it is unsubstituted or substituted with one or more substituents selected from Ra, wherein Ra is as defined above.

In the compounds of formula (I-c) when $R_8$ is a heteroaryl group, it is preferably a 5- to 6-membered heteroaryl group containing one or two nitrogen atoms. Pyridyl is preferred. Preferably, when $R_8$ is a heteroaryl group it is unsubstituted or substituted with one or more halogen atoms.

In the compound of formula (I-c) when $R_8$ is a heterocyclyl group it is preferably a 5- or 6-membered heterocyclyl group, e.g. a 6-membered heterocyclyl group, containing one or two heteroatoms selected from N and O, more preferably containing one or two nitrogen atoms. Tetrahydropyranyl and piperidinyl groups are preferred. Piperidinyl is more preferred. Preferably, the heterocyclyl group is linked to the rest of the molecule via a ring carbon atom, in other words it is linked to the group $-Z-(CR_6R_7)_m-$ via a ring carbon atom. Substituents on a piperidinyl group are typically at least present on the nitrogen atom and may optionally be present on any other ring atom.

Most preferably, in the compound of the invention of formula (I-c) $R_8$ represents a linear or branched $C_1$-$C_6$ alkyl group; a $C_1$-$C_4$ haloalkyl group; a $C_3$-$C_7$ cycloalkyl group, which cycloalkyl group is unsubstituted or substituted by one or more substituents selected from halogen atoms and hydroxyl groups; a phenyl group, which phenyl group is unsubstituted or substituted by one or more halogen atoms; a $-(CH_2)-OR$ group wherein n is 0 or 1 and R represents a linear or branched $C_1$-$C_3$ alkyl group; a pyridyl group, which pyridyl group is unsubstituted or substituted by one or more substituents selected from halogen atoms and hydroxyl groups; a tetrahydropyranyl group, which tetrahydropyranyl group is unsubstituted or substituted by one or more substituents selected from halogen atoms and hydroxyl groups; or a piperidinyl group, which piperidinyl group is unsubstituted or substituted by one or more substituents selected from
- a linear or branched $C_1$-$C_3$ alkyl group;
- a halogen atom;
- a pyridyl group, which pyridyl group is unsubstituted or substituted by one or more cyano groups;
- a 1,2,4-triazolyl group; and
- a $-C(O)-(CH_2)_n-R''$ group, wherein n is 0 or 1 and R'' is a cyano group, a linear or branched $C_1$-$C_6$ alkyl group, a $C_1$-$C_4$ haloalkyl group or a $C_3$-$C_7$ cycloalkyl group.

In another embodiment, in the compound of the invention of formula (I-c) $R_8$ represents a linear or branched $C_1$-$C_6$ alkyl group, a $C_1$-$C_4$ haloalkyl group, a $C_3$-$C_7$ cycloalkyl group, a phenyl group, a 5- to 6-membered monocyclic heteroaryl group containing 1, 2 or 3 heteroatoms selected from N, O and S, a 5- to 7-membered heterocyclyl group containing 1, 2 or 3 heteroatoms selected from N, O and S, or a $-(CH_2)_nOR$ group wherein n is 0 or 1 and R represents a linear or branched $C_1$-$C_6$ alkyl group or a $C_1$-$C_4$ haloalkyl group;
wherein the haloalkyl, cycloalkyl, phenyl, and heterocyclyl groups are unsubstituted or substituted by one or more substituents selected from Ra; and the alkyl group is unsubstituted or substituted by one or more substituents selected from Rb, wherein Ra and Rb, are as defined above.

Alternatively, $R_8$ may represent a linear or branched $C_1$-$C_6$ alkyl group; a $C_1$-$C_4$ haloalkyl group; a $C_3$-$C_7$ cycloalkyl group, which cycloalkyl group is unsubstituted or substituted by one or more substituents selected from halogen atoms and hydroxyl groups; a $-(CH_2)_n-OR$ group wherein n is 0 or 1 and R represents a linear or branched $C_1$-$C_3$ alkyl group; a tetrahydropyranyl group, which tetrahydropyranyl group is unsubstituted or substituted by one or more substituents selected from halogen atoms and hydroxyl groups; or a piperidinyl group, which piperidinyl group is unsubstituted or substituted by one or more substituents selected from
- a linear or branched $C_1$-$C_3$ alkyl group;
- a halogen atom;
- a pyridyl group, which pyridyl group is unsubstituted or substituted by one or more cyano groups;
- a 1,2,4-triazolyl group; and
- a $-C(O)-(CH_2)-R''$ group, wherein n is 0 or 1 and R'' is a cyano group, a linear or branched $C_1$-$C_6$ alkyl group, a $C_1$-$C_4$ haloalkyl group or a $C_3$-$C_7$ cycloalkyl group.

Particularly preferred substituents on the ring nitrogen of the piperidinyl group at $R_8$ in the compound of the invention of formula (I-c) are substituents selected from
- a pyridyl group, which pyridyl group is unsubstituted or substituted by one or more cyano groups;
- a 1,2,4-triazolyl group; and
- a $-C(O)-(CH_2)_n-R''$ group, wherein n is 0 or 1 and R'' is a cyano group or a linear or branched $C_1$-$C_3$ alkyl group.

In one embodiment $R_8$ represents a 6-membered heterocyclyl group, e.g. a tetrahydropyranyl group or a piperidinyl group, e.g. a piperidinyl group. Preferred substituents on these groups are defined above.

In one embodiment, when $R_8$ of formula (Ic) represents a 5- to 7-membered heterocyclyl group containing one nitrogen atom, said heterocyclyl group is substituted by one or more substituents, wherein said substitution is at least on the ring nitrogen atom of the heterocyclyl group, and wherein this substituent is other than a tert-butoxycarbonyl group. Preferably, said heterocyclyl group is a piperidinyl group which is substituted by one or more substituents, wherein said substitution is at least on the ring nitrogen of the piperidinyl group, the substituents being selected from
- a linear or branched $C_1$-$C_3$ alkyl group;
- a halogen atom;
- a pyridyl group, which pyridyl group is unsubstituted or substituted by one or more cyano groups;
- a 1,2,4-triazolyl group; and
- a $-C(O)-(CH_2),-R''$ group, wherein n is 0 or 1 and R'' is a cyano group, a linear or branched $C_1$-$C_6$ alkyl group, a $C_1$-$C_4$ haloalkyl group or a $C_3$-$C_7$ cycloalkyl group. Preferred substituents are selected from:
- a pyridyl group, which pyridyl group is unsubstituted or substituted by one or more cyano groups;
- a 1,2,4-triazolyl group; and
- a $-C(O)-(CH_2)_n-R''$ group, wherein n is 0 or 1 and R'' is a cyano group or a linear or branched $C_1$-$C_3$ alkyl group.

Typically, in the compound of the invention of formula (I-c) $R_9$ represents a hydrogen atom, a halogen atom, a hydroxyl group, a cyano group, a linear or branched $C_1$-$C_6$ alkyl group or a $-NR'R''$ group, wherein R' and R'' are the same or different and each represents a hydrogen atom, a linear or branched $C_1$-$C_6$ alkyl group or a $C_1$-$C_4$ haloalkyl group; preferably $R_9$ represents a hydrogen atom, a halogen atom, a linear or branched $C_1$-$C_3$ alkyl group or a $-NH_2$ group.

Typically, in the compound of formula (I-c), m is 0, 1 or 2, preferably 0 or 1.

In a further particular preferred embodiment, in the compound of formula (I-c):
m is 0, 1 or 2;
W represents a nitrogen atom or a $-CR_3$ group, preferably a $-CR_3$ group;
X and Y independently represent a nitrogen atom or a $-CR_9$ group, wherein at least one of X and Y represents a nitrogen atom, and the other represents a $-CR_9$ group;
$R_1$ represents a hydrogen atom or a $-NH_2$ group;
$R_2$ represents a hydrogen atom or a linear or branched $C_1$-$C_3$ alkyl group;

$R_3$ represents a hydrogen atom, a cyano group or a linear or branched $C_1$-$C_3$ alkyl group;

$R_4$ represents a hydrogen atom or a linear or branched $C_1$-$C_3$ alkyl group;

$R_5$ represents a hydrogen atom or a linear or branched $C_1$-$C_3$ alkyl group;

$R_6$ and $R_7$ independently represent a hydrogen atom or a linear or branched $C_1$-$C_3$ alkyl group, $R_8$ represents a linear or branched $C_1$-$C_6$ alkyl group; a $C_1$-$C_4$ haloalkyl group; a $C_3$-$C_7$ cycloalkyl group, which cycloalkyl group is unsubstituted or substituted by one or more substituents selected from halogen atoms and hydroxyl groups; a phenyl group, which phenyl group is unsubstituted or substituted by one or more halogen atoms; a —$(CH_2)_n$—OR group wherein n is 0 or 1 and R represents a linear or branched $C_1$-$C_3$ alkyl group; a pyridyl group, which pyridyl group is unsubstituted or substituted by one or more substituents selected from halogen atoms and hydroxyl groups; a tetrahydropyranyl group, which tetrahydropyranyl group is unsubstituted or substituted by one or more substituents selected from halogen atoms and hydroxyl groups; and a piperidinyl group, which piperidinyl group is unsubstituted or substituted by one or more substituents selected from
- a linear or branched $C_1$-$C_3$ alkyl group;
- a halogen atom;
- a pyridyl group, which pyridyl group is unsubstituted or substituted by one or more cyano groups; and
- a —C(O)—$(CH_2)_n$—R" group, wherein n is 0 or 1 and R" is a cyano group, a linear or branched $C_1$-$C_6$ alkyl group, a $C_1$-$C_4$ haloalkyl group or a $C_3$-$C_7$ cycloalkyl group; and $R_9$ represents a hydrogen atom, a halogen atom, a linear or branched $C_1$-$C_3$ alkyl group or a —$NH_2$ group.

In another preferred embodiment, in the compound of formula (I-c):

m is 0, 1 or 2;

W represents a nitrogen atom or a —$CR_3$ group, preferably a —$CR_3$ group;

Z represents a $NR_5$ group;

X and Y independently represent a nitrogen atom or a —$CR_9$ group, wherein at least one of X and Y represents a nitrogen atom, and the other represents a —$CR_9$ group;

$R_1$ represents a hydrogen atom or a —$NH_2$ group;

$R_2$ represents a hydrogen atom or a linear or branched $C_1$-$C_3$ alkyl group;

$R_3$ represents a hydrogen atom, a cyano group or a linear or branched $C_1$-$C_3$ alkyl group;

$R_4$ represents a hydrogen atom or a linear or branched $C_1$-$C_3$ alkyl group;

$R_5$ represents a hydrogen atom or a linear or branched $C_1$-$C_3$ alkyl group;

$R_6$ and $R_7$ independently represent a hydrogen atom or a linear or branched $C_1$-$C_3$ alkyl group, $R_8$ represents a linear or branched $C_1$-$C_6$ alkyl group; a $C_1$-$C_4$ haloalkyl group; a $C_3$-$C_7$ cycloalkyl group, which cycloalkyl group is unsubstituted or substituted by one or more substituents selected from halogen atoms and hydroxyl groups; a phenyl group, which phenyl group is unsubstituted or substituted by one or more halogen atoms; a —$(CH_2)_n$—OR group wherein n is 0 or 1 and R represents a linear or branched $C_1$-$C_3$ alkyl group; a pyridyl group, which pyridyl group is unsubstituted or substituted by one or more substituents selected from halogen atoms and hydroxyl groups; a tetrahydropyranyl group, which tetrahydropyranyl group is unsubstituted or substituted by one or more substituents selected from halogen atoms and hydroxyl groups; and a piperidinyl group, which piperidinyl group is unsubstituted or substituted by one or more substituents selected from
- a linear or branched $C_1$-$C_3$ alkyl group;
- a halogen atom;
- a pyridyl group, which pyridyl group is unsubstituted or substituted by one or more cyano groups;
- a 1,2,4-triazolyl group; and
- a —C(O)—$(CH_2)_n$—R" group, wherein n is 0 or 1 and R" is a cyano group, a linear or branched $C_1$-$C_6$ alkyl group, a $C_1$-$C_4$ haloalkyl group or a $C_3$-$C_7$ cycloalkyl group; and $R_9$ represents a hydrogen atom, a halogen atom, a linear or branched $C_1$-$C_3$ alkyl group or a —$NH_2$ group.

Typically, when $R_8$ is a piperidinyl group, it is substituted by one or more substituents, wherein said substitution is at least on the ring nitrogen of the piperidinyl group, the substituents being selected from
- a linear or branched $C_1$-$C_3$ alkyl group;
- a halogen atom;
- a pyridyl group, which pyridyl group is unsubstituted or substituted by one or more cyano groups;
- a 1,2,4-triazolyl group; and
- a —C(O)—$(CH_2)_n$—R" group, wherein n is 0 or 1 and R" is a cyano group, a linear or branched $C_1$-$C_6$ alkyl group, a $C_1$-$C_4$ haloalkyl group or a $C_3$-$C_7$ cycloalkyl group More typically, said substituents are selected from
- a linear or branched $C_1$-$C_3$ alkyl group;
- a halogen atom;
- a pyridyl group, which pyridyl group is unsubstituted or substituted by one or more cyano groups; and
- a —C(O)—$(CH_2)_n$—R" group, wherein n is 0 or 1 and R" is a cyano group, a linear or branched $C_1$-$C_6$ alkyl group, a $C_1$-$C_4$ haloalkyl group or a $C_3$-$C_7$ cycloalkyl group.

In a particularly preferred embodiment, in the compound of formula (I)

m is 0, 1 or 2;

W represents a nitrogen atom or a —$CR_3$ group, preferably a —$CR_3$ group;

Z represents a $NR_5$ group;

X and Y independently represent a nitrogen atom or a —$CR_9$ group, wherein when one of X and Y represents a nitrogen atom, the other represents a —$CR_9$ group;

T represents a —$CR_9$ group;

$R_1$ represents a hydrogen atom or a —$NH_2$ group;

$R_2$ represents a hydrogen atom or a linear or branched $C_1$-$C_3$ alkyl group;

$R_3$ represents a hydrogen atom, a cyano group or a linear or branched $C_1$-$C_3$ alkyl group;

$R_4$ represents a hydrogen atom or a linear or branched $C_1$-$C_3$ alkyl group;

$R_5$ represents a hydrogen atom or a linear or branched $C_1$-$C_3$ alkyl group;

$R_6$ and $R_7$ independently represent a hydrogen atom or a linear or branched $C_1$-$C_3$ alkyl group, $R_8$ represents a linear or branched $C_1$-$C_6$ alkyl group; a $C_1$-$C_4$ haloalkyl group; a $C_3$-$C_7$ cycloalkyl group, which cycloalkyl group is unsubstituted or substituted by one or more hydroxyl groups; a phenyl group, which phenyl group is unsubstituted or substituted by one or more halogen atoms; a —$(CH_2)_n$—OR group wherein n is 0 or 1 and R represents a linear or branched $C_1$-$C_3$ alkyl group; and a piperidinyl group, which piperidinyl group is unsubstituted or substituted by one or more substituents selected from
- a pyridyl group, which pyridyl group is unsubstituted or substituted by one or more cyano groups; and
- a —C(O)—$(CH_2)_n$—R" group, wherein n is 0 or 1 and R" is a cyano group, a linear or branched $C_1$-$C_6$ alkyl group, a $C_1$-$C_4$ haloalkyl group or a $C_3$-$C_7$ cycloalkyl group; and $R_9$ represents a hydrogen atom, a halogen atom or a linear or branched $C_1$-$C_3$ alkyl group.

In a further particularly preferred embodiment, the compound is of formula (I-a)

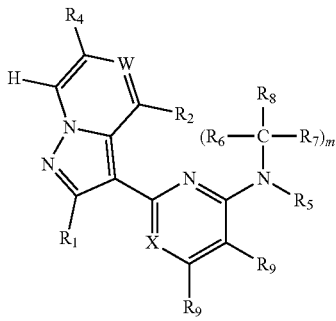

Formula (I-a)

wherein
m is 0, 1 or 2;
W represents a nitrogen atom or a —CR$_3$ group, preferably a —CR$_3$ group;
X represents a nitrogen atom or a —CR$_9$ group;
R$_1$ represents a hydrogen atom or a —NH$_2$ group;
R$_2$ represents a hydrogen atom or a linear or branched C$_1$-C$_3$ alkyl group;
R$_3$ represents a hydrogen atom, a cyano group or a linear or branched C$_1$-C$_3$ alkyl group;
R$_4$ represents a hydrogen atom or a linear or branched C$_1$-C$_3$ alkyl group;
R$_5$ represents a hydrogen atom or a linear or branched C$_1$-C$_3$ alkyl group;
R$_6$ and R$_7$ independently represent a hydrogen atom or a linear or branched C$_1$-C$_3$ alkyl group,
R$_8$ represents a linear or branched C$_1$-C$_6$ alkyl group; a C$_1$-C$_4$ haloalkyl group; a C$_3$-C$_7$ cycloalkyl group, which cycloalkyl group is unsubstituted or substituted by one or more hydroxyl groups; a phenyl group, which phenyl group is unsubstituted or substituted by one or more halogen atoms; a (CH$_2$)$_n$—OR group wherein n is 0 or 1 and R represents a linear or branched C$_1$-C$_3$ alkyl group; and a piperidinyl group, which piperidinyl group is unsubstituted or substituted by one or more substituents selected from
  a pyridyl group, which pyridyl group is unsubstituted or substituted by one or more cyano groups; and
  a —C(O)—(CH$_2$)$_n$—R" group, wherein n is 0 or 1 and R" is a cyano group, a linear or branched C$_1$-C$_6$ alkyl group, a C$_1$-C$_4$ haloalkyl group or a C$_3$-C$_7$ cycloalkyl group; and
R$_9$ represents a hydrogen atom, a halogen atom or a linear or branched C$_1$-C$_3$ alkyl group.

In a further particular preferred embodiment, in the compound of formula (I-a):
m is 0 or 1;
W represents a nitrogen atom or a —CR$_3$ group, preferably a —CR$_3$ group;
X represents a nitrogen atom or a —CR$_9$ group;
R$_1$ represents a hydrogen atom;
R$_2$ represents a hydrogen atom;
R$_3$ represents a hydrogen atom or a cyano group;
R$_4$ represents a hydrogen atom;
R$_5$ represents a hydrogen atom or a linear or branched C$_1$-C$_3$ alkyl group;
R$_6$ and R$_7$ independently represent a hydrogen atom or a linear or branched C$_1$-C$_3$ alkyl group;
R$_8$ represents a linear or branched C$_1$-C$_6$ alkyl group; a C$_1$-C$_4$ haloalkyl group; a C$_3$-C$_7$ cycloalkyl group, which cycloalkyl group is unsubstituted or substituted by one or more hydroxyl groups; a phenyl group, which phenyl group is unsubstituted or substituted by one or more halogen atoms; a (CH$_2$)$_n$—OR group wherein n is 0 or 1 and R represents a linear or branched C$_1$-C$_3$ alkyl group; and a piperidinyl group, which piperidinyl group is unsubstituted or substituted by one or more substituents selected from
  a pyridyl group, which pyridyl group is unsubstituted or substituted by one or more cyano groups; and
  a —C(O)—(CH$_2$)$_n$—R" group, wherein n is 0 or 1 and R" is a cyano group, a linear or branched C$_1$-C$_3$ alkyl group, or a C$_1$-C$_4$ haloalkyl group; and
R$_9$ represents a hydrogen atom, a halogen atom or a linear or branched C$_1$-C$_3$ alkyl group.

In an alternative particularly preferred embodiment, the compound is of formula (I-b):

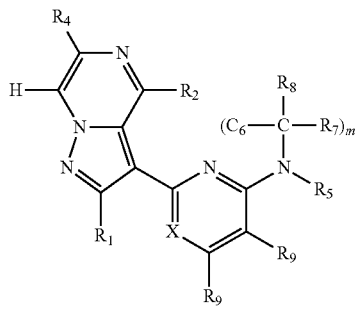

Formula (I-b)

wherein
m is 0, 1 or 2;
X represents a nitrogen atom or a —CR$_9$ group;
R$_1$ represents a hydrogen atom or a —NH$_2$ group;
R$_2$ represents a hydrogen atom or a linear or branched C$_1$-C$_3$ alkyl group;
R$_4$ represents a hydrogen atom or a linear or branched C$_1$-C$_3$ alkyl group;
R$_5$ represents a hydrogen atom or a linear or branched C$_1$-C$_3$ alkyl group;
R$_6$ and R$_7$ independently represent a hydrogen atom or a linear or branched C$_1$-C$_3$ alkyl group,
R$_8$ represents a linear or branched C$_1$-C$_6$ alkyl group; a C$_1$-C$_4$ haloalkyl group; a C$_3$-C$_7$ cycloalkyl group, which cycloalkyl group is unsubstituted or substituted by one or more hydroxyl groups; a phenyl group, which phenyl group is unsubstituted or substituted by one or more halogen atoms; a (CH$_2$)$_n$—OR group wherein n is 0 or 1 and R represents a linear or branched C$_1$-C$_3$ alkyl group; and a piperidinyl group, which piperidinyl group is unsubstituted or substituted by one or more substituents selected from
  a pyridyl group, which pyridyl group is unsubstituted or substituted by one or more cyano groups; and
  a —C(O)—(CH$_2$), —R" group, wherein n is 0 or 1 and R" is a cyano group, a linear or branched C$_1$-C$_6$ alkyl group, a C$_1$-C$_4$ haloalkyl group or a C$_3$-C$_7$ cycloalkyl group; and
R$_9$ represents a hydrogen atom, a halogen atom or a linear or branched C$_1$-C$_3$ alkyl group.

In a further particular preferred embodiment, in the compound of formula (I-b):
m is 0 or 1;
X represents a nitrogen atom;
R$_1$ represents a hydrogen atom;
R$_2$ represents a hydrogen atom;

R$_4$ represents a hydrogen atom or a linear or branched C$_1$-C$_3$ alkyl group;

R$_5$ represents a hydrogen atom or a linear or branched C$_1$-C$_3$ alkyl group;

R$_6$ and R$_7$ independently represent a hydrogen atom or a linear or branched C$_1$-C$_3$ alkyl group, R$_8$ represents a linear or branched C$_1$-C$_6$ alkyl group; a C$_3$-C$_7$ cycloalkyl group, which cycloalkyl group is unsubstituted or substituted by one or more hydroxyl groups; a phenyl group, which phenyl group is unsubstituted or substituted by one or more halogen atoms; and a piperidinyl group, which piperidinyl group is unsubstituted or substituted by one or more substituents selected from
- a pyridyl group, which pyridyl group is unsubstituted or substituted by one or more cyano groups; and
- a —C(O)—(CH$_2$)$_n$—R" group, wherein n is 0 or 1 and R" is a cyano group, a linear or branched C$_1$-C$_3$ alkyl group or a C$_1$-C$_3$ haloalkyl group; and R$_9$ represents a hydrogen atom, a halogen atom or a linear or branched C$_1$-C$_3$ alkyl group.

Particular individual compounds of the invention include:
3-(4-{[(1S)-1-Phenylethyl]amino}pyrimidin-2-yl)pyrazolo[1,5-a]pyridine-5-carbonitrile;
3-{4-[(Cyclohexylmethyl)amino]pyrimidin-2-yl}pyrazolo[1,5-a]pyridine-5-carbonitrile;
3-[4-(Benzylamino)pyrimidin-2-yl]pyrazolo[1,5-a]pyridine-5-carbonitrile;
3-{4-[(2,2-Dimethylpropyl)amino]pyrimidin-2-yl}pyrazolo[1,5-a]pyridine-5-carbonitrile;
3-(4-{[(1S)-2-Methoxy-1-methylethyl]amino}pyrimidin-2-yl)pyrazolo[1,5-a]pyridine-5-carbonitrile;
3-{4-[(Cyclopropylmethyl)amino]pyrimidin-2-yl}pyrazolo[1,5-a]pyridine-5-carbonitrile;
3-{4-[(2,2,2-Trifluoroethyl)amino]pyrimidin-2-yl}pyrazolo[1,5-a]pyridine-5-carbonitrile;
N-(1-Phenylethyl)-2-pyrazolo[1,5-a]pyridin-3-ylpyrimidin-4-amine;
3-{6-[(Cyclohexylmethyl)amino]pyridin-2-yl}pyrazolo[1,5-a]pyridine-5-carbonitrile;
3-{6-[(2,2-Dimethylpropyl)amino]pyridin-2-yl}pyrazolo[1,5-a]pyridine-5-carbonitrile;
3-{6-[(3-Fluorobenzyl)amino]pyridin-2-yl}pyrazolo[1,5-a]pyridine-5-carbonitrile;
3-[6-(Benzylamino)pyridin-2-yl]pyrazolo[1,5-a]pyridine-5-carbonitrile;
3-(6-{[(1S)-1-Phenylethyl]amino}pyridin-2-yl)pyrazolo[1,5-a]pyridine-5-carbonitrile;
3-(4-{[(3R)-1-(Cyanoacetyl)piperidin-3-yl]amino}pyrimidin-2-yl)pyrazolo[1,5-a]pyridine-5-carbonitrile;
3-(4-{[(3R)-1-Acetylpiperidin-3-yl]amino}pyrimidin-2-yl}pyrazolo[1,5-a]pyridine-5-carbonitrile;
3-(4-{[(3R)-1-(5-Cyanopyridin-2-yl)piperidin-3-yl]amino}pyrimidin-2-yl)pyrazolo[1,5-a]pyridine-5-carbonitrile;
3-(4-{[(3R)-1-(3,3,3-Trifluoropropanoyl)piperidin-3-yl]amino}pyrimidin-2-yl)pyrazolo[1,5-a]pyridine-5-carbonitrile;
3-{4-[[(3R)-1-(Cyanocarbonyl)piperidin-3-yl](methyl)amino]pyrimidin-2-yl}pyrazolo[1,5-a]pyridine-5-carbonitrile;
3-(4-((Trans)-4-Hydroxycyclohexylamino)pyrimidin-2-yl)pyrazolo[1,5-a]pyridine-5-carbonitrile;
N-(Cyclohexylmethyl)-2-pyrazolo[1,5-a]pyrazin-3-ylpyrimidin-4-amine;
(S)—N-(1-phenylethyl)-2-(pyrazolo[1,5-a]pyrazin-3-yl)pyrimidin-4-amine;
N-Benzyl-2-pyrazolo[1,5-a]pyrazin-3-ylpyrimidin-4-amine;
N-(2,2-Dimethylpropyl)-2-pyrazolo[1,5-a]pyrazin-3-ylpyrimidin-4-amine;
3-Oxo-3-{(3R)-3-[(2-pyrazolo[1,5-a]pyrazin-3-ylpyrimidin-4-yl)amino]piperidin-1-yl}propanenitrile;
6-{(3R)-3-[(2-Pyrazolo[1,5-a]pyrazin-3-ylpyrimidin-4-yl)amino]piperidin-1-yl}nicotinonitrile;
2-Pyrazolo[1,5-a]pyrazin-3-yl-N-[(3R)-1-(3,3,3-trifluoropropanoyl)piperidin-3-yl]pyrimidin-4-amine;
3-{(3R)-3-[Methyl(2-pyrazolo[1,5-a]pyrazin-3-ylpyrimidin-4-yl)amino]piperidin-1-yl}-3-oxopropanenitrile;
3-{(3R)-3-[(5-Chloro-2-pyrazolo[1,5-a]pyrazin-3-ylpyrimidin-4-yl)amino]piperidin-1-yl}-3-oxopropanenitrile;
3-{(3R)-3-[(5-Fluoro-2-pyrazolo[1,5-a]pyrazin-3-ylpyrimidin-4-yl)amino]piperidin-1-yl}-3-oxopropanenitrile;
5-Fluoro-2-pyrazolo[1,5-a]pyrazin-3-yl-N-[(3R)-1-(3,3,3-trifluoropropanoyl)piperidin-3-yl]pyrimidin-4-amine;
3-{(3R)-3-[(5-Methyl-2-pyrazolo[1,5-a]pyrazin-3-ylpyrimidin-4-yl)amino]piperidin-1-yl}-3-oxopropanenitrile;
(S)—N-(1-(5-fluoropyridin-2-yl)ethyl)-2-(pyrazolo[1,5-a]pyrazin-3-yl)pyrimidin-4-amine;
N-((5-fluoropyridin-2-yl)methyl)-2-(pyrazolo[1,5-a]pyrazin-3-yl)pyrimidin-4-amine;
5-chloro-N-((5-fluoropyridin-2-yl)methyl)-2-(pyrazolo[1,5-a]pyrazin-3-yl)pyrimidin-4-amine;
N$^4$-(4,4-difluorocyclohexyl)-2-(pyrazolo[1,5-a]pyrazin-3-yl)pyrimidine-4,5-diamine;
(S)-5-chloro-N-(1-(5-fluoropyridin-2-yl)ethyl)-2-(pyrazolo[1,5-a]pyrazin-3-yl)pyrimidin-4-amine;
2-(pyrazolo[1,5-a]pyrazin-3-yl)-N$^4$-(tetrahydro-2H-pyran-4-yl)pyrimidine-4,5-diamine;
(R)-3-oxo-3-(3-(6-(pyrazolo[1,5-a]pyrazin-3-yl)pyrazin-2-ylamino)piperidin-1-yl)propanenitrile;
(R)-3-oxo-3-(3-(6-(pyrazolo[1,5-a]pyridin-3-yl)pyrazin-2-ylamino)piperidin-1-yl)propanenitrile;
(R)-3-oxo-3-(3-(2-(pyrazolo[1,5-a]pyridin-3-yl)pyrimidin-4-ylamino)piperidin-1-yl)propanenitrile;
3-(3-(5-fluoro-2-(pyrazolo[1,5-a]pyridin-3-yl)pyrimidin-4-ylamino)piperidin-1-yl)-3-oxopropanenitrile;
3-(3-(5-chloro-2-(pyrazolo[1,5-a]pyridin-3-yl)pyrimidin-4-ylamino)piperidin-1-yl)-3-oxopropanenitrile;
3-(4-fluoro-3-(6-(pyrazolo[1,5-a]pyridin-3-yl)pyrazin-2-ylamino)piperidin-1-yl)-3-oxopropanenitrile;
3-(4-methyl-3-(6-(pyrazolo[1,5-a]pyridin-3-yl)pyrazin-2-ylamino)piperidin-1-yl)-3-oxopropanenitrile;
N-(1-(4H-1,2,4-Triazol-3-yl)piperidin-3-yl)-6-(pyrazolo[1,5-a]pyridin-3-yl)pyrazin-2-amine;
N-(1-(4H-1,2,4-Triazol-3-yl)piperidin-3-yl)-2-(pyrazolo[1,5-a]pyridin-3-yl)pyrimidin-4-amine;
and pharmaceutically acceptable salts, solvates, N-oxides or deuterated derivatives thereof.

Examples of the preferred compounds are
3-(4{[(1S)-1-Phenylethyl]amino}pyrimidin-2-yl)pyrazolo[1,5-a]pyridine-5-carbonitrile;
3-{4-[(Cyclohexylmethyl)amino]pyrimidin-2-yl}pyrazolo[1,5-a]pyridine-5-carbonitrile;
3-[4-(Benzylamino)pyrimidin-2-yl]pyrazolo[1,5-a]pyridine-5-carbonitrile;
3-{4-[(2,2-Dimethylpropyl)amino]pyrimidin-2-yl}pyrazolo[1,5-a]pyridine-5-carbonitrile;
3-(4-{[(1S)-2-Methoxy-1-methylethyl]amino}pyrimidin-2-yl)pyrazolo[1,5-a]pyridine-5-carbonitrile;
3-{4-[(Cyclopropylmethyl)amino]pyrimidin-2-yl}pyrazolo[1,5-a]pyridine-5-carbonitrile;
3-{4-[(2,2,2-Trifluoroethyl)amino]pyrimidin-2-yl}pyrazolo[1,5-a]pyridine-5-carbonitrile;

N-(1-Phenylethyl)-2-pyrazolo[1,5-a]pyridin-3-ylpyrimidin-4-amine;
3-{6-[(Cyclohexylmethyl)amino]pyridin-2-yl}pyrazolo[1,5-a]pyridine-5-carbonitrile;
3-{6-[(2,2-Dimethylpropyl)amino]pyridin-2-yl}pyrazolo[1,5-a]pyridine-5-carbonitrile;
3-{6-[(3-Fluorobenzyl)amino]pyridin-2-yl}pyrazolo[1,5-a]pyridine-5-carbonitrile;
3-[6-(Benzylamino)pyridin-2-yl]pyrazolo[1,5-a]pyridine-5-carbonitrile;
3-(6{[(1S)-1-Phenylethyl]amino}pyridin-2-yl)pyrazolo[1,5-a]pyridine-5-carbonitrile;
3-(4-{[(3R)-1-(Cyanoacetyl)piperidin-3-yl]amino}pyrimidin-2-yl)pyrazolo[1,5-a]pyridine-5-carbonitrile;
3-(4-{[(3R)-1-Acetylpiperidin-3-yl]amino}pyrimidin-2-yl)pyrazolo[1,5-a]pyridine-5-carbonitrile;
3-(4-{[(3R)-1-(5-Cyanopyridin-2-yl)piperidin-3-yl]amino}pyrimidin-2-yl)pyrazolo[1,5-a]pyridine-5-carbonitrile;
3-(4-{[(3R)-1-(3,3,3-Trifluoropropanoyl)piperidin-3-yl]amino}pyrimidin-2-yl) pyrazolo[1,5-a]pyridine-5-carbonitrile;
3-{4-[[(3R)-1-(Cyanocarbonyl)piperidin-3-yl]methyl)amino]pyrimidin-2-yl}pyrazolo[1,5-a]pyridine-5-carbonitrile;
3-(4-((Trans)-4-Hydroxycyclohexylamino)pyrimidin-2-yl)pyrazolo[1,5-a]pyridine-5-carbonitrile;
N-(Cyclohexylmethyl)-2-pyrazolo[1,5-a]pyrazin-3-ylpyrimidin-4-amine;
(S)—N-(1-phenylethyl)-2-(pyrazolo[1,5-a]pyrazin-3-yl)pyrimidin-4-amine;
N-Benzyl-2-pyrazolo[1,5-a]pyrazin-3-ylpyrimidin-4-amine;
N-(2,2-Dimethylpropyl)-2-pyrazolo[1,5-a]pyrazin-3-ylpyrimidin-4-amine;
3-Oxo-3-{(3R)-3-[(2-pyrazolo[1,5-a]pyrazin-3-ylpyrimidin-4-yl)amino]piperidin-1-yl}propanenitrile;
6-{(3R)-3-[(2-Pyrazolo[1,5-a]pyrazin-3-ylpyrimidin-4-yl)amino]piperidin-1-yl}nicotinonitrile;
2-Pyrazolo[1,5-a]pyrazin-3-yl-N-[(3R)-1-(3,3,3-trifluoropropanoyl)piperidin-3-yl]pyrimidin-4-amine;
3-{(3R)-3-[Methyl(2-pyrazolo[1,5-a]pyrazin-3-ylpyrimidin-4-yl)amino]piperidin-1-yl}-3-oxopropanenitrile;
3-{(3R)-3-[(5-Chloro-2-pyrazolo[1,5-a]pyrazin-3-ylpyrimidin-4-yl)amino]piperidin-1-yl}-3-oxopropanenitrile;
3-{(3R)-3-[(5-Fluoro-2-pyrazolo[1,5-a]pyrazin-3-ylpyrimidin-4-yl)amino]piperidin-1-yl}-3-oxopropanenitrile;
5-Fluoro-2-pyrazolo[1,5-a]pyrazin-3-yl-N-[(3R)-1-(3,3,3-trifluoropropanoyl) piperidin-3-yl]pyrimidin-4-amine;
3-{(3R)-3-[(5-Methyl-2-pyrazolo[1,5-a]pyrazin-3-ylpyrimidin-4-yl)amino]piperidin-1-yl}-3-oxopropanenitrile;
and pharmaceutically acceptable salts, solvates, N-oxides or deuterated derivatives thereof.

Of outstanding interest are:
3-(4-{[(1S)-1-Phenylethyl]amino}pyrimidin-2-yl)pyrazolo[1,5-a]pyridine-5-carbonitrile;
3-{4-[(2,2-Dimethylpropyl)amino]pyrimidin-2-yl}pyrazolo[1,5-a]pyridine-5-carbonitrile;
3-(4-{[(1S)-2-Methoxy-1-methylethyl]amino}pyrimidin-2-yl)pyrazolo[1,5-a]pyridine-5-carbonitrile;
N-(1-Phenylethyl)-2-pyrazolo[1,5-a]pyridin-3-ylpyrimidin-4-amine;
3-(4-{[(3R)-1-(Cyanoacetyl)piperidin-3-yl]amino}pyrimidin-2-yl)pyrazolo[1,5-a]pyridine-5-carbonitrile;
3-(4-{[(3R)-1-(3,3,3-Trifluoropropanoyl)piperidin-3-yl]amino}pyrimidin-2-yl) pyrazolo[1,5-a]pyridine-5-carbonitrile;
3-{4-[[(3R)-1-(Cyanocarbonyl)piperidin-3-yl]methyl)amino]pyrimidin-2-yl}pyrazolo[1,5-a]pyridine-5-carbonitrile;
3-(4-((Trans)-4-Hydroxycyclohexylamino)pyrimidin-2-yl)pyrazolo[1,5-a]pyridine-5-carbonitrile;
(S)—N-(1-phenylethyl)-2-(pyrazolo[1,5-a]pyrazin-3-yl)pyrimidin-4-amine;
N-Benzyl-2-pyrazolo[1,5-a]pyrazin-3-ylpyrimidin-4-amine;
N-(2,2-Dimethylpropyl)-2-pyrazolo[1,5-a]pyrazin-3-ylpyrimidin-4-amine;
3-Oxo-3-{(3R)-3-[(2-pyrazolo[1,5-a]pyrazin-3-ylpyrimidin-4-yl)amino]piperidin-1-yl}propanenitrile;
6-{(3R)-3-[(2-Pyrazolo[1,5-a]pyrazin-3-ylpyrimidin-4-yl)amino]piperidin-1-yl}nicotinonitrile;
3-{(3R)-3-[Methyl(2-pyrazolo[1,5-a]pyrazin-3-ylpyrimidin-4-yl)amino]piperidin-1-yl}-3-oxopropanenitrile;
3-{(3R)-3-[(5-Chloro-2-pyrazolo[1,5-a]pyrazin-3-ylpyrimidin-4-yl)amino]piperidin-1-yl}-3-oxopropanenitrile;
3-{(3R)-3-[(5-Fluoro-2-pyrazolo[1,5-a]pyrazin-3-ylpyrimidin-4-yl)amino]piperidin-1-yl}-3-oxopropanenitrile;
5-Fluoro-2-pyrazolo[1,5-a]pyrazin-3-yl-N-[(3R)-1-(3,3,3-trifluoropropanoyl) piperidin-3-yl]pyrimidin-4-amine;
3-{(3R)-3-[(5-Methyl-2-pyrazolo[1,5-a]pyrazin-3-ylpyrimidin-4-yl)amino]piperidin-1-yl}-3-oxopropanenitrile;
(S)—N-(1-(5-fluoropyridin-2-yl)ethyl)-2-(pyrazolo[1,5-a]pyrazin-3-yl)pyrimidin-4-amine;
N-((5-fluoropyridin-2-yl)methyl)-2-(pyrazolo[1,5-a]pyrazin-3-yl)pyrimidin-4-amine;
5-chloro-N-((5-fluoropyridin-2-yl)methyl)-2-(pyrazolo[1,5-a]pyrazin-3-yl)pyrimidin-4-amine;
$N^4$-(4,4-difluorocyclohexyl)-2-(pyrazolo[1,5-a]pyrazin-3-yl)pyrimidine-4,5-diamine;
(S)-5-chloro-N-(1-(5-fluoropyridin-2-yl)ethyl)-2-(pyrazolo[1,5-a]pyrazin-3-yl)pyrimidin-4-amine;
2-(pyrazolo[1,5-a]pyrazin-3-yl)-$N^4$-(tetrahydro-2H-pyran-4-yl)pyrimidine-4,5-diamine;
(R)-3-oxo-3-(3-(6-(pyrazolo[1,5-a]pyrazin-3-yl)pyrazin-2-ylamino)piperidin-1-yl)propanenitrile;
(R)-3-oxo-3-(3-(6-(pyrazolo[1,5-a]pyridin-3-yl)pyrazin-2-ylamino)piperidin-1-yl)propanenitrile;
(R)-3-oxo-3-(3-(2-(pyrazolo[1,5-a]pyridin-3-yl)pyrimidin-4-ylamino)piperidin-1-yl)propanenitrile;
3-(3-(5-fluoro-2-(pyrazolo[1,5-a]pyridin-3-yl)pyrimidin-4-ylamino)piperidin-1-yl)-3-oxopropanenitrile;
3-(3-(5-chloro-2-(pyrazolo[1,5-a]pyridin-3-yl)pyrimidin-4-ylamino)piperidin-1-yl)-3-oxopropanenitrile;
3-(4-fluoro-3-(6-(pyrazolo[1,5-a]pyridin-3-yl)pyrazin-2-ylamino)piperidin-1-yl)-3-oxopropanenitrile;
3-(4-methyl-3-(6-(pyrazolo[1,5-a]pyridin-3-yl)pyrazin-2-ylamino)piperidin-1-yl)-3-oxopropanenitrile;
N-(1-(4H-1,2,4-Triazol-3-yl)piperidin-3-yl)-6-(pyrazolo[1,5-a]pyridin-3-yl)pyrazin-2-amine;
N-(1-(4H-1,2,4-Triazol-3-yl)piperidin-3-yl)-2-(pyrazolo[1,5-a]pyridin-3-yl)pyrimidin-4-amine;
and pharmaceutically acceptable salts, solvates, N-oxides or deuterated derivatives thereof.

Preferred individual compounds of the invention include:
3-(4-{[(1S)-1-Phenylethyl]amino}pyrimidin-2-yl)pyrazolo[1,5-a]pyridine-5-carbonitrile;
3-{4-[(2,2-Dimethylpropyl)amino]pyrimidin-2-yl}pyrazolo[1,5-a]pyridine-5-carbonitrile;
3-(4-{[(1S)-2-Methoxy-1-methylethyl]amino}pyrimidin-2-yl)pyrazolo[1,5-a]pyridine-5-carbonitrile;

N-(1-Phenylethyl)-2-pyrazolo[1,5-a]pyridin-3-ylpyrimidin-4-amine;
3-(4-{[(3R)-1-(Cyanoacetyl)piperidin-3-yl]amino}pyrimidin-2-yl)pyrazolo[1,5-a]pyridine-5-carbonitrile;
3-(4-{[(3R)-1-(3,3,3-Trifluoropropanoyl)piperidin-3-yl]amino}pyrimidin-2-yl) pyrazolo[1,5-a]pyridine-5-carbonitrile;
3-{4-[[(3R)-1-(Cyanocarbonyl)piperidin-3-yl]methyl)amino]pyrimidin-2-yl}pyrazolo[1,5-a]pyridine-5-carbonitrile;
3-(4-((Trans)-4-Hydroxycyclohexylamino)pyrimidin-2-yl)pyrazolo[1,5-a]pyridine-5-carbonitrile;
(S)—N-(1-phenylethyl)-2-(pyrazolo[1,5-a]pyrazin-3-yl)pyrimidin-4-amine;
N-Benzyl-2-pyrazolo[1,5-a]pyrazin-3-ylpyrimidin-4-amine;
N-(2,2-Dimethylpropyl)-2-pyrazolo[1,5-a]pyrazin-3-ylpyrimidin-4-amine;
3-Oxo-3-{(3R)-3-[(2-pyrazolo[1,5-a]pyrazin-3-ylpyrimidin-4-yl)amino]piperidin-1-yl}propanenitrile;
6-{(3R)-3-[(2-Pyrazolo[1,5-a]pyrazin-3-ylpyrimidin-4-yl)amino]piperidin-1-yl}nicotinonitrile;
3-{(3R)-3-[Methyl(2-pyrazolo[1,5-a]pyrazin-3-ylpyrimidin-4-yl)amino]piperidin-1-yl}-3-oxopropanenitrile;
3-{(3R)-3-[(5-Chloro-2-pyrazolo[1,5-a]pyrazin-3-ylpyrimidin-4-yl)amino]piperidin-1-yl}-3-oxopropanenitrile;
3-{(3R)-3-[(5-Fluoro-2-pyrazolo[1,5-a]pyrazin-3-ylpyrimidin-4-yl)amino]piperidin-1-yl}-3-oxopropanenitrile;
5-Fluoro-2-pyrazolo[1,5-a]pyrazin-3-yl-N-[(3R)-1-(3,3,3-trifluoropropanoyl) piperidin-3-yl]pyrimidin-4-amine;
3-{(3R)-3-[(5-Methyl-2-pyrazolo[1,5-a]pyrazin-3-ylpyrimidin-4-yl)amino]piperidin-1-yl}-3-oxopropanenitrile;
(S)—N-(1-(5-fluoropyridin-2-yl)ethyl)-2-(pyrazolo[1,5-a]pyrazin-3-yl)pyrimidin-4-amine;
N-((5-fluoropyridin-2-yl)methyl)-2-(pyrazolo[1,5-a]pyrazin-3-yl)pyrimidin-4-amine;
5-chloro-N-((5-fluoropyridin-2-yl)methyl)-2-(pyrazolo[1,5-a]pyrazin-3-yl)pyrimidin-4-amine;
$N^4$-(4,4-difluorocyclohexyl)-2-(pyrazolo[1,5-a]pyrazin-3-yl)pyrimidine-4,5-diamine;
(S)-5-chloro-N-(1-(5-fluoropyridin-2-yl)ethyl)-2-(pyrazolo[1,5-a]pyrazin-3-yl)pyrimidin-4-amine;
2-(pyrazolo[1,5-a]pyrazin-3-yl)-$N^4$-(tetrahydro-2H-pyran-4-yl)pyrimidine-4,5-diamine;
(R)-3-oxo-3-(3-(6-(pyrazolo[1,5-a]pyrazin-3-yl)pyrazin-2-ylamino)piperidin-1-yl)propanenitrile;
(R)-3-oxo-3-(3-(6-(pyrazolo[1,5-a]pyridin-3-yl)pyrazin-2-ylamino)piperidin-1-yl)propanenitrile;
(R)-3-oxo-3-(3-(2-(pyrazolo[1,5-a]pyridin-3-yl)pyrimidin-4-ylamino)piperidin-1-yl)propanenitrile;
3-(3-(5-fluoro-2-(pyrazolo[1,5-a]pyridin-3-yl)pyrimidin-4-ylamino)piperidin-1-yl)-3-oxopropanenitrile;
3-(3-(5-chloro-2-(pyrazolo[1,5-a]pyridin-3-yl)pyrimidin-4-ylamino)piperidin-1-yl)-3-oxopropanenitrile;
3-(4-fluoro-3-(6-(pyrazolo[1,5-a]pyridin-3-yl)pyrazin-2-ylamino)piperidin-1-yl)-3-oxopropanenitrile;
3-(4-methyl-3-(6-(pyrazolo[1,5-a]pyridin-3-yl)pyrazin-2-ylamino)piperidin-1-yl)-3-oxopropanenitrile;
N-(1-(4H-1,2,4-Triazol-3-yl)piperidin-3-yl)-6-(pyrazolo[1,5-a]pyridin-3-yl)pyrazin-2-amine;
N-(1-(4H-1,2,4-Triazol-3-yl)piperidin-3-yl)-2-(pyrazolo[1,5-a]pyridin-3-yl)pyrimidin-4-amine;
and pharmaceutically acceptable salts, solvates, N-oxides or deuterated derivatives thereof.

According to one embodiment of the present invention, compounds of general formula (I-d), a subformula of claimed compounds of general formula (I) where the central heteroaryl moiety is a pyrimidine ring, may be prepared by the following synthetic route as illustrated in Scheme 1:

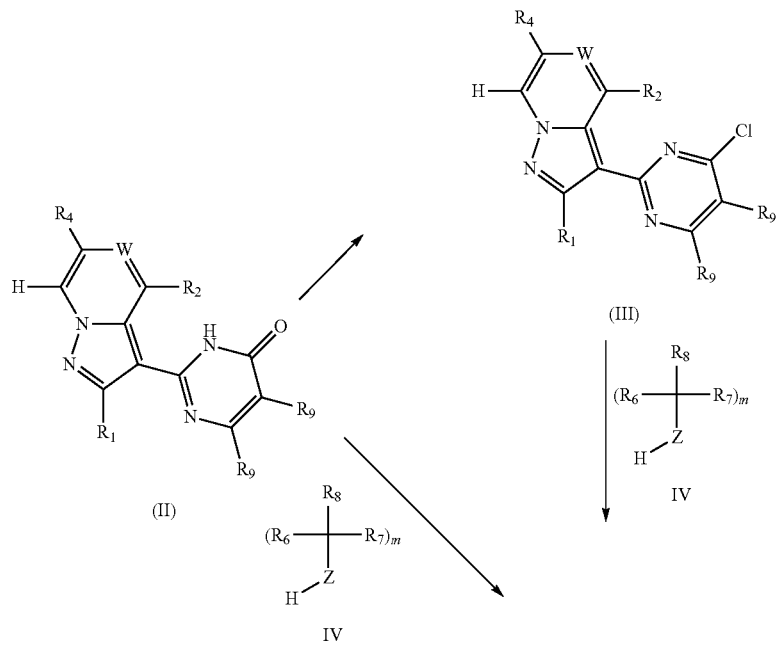

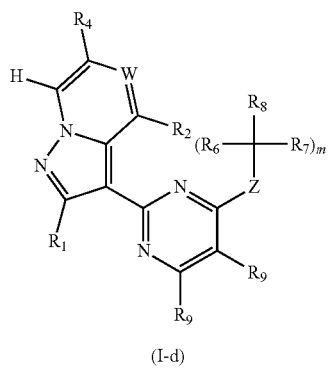

(I-d)

Compounds of formula (I-d) may be obtained from chlorine-containing heteroaromatic compounds of formula (III) by reaction with an appropriate nucleophile of formula (IV), such as an amine or an alcohol, in the presence of a base such as N,N'-diisopropylethylamine or triethylamine in a solvent such as N,N'-dimethylformamide, dimethylsulfoxide, tetrahydrofuran or ethanol at temperatures ranging from ambient temperature to 150° C. with or without the use of microwave irradiation. Compounds of formula (III) may be prepared by treatment of pyrimidones of formula (II) with a suitable chlorinating agent, for example phosphorous (V) oxychloride or phosphorous (V) chloride, at temperatures ranging from 25° C. to reflux. In the particular case where Z=NR$_5$, compounds of formula (I-d) may be obtained directly from compounds of formula (II) by treatment with an appropriate activating agent such as benzotriazolyloxy-tris-(dimethylamino)phosphonium hexafluorophosphate in the presence of a suitable base such as 1,8-diazabiciclo[5.4.0]undec-7-ene at temperatures ranging from 25 to 80° C. in a suitable solvent such as N,N'-dimethylformamide in the presence of a nucleophile of type (IV) following the protocol as described in the literature (*J. Org. Chem.*, 2007, 72 (26), 10194-10210).

Compounds of general formula (II-a), a subformula of intermediates of formula (II) in which R$_1$ is an hydrogen atom, may be obtained as shown in Scheme 2:

Scheme 2

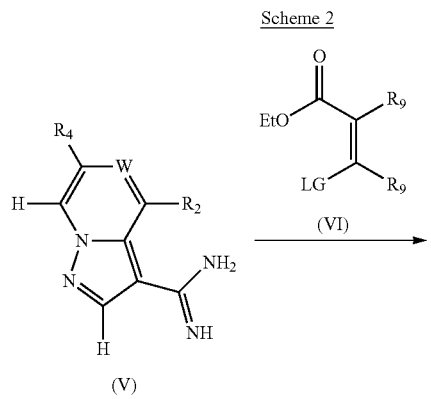

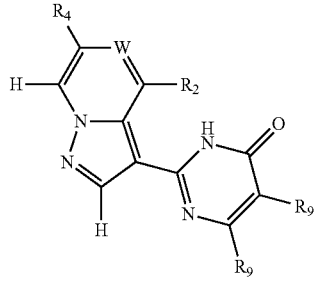

(II-a)

Amidines of formula (V) may be reacted with unsaturated esters of formula (VI) (where LG is OH, —OMe, —OEt or NMe$_2$) to give pyrimidones of formula (II-a). Such reactions may be carried out in the presence of a suitable base such as triethylamine in a solvent such as ethanol at temperatures ranging from ambient temperature to reflux.

Intermediate amidines of general formula (V) may be prepared by the following synthetic route as illustrated in Scheme 3:

Scheme 3

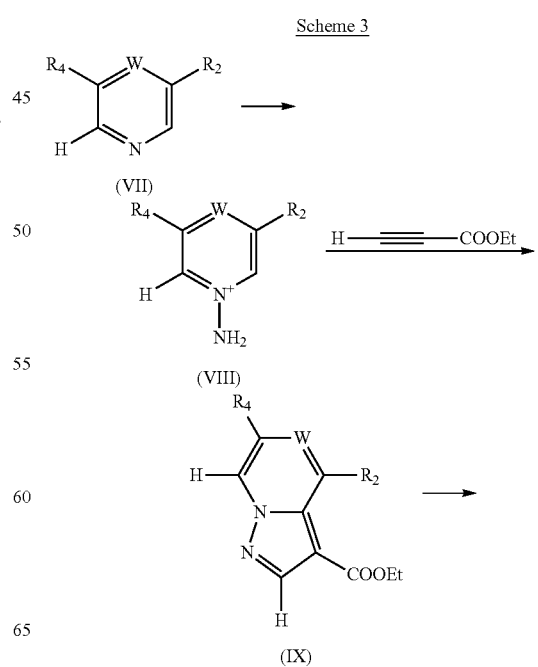

-continued

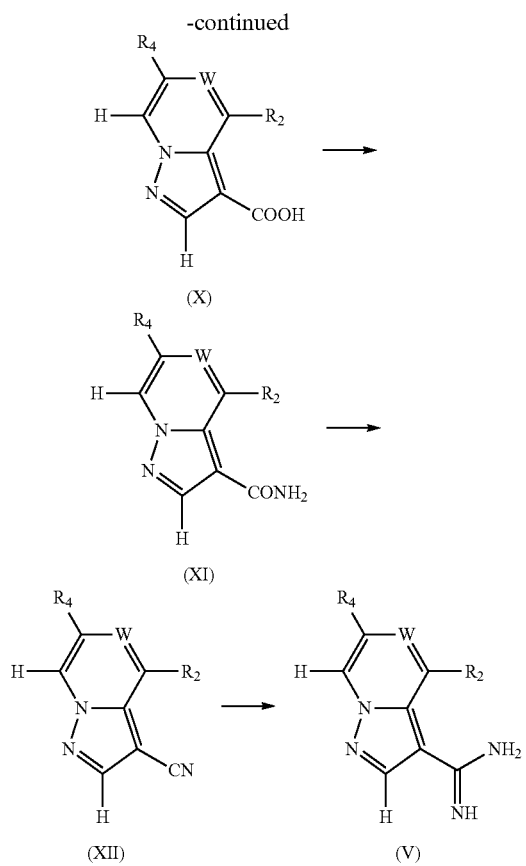

Reaction of ethyl propiolate with N-aminopyridinium (in the particular case where W=CR$_3$) or N-aminopyrazinium salts (in the particular case where W=N) of formula (VIII) in the presence of a base, for example potassium carbonate, in a solvent such as N,N' dimethylformamide at temperatures ranging from 0° C. to ambient temperature, furnishes esters of formula (IX). N-aminopyridinium and N-aminopyrazinium salts of formula (VIII) may be commercially available or may be prepared by reaction of the corresponding pyridines (in the particular case where W=CR$_3$) or pyrazines (in the particular case where W=N) of formula (VII) with O-(mesitylsulfonyl) hydroxylamine in a suitable solvent such as dichloromethane at temperatures ranging from 0° C. to ambient temperature. Carboxylic acids of formula (X) may be prepared by treatment of esters of formula (IX) with a suitable base such as sodium hydroxide in a solvent such as ethanol at temperatures ranging from ambient temperature to reflux. Treatment of compounds of formula (X) with a suitable chlorinating reagent such as thionyl chloride at temperatures ranging from ambient temperature to reflux furnishes intermediate acid chlorides which when treated with an ammonia source, such as aqueous ammonium hydroxide, gives rise to amides of formula (XI). Reaction of amides of formula (XI) with a suitable dehydrating reagent such as phosphoryl trichloride at temperatures ranging from ambient temperature to reflux furnishes nitriles of formula (XII). Treatment of nitriles of formula (XII) with catalytic sodium methoxide in methanol at ambient temperature followed by treatment of the corresponding imidate intermediates with ammonium chloride in methanol at refluxing temperatures furnishes amidine intermediates of formula (V).

In another synthetic pathway, compounds of general formula (II-a) may be prepared by the following synthetic route as described in Scheme 4:

Scheme 4

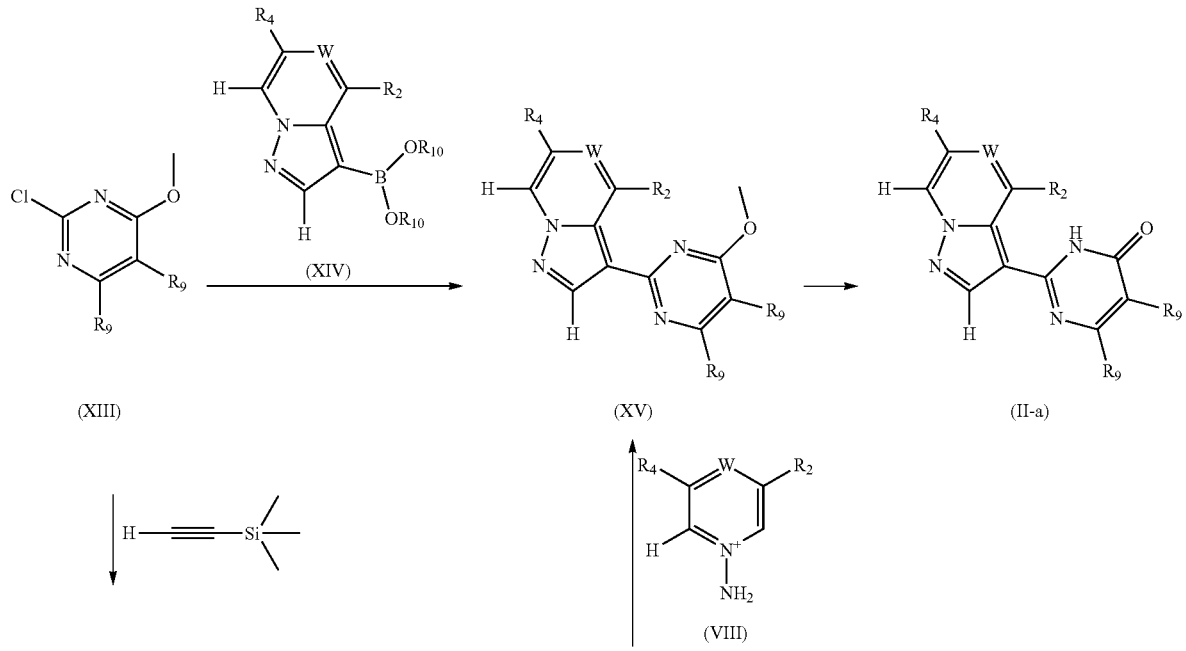

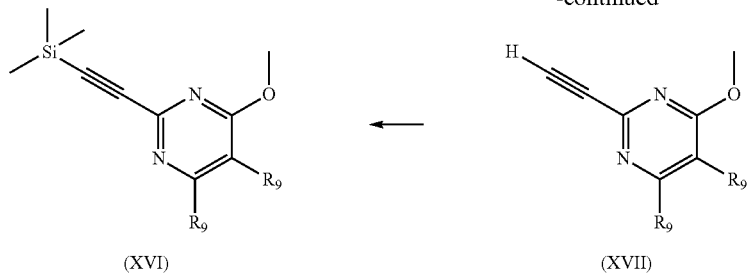

(XVI) ← (XVII)

Reaction of 2-chloropyrimidines of formula (XIII) with ethynyltrimethylsilane under palladium and copper-catalyzed coupling conditions with suitable catalysts such as bis(triphenylphosphine)palladium (II) dichloride and copper(I) iodide in the presence of a base, for example triethylamine, in a solvent such as tetrahydrofuran at temperatures ranging from room temperature to reflux, with or without the use of microwave irradiation, furnishes alkynes of formula (XVI). Treatment of compounds of formula (XVI) with a suitable reagent such as tetrabutylammonium fluoride in the presence of a catalytic amount of acetic acid in a suitable solvent such as tetrahydrofuran at ambient temperature, gives rise to desired terminal alkynes of formula (XVII). Reaction of alkynes of formula (XVII) with N-aminopyridinium (in the particular case where W=$CR_3$) or N-aminopyrazinium salts (in the particular case where W=N) of formula (VIII) in the presence of a base, for example potassium carbonate, in a solvent such as N,N' dimethylformamide at temperatures ranging from 0° C. to room temperature, furnishes compounds of formula (XV). Alternatively, compounds of formula (XV) may be prepared directly from 2-chloropyrimidines of formula (XIII) by reaction with boronic esters of formula (XIV) under Suzuki-Miyaura reaction conditions (Miyaura, N.; Suzuki, A. Chem. Rev. 1995, 95, 2457). Such reactions may be catalyzed by a suitable palladium catalyst such as tris(dibencylidenoacetone)dipalladium (0), in the presence of a ligand such as tricyclohexylphosphine, in a solvent such as N,N'-dimethylformamide, in the presence of a base such as potassium phosphate, at temperatures ranging from 80-120° C. with or without the use of microwave irradiation. Treatment of compounds of formula (XV) with suitable reagents such as trimethylsilylchloride/sodium iodide in a suitable solvent such as acetonitrile at reflux, with potassium hydroxide in a mixture of ethanol and water under microwave heating at 130° C. or with an aqueous hydrogen chloride or hydrogen bromide solution at 100° C., gives rise to desired pyrimidones of formula (II-a).

Intermediate boronic esters of general formula (XIV) may be prepared as shown in Scheme 5:

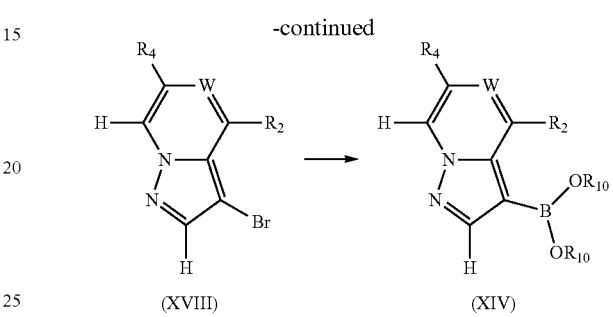

(XVIII) (XIV)

Carboxylic acids of formula (X) may be transformed into bromo derivatives of formula (XVIII) by treatment with a brominating reagent such as N-bromosuccinimide in the presence of a base, such as sodium hydrogen carbonate, in a solvent such as N,N'-dimethylformamide at ambient temperature. Treatment of bromo derivatives of formula (XVIII) with an appropriate boron reagent such as bis(pinacolato)diboron with a palladium catalyst such as palladium (II) acetate, in the presence of a ligand such as tricyclohexylphosphine, in a solvent such as diglyme or water, in the presence of a base such as potassium carbonate, at temperatures ranging from 80-120° C. with or without the use of microwave irradiation provides boronic esters of formula (XIV).

Compounds of general formula (I-e), a subformula of claimed compounds of general formula (I) where the central heteroaryl moiety is a pyridine ring and $R_1$ is an hydrogen atom, may be prepared by the following synthetic route as illustrated in Scheme 6:

Scheme 5

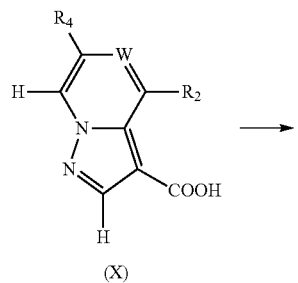

(X)

Scheme 6

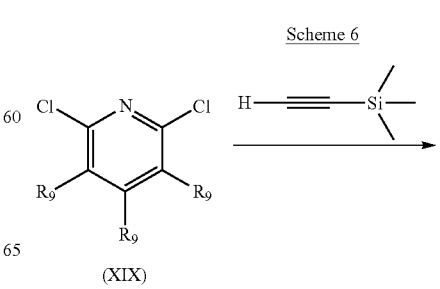

(XIX)

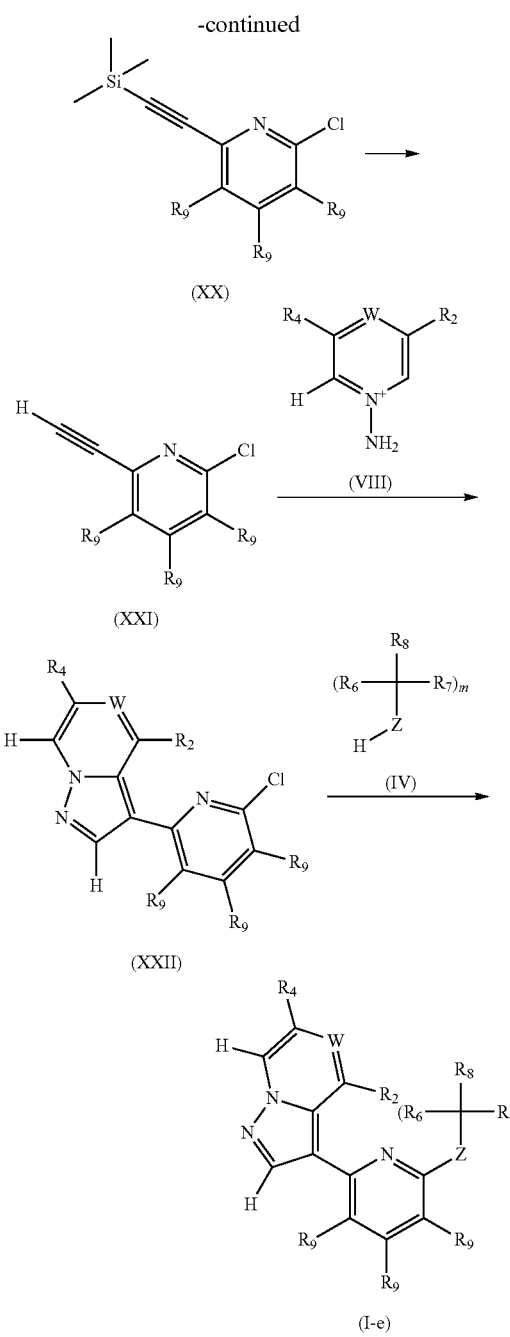

(XX)

(XXI)

(XXII)

(I-e)

solvent such as N,N'-dimethylformamide at temperatures ranging from 0° C. to ambient temperature, furnishes compounds of formula (XXII). Treatment of chloropyridines of formula (XXII) with nucleophiles of formula (IV) such as an amine or an alcohol, in the presence of a base, such as N,N'-diisopropylethylamine or triethylamine, in an aprotic solvent such as N,N'-dimethylformamide or dimethylsulfoxide at temperatures ranging from ambient temperature to 140° C. gives rises to compounds of formula (I-e). In the particular case where Z=NR$_5$, compounds of formula (I-e) may be prepared by reaction of compounds of formula (XXII) with nitrogen nucleophiles of formula (IV) using a suitable catalyst such as palladium (II) acetate in the presence of a ligand such as 1,1'-binaphthalene-2,2'-diylbis(diphenylphosphine) and a base, for example cesium carbonate, in a solvent such as toluene at a temperature ranging from 80-120° C. with or without the use of microwave irradiation.

Compounds of general formula (I-f), a subformula of claimed compounds of general formula (I) where the central heteroaryl moiety is a pyrazine ring and R$_1$ is an hydrogen atom, may be prepared by the following synthetic route as described in Scheme 7:

Scheme 7

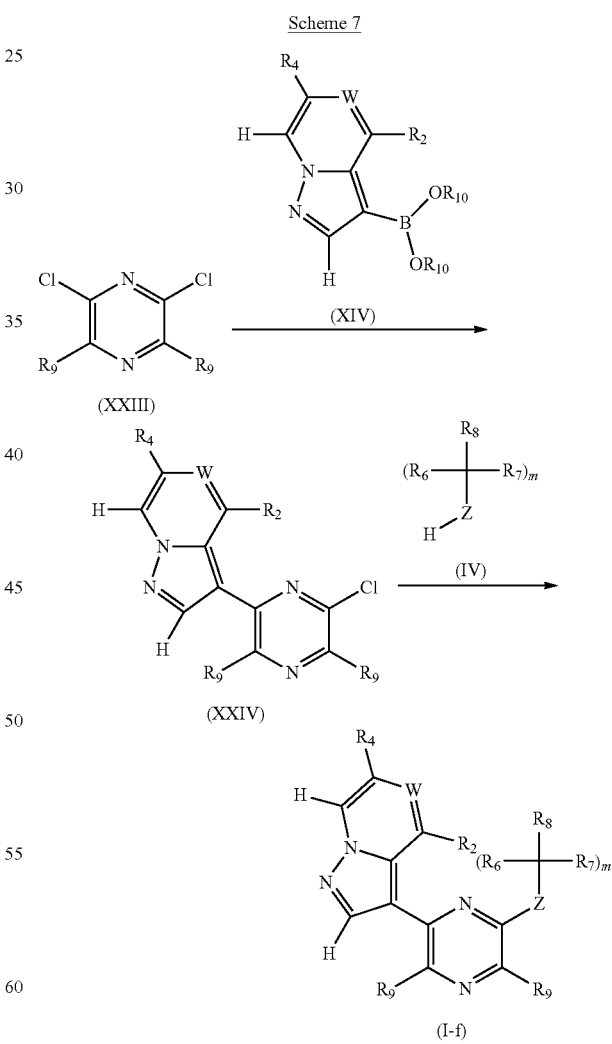

Alkynes of formula (XX) may be prepared by reaction of dichloropyridines of formula (XIX) with ethynyltrimethylsilane under palladium and copper-catalyzed coupling conditions with suitable catalysts such as bis(triphenylphosphine) palladium (II) dichloride and copper (I) iodide in the presence of a base, for example triethylamine, in a solvent such as tetrahydrofuran at temperatures ranging from ambient temperature to reflux with or without the use of microwave irradiation. Treatment of compounds of formula (XX) with a suitable reagent such as tetrabutylammonium fluoride in the presence of a catalytic amount of acetic acid in a suitable solvent such as tetrahydrofuran at room temperature, gives rise to desired terminal alkynes of formula (XXI). Reaction of alkynes of formula (XXI) with N-aminopyridinium (in the particular case where W=CR$_3$) or N-aminopyrazinium salts (in the particular case where W=N) of formula (VIII) in the presence of a base, for example potassium carbonate, in a Boronic esters of formula (XIV) may be reacted with 2,6-dichloropyrazines of formula (XXIII) under Suzuki-Miyaura reaction conditions (Miyaura, N.; Suzuki, A. Chem. Rev. 1995, 95, 2457) to give compounds of formula (XXIV). Such reactions may be catalyzed by a suitable palladium catalyst such as tris(dibencylidenoacetone)dipalladium (0), in the presence of a ligand such as tricyclohexylphosphine, in a solvent such as N,N'-dimethylformamide, in the presence of a base such as potassium phosphate, at temperatures ranging from 80-120° C. with or without the use of microwave irradiation. Treatment of chloropyrazines of formula (XXIV) with nucleophiles of formula (IV) in the presence of a base, such as cesium fluoride, in an aprotic solvent such as dimethylsulfoxide at temperatures ranging from ambient temperature to 140° C. gives rises to compounds of formula (I-f). In the particular case where $Z=NR_5$, compounds of formula (I-f) may be prepared by reaction of compounds of formula (XXIV) with nitrogen nucleophiles of formula (IV) using a suitable catalyst such as tris(dibencylidenoacetone)dipalladium (0), in the presence of a ligand such as 9,9-dimethyl-4,5-bis(diphenylphosphino)xanthene and a base, for example cesium carbonate, in a solvent such as N,N'-dimethylformamide at a temperature ranging from 80-120° C. with or without the use of microwave irradiation.

In another particular case, compounds of formula (I-d), (I-e) or (I-f) where Z is $NR_5$ and $R_5$ is an hydrogen atom, may undergo further reaction with a suitable base such as sodium hydride in a solvent such as N,N'-dimethylformamide followed by the addition of an alkylating agent, such as methyl iodide at temperatures ranging from 0° C. to reflux, to furnish compounds of formula (I-d), (I-e) or (I-f) where $R_5$ is now an alkyl group.

In yet another particular case, compounds of formula (I-d), (I-e) or (I-f) in which the residue at $R_9$ is a nitro group, may undergo further reaction with hydrogen gas at atmospheric pressure using a suitable catalyst such as palladium or platinum on carbon in a solvent such as ethanol or methanol at ambient temperature to furnish compounds of formula (I-d), (I-e) or (I-f) where $R_9$ is now an amino group.

In yet another particular case, compounds of formula (I-d), (I-e) or (I-f) in which the residue at $R_6$, $R_7$ or $R_8$ contains, in part, an amine moiety functionalized with an appropriate protecting group such as tert-butoxycarbonyl (BOC) or benzyloxycarbonyl (CBZ), may be deprotected at the amine moiety under standard conditions (*Greene's Protective Groups in Organic Synthesis*, ISBN: 0471697540). The corresponding free amine may then be further functionalized under standard conditions to give the corresponding amides, sulphonamides, ureas, and N-alkylated and N-arylated amines. The syntheses of the compounds of the invention and of the intermediates for use therein are illustrated by the following Examples (1-47) (including Preparation Examples (Preparations 1-41)) and are given in order to provide a person skilled in the art with a sufficiently clear and complete explanation of the present invention, but should not be considered as limiting of the essential aspects of its subject, as set out in the preceding portions of this description.

Preparation 1

2-Ethynyl-4-methoxypyrimidine

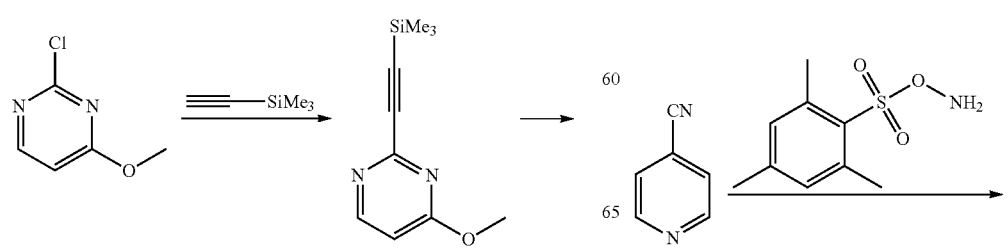

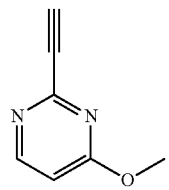

a) 4-Methoxy-2-[(trimethylsilyl)ethynyl]pyrimidine

An oven-dried resealable Schlenk tube was charged with 2-chloro-4-methoxypyrimidine (2.60 g, 17.99 mmol), ethynyltrimethylsilane (3.05 mL, 21.58 mmol), tetrahydrofuran (24 mL) and triethylamine (12.53 mL, 89.90 mmol). The Schlenk tube was subjected to three cycles of evacuation-backfilling with argon and then copper(I) iodide (0.14 g, 0.72 mmol) and bis(triphenylphosphine)palladium(II) dichloride (0.51 g, 0.72 mmol) were added. After three further cycles of evacuation-backfilling with argon, the Schlenk tube was sealed and the mixture was stirred and heated in an oil bath at 90° C. After 16 hours, the mixture was filtered and the solvent was removed under reduced pressure. The residue was taken up in a mixture of ethyl acetate and water and the organic layer was separated, washed with 4% aqueous sodium hydrogencarbonate solution, dried ($MgSO_4$) and evaporated. Purification of the residue by flash chromatography (9:1 hexane/ethyl acetate) gave the title compound (2.85 g, 77%) as an oil.

LRMS (m/z): 207 $(M+1)^+$.

$^1$H-NMR δ (300 MHz, $CDCl_3$): 0.0 (s, 9H), 3.7 (s, 3H), 6.4 (d, 1H), 8.1 (d, 1H).

b) 2-Ethynyl-4-methoxypyrimidine

Tetrabutylammonium fluoride (0.97 mL of a 1M solution in tetrahydrofuran, 0.97 mmol) was added to a stirred solution of 4-methoxy-2-[(trimethylsilyl)ethynyl]pyrimidine (Preparation 1a, 0.20 g, 0.97 mmol) in tetrahydrofuran (1.4 mL) and acetic acid (56 pt) at room temperature. After 5 minutes, 10% aqueous potassium carbonate solution was added to the reaction mixture and the mixture was extracted with dichloromethane. The organic layer was separated, dried ($MgSO_4$) and evaporated. Purification of the residue by flash chromatography (dichloromethane) gave the title compound (0.11 g, 85%) as a pale orange solid.

LRMS (m/z): 135 $(M+1)^+$.

$^1$H-NMR δ (300 MHz, $CDCl_3$): 3.1 (s, 1H), 4.0 (s, 3H), 6.7 (d, 1H), 8.4 (d, 1H).

Preparation 2

1-Amino-4-cyanopyridinium 2,4,6-trimethylbenzenesulfonate

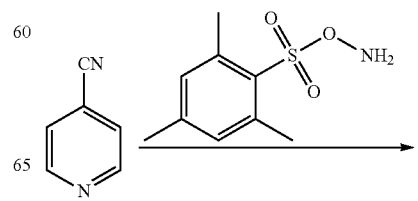

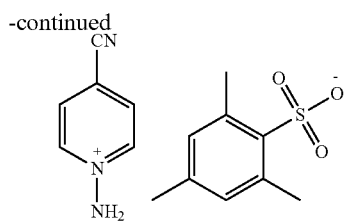

A solution of O-(mesitylsulfonyl)hydroxylamine (prepared as described in *Synthesis*, 1977, 1; 2.17 g, 10.1 mmol) in anhydrous dichloromethane (21 mL) was added dropwise to a stirred solution of isonicotinonitrile (1.05 g, 10.1 mmol) in anhydrous dichloromethane (10 mL) at 0° C. and the mixture was stirred at ambient temperature for 1 hour and 30 minutes. Diethyl ether was then added to the mixture and the precipitate that formed was collected by filtration, washed with diethyl ether and dried in vacuo to give the title compound (3.03 g, 94%) as a white solid.

LRMS (m/z): 120 (M+1)$^+$, 199 (M−1)$^−$.

$^1$H-NMR δ (300 MHz, CD$_3$OD): 2.2 (s, 3H), 2.6 (s, 6H), 6.9 (bs, 2H), 8.3 (d, 1H), 8.9 (d, 1H).

Preparation 3

3-(4-Hydroxypyrimidin-2-yl)pyrazolo[1,5-a]pyridine-5-carbonitrile

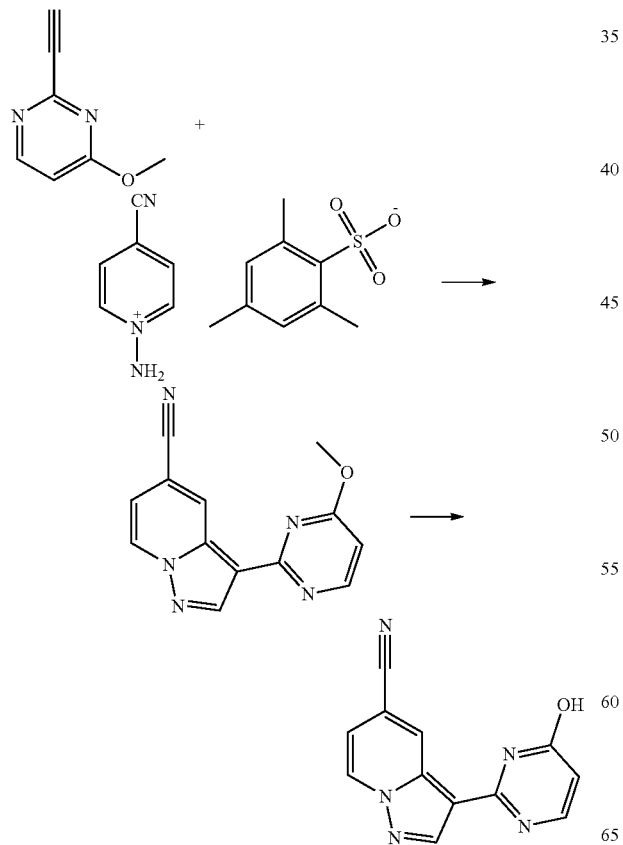

a) 3-(4-Methoxypyrimidin-2-yl)pyrazolo[1,5-a]pyridine-5-carbonitrile

1-Amino-4-cyanopyridinium 2,4,6-trimethylbenzenesulfonate (Preparation 2, 12.10 g, 37.88 mmol) was added in portions over 6 hours to a stirred suspension of 2-ethynyl-4-methoxypyrimidine (Preparation 1b, 2.54 g, 18.94 mmol) and potassium carbonate (3.93 g, 28.43 mmol) in anhydrous N,N'-dimethylformamide (47 mL) at 0° C. and the resulting mixture was stirred at ambient temperature for 48 hours. The solvent was evaporated and dichloromethane was added to the residue. The solid formed was filtered and the filtrate evaporated to dryness. The crude product was purified by flash chromatography (4:1 hexanes/ethyl acetate) to give the title compound (3.51 g, 74%) as a solid.

LRMS (m/z): 252 (M+1)$^+$.

$^1$H-NMR δ (300 MHz, CDCl$_3$): 4.1 (s, 3H), 6.6 (d, 1H), 7.0 (d, 1H), 8.5 (d, 1H), 8.6 (d, 1H), 8.8 (s, 1H), 9.1 (s, 1H).

b) 3-(4-Hydroxypyrimidin-2-yl)pyrazolo[1,5-a]pyridine-5-carbonitrile

Chlorotrimethylsilane (0.61 mL, 4.83 mmol) and sodium iodide (0.72 g, 4.83 mmol) were added to a stirred suspension of 3-(4-methoxypyrimidin-2-yl)pyrazolo[1,5-a]pyridine-5-carbonitrile (Preparation 3a, 0.14 g, 0.54 mmol) in acetonitrile (11 mL) and the mixture was heated at 70° C. in a sealed tube and left overnight. The mixture was then cooled and the solvent evaporated. Water (4 mL) and 10% aqueous sodium thiosulfate solution (5 mL) were added to the residue and the suspension was stirred for 20 minutes. The suspension was filtered and the precipitate was dried in vacuo to give the title compound in quantitative yield which was used in the next synthetic step without further purification.

LRMS (m/z): 238 (M+1)$^+$.

$^1$H-NMR δ (300 MHz, DMSO-d$_6$): 6.3 (d, 1H), 7.5 (d, 1H), 8.1 (d, 1H), 9.0 (s, 1H), 9.1 (s, 1H), 9.1 (d, 1H).

Preparation 4

2-Pyrazolo[1,5-a]pyridin-3-ylpyrimidin-4-ol

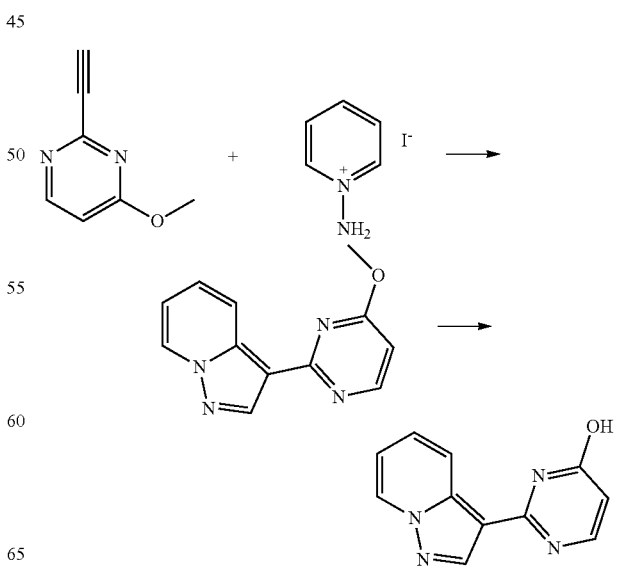

a) 3-(4-Methoxypyrimidin-2-yl)pyrazolo[1,5-a]pyridine

Obtained as a solid (49%) from 2-ethynyl-4-methoxypyrimidine (Preparation 1b) and 1-aminopyridinium iodide following the experimental procedure as described in Preparation 3a followed by purification by flash chromatography (4:1 hexane/ethyl acetate).

LRMS (m/z): 227 (M+1)$^+$.

$^1$H-NMR δ (300 MHz, CDCl$_3$): 4.1 (s, 3H), 6.5 (dd, 1H), 6.9 (t, 1H), 7.4 (dd, 1H), 8.5 (dd, 1H), 8.6 (dd, 1H), 8.6 (d, 1H), 8.7 (s, 1H).

b) 2-Pyrazolo[1,5-a]pyridin-3-ylpyrimidin-4-ol

48% Aqueous hydrogen bromide (19.50 mL) was added to 3-(4-methoxypyrimidin-2-yl) pyrazolo[1,5-a]pyridine (Preparation 4a, 0.30 g, 1.32 mmol) and the resulting mixture was heated to 100° C. with stirring. After 3 hours, the mixture was cooled and the resultant precipitate was filtered and dried in vacuo to give the title compound (0.28 g, 99%) as the hydrobromide salt.

LRMS (m/z): 213 (M+1)$^+$.

Preparation 5

2-Chloro-6-ethynylpyridine

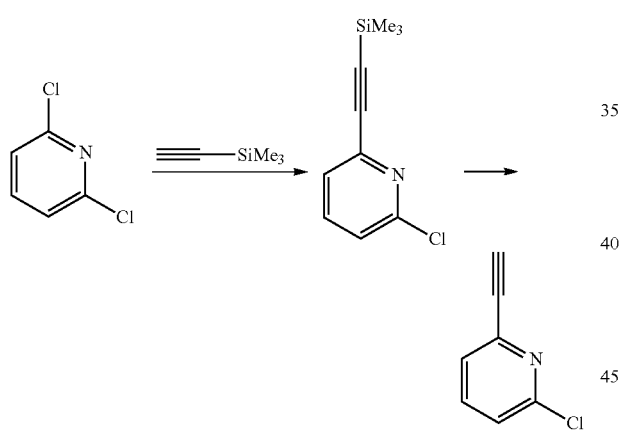

a) 2-Chloro-6-[(trimethylsilyl)ethynyl]pyridine

Obtained as an oil (38%) from 2,6-dichloropyridine and ethynyltrimethylsilane following the experimental procedure as described in Preparation 1a followed by purification by flash chromatography (hexane to 30:1 hexane/ethyl acetate).

LRMS (m/z): 210 (M+1)$^+$.

b) 2-Chloro-6-ethynylpyridine

Obtained as an oil (29%) from 2-chloro-6-[(trimethylsilyl)ethynyl]pyridine (Preparation 5a) following the experimental procedure as described in Preparation 1b followed by purification by flash chromatography (hexane to 10:1 hexane/ethyl acetate).

$^1$H-NMR δ (300 MHz, CDCl$_3$): 3.2 (s, 1H), 7.3 (d, 1H), 7.4 (d, 1H), 7.6 (t, 1H).

Preparation 6

3-(6-Chloropyridin-2-yl)pyrazolo[1,5-a]pyridine-5-carbonitrile

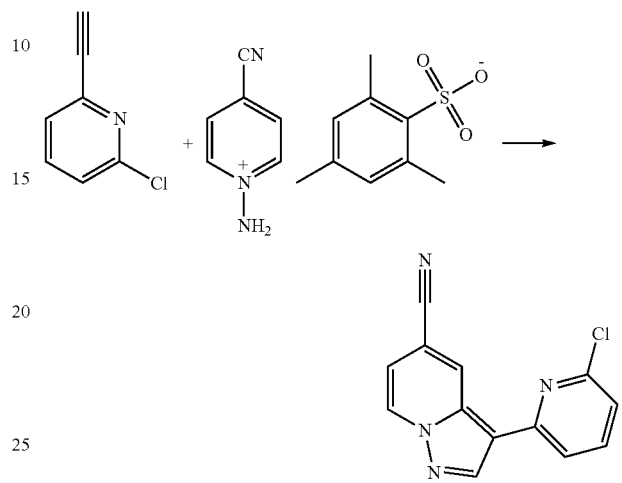

Obtained as a solid (30%) from 2-chloro-6-ethynylpyridine (Preparation 5b) and 1-amino-4-cyanopyridinium 2,4,6-trimethylbenzenesulfonate (Preparation 2) following the experimental procedure as described in Preparation 3a followed by purification by flash chromatography (99:1 dichloromethane/methanol).

LRMS (m/z): 255 (M+1)$^+$.

$^1$H-NMR δ (300 MHz, CDCl$_3$): 6.9-7.1 (m, 1H), 7.2-7.3 (m, 1H), 7.5-7.8 (m, 2H), 8.4-8.7 (m, 2H), 9.0-9.1 (m, 1H).

Preparation 7

3-{4-[(3R)-Piperidin-3-ylamino]pyrimidin-2-yl}pyrazolo[1,5-a]pyridine-5-carbonitrile

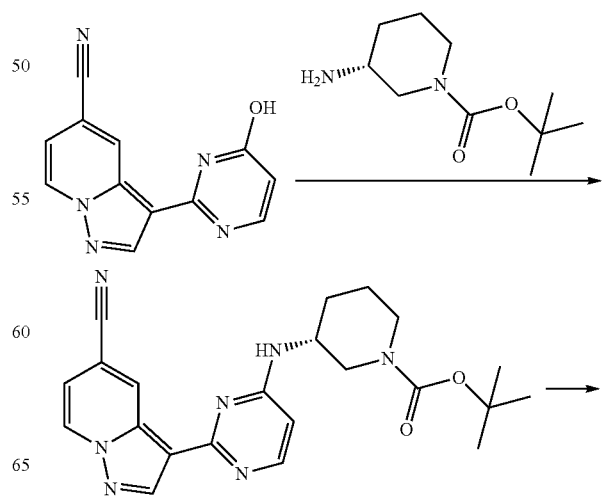

-continued

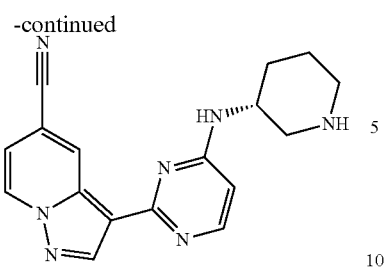

a) Tert-butyl (3R)-3-{[2-(5-cyanopyrazolo[1,5-a]pyridin-3-yl)pyrimidin-4-yl]amino}piperidine-1-carboxylate Tert-butyl (3R)-3-aminopiperidine-1-carboxylate (1.49 g, 7.46 mmol) was added to a stirred solution of 3-(4-hydroxypyrimidin-2-yl)pyrazolo[1,5-a]pyridine-5-carbonitrile (Preparation 3b, 0.70 g, 2.98 mmol), (benzotriazol-1-yloxy)tris(dimethylamino)phosphonium hexafluorophosphate (1.71 g, 3.88 mmol) and 1,8-diazabicyclo[5.4.0]undec-7-ene (0.67 mL g, 4.48 mmol) in N,N'-dimethylformamide (15 mL) and the resulting mixture was stirred at room temperature for 16 hours. Then the solvent was removed under reduced pressure and the residue was taken up in a mixture of dichloromethane and 4% aqueous sodium hydrogencarbonate solution. The organic layer was separated, dried (MgSO$_4$) and evaporated in vacuo. The crude product was purified by flash chromatography (99:1 dichloromethane/methanol) to give a residue that was repurified by reverse phase chromatography (C-18 silica from Waters, water/acetonitrile/methanol as eluents [0.1% v/v formic acid buffered] 0% to 100%) to give the title compound (0.83 g, 66%) and 3-(4-(1H-benzo[d][1,2,3]triazol-1-yloxy) pyrimidin-2-yl)pyrazolo[1,5-a]pyridine-5-carbonitrile (0.10 g) as the main reaction byproduct.

LRMS (m/z): 420 (M+1)$^+$, 418 (M−1)$^−$.

$^1$H-NMR δ (300 MHz, CDCl$_3$): 0.7-0.9 (m, 4H), 1.5 (s, 9H), 1.6-1.7 (m, 2H), 1.7-1.9 (m, 2H), 2.0-2.1 (m, 1H), 5.0 (bs, 1H), 6.3 (d, 1H), 7.0 (dd, 1H), 8.3 (d, 1H), 8.6 (d, 1H), 8.8 (s, 1H), 9.1 (t, 1H).

b) 3-{4-[(3R)-Piperidin-3-ylamino]pyrimidin-2-yl}pyrazolo[1,5-a]pyridine-5-carbonitrile Trifluoroacetic acid (0.61 mL, 7.97 mmol) was added to a stirred solution of (R)-tert-butyl 3-(2-(5-cyanopyrazolo[1,5-a]pyridin-3-yl)pyrimidin-4-ylamino)piperidine-1-carboxylate (Preparation 7a, 0.12 g, 0.27 mmol) in dichloromethane (4 mL) and the mixture was stirred at room temperature for 4 hours. 4% Aqueous sodium hydrogencarbonate solution and solid sodium hydrogencarbonate were then added until the pH was basic and the mixture was further extracted with more dichloromethane. The organic layer was separated, dried (MgSO$_4$) and evaporated to give the title compound (0.06 g, 62%) as a pale yellow solid which was used in the next synthetic step without further purification.

LRMS (m/z): 320 (M+1)$^+$, 318 (M−1)$^−$.

$^1$H-NMR δ (300 MHz, CDCl$_3$): 0.8-0.9 (m, 4H), 1.5 (s, 9H), 1.8-2.3 (m, 5H), 5.7 (bs, 1H), 6.3 (d, 1H), 7.0 (dd, 1H), 8.2 (d, 1H), 8.6 (d, 1H), 8.7 (s, 1H), 9.1 (bs, 1H).

Preparation 8

(R)-3-(4-(Methyl(piperidin-3-yl)amino)pyrimidin-2-yl)pyrazolo[1,5-a]pyridine-5-carbonitrile

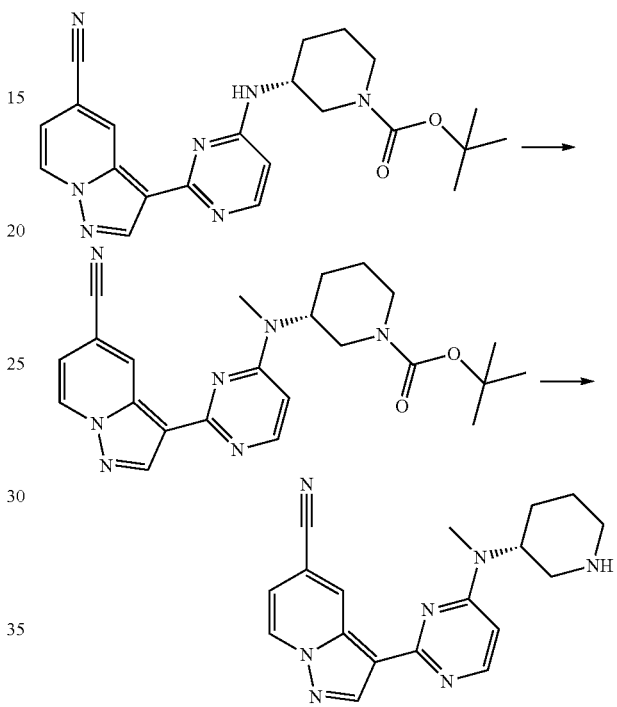

a) (R)-Tert-butyl 3-((2-(5-cyanopyrazolo[1,5-a]pyridin-3-yl)pyrimidin-4-yl)(methyl)amino)piperidine-1-carboxylate Sodium hydride (60% dispersion in mineral oil, 102 mg, 2.55 mmol) was added to a cooled (0° C.) solution of tert-butyl (3R)-3-{[2-(5-cyanopyrazolo[1,5-a]pyridin-3-yl) pyrimidin-4-yl]amino}piperidine-1-carboxylate (Preparation 7a, 0.83 g, 1.98 mmol) in NIP-dimethylformamide (5 mL) and the reaction mixture was stirred at the same temperature for 30 minutes. Methyl iodide (0.135 mL, 2.17 mmol) was then added and the reaction mixture was stirred at room temperature for 2 hours. The solvent was concentrated in vacuo and the residue was partitioned between water and ethyl acetate. The organic layer was separated, washed with water and brine, dried (MgSO$_4$) and the solvent was evaporated to give the title compound (0.39 g, 80%) as a beige solid.

LRMS (m/z): 434 (M+1)$^+$.

b) (R)-3-(4-(Methyl(piperidin-3-yl)amino)pyrimidin-2-yl)pyrazolo[1,5-a]pyridine-5-carbonitrile Obtained as a pale orange solid (77%) from (R)-tert-butyl 3-((2-(5-cyanopyrazolo[1,5-a]pyridin-3-yl)pyrimidin-4-yl)(methyl)amino)piperidine-1-carboxylate (Preparation 8a) following the experimental procedure as described in Preparation 7b.

LRMS (m/z): 334 (M+1)+.
1H-NMR δ (400 MHz, DMSO-d6): 1.5-1.9 (m, 5H), 2.3-2.5 (m, 2H), 2.7 (t, 1H), 2.8-3.1 (m, 5H), 6.6 (bs, 1H), 7.3 (dd, 1H), 8.3 (d, 1H), 8.8 (s, 1H), 8.9-9.0 (m, 2H).

Preparation 9

1-Aminopyrazin-1-ium 2,4,6-trimethylbenzenesulfonate

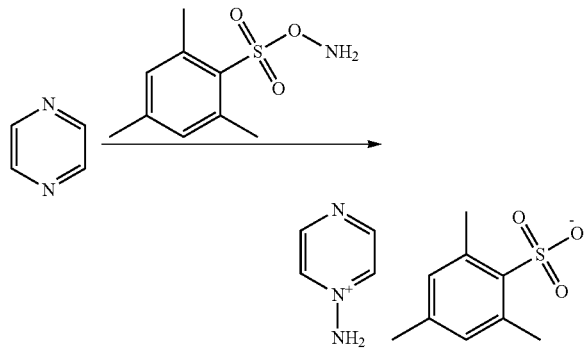

Obtained as a white solid (75%) from pyrazine and O-(mesitylsulfonyl)hydroxylamine (prepared as described in *Synthesis*, 1977, 1) following the experimental procedure as described in Preparation 2.

1H-NMR δ (400 MHz, DMSO-d6): 2.2 (s, 3H), 2.5 (s, 6H), 6.8 (s, 2H), 8.7 (d, 2H), 9.2 (d, 2H), 9.6 (s, 2H).

Preparation 10

2-(Pyrazolo[1,5-a]pyrazin-3-yl)pyrimidin-4-ol

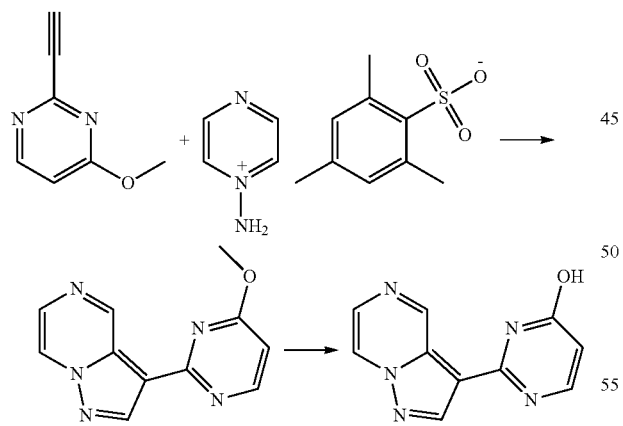

a) 3-(4-Methoxypyrimidin-2-yl)pyrazolo[1,5-a]pyrazine

Obtained as a solid (43%) from 2-ethynyl-4-methoxypyrimidine (Preparation 1b) and 1-aminopyrazin-1-ium 2,4,6-trimethylbenzenesulfonate (Preparation 9) following the experimental procedure as described in Preparation 3a.

LRMS (m/z): 228 (M+1)+.

1H-NMR δ (400 MHz, CDCl3): 4.1 (s, 3H), 6.6 (d, 1H), 8.0 (d, 1H), 8.4 (dd, 1H), 8.5 (d, 1H), 8.8 (s, 1H), 10.0 (s, 1H).

b) 2-(Pyrazolo[1,5-a]pyrazin-3-yl)pyrimidin-4-ol

Obtained (83%) from 3-(4-methoxypyrimidin-2-yl)pyrazolo[1,5-a]pyrazine (Preparation 10a) following the experimental procedure as described in Preparation 4b.

LRMS (m/z): 214 (M+1)+, 212 (M−1)−.

1H-NMR δ (300 MHz, DMSO-d6): 6.4 (d, 1H), 8.2 (d, 1H), 8.2 (s, 1H), 9.0 (dd, 1H), 9.0 (s, 1H), 9.9 (d, 1H).

Preparation 11

(R)—N-(Piperidin-3-yl)-2-(pyrazolo[1,5-a]pyrazin-3-yl)pyrimidin-4-amine

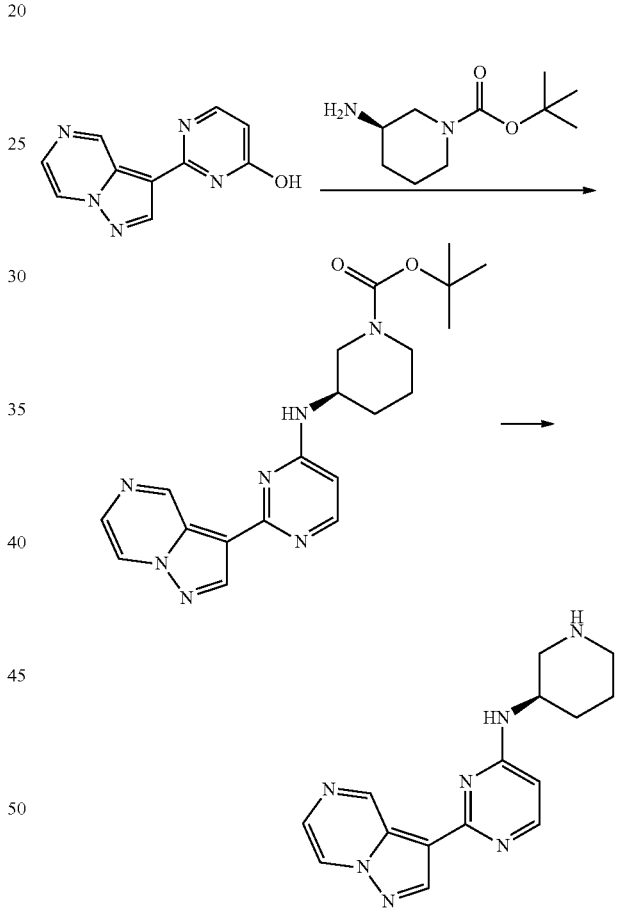

a) (R)-Tert-butyl 3-(2-(pyrazolo[1,5-a]pyrazin-3-yl)pyrimidin-4-ylamino)piperidine-1-carboxylate Obtained (50%) from 2-(pyrazolo[1,5-a]pyrazin-3-yl)pyrimidin-4-ol (Preparation 10b) and tert-butyl (3R)-3-aminopiperidine-1-carboxylate following the experimental procedure as described in Preparation 7a followed by purification by flash chromatography (dichloromethane to 97:3 dichloromethane/methanol).

LRMS (m/z): 396 (M+1)+.

b) (R)—N-(Piperidin-3-yl)-2-(pyrazolo[1,5-a]pyrazin-3-yl)pyrimidin-4-amine

Obtained (91%) from (R)-tert-butyl 3-(2-(pyrazolo[1,5-a]pyrazin-3-yl)pyrimidin-4-ylamino)piperidine-1-carboxylate (Preparation 11a) and trifluoroacetic acid following the experimental procedure as described in Preparation 7b.

LRMS (m/z): 296 (M+1)+.

$^1$H-NMR δ (400 MHz, CDCl$_3$): 1.6-1.7 (m, 2H), 1.7-1.9 (m, 3H), 2.7-3.0 (m, 4H), 3.2-3.3 (m, 1H), 5.5 (bs, 1H), 6.2 (d, 1H), 8.0 (d, 1H), 8.2 (d, 1H), 8.4 (dd, 1H), 8.7 (s, 1H), 10.0 (s, 1H).

Preparation 12

N-Methyl-N-[(3R)-piperidin-3-yl]-2-pyrazolo[1,5-a]pyrazin-3-ylpyrimidin-4-amine

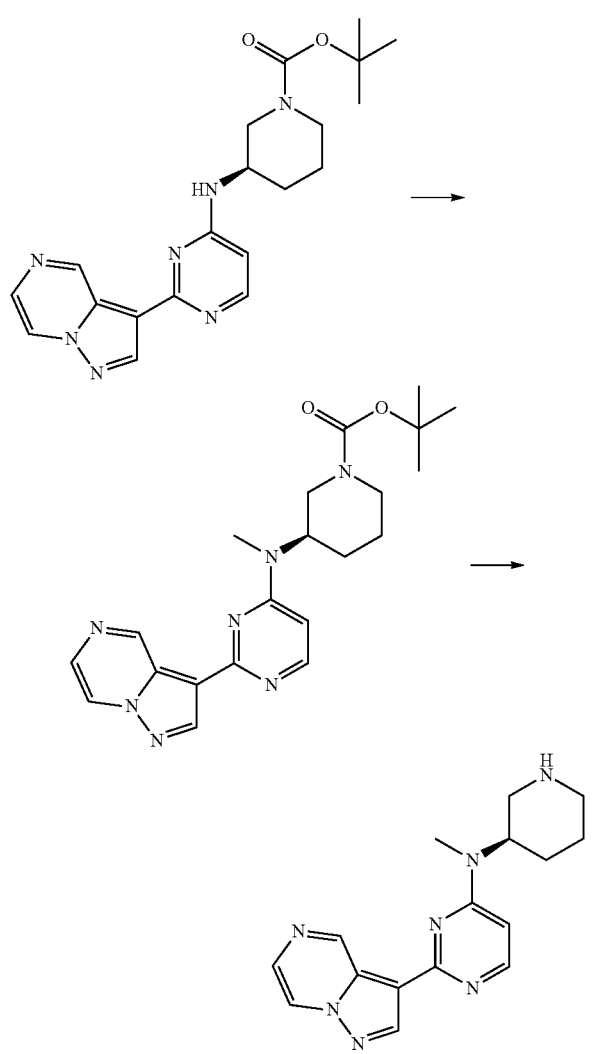

a) Tert-butyl (3R)-3-[methyl(2-pyrazolo[1,5-a]pyrazin-3-ylpyrimidin-4-yl)amino]piperidine-1-carboxylate Obtained (9%) from (R)-tert-butyl 3-(2-(pyrazolo[1,5-a]pyrazin-3-yl)pyrimidin-4-ylamino) piperidine-1-carboxylate (Preparation 11a) and methyl iodide following the experimental procedure as described in Preparation 8a followed by purification by reverse phase chromatography (C-18 silica from Waters, water/acetonitrile/methanol as eluents [0.1% v/v formic acid buffered] 5% to 50%).

LRMS (m/z): 410 (M+1)$^4$.

b) N-Methyl-N-[(3R)-piperidin-3-yl]-2-pyrazolo[1,5-a]pyrazin-3-ylpyrimidin-4-amine Obtained (94%) from tert-butyl (3R)-3-[methyl(2-pyrazolo[1,5-a]pyrazin-3-ylpyrimidin-4-yl)amino]piperidine-1-carboxylate (Preparation 12a) and trifluoroacetic acid following the experimental procedure as described in Preparation 7b.

LRMS (m/z): 310 (M+1)+.

Preparation 13

5-Chloro-2-ethynyl-4-methoxypyrimidine

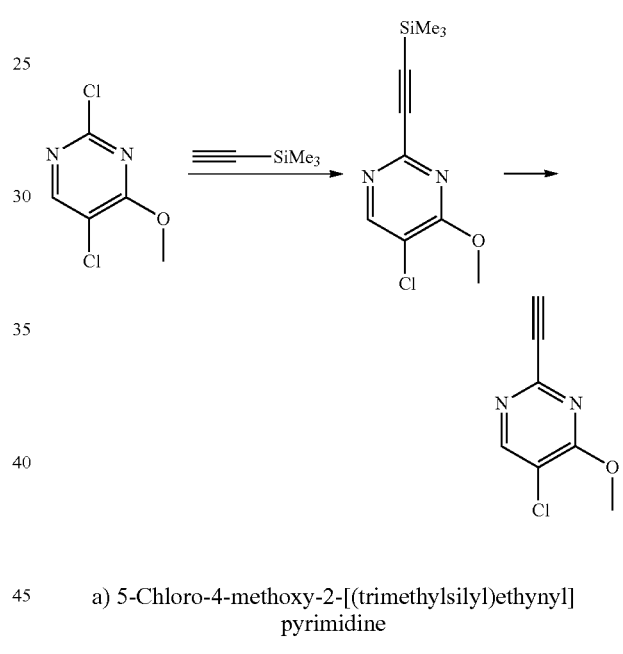

a) 5-Chloro-4-methoxy-2-[(trimethylsilyl)ethynyl]pyrimidine

Obtained (44%) from 2,5-dichloro-4-methoxypyrimidine (prepared as described in *Tetrahedron Lett.* 2006, 47, 4415) and ethynyltrimethylsilane following the experimental procedure as described in Preparation 1a followed by purification by flash chromatography (dichloromethane to 4:6 dichloromethane/hexane).

LRMS (m/z): 241 (M+1)+.

$^1$H-NMR δ (300 MHz, CDCl$_3$): 0.1 (bs, 9H), 3.8 (bs, 3H), 8.1 (s, 1H).

b) 5-Chloro-2-ethynyl-4-methoxypyrimidine

Obtained as a grey solid (78%) from 5-chloro-4-methoxy-2-((trimethylsilyl)ethynyl) pyrimidine (Preparation 13a) following the experimental procedure as described in Preparation 1b followed by purification by flash chromatography (9:1 hexane/ethyl acetate).

LRMS (m/z): 169 (M+1)+.

$^1$H-NMR δ (300 MHz, CDCl$_3$): 3.1 (s, 1H), 4.1 (s, 3H), 8.4 (s, 1H).

Preparation 14

5-Chloro-2-pyrazolo[1,5-a]pyrazin-3-ylpyrimidin-4-ol

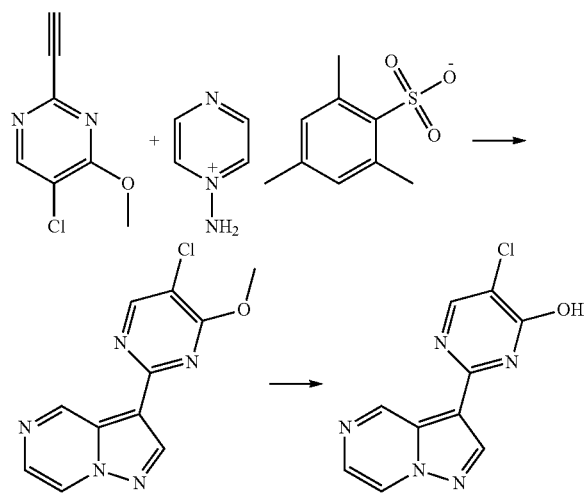

a) 3-(5-Chloro-4-methoxypyrimidin-2-yl)pyrazolo[1,5-a]pyrazine

Obtained as an orange solid (84%) from 5-chloro-2-ethynyl-4-methoxypyrimidine (Preparation 13b) and 1-aminopyrazin-1-ium trimethylbenzene sulfonate (Preparation 9) following the experimental procedure as described in preparation 3a followed by purification by flash chromatography (dichloromethane to 7:3 dichloromethane/methanol).

LRMS (m/z): 262 (M+1)$^+$.

$^1$H-NMR δ (300 MHz, CDCl$_3$): 4.2 (s, 3H), 8.0 (d, 1H), 8.5 (d, 1H), 8.5 (s, 1H), 8.7 (s, 1H), 10.0 (s, 1H).

b) 5-Chloro-2-pyrazolo[1,5-a]pyrazin-3-ylpyrimidin-4-ol

Obtained as a green solid (62%) from 3-(5-chloro-4-methoxypyrimidin-2-yl)pyrazolo[1,5-a]pyrazine (Preparation 14a) following the experimental procedure as described in Preparation 4b.

Preparation 15

5-Chloro-N-[(3R)-piperidin-3-yl]-2-pyrazolo[1,5-a]pyrazin-3-ylpyrimidin-4-amine

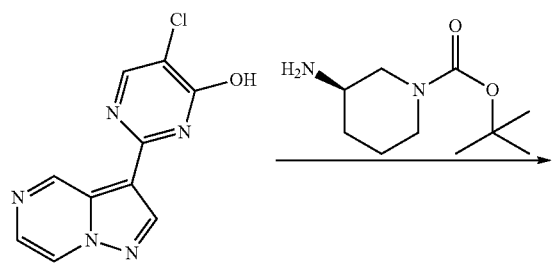

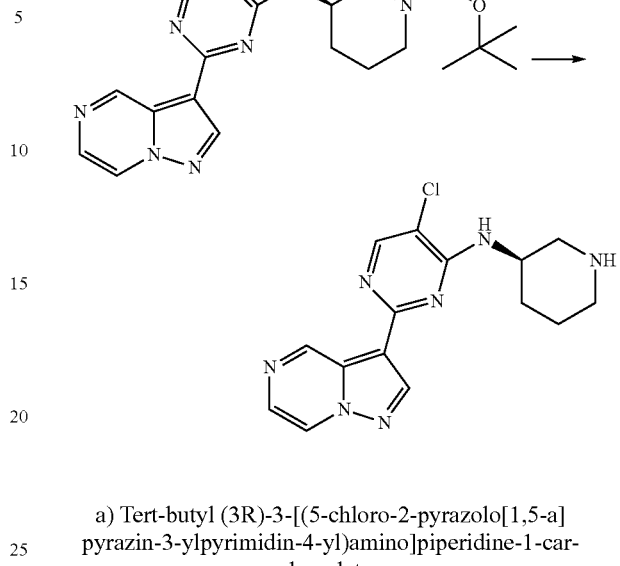

a) Tert-butyl (3R)-3-[(5-chloro-2-pyrazolo[1,5-a]pyrazin-3-ylpyrimidin-4-yl)amino]piperidine-1-carboxylate Obtained as a yellow solid (40%) from 5-chloro-2-(pyrazolo[1,5-a]pyrazin-3-yl) pyrimidin-4-ol (Preparation 14b) and (R)-tert-butyl 3-aminopiperidine 1-carboxylate following the experimental procedure as described in Preparation 7a followed by purification by flash chromatography (hexane to 6:4 hexane/ethyl acetate).

LRMS (m/z): 430 (M+1)$^+$.

$^1$H-NMR δ (300 MHz, CDCl$_3$): 1.4 (bs, 9H), 1.7 (bs, 3H), 1.9-2.1 (m, 2H), 3.4 (bs, 1H), 3.7 (bs, 2H), 4.3 (bs, 1H), 5.6 (bs, 1H), 8.0 (d, 1H), 8.3 (s, 1H), 8.4 (d, 1H), 8.7 (s, 1H), 9.9 (s, 1H).

b) 5-Chloro-N-[(3R)-piperidin-3-yl]-2-pyrazolo[1,5-a]pyrazin-3-ylpyrimidin-4-amine Obtained as a yellow solid (87%) from tert-butyl 3-(5-chloro-2-(pyrazolo[1,5-a]pyrazin-3-yl)pyrimidin-4-ylamino)piperidine-1-carboxylate (Preparation 15a) and trifluoroacetic acid following the experimental procedure as described in Preparation 7b.

LRMS (m/z): 330 (M+1)$^+$.

$^1$H-NMR δ (300 MHz, CDCl$_3$): 1.3 (bs, 2H), 1.9 (bs, 3H), 2.9 (bs, 3H), 3.2-3.3 (m, 1H), 4.4 (bs, 1H), 5.9 (bs, 1H), 8.0 (d, 1H), 8.2 (s, 1H), 8.4 (d, 1H), 8.7 (s, 1H), 9.9 (s, 1H).

Preparation 16

2-Ethynyl-5-fluoro-4-methoxypyrimidine

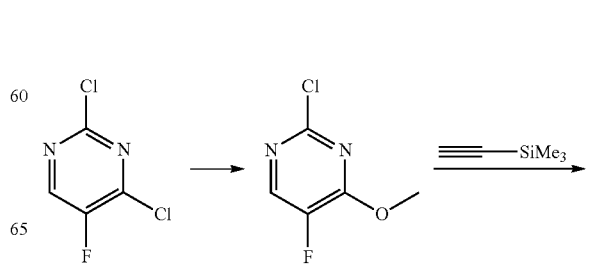

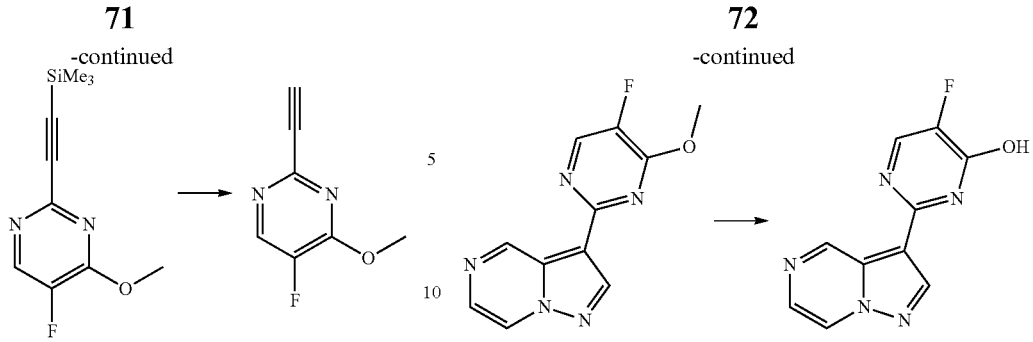

a) 2-Chloro-5-fluoro-4-methoxypyrimidine

To a mixture of sodium (450 mg, 19 mmol) in methanol (20 mL) was added a solution of 2,4-dichloro-5-fluoropyrimidine (3.25 g, 19 mmol) in methanol (10 mL). The reaction mixture was stirred at room temperature overnight before being partitioned between water and diethyl ether. The organic phase was separated, washed with brine and evaporated to dryness to give the title compound as an orange oil (80%), which was used in the next step without further purification.

$^1$H-NMR δ (400 MHz, CDCl$_3$): 4.1 (s, 3H), 8.2 (s, 1H).

b) 5-Fluoro-4-methoxy-2-[(trimethylsilyl)ethynyl]pyrimidine

Obtained (17%) from 2-chloro-5-fluoro-4-methoxypyrimidine (Preparation 16a) and ethynyltrimethylsilane following the experimental procedure as described in Preparation 1a followed by purification by flash chromatography (2:8 hexane/dichloromethane to 100% dichloromethane).

LRMS (m/z): 225 (M+1)$^+$.

$^1$H-NMR δ (400 MHz, CDCl$_3$): 0.1 (s, 9H), 3.8 (s, 3H), 8.0 (d, 1H).

c) 2-Ethynyl-5-fluoro-4-methoxypyrimidine

Obtained (82%) from 5-fluoro-4-methoxy-2-((trimethylsilyl)ethynyl)pyrimidine (Preparation 16b) following the experimental procedure as described in Preparation 1b followed by purification by flash chromatography (99:1 dichloromethane/methanol).

$^1$H-NMR δ (400 MHz, CDCl$_3$): 3.1 (d, 1H), 4.1 (s, 3H), 8.3 (d, 1H).

Preparation 17

5-Fluoro-2-pyrazolo[1,5-a]pyrazin-3-ylpyrimidin-4-ol

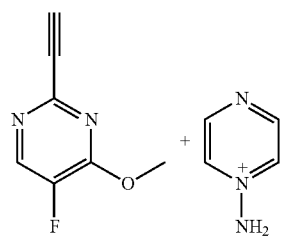

a) 3-(5-Fluoro-4-methoxypyrimidin-2-yl)pyrazolo[1,5-a]pyrazine

Obtained (72%) from 2-ethynyl-5-fluoro-4-methoxypyrimidine (Preparation 16c) and 1-aminopyrazin-1-ium 2,4,6-trimethylbenzenesulfonate (Preparation 9) following the experimental procedure as described in Preparation 3a followed by purification by flash chromatography (dichloromethane to 97:3 dichloromethane/methanol).

LRMS (m/z): 246 (M+1)$^+$.

$^1$H-NMR δ (400 MHz, CDCl$_3$): 4.2 (s, 3H), 8.0 (d, 1H), 8.4 (d, 1H), 8.4 (dd, 1H), 8.7 (s, 1H), 10.0 (d, 1H).

b) 5-Fluoro-2-pyrazolo[1,5-a]pyrazin-3-ylpyrimidin-4-ol

Aqueous hydrogen chloride (13 mL of a 6N solution, 78 mmol) was added to 3-(5-fluoro-4-methoxypyrimidin-2-yl)pyrazolo[1,5-a]pyrazine (Preparation 17a, 0.38 g, 1 mmol) in a microwave vessel. The resulting mixture was subjected to microwave irradiation for 1 hour at 120° C. After cooling to room temperature, 8N aqueous sodium hydroxide solution was added until a basic pH was reached. The solid formed was filtered and dried to yield the title compound (72%), which was used in the next step without further purification.

LRMS (m/z): 232 (M+1)$^+$.

$^1$H-NMR δ (400 MHz, DMSO-d$_6$): 8.1-8.2 (m, 3H), 9.0 (bs, 1H), 9.8 (bs, 1H).

Preparation 18

5-Fluoro-N-[(3R)-piperidin-3-yl]-2-pyrazolo[1,5-a]pyrazin-3-ylpyrimidin-4-amine

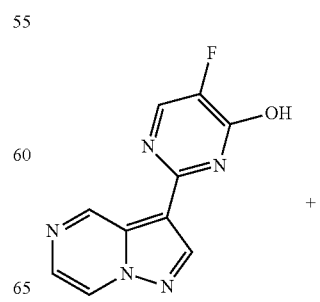

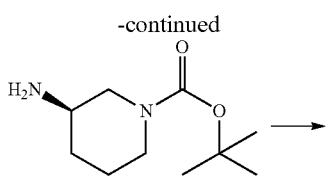

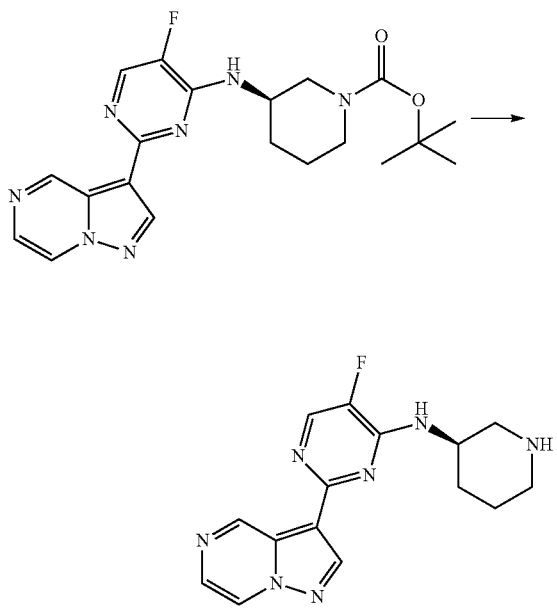

a) Tert-butyl (3R)-3-[(5-fluoro-2-pyrazolo[1,5-a]pyrazin-3-ylpyrimidin-4-yl)amino]piperidine-1-carboxylate Obtained as a white solid (50%) from 5-fluoro-2-(pyrazolo[1,5-a]pyrazin-3-yl)pyrimidin-4-ol (Preparation 17b) and tert-butyl (3R)-3-aminopiperidine-1-carboxylate following the experimental procedure as described in Preparation 7a followed by purification by flash chromatography (dichloromethane to 95:5 dichloromethane/methanol).

LRMS (m/z): 414 (M+1)$^+$.

$^1$H-NMR δ (400 MHz, CDCl$_3$): 1.4-1.5 (m, 2H), 1.7 (s, 9H), 1.8 (m, 1H), 1.9-2.0 (m, 1H), 2.0-2.1, (m, 1H), 3.4 (bs, 1H), 3.6 (bs, 1H), 3.7 (bs, 1H), 4.3-4.4 (m, 1H), 8.0 (d, 1H), 8.1 (d, 1H), 8.4 (dd, 1H), 8.7 (s, 1H), 9.9 (d, 1H).

b) 5-Fluoro-N-[(3R)-piperidin-3-yl]-2-pyrazolo[1,5-a]pyrazin-3-ylpyrimidin-4-amine Obtained as a solid (94%) from (R)-tert-butyl 3-(5-fluoro-2-(pyrazolo[1,5-a]pyrazin-3-yl) pyrimidin-4-ylamino)piperidine-1-carboxylate (Preparation 18a) and trifluoroacetic acid following the experimental procedure as described in Preparation 7b followed by purification by flash chromatography (dichloromethane to 92:8 dichloromethane/methanol).

LRMS (m/z): 314 (M+1)$^+$.

$^1$H-NMR δ (400 MHz, CDCl$_3$): 1.6 (m, 1H), 1.7-1.9 (m, 2H), 2.0 (m, 1H), 2.1 (bs, 1H), 2.8-2.9 (m, 2H), 3.3 (bs, 1H), 4.3-4.4 (m, 1H), 5.7 (d, 1H), 8.0 (d, 1H), 8.1 (d, 1H), 8.4 (dd, 1H), 8.6 (s, 1H), 9.9 (d, 1H).

Preparation 19

2-Ethynyl-4-methoxy-5-methylpyrimidine

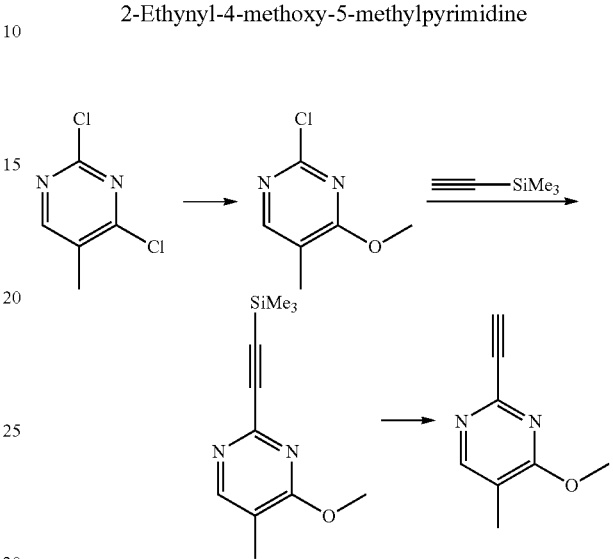

a) 2-Chloro-4-methoxy-5-methylpyrimidine

Obtained as a white solid (85%) from 2,4-dichloro-5-methylpyrimidine following the experimental procedure as described in Preparation 16a followed by purification by flash chromatography (hexane to 95:5 hexane/ethyl acetate).

LRMS (m/z): 159 (M+1)$^+$.

$^1$H-NMR δ (400 MHz, CDCl$_3$): 2.1 (d, 3H), 4.0 (s, 3H), 8.1 (d, 1H).

b) 4-Methoxy-5-methyl-2-[(trimethylsilyl)ethynyl]pyrimidine

Obtained as a yellow solid (19%) from 2-chloro-4-methoxy-5-methylpyrimidine (Preparation 19a) and ethynyltrimethylsilane following the experimental procedure as described in Preparation 1a followed by purification by flash chromatography (hexane to 93:7 hexane/diethyl ether).

LRMS (m/z): 221 (M+1)$^+$.

$^1$H-NMR δ (400 MHz, CDCl$_3$): 0.1 (s, 9H), 1.9 (d, 3H), 3.7 (s, 3H), 7.9 (s, 1H).

c) 2-Ethynyl-4-methoxy-5-methylpyrimidine

Obtained as a white solid (55%) from 4-methoxy-5-methyl-2-((trimethylsilyl)ethynyl) pyrimidine (Preparation 19b) following the experimental procedure as described in Preparation 1b followed by purification by flash chromatography (dichloromethane).

LRMS (m/z): 149 (M+1)$^+$.

$^1$H-NMR δ (400 MHz, CDCl$_3$): 2.2 (s, 3H), 3.0 (s, 1H), 4.0 (s, 3H), 8.2 (s, 1H).

Preparation 20

3-(4-Methoxy-5-methylpyrimidin-2-yl)pyrazolo[1,5-a]pyrazine

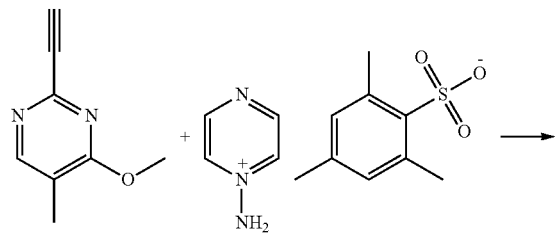

a) 3-(4-Methoxy-5-methylpyrimidin-2-yl)pyrazolo[1,5-a]pyrazine

Obtained as a yellow solid (99%) from 2-ethynyl-4-methoxy-5-methylpyrimidine (Preparation 19c) and 1-aminopyrazin-1-ium 2,4,6-trimethylbenzene sulfonate (Preparation 9) following the experimental procedure as described in Preparation 3a followed by purification by flash chromatography (dichloromethane to 95:5 dichloromethane/methanol).

LRMS (m/z): 242 (M4-1)$^+$.

$^1$H-NMR δ (400 MHz, CDCl$_3$): 3.0 (s, 3H), 4.2 (s, 3H), 8.0 (d, 1H), 8.3 (d, 1H), 8.4 (dd, 1H), 8.7 (s, 1H), 10.0 (d, 1H).

b) 3-(4-Methoxy-5-methylpyrimidin-2-yl)pyrazolo[1,5-a]pyrazine

35% Aqueous potassium hydroxide solution (5 mL) was added to a solution of 3-(4-methoxy-5-methylpyrimidin-2-yl)pyrazolo[1,5-a]pyrazine (Preparation 20a, 0.70 g, 2.89 mmol) in ethanol (10 mL). The mixture was placed in a microwave vessel and was subjected to microwave irradiation for 1 hour at 130° C. After cooling to room temperature, the organic solvent was removed under reduced pressure and the residue was acidified with 5N aqueous hydrogen chloride solution. The solid formed was filtered, washed with water and dried to give the title compound (64%) as a brown solid.

LRMS (m/z): 228 (M+1)$^+$.

$^1$H-NMR δ (400 MHz, DMSO-d$_6$): 3.3 (bs, 3H), 8.0 (bs, 1H), 8.1 (bs, 1H), 9.0 (bs, 2H), 9.8 (bs, 1H).

Preparation 21

5-Methyl-N-[(3R)-piperidin-3-yl]-2-pyrazolo[1,5-a]pyrazin-3-ylpyrimidin-4-amine

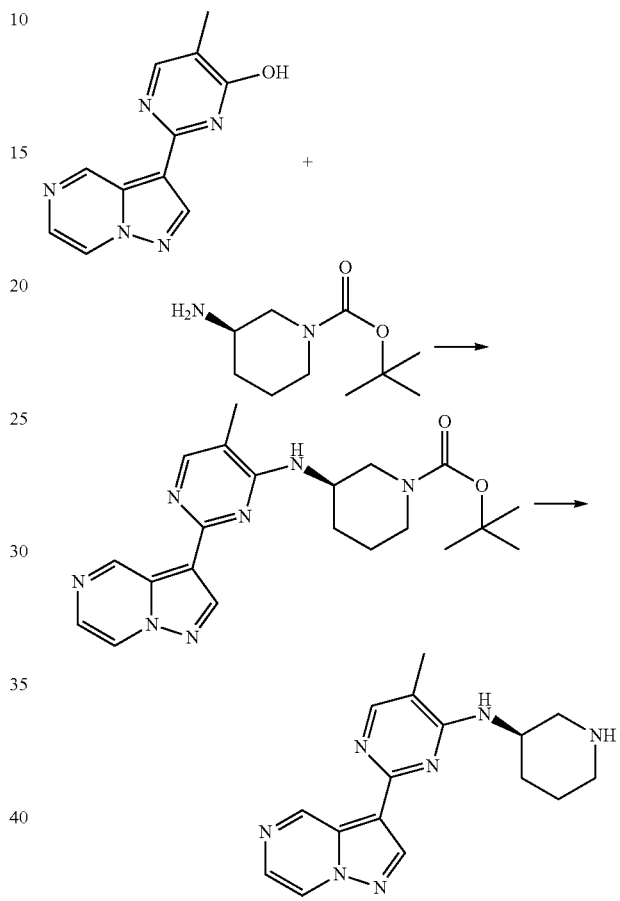

a) Tert-butyl (3R)-3-[(5-methyl-2-pyrazolo[1,5-a]pyrazin-3-ylpyrimidin-4-yl)amino]piperidine-1-carboxylate Obtained as a yellow oil (58%) from 5-methyl-2-(pyrazolo[1,5-a]pyrazin-3-yl)pyrimidin-4-ol (Preparation 20b) and tert-butyl (3R)-3-aminopiperidine-1-carboxylate following the experimental procedure as described in Preparation 7a followed by purification by flash chromatography (hexane to 30:70 hexane/ethyl acetate).

LRMS (m/z): 410 (M+1)$^+$.

$^1$H-NMR δ (400 MHz, DMSO-d$_6$) δ 1.2 (bs, 1H), 1.4 (bs, 1H), 1.7 (bs, 1H), 1.8 (bs, 1H), 2.1 (s, 6H), 2.0 (s, 3H), 2.8-2.9 (m, 1H), 3.4 (s, 3H), 3.9 (bs, 2H), 4.0 (q, 1H), 4.1 (bs, 1H), 8.0 (d, 1H), 8.1 (s, 1H), 8.9 (bs, 2H), 9.8 (s, 1H).

b) 5-Methyl-N-[(3R)-piperidin-3-yl]-2-pyrazolo[1,5-a]pyrazin-3-ylpyrimidin-4-amine Obtained as a yellow oil (85%) from (R)-tert-butyl 3-(5-methyl-2-(pyrazolo[1,5-a]pyrazin-3-yl)pyrimidin-4-ylamino)piperidine-1-carboxylate (Preparation 21a) and trifluoroacetic acid following the experimental procedure as described in Preparation 7b.

LRMS (m/z): 310 (M+1)+.
1H-NMR δ (400 MHz, CDCl3): 1.6 (bs, 2H), 1.8 (bs, 2H), 2.1 (s, 3H), 2.7-2.9 (m, 1H), 3.2-3.3 (m, 2H), 4.4 (bs, 2H), 7.9 (d, 1H), 8.0 (s, 1H), 8.4 (d, 1H), 8.7 (s, 1H), 10.0 (s, 1H).

Preparation 22

3-Bromopyrazolo[1,5-a]pyridine

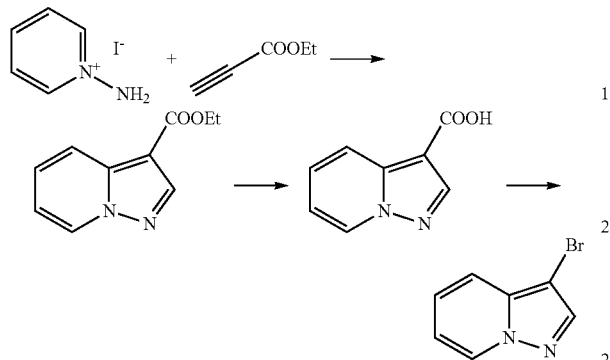

a) Ethyl pyrazolo[1,5-a]pyridine-3-carboxylate

Ethyl propionate (50.2 mL, 49.54 mmol) and 1-aminopyridinium iodide (10.0 g, 45 mmol) were added to a suspension of potassium carbonate (8.71 g, 63.02 mmol) in N,N'-dimethylformamide (100 mL) and the resulting mixture was stirred at room temperature for 2 h before being poured into 100 mL of water. Ethyl acetate was then added and the aqueous layer was separated and washed with ethyl acetate (×2). The combined organic layers were dried over magnesium sulphate, filtered and evaporated. The crude product was purified by flash chromatography (hexanes to 4:1 hexanes/ethyl acetate) to give the title compound (4.30 g, 50%) as an orange solid.

LRMS (m/z): 191 (M+1)+.
1H-NMR δ (250 MHz, CDCl3): 1.4 (t, 3H), 4.3 (q, 2H), 6.9 (t, 1H), 7.4 (t, 1H), 8.1 (s, 1H), 8.4 (s, 1H), 8.5 (d, 1H).

b) Pyrazolo[1,5-a]pyridine-3-carboxylic acid

A 2.5 N aqueous solution of sodium hydroxide (36 mL) was added to a solution of ethyl pyrazolo[1,5-a]pyridine-3-carboxylate (Preparation 22a, 4.3 g, 22.6 mmol) in ethanol (70 mL) and the resulting reaction mixture was heated to reflux for 1 h. After evaporation of the ethanol, the reaction mixture was acidified with 15% aqueous hydrochloric acid solution. The solid formed was filtered, washed with water and diethyl ether and dried to give the title compound (2.81 g, 77%) as a pale pink solid.

LRMS (m/z): 163 (M+1)+.
1H-NMR δ (250 MHz, DMSO-d6): 7.1 (t, 1H), 7.6 (t, 1H), 8.1 (dd, 1H), 8.4 (s, 1H), 8.9 (d, 1H), 12.5 (s, 1H).

c) 3-Bromopyrazolo[1,5-a]pyridine

N-Bromosuccinimide (3.06 g, 17.22 mmol) and sodium hydrogen carbonate (4.34 g, 51.66 mmol) were added to a solution of pyrazolo[1,5-a]pyridine-3-carboxylic acid (Preparation 22b, 2.81 g, 17.22 mmol) in NN-dimethylformamide (40 mL) and the resulting mixture was stirred at room temperature for 4 h before being poured over 100 mL of water. The resulting suspension was extracted twice with ethyl acetate and the combined organic layers were dried over magnesium sulphate, filtered and the solvent was evaporated. The crude product was purified by flash chromatography (8:2 hexane/ethyl acetate) to yield the title compound (2.58 g, 76%).

LRMS (m/z): 197 (M+1)+.
1H-NMR δ (250 MHz, CDCl3): 6.8 (t, 1H), 7.2 (t, 1H), 7.5 (d, 1H), 7.9 (s, 1H), 8.4 (d, 1H).

Preparation 23

3-Bromopyrazolo[1,5-a]pyrazine

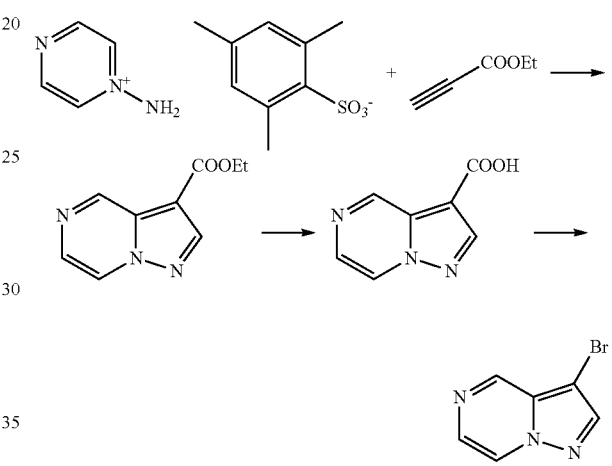

a) Ethyl pyrazolo[1,5-a]pyrazine-3-carboxylate

Obtained as an orange solid (28%) from 1-aminopyrazin-1-ium 2,4,6-trimethyl benzenesulfonate (Preparation 9) and ethyl propionate following the experimental procedure as described in Preparation 22a followed by purification by flash chromatography (hexane to 4:6 hexane/ethyl acetate).

LRMS (m/z): 192 (M+1)+.

b) Pyrazolo[1,5-a]pyrazine-3-carboxylic acid

Obtained as a white solid (99%) from ethyl pyrazolo[1,5-a]pyrazine-3-carboxylate (Preparation 23a) following the experimental procedure as described in Preparation 22b.

LRMS (m/z): 164 (M+1)+.

c) 3-Bromopyrazolo[1,5-a]pyrazine

Obtained as a yellowish solid (69%) from pyrazolo[1,5-a]pyrazine-3-carboxylic acid (Preparation 23b) according to the experimental procedure as described in Preparation 22c followed by purification by flash chromatography (2:8 to 6:4 ethyl acetate/hexane).

LRMS (m/z): 198 (M+1)+.

Preparation 24

3-(4-Chloro-5-nitropyrimidin-2-yl)pyrazolo[1,5-a]pyrazine

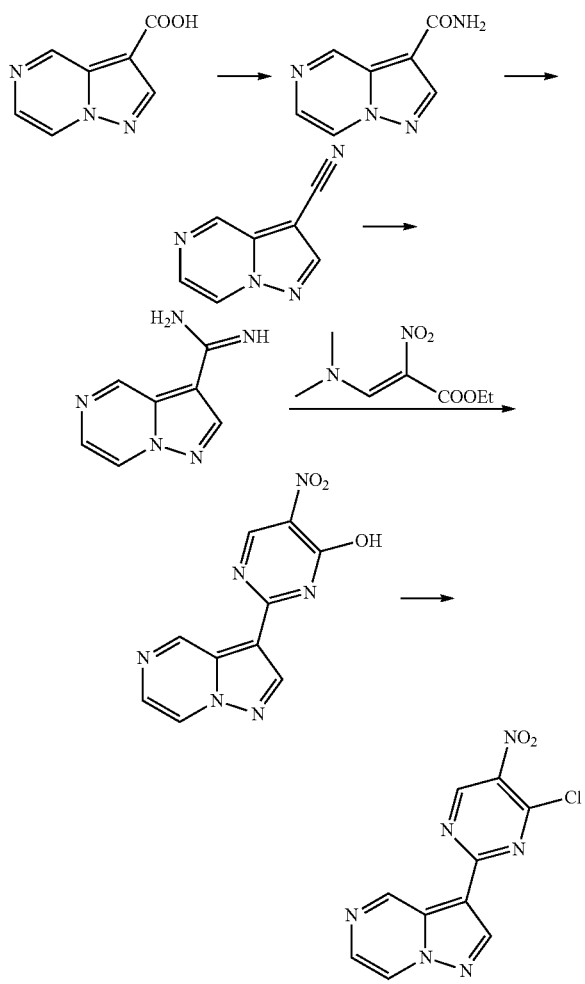

a) Pyrazolo[1,5-a]pyrazine-3-carboxamide

A suspension of pyrazolo[1,5-a]pyrazine-3-carboxylic acid (Preparation 23b, 6.70 g, 41.1 mmol) in thionyl chloride (50 mL) was heated to reflux for 7 hours. After cooling, the reaction mixture was concentrated in vacuo and the residue was azeotroped with toluene (2×30 mL). The resultant solid was suspended in 25% aqueous ammonium hydroxide solution (80 mL) and the mixture was stirred for 16 hours at ambient temperature. The mixture was concentrated to dryness to give the crude title compound (10.0 g, >100%) as a beige solid which was used in the next synthetic step without further purification.

LRMS (m/z): 163 (M+1)$^+$.

$^1$H NMR δ (300 MHz, DMSO-$d_6$): 8.1 (d, 1H), 8.7 (s, 1H), 8.9 (d, 1H), 9.6 (s, 1H).

b) Pyrazolo[1,5-a]pyrazine-3-carbonitrile

A suspension of crude pyrazolo[1,5-a]pyrazine-3-carboxamide (Preparation 24a, 6.66 g) in phosphoryl trichloride (80 mL) was heated to reflux for 2.5 hours. The reaction mixture was then poured onto a saturated aqueous sodium hydrogen carbonate solution (200 mL) and then the pH was adjusted to 7-8 by addition of a 10% aqueous sodium hydroxide solution. The mixture was extracted with ethyl acetate, the organic layer was dried (MgSO$_4$) and evaporated and the resulting residue was purified by flash chromatography (1:1 hexanes/ethyl acetate) to give the title compound (3.10 g, 52%) as a yellow solid.

LRMS (m/z): 145 (M+1)$^+$.

$^1$H NMR δ (300 MHz, DMSO-$d_6$): 8.3 (d, 1H), 8.8 (s, 1H), 9.1 (d, 1H), 9.5 (s, 1H).

c) Pyrazolo[1,5-a]pyrazine-3-carboximidamide hydrochloride

Freshly prepared sodium methoxide (0.44 g, 8.1 mmol) was added to a suspension of pyrazolo[1,5-a]pyrazine-3-carbonitrile (Preparation 24b, 6.09 g, 42.3 mmol) in anhydrous methanol (350 mL) and the mixture was stirred at ambient temperature. After 20 hours, further sodium methoxide (0.44 g, 8.1 mmol) was added and the reaction mixture was stirred for a further 48 hours. Ammonium chloride (3.91 g, 73.1 mmol) was added and the mixture was stirred and heated to 70° C. in a sealed tube. After 3 days, the mixture was concentrated to dryness to give a solid which was suspended in ethyl acetate and stirred overnight. The precipitate was filtered and dried in vacuo to give the crude title compound (8.50 g, >100%) as a white solid which was used in the next synthetic step without further purification.

LRMS (m/z): 162 (M+1)$^+$.

$^1$H NMR δ (300 MHz, DMSO-$d_6$): 8.2 (d, 1H), 8.8 (s, 1H), 9.0 (d, 1H), 9.5 (s, 1H).

d) 5-Nitro-2-(pyrazolo[1,5-a]pyrazin-3-yl)pyrimidin-4-ol

A mixture of crude pyrazolo[1,5-a]pyrazine-3-carboximidamide hydrochloride (Preparation 24c, 4.88 g), (Z)-ethyl 3-(dimethylamino)-2-nitroacrylate (8.04 g, 42.7 mmol) and triethylamine (6.25 mL, 44.8 mmol) in ethanol (165 mL) was stirred and heated to 90° C. in a sealed tube. After 22 hours, the reaction mixture was cooled and the precipitate was filtered, washed with ethanol and diethyl ether and dried to give the title compound (3.12 g, 66%) as a yellow solid.

LRMS (m/z): 257 (M−1)$^+$.

$^1$H NMR δ (300 MHz, DMSO-$d_6$): 8.1 (d, 1H), 8.7 (s, 1H), 8.8 (s, 1H), 8.9 (d, 1H), 9.9 (s, 1H).

e) 3-(4-Chloro-5-nitropyrimidin-2-yl)pyrazolo[1,5-a]pyrazine

A suspension of 5-nitro-2-(pyrazolo[1,5-a]pyrazin-3-yl)pyrimidin-4-ol (Preparation 24d, 1.50 g, 5.8 mmol) in phosphoryl trichloride (12 mL) was stirred and heated to 90° C. in a sealed tube. After 2 hours, the mixture was concentrated in vacuo and the residue was azeotroped with toluene. The resultant solid was treated with saturated aqueous sodium hydrogen carbonate solution and, upon scratching, a solid formed which was filtered, washed with water (40 mL) and dried to give the title compound (1.38 g, 86%) as a yellow solid.

LRMS (m/z): 277 (M+1)$^+$.

$^1$H NMR δ (300 MHz, DMSO-$d_6$): 8.3 (d, 1H), 9.0 (s, 1H), 9.1 (d, 1H), 9.6 (s, 1H), 9.9 (s, 1H).

Preparation 25

5-Nitro-2-(pyrazolo[1,5-a]pyrazin-3-yl)-N-(tetrahydro-2H-pyran-4-yl)pyrimidin-4-amine

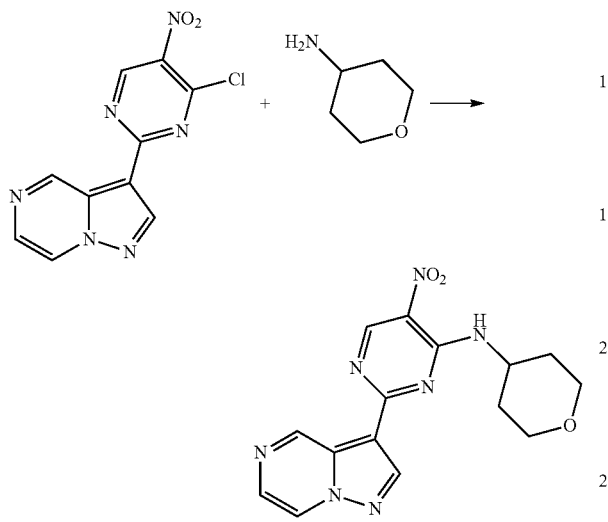

Diisopropylethylamine (2.30 mL, 13.20 mmol) and tetrahydro-2H-pyran-4-amine acetate (526 mg, 3.28 mmol) were added to a stirred suspension of 3-(4-chloro-5-nitropyrimidin-2-yl)pyrazolo[1,5-a]pyrazine (Preparation 24e, 0.91 g, 3.29 mmol) in tetrahydrofuran (15 mL) and the mixture was stirred at room temperature for 3 hours. The solvent was evaporated and water was added. The mixture was filtered to give the title compound (0.785 g, 70%) as a yellow solid.
LRMS (m/z): 342 (M+1)$^+$.

Preparation 26

N-(4,4-Difluorocyclohexyl)-5-nitro-2-(pyrazolo[1,5-a]pyrazin-3-yl)pyrimidin-4-amine

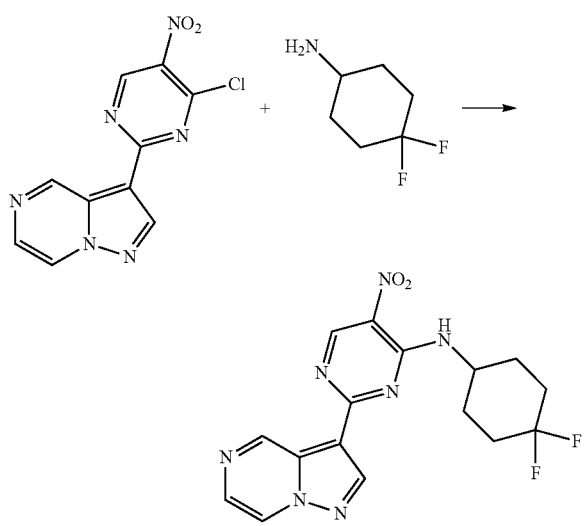

Obtained as a yellow solid (86%) from 3-(4-chloro-5-nitropyrimidin-2-yl)pyrazolo[1,5-a]pyrazine (Preparation 24e) and 4,4-difluorocyclohexanamine following the experimental procedure as described in Preparation 25.
LRMS (m/z): 376 (M+1)$^+$.
$^1$H NMR δ (300 MHz, DMSO-d$_6$): 1.9-2.2 (m, 8H), 4.6 (m, 1H), 8.2 (d, 1H), 8.5 (d, 1H), 8.9 (s, 1H), 9.0 (d, 1H), 9.2 (s, 1H), 9.9 (s, 1H).

Preparation 27

3-(6-Chloropyrazin-2-yl)pyrazolo[1,5-a]pyridine

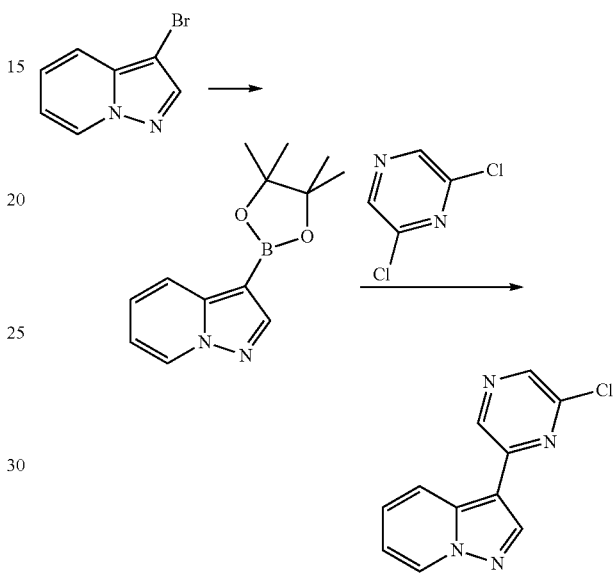

a) 3-(4,4,5,5-Tetramethyl-1,3,2-dioxaborolan-2-yl)pyrazolo[1,5-a]pyridine 4,4,4',4',5,5,5',5'-Octamethyl-2,2'-bi(1,3,2-dioxaborolane) (1.27 g, 5.0 mmol), palladium (II) acetate (0.050 g, 0.228 mmol), tricyclohexylphosphine (0.127 g, 0.46 mmol), potassium carbonate (0.945 g, 6.84 mmol) and water (0.05 mL) were added to a solution of 3-bromopyrazolo[1,5-a]pyridine (Preparation 22c, 0.90 g, 4.56 mmol)) in diglyme (10 mL) and the resulting mixture was heated at 100° C. for 2 h. After cooling, the reaction mixture was filtered through Celite®, eluting with methanol. The filtrate was evaporated and the crude product was used with no further purification in the next synthetic step.
LRMS (m/z): 245 (M+1)$^+$.

b) 3-(6-Chloropyrazin-2-yl)pyrazolo[1,5-a]pyridine 2,6-Dichloropyrazine (0.316 g, 2.12 mmol), tris(dibenzylideneacetone)dipalladium (0), (0.097 g, 0.106 mmol), tricyclohexylphosphine (0.06 g, 0.212 mmol) and potassium phosphate (1.35 g, 6.36 mmol) were added to a suspension of 3-(4,4,5,5-tetramethyl-1,3,2-dioxaborolan-2-yl)pyrazolo[1,5-a]pyridine (Preparation 27a, 0.518 g, 2.12 mmol)) in N,N'-dimethylformamide (10 mL). This mixture was subjected to microwave irradiation at 100° C. for 40 min. The reaction mixture was filtered through Celite®, eluting with methanol, and the filtrate was evaporated. The resulting residue was purified by flash chromatography (2:8 to 3:7 ethyl acetate/hexane) to yield the title compound (0.162 g, 33%, two steps) as a pale yellow solid.

LRMS (m/z): 231 (M+1)⁺.
¹H-NMR δ (250 MHz, CDCl₃): 7.0 (t, 1H), 7.4 (t, 1H), 8.3 (s, 1H), 8.5 (s, 1H), 8.5 (m, 2H), 8.8 (s, 1H).

Preparation 28

(R)—N-(Piperidin-3-yl)-6-(pyrazolo[1,5-a]pyridin-3-yl)pyrazin-2-amine

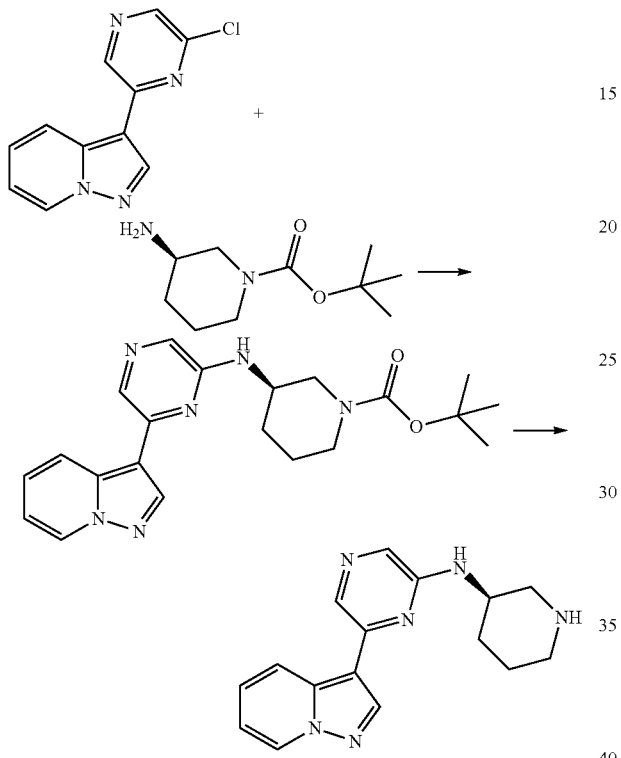

a) (R)-tert-Butyl 3-(6-(pyrazolo[1,5-a]pyridin-3-yl)pyrazin-2-ylamino)piperidine-1-carboxylate Tert-Butyl (3R)-3-aminopiperidine-1-carboxylate (0.51 g, 2.54 mmol) and cesium fluoride (0.83 g, 5.46 mmol) were added to a stirred solution of 3-(6-chloropyrazin-2-yl)pyrazolo[1,5-a]pyridine (Preparation 27b, 0.42 g, 1.82 mmol) in dimethylsulfoxide (20 mL). The resulting mixture was stirred at 100° C. for 22 h before being poured onto 50 mL of water. The resultant suspension was extracted with ethyl acetate (×2) and the combined organic layers were dried over magnesium sulphate, filtered and evaporated to dryness. The crude product was purified by flash chromatography (3:7 to 7:3 ethyl acetate/hexane) to give the title compound (0.244 g, 34%) as a yellowish foam.
LRMS (m/z): 395 (M+1)⁺.

b) (R)—N-(Piperidin-3-yl)-6-(pyrazolo[1,5-a]pyridin-3-yl)pyrazin-2-amine

Trifluoroacetic acid (0.35 mL, 4.56 mmol) was added to a solution of (R)-tert-butyl 3-(6-(pyrazolo[1,5-a]pyridin-3-yl)pyrazin-2-ylamino)piperidine-1-carboxylate (Preparation 28a, 0.30 g, 0.76 mmol) in methylene chloride (10 mL) and the resulting solution was stirred at ambient temperature overnight and then at 50° C. for additional 24 h. The solvent was then evaporated and the residue was redissolved in methylene chloride and washed with a 10% aqueous sodium hydroxide solution. The organic phase was dried over magnesium sulphate, filtered and the solvent was evaporated. The crude product was purified by flash chromatography (10-15% MeOH/CH₂Cl₂/NH₃) to yield the title compound (0.125 g, 56%) as an oil.
LRMS (m/z): 295 (M+1)⁺.

Preparation 29

3-(6-Chloropyrazin-2-yl)pyrazolo[1,5-a]pyrazine

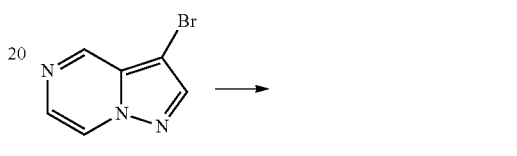

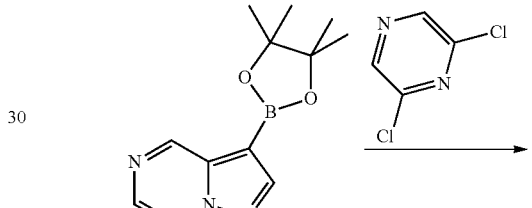

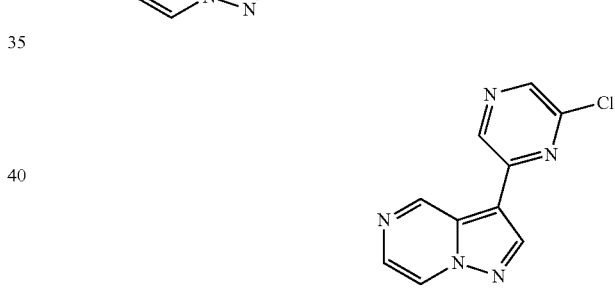

a) 3-(4,4,5,5-Tetramethyl-1,3,2-dioxaborolan-2-yl)pyrazolo[1,5-a]pyrazine

Obtained from 3-bromopyrazolo[1,5-a]pyrazine (Preparation 23c) following the experimental procedure as described in Preparation 27a, irradiating the reaction mixture at 100° C. for 1 h. The crude product was used without further purification in the next synthetic step.
LRMS (m/z): 246 (M+1)⁺.

b) 3-(6-Chloropyrazin-2-yl)pyrazolo[1,5-a]pyrazine

Obtained as a yellow solid (28% yield, two steps) from 3-(4,4,5,5-tetramethyl-1,3,2-dioxaborolan-2-yl)pyrazolo[1,5-a]pyrazine (Preparation 29a) according to the experimental procedure as described in Preparation 27b followed by purification by flash chromatography (2:8 ethyl acetate/hexane).
LRMS (m/z): 232 (M+1)⁺.

Preparation 30

(R)—N-(Piperidin-3-yl)-6-(pyrazolo[1,5-a]pyrazin-3-yl)pyrazin-2-amine

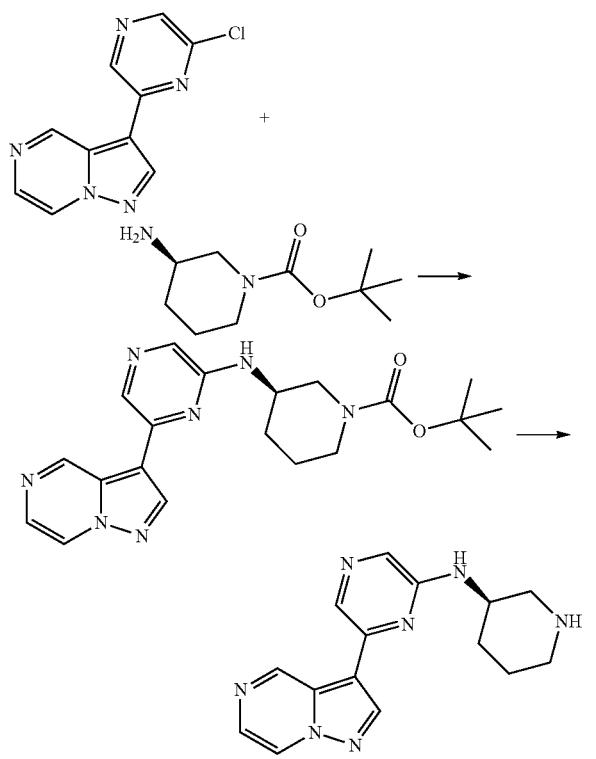

a) (R)-tert-Butyl 3-(6-(pyrazolo[1,5-a]pyrazin-3-yl)pyrazin-2-ylamino)piperidine-1-carboxylate Tert-butyl (3R)-3-aminopiperidine-1-carboxylate (0.41 g, 2.05 mmol), tris(dibencylidenoacetone)dipalladium(0) (0.034 g, 0.037 mmol), 9,9-dimethyl-4,5-bis(diphenylphosphino)xanthene (0.043 g, 0.074 mmol) and cesium carbonate (0.848 g, 2.6 mmol) were added to a suspension of 3-(6-chloropyrazin-2-yl)pyrazolo[1,5-a]pyrazine (Preparation 29b, 0.43 g, 1.86 mmol)) in N,N'-dimethylformamide (10 mL) and the resulting mixture was purged with argon before being heated to 100° C. for 7 h. After cooling to ambient temperature, the reaction mixture was filtered though Celite®, eluting with methanol. The filtrate was evaporated and the residue was purified by flash chromatography (7:3 ethyl acetate/hexane to 100% ethyl acetate) to yield the title compound (0.320 g, 44%) as a greenish solid.

LRMS (m/z): 396 (M+1)$^+$.

$^1$H-NMR δ (250 MHz, CDCl$_3$): 1.4 (s, 9H), 1.8 (m, 2H), 2.0 (m, 2H), 3.5 (m, 3H), 3.7 (m, 1H), 4.1 (m, 1H), 4.8 (m, 1H), 7.8 (s, 1H), 8.0 (d, 1H), 8.3 (s, 1H), 8.4 (dd, 1H), 8.5 (s, 1H), 9.8 (d, 1H).

b) (R)—N-(Piperidin-3-yl)-6-(pyrazolo[1,5-a]pyrazin-3-yl)pyrazin-2-amine

Obtained as a yellow foam (99%) from (R)-tert-butyl 3-(6-(pyrazolo[1,5-a]pyrazin-3-yl)pyrazin-2-ylamino)piperidine-1-carboxylate (Preparation 30a) and trifluoroacetic acid following the experimental procedure as described in Preparation 28b. The crude product was used in the next synthetic step without further purification.

LRMS (m/z): 296 (M+1)$^+$.

Preparation 31

3-(4-Chloropyrimidin-2-yl)pyrazolo[1,5-a]pyrazine

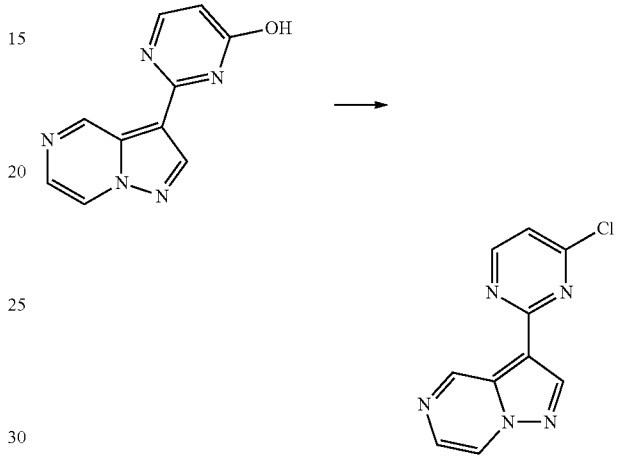

A solution of 2-(pyrazolo[1,5-a]pyrazin-3-yl)pyrimidin-4-ol (Preparation 10b, 150 mg, 0.7 mmol) in phosphorous oxychloride (1.42 mL, 15.51 mmol) was heated overnight at 110° C. After cooling to ambient temperature, the reaction mixture was poured with caution onto water and basified by addition of a 2N aqueous sodium hydroxide solution. Ethyl acetate was then added and the organic phase was separated, washed with water and brine, dried (MgSO$_4$), filtered and evaporated under reduced pressure to yield the title compound (170 mg, 87%) as a solid which was used in the next synthetic step without further purification.

LRMS (m/z): 232 (M+1)$^+$ $^1$H NMR δ (300 MHz, CDCl$_3$): 7.0 (t, 1H), 7.1 (d, 1H), 7.4 (d, 1H), 8.6 (dd, 2H), 8.8 (s, 1H).

Preparation 32

3-(4,5-Dichloropyrimidin-2-yl)pyrazolo[1,5-a]pyrazine

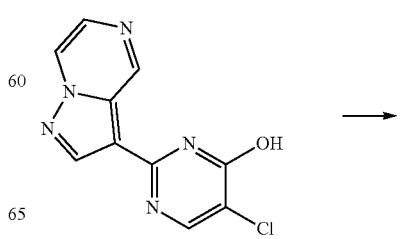

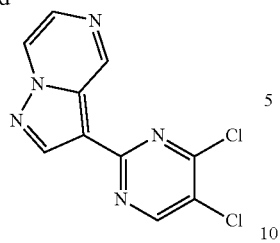

Obtained as a solid (57%) from 5-chloro-2-(pyrazolo[1,5-a]pyrazin-3-yl)pyrimidin-4-ol (Preparation 14b) and phosphorous oxychloride following the experimental procedure as described in Preparation 31.

LRMS (m/z): 267 (M+1)$^+$

Preparation 33

3-(4-Chloropyrimidin-2-yl)pyrazolo[1,5-a]pyridine

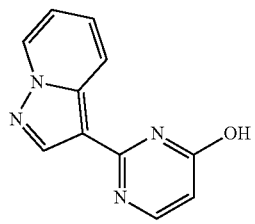

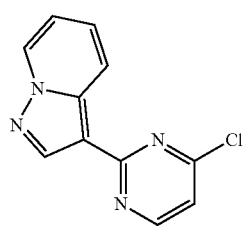

Obtained as a yellowish solid (99%) from 2-(pyrazolo[1,5-a]pyrazin-3-yl)pyrimidin-4-ol (Preparation 4b) and phosphorous oxychloride following the experimental procedure as described in Preparation 31.

LRMS (m/z): 231 (M+1)$^+$ $^1$H NMR δ (300 MHz, CDCl$_3$): 7.0 (t, 1H), 7.1 (d, 1H), 7.4 (d, 1H), 8.6 (dd, 3H), 8.8 (s, 1H).

Preparation 34

(R)—N-(Piperidin-3-yl)-2-(pyrazolo[1,5-a]pyridin-3-yl)pyrimidin-4-amine

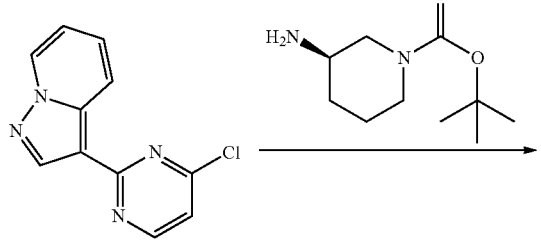

a) (R)-Tert-Butyl 3-(2-(pyrazolo[1,5-a]pyridin-3-yl)pyrimidin-4-ylamino)piperidine-1-carboxylate A solution of 3-(4-chloropyrimidin-2-yl)pyrazolo[1,5-a]pyridine (Preparation 33, 130 mg, 0.56 mmol) and (R)-tert-butyl 3-aminopiperidine-1-carboxylate (326 mg, 1.63 mmol) in ethanol (5 mL) was heated overnight at 100° C. After cooling to ambient temperature, the solvent was evaporated under reduced pressure and the residue was taken up in a mixture of chloroform and water. The aqueous layer was separated and washed with chloroform (×2). The combined organic extracts were dried (MgSO$_4$) and evaporated in vacuo. The crude product was purified by flash chromatography (dichloromethane to 95:5 dichloromethane/methanol) to give the title compound (150 mg, 68%).

LRMS (m/z): 395 (M+1)$^+$ $^1$H NMR δ (300 MHz, CDCl$_3$): 1.5 (s, 9H), 2.1 (m, 2H), 3.0-4.2 (m, 7H), 5.0-5.1 (m, 1H), 6.2 (d, 1H), 6.9 (t, 1H), 7.3 (d, 1H), 8.2 (d, 1H), 8.5 (d, 1H), 8.6 (d, 1H), 8.7 (s, 1H).

b) (R)—N-(Piperidin-3-yl)-2-(pyrazolo[1,5-a]pyridin-3-yl)pyrimidin-4-amine

Obtained as a pale yellow solid (89%) from (R)-tert-butyl 3-(2-(pyrazolo[1,5-a]pyridin-3-yl)pyrimidin-4-ylamino)piperidine-1-carboxylate (Preparation 34a) and trifluoroacetic acid following the experimental procedure as described in Preparation 7b.

LRMS (m/z): 295 (M+1)$^+$, 293 (M−1)$^−$.

$^1$H NMR δ (300 MHz, CDCl$_3$): 1.5-1.9 (m, 4H), 2.0 (td, 2H), 2.3 (bs, 1H), 2.6-3.0 (m, 2H), 3.2 (dd, 1H), 5.4 (bs, 1H), 6.2 (d, 1H), 6.9 (t, 1H), 7.3 (d, 1H), 8.2 (d, 1H), 8.5 (d, 1H), 8.6 (d, 1H), 8.7 (s, 1H).

Preparation 35

5-Chloro-2-(pyrazolo[1,5-a]pyridin-3-yl)pyrimidin-4-ol

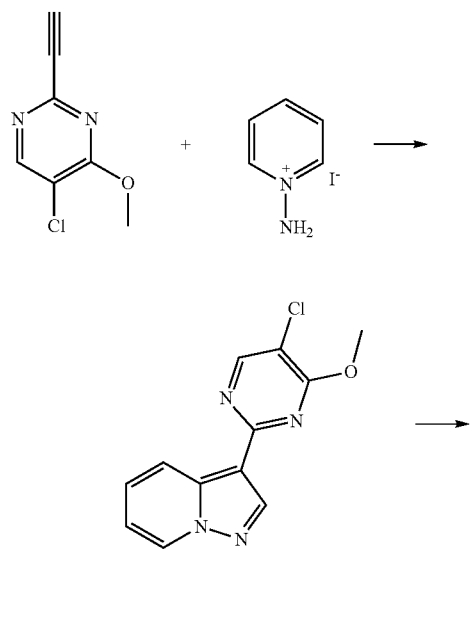

a) 3-(5-Chloro-4-methoxypyrimidin-2-yl)pyrazolo[1,5-a]pyridine

Obtained as a yellowish solid (69%) from 5-chloro-2-ethynyl-4-methoxypyrimidine (Preparation 13b) and 1-aminopyridinium iodide following the experimental procedure as described in Preparation 3a. After usual work up, the crude material was triturated with ethyl ether and the insoluble solid was isolated by filtration to yield the title compound which was used in the next synthetic step without further purification.

LRMS (m/z): 262 (M+1)$^+$.

b) 5-Chloro-2-pyrazolo[1,5-a]pyridin-3-ylpyrimidin-4-ol

Obtained as a dark solid (61%) from 3-(5-chloro-4-methoxypyrimidin-2-yl)pyrazolo[1,5-a]pyridine (Preparation 35a) following the experimental procedure as described in Preparation 4b.

LRMS (m/z): 247 (M−1-1)$^+$.

Preparation 36

3-(4,5-Dichloropyrimidin-2-yl)pyrazolo[1,5-a]pyridine

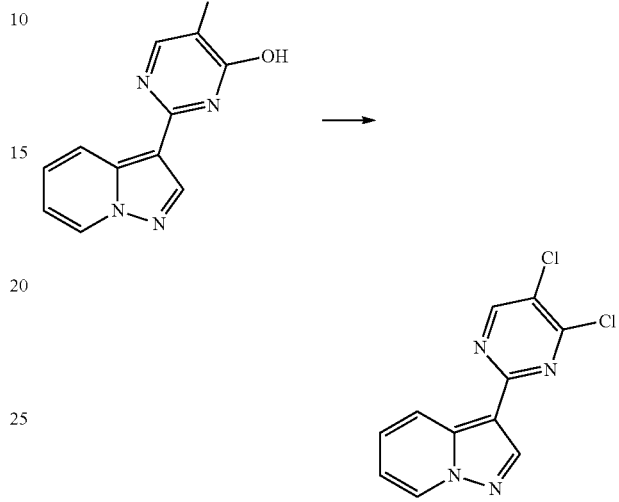

Obtained as a yellowish solid (84%) from 5-chloro-2-pyrazolo[1,5-a]pyridin-3-ylpyrimidin-4-ol (Preparation 35b) and phosphorous oxychloride following the experimental procedure as described in Preparation 31.

LRMS (m/z): 266 (M+1)$^+$ $^1$H NMR δ (300 MHz, CDCl$_3$): 6.9-7.0 (m, 1H), 7.4-7.5 (m, 1H), 8.6 (ddt, 2H), 8.6 (d, 1H), 8.7 (s, 1H).

Preparation 37

(R)-5-Chloro-N-(piperidin-3-yl)-2-(pyrazolo[1,5-a]pyridin-3-yl)pyrimidin-4-amine

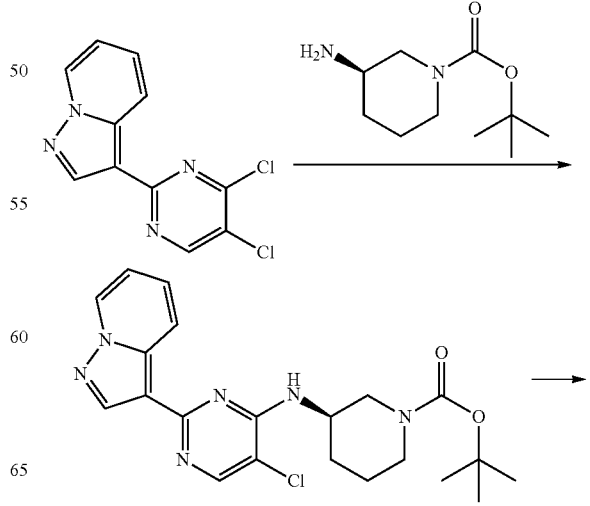

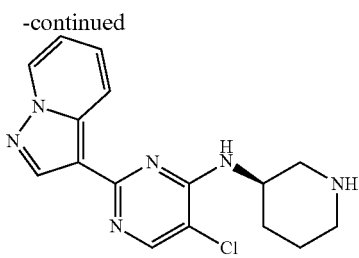

a) (R)-Tert-butyl 3-(5-chloro-2-(pyrazolo[1,5-a]pyridin-3-yl) pyrimidin-4-ylamino) piperidine-1-carboxylate Obtained as an oil (100%) from 3-(4,5-dichloropyrimidin-2-yl)pyrazolo[1,5-a]pyridine (Preparation 36) and (R)-tert-butyl 3-aminopiperidine-1-carboxylate following the experimental procedure as described in Preparation 34a.

LRMS (m/z): 429 (M+1)$^+$ $^1$H NMR δ (300 MHz, CDCl$_3$): 1.8 (s, 9H), 2.1 (s, 2H), 3.0 (s, 4H), 4.0 (s, 2H), 4.3 (s, 1H), 5.4 (bs, 1H), 6.9 (t, 1H), 7.3-7.4 (m, 1H), 8.2 (s, 1H), 8.5 (t, 2H), 8.7 (s, H).

b) (R)-5-Chloro-N-(piperidin-3-yl)-2-(pyrazolo[1,5-a]pyridin-3-yl)pyrimidin-4-amine Obtained as an oil (100%) from (R)-tert-butyl 3-(5-chloro-2-(pyrazolo[1,5-a]pyridin-3-yl) pyrimidin-4-ylamino)piperidine-1-carboxylate (Preparation 37a) and trifluoroacetic acid following the experimental procedure as described in Preparation 7b.

LRMS (m/z): 329 (M+1)$^+$

Preparation 38

Tert-Butyl (2-oxo-2-{(3R)-3-[(6-pyrazolo[1,5-a]pyridin-3-ylpyrazin-2-yl)amino]piperidin-1-yl}ethyl)carbamate

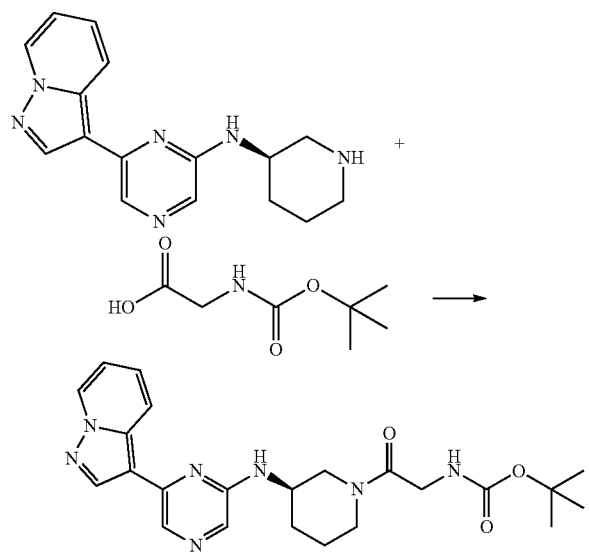

[(Tert-Butoxycarbonyl)amino]acetic acid (65 mg, 0.37 mmol), 0-(7-azabenzotriazol-1-yl)-N,N,N',N'-tetramethyluronium hexafluorophosphate (142 mg, 0.37 mmol) and diisopropylethylamine (65 mL, 0.37 mmol) were added to a solution of (R)—N-(piperidin-3-yl)-6-(pyrazolo[1,5-a]pyridin-3-yl)pyrazin-2-amine (Preparation 28b, 100 mg, 0.34 mmol) in N,N'-dimethylformamide (2 mL) and the resulting mixture was stirred at ambient temperature overnight. The reaction mixture was then partitioned between ethyl acetate and water and the organic layer was separated, washed with brine, dried (MgSO$_4$) and evaporated. The residue was purified by reverse phase chromatography (C-18 silica from Waters, water/1:1 acetonitrile-methanol as eluents [0.1% v/v formic acid buffered] 0% to 100%) to yield the title compound (88 mg, 57%).

LRMS (m/z): 452 (M+1)$^+$.

$^1$H NMR δ (400 MHz, CDCl$_3$): 1.5 (s, 9H), 1.6-2.2 (m, 5H), 3.2-4.2 (m, 7H), 4.8 (m, 1H), 5.6 (s, 1H), 6.9 (t, 1H), 7.3 (m, 1H), 7.7 (s, 1H), 8.2 (m, 1H), 8.4 (m, 1H), 8.4 (m, 1H).

Preparation 39

5-Fluoro-2-pyrazolo[1,5-a]pyridin-3-ylpyrimidin-4-ol

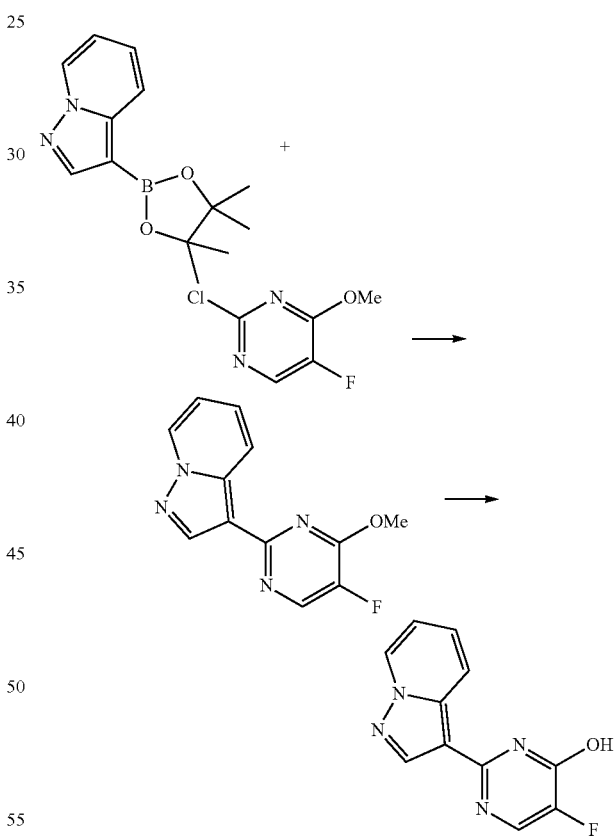

a) 3-(5-Fluoro-4-methoxypyrimidin-2-yl)pyrazolo[1,5-a]pyridine

Obtained as a solid (23%) from 3-(4,4,5,5-tetramethyl-1,3,2-dioxaborolan-2-yl)pyrazolo[1,5-a]pyridine (Preparation 27a) and 2-chloro-5-fluoro-4-methoxypyrimidine (Preparation 16a) following the experimental procedure as described in Preparation 27b.

LRMS (m/z): 245 (M+1)$^+$.

¹H NMR δ (400 MHz, CDCl₃): 4.2 (s, 3H), 6.9-7.0 (m, 1H), 7.3-7.4 (m, 1H), 8.3 (d, 1H), 8.5-8.6 (m, 2H), 8.7 (bs, 1H).

b) 5-Fluoro-2-pyrazolo[1,5-a]pyridin-3-ylpyrimidin-4-ol

Obtained as a solid (74%) from 3-(5-fluoro-4-methoxypyrimidin-2-yl)pyrazolo[1,5-a]pyridine (Preparation 39a) and 48% aqueous hydrogen bromide following the experimental procedure as described in Preparation 4b.
LRMS (m/z): 231 (M+1)+

Preparation 40

5-Fluoro-N-[(3R)-piperidin-3-yl]-2-pyrazolo[1,5-a]pyridin-3-ylpyrimidin-4-amine

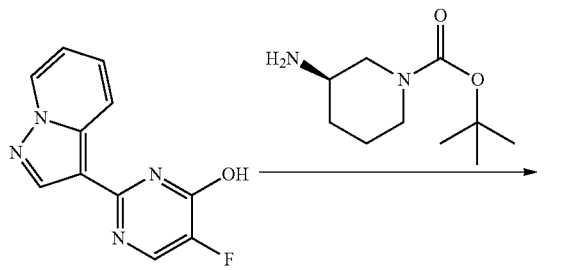

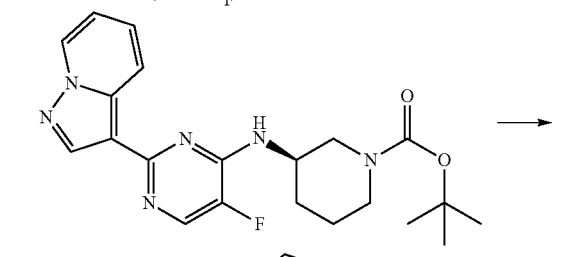

a) Tert-Butyl (3R)-3-[(5-fluoro-2-pyrazolo[1,5-a]pyridin-3-ylpyrimidin-4-yl)amino]piperidine-1-carboxylate Obtained as an oil (88%) from 5-fluoro-2-pyrazolo[1,5-a]pyridin-3-ylpyrimidin-4-ol (Preparation 39b) and tert-butyl (3R)-3-aminopiperidine-1-carboxylate following the experimental procedure as described in Preparation 7a.
LRMS (m/z): 413 (M+1)+ b) 5-Fluoro-N-[(3R)-piperidin-3-yl]-2-pyrazolo-[1,5-a]pyridin-3-ylpyrimidin-4-amine Obtained as an oil (98%) from tert-butyl (3R)-3-[(5-fluoro-2-pyrazolo[1,5-a]pyridin-3-ylpyrimidin-4-yl)amino]piperidine-1-carboxylate (Preparation 40a) and trifluoroacetic acid following the experimental procedure as described in Preparation 7b.
LRMS (m/z): 313 (M+1)⁺.

Preparation 41

N-[(3s,4r)-4-fluoropiperidin-3-yl]-6-pyrazolo[1,5-a]pyridin-3-ylpyrazin-2-amine

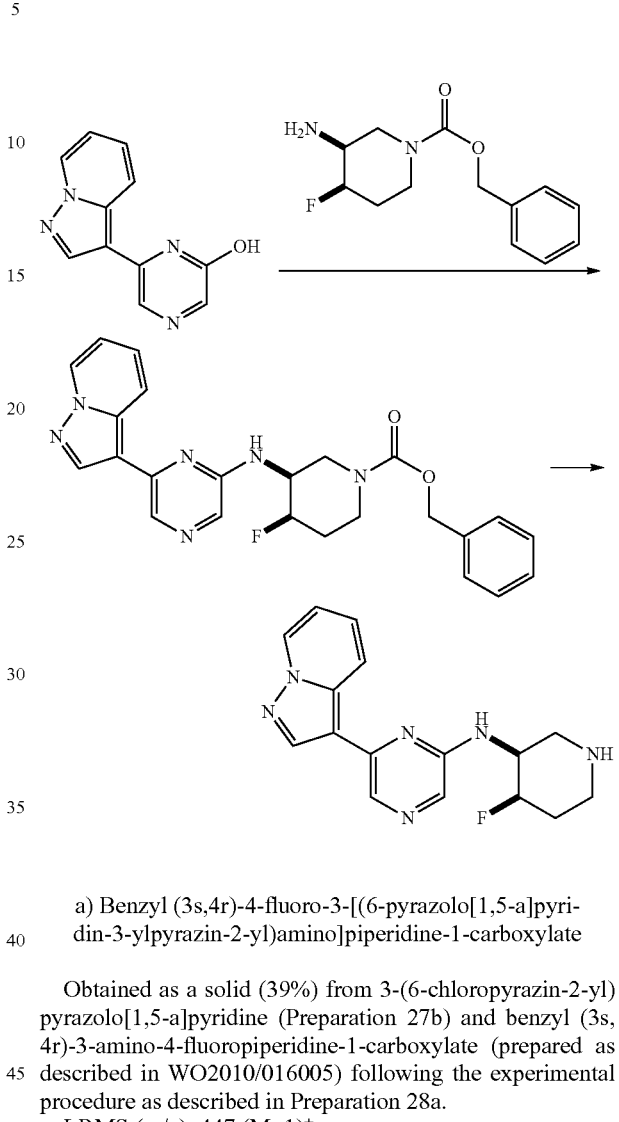

a) Benzyl (3s,4r)-4-fluoro-3-[(6-pyrazolo[1,5-a]pyridin-3-ylpyrazin-2-yl)amino]piperidine-1-carboxylate Obtained as a solid (39%) from 3-(6-chloropyrazin-2-yl)pyrazolo[1,5-a]pyridine (Preparation 27b) and benzyl (3s,4r)-3-amino-4-fluoropiperidine-1-carboxylate (prepared as described in WO2010/016005) following the experimental procedure as described in Preparation 28a.
LRMS (m/z): 447 (M+1)⁺.

b) N-[(3s,4r)-4-fluoropiperidin-3-yl]-6-pyrazolo[1,5-a]pyridin-3-ylpyrazin-2-amine Benzyl (3s,4r)-4-fluoro-3-[(6-pyrazolo[1,5-a]pyridin-3-ylpyrazin-2-yl)amino]piperidine-1-carboxylate (Preparation 41a, 229 mg, 0.51 mmol) was added to a 3N hydrochloric acid solution in methanol (45 mL) and the resulting mixture was heated overnight at 100° C. in a sealed tube. A 37% aqueous hydrochloric acid solution (10 mL) was then added and the reaction mixture was stirred at 100° C. for four additional hours. After cooling to ambient temperature, water was added and the organic solvent was evaporated under reduced pressure. The resulting aqueous phase was washed with methylene chloride, basified by addition of an aqueous 2N sodium hydroxide solution until a basic pH was reached and washed again with methylene chloride (×3). The combined organic phases were washed with brine, dried (MgSO₄) and the solvent was evaporated in vacuo to yield the title compound (153 mg, 95%) as an oil.

LRMS (m/z): 313 (M+1)⁺.

¹H NMR δ (400 MHz, CDCl₃): 2.0-2.3 (m, 2H), 2.9-3.8 (m, 5H), 4.3-5.2 (m, 1H), 4.9-5.2 (m, 2H), 6.9 (m, 1H), 7.4 (m, 1H), 7.8 (s, 1H), 8.3 (s, 1H), 8.4 (s, 1H), 8.5 (m, 1H).

Example 1

3-(4-{[(1S)-1-Phenylethyl]amino}pyrimidin-2-yl)pyrazolo[1,5-a]pyridine-5-carbonitrile

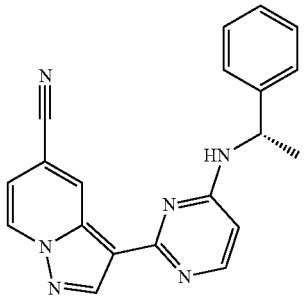 [SMILES: C[C@H](Nc1ccnc(-c2cnn3ccc(C#N)cc23)n1)c1ccccc1]

Obtained as monoformate salt (15%) from 3-(4-hydroxypyrimidin-2-yl)pyrazolo[1,5-a]pyridine-5-carbonitrile (Preparation 3b) and (S)-1-phenylethanamine following the experimental procedure as described in Preparation 7a followed by purification by flash chromatography (99:1 dichloromethane/methanol) to give a residue that was repurified by reverse phase chromatography (C-18 silica from Waters, water/acetonitrile/methanol as eluents [0.1% v/v formic acid buffered] 0% to 100%).

LRMS (m/z): 341 (M)⁺.

¹H-NMR δ (300 MHz, CD₃OD): 1.6 (d, 3H), 5.3 (bs, 1H), 5.5 (bs, 1H), 7.1 (d, 1H), 7.2 (t, 1H), 7.4 (t, 2H), 7.5 (d, 2H), 8.1 (d, 1H), 8.5 (bs, 1H), 8.6 (s, 1H), 8.7 (d, 1H).

Example 2

3-{4-[(Cyclohexylmethyl)amino]pyrimidin-2-yl}pyrazolo[1,5-a]pyridine-5-carbonitrile

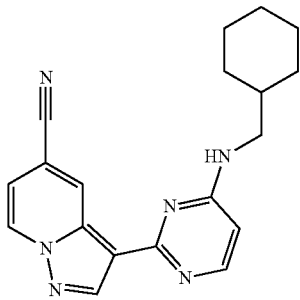 [SMILES: N#Cc1ccn2ncc(-c3nccc(NCC4CCCCC4)n3)c2c1]

Obtained as monoformate salt (22%) from 3-(4-hydroxypyrimidin-2-yl)pyrazolo[1,5-a]pyridine-5-carbonitrile (Preparation 3b) and cyclohexylmethanamine following the experimental procedure as described in Preparation 7a followed by purification by reverse phase chromatography (C-18 silica from Waters, water/acetonitrile/methanol as eluents [0.1% v/v formic acid buffered] 5% to 50%).

LRMS (m/z): 333 (M)⁺.

¹H-NMR δ (300 MHz, CD₃OD): 1.1-1.3 (m, 4H), 1.7-1.8 (m, 5H), 1.9-1.9 (m, 2H), 3.3-3.4 (m, 2H), 6.3 (d, 1H), 7.2 (d, 1H), 8.0 (bs, 1H), 8.5 (s, 2H), 8.7 (s, 1H), 8.8 (d, 1H), 9.1 (bs, 1H).

Example 3

3-[4-(Benzylamino)pyrimidin-2-yl]pyrazolo[1,5-a]pyridine-5-carbonitrile

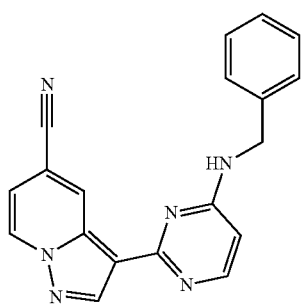 [SMILES: N#Cc1ccn2ncc(-c3nccc(NCc4ccccc4)n3)c2c1]

Obtained as monoformate salt (8%) from 3-(4-hydroxypyrimidin-2-yl)pyrazolo[1,5-a]pyridine-5-carbonitrile (Preparation 3b) and phenylmethanamine following the experimental procedure as described in Preparation 7a followed by purification by reverse phase chromatography (C-18 silica from Waters, water/acetonitrile/methanol as eluents [0.1% v/v formic acid buffered] 5% to 50%).

LRMS (m/z): 327 (M+1)⁺, 325 (M–1)⁻.

¹H-NMR δ (300 MHz, CDCl₃): 4.7 (bs, 2H), 6.3 (d, 1H), 6.9 (d, 1H), 7.3-7.4 (m, 1H), 7.4 (d, 4H), 8.3 (d, 1H), 8.6 (d, 1H), 8.8 (s, 1H), 9.0 (bs, 1H).

Example 4

3-{4-[(2,2-Dimethylpropyl)amino]pyrimidin-2-yl}pyrazolo[1,5-a]pyridine-5-carbonitrile

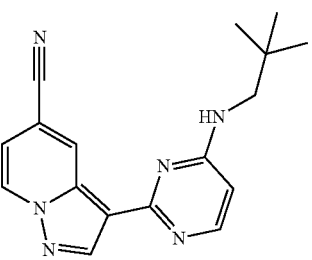 [SMILES: CC(C)(C)CNc1ccnc(-c2cnn3ccc(C#N)cc23)n1]

Obtained as a yellow solid (11%) from 3-(4-hydroxypyrimidin-2-yl)pyrazolo[1,5-a]pyridine-5-carbonitrile (Preparation 3b) and (2,2-dimethylpropyl)amine following the experimental procedure as described in Preparation 7a followed by purification by flash chromatography (10:1 hexane/ethyl acetate to 100% ethyl acetate).

LRMS (m/z): 307 (M+1)⁺, 305 (M–1)⁻.

¹H-NMR δ (300 MHz, CDCl₃): 1.1 (s, 9H), 3.3 (s, 2H) 5.2 (bs, 1H), 6.3 (d, 1H), 7.0 (d, 1H), 8.3 (d, 1H), 8.6 (d, 1H), 8.8 (s, 1H), 9.2 (bs, 1H).

Example 5

3-(4-{[(1S)-2-Methoxy-1-methylethyl]amino}pyrimidin-2-yl)pyrazolo[1,5-a]pyridine-5-carbonitrile

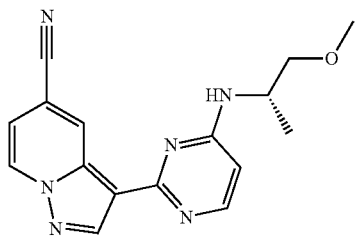 [SMILES: COC[C@H](C)Nc1ccnc(-c2cnn3ccc(C#N)cc23)n1]

Obtained as a yellow solid (10%) from 3-(4-hydroxypyrimidin-2-yl)pyrazolo[1,5-a]pyridine-5-carbonitrile (Preparation 3b) and [(1S)-2-methoxy-1-methylethyl]amine following the experimental procedure as described in Preparation 7a followed by purification by flash chromatography (10:1 hexane/ethyl acetate to 100% ethyl acetate).

LRMS (m/z): 309 (M+1)⁺, 307 (M−1)⁻.

¹H-NMR δ (300 MHz, CDCl₃): 1.4 (d, 3H), 3.4 (s, 3H), 3.5 (d, 2H), 4.2 (m, 1H), 5.1 (bs, 1H), 6.2 (d, 1H), 7.0 (dd, 1H), 8.2 (d, 1H), 8.6 (d, 1H), 8.8 (s, 1H), 9.1 (s, 1H).

Example 6

3-{4-[(Cyclopropylmethyl)amino]pyrimidin-2-yl}pyrazolo[1,5-a]pyridine-5-carbonitrile

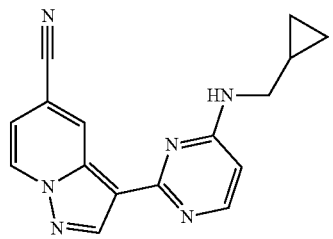 [SMILES: N#Cc1ccn2ncc(-c3nccc(NCC4CC4)n3)c2c1]

Obtained as a pale yellow solid (15%) from 3-(4-hydroxypyrimidin-2-yl)pyrazolo[1,5-a]pyridine-5-carbonitrile (Preparation 3b) and (cyclopropylmethyl)amine following the experimental procedure as described in Preparation 7a followed by purification by flash chromatography (10:1 hexane/ethyl acetate to 100% ethyl acetate).

LRMS (m/z): 291 (M+1)⁺, 289 (M−1)⁻.

¹H-NMR δ (300 MHz, CDCl₃): 0.4 (m, 2H), 0.7 (m, 2H), 1.2 (m, 1H), 3.3 (bs, 2H), 5.1 (bs, 1H), 6.2 (d, 1H), 7.0 (dd, 1H), 8.3 (d, 1H), 8.6 (d, 1H), 8.8 (s, 1H), 9.1 (s, 1H).

Example 7

3-{4-[(2,2,2-Trifluoroethyl)amino]pyrimidin-2-yl}pyrazolo[1,5-a]pyridine-5-carbonitrile

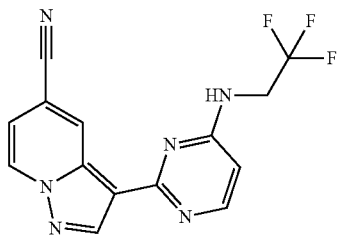 [SMILES: N#Cc1ccn2ncc(-c3nccc(NCC(F)(F)F)n3)c2c1]

Obtained as a pale yellow solid (10%) from 3-(4-hydroxypyrimidin-2-yl)pyrazolo[1,5-a]pyridine-5-carbonitrile (Preparation 3b) and (2,2,2-trifluoroethyl)amine following the experimental procedure as described in Preparation 7a followed by purification by flash chromatography (10:1 to 1:1 hexane/ethyl acetate).

LRMS (m/z): 319 (M+1)⁺, 317 (M−1)⁻.

¹H-NMR δ (300 MHz, CDCl₃): 4.2 (m, 2H), 5.1 (bs, 1H), 6.3 (d, 1H), 7.0 (dd, 1H), 8.3 (d, 1H), 8.6 (d, 1H), 8.8 (s, 1H), 9.0 (s, 1H).

Example 8

N-(1-Phenylethyl)-2-pyrazolo[1,5-a]pyridin-3-ylpyrimidin-4-amine

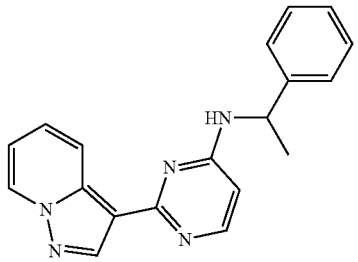 [SMILES: CC(Nc1ccnc(-c2cnn3ccccc23)n1)c1ccccc1]

Obtained as a solid (5%) from 2-pyrazolo[1,5-a]pyridin-3-ylpyrimidin-4-ol (Preparation 4b) and 1-phenylethanamine following the experimental procedure as described in Preparation 7a.

LRMS (m/z): 316 (M+1)⁺.

¹H-NMR δ (300 MHz, CD₃OD): 1.6 (d, 3H), 4.6 (bs, 1H), 6.4 (bs, 1H), 7.0 (t, 1H), 7.2-7.3 (m, 2H), 7.3 (t, 2H), 7.4 (d, 2H), 8.0 (d, 2H), 8.5 (s, 1H), 8.5 (d, 1H).

Example 9

3-{6-[(Cyclohexylmethyl)amino]pyridin-2-yl}pyrazolo[1,5-a]pyridine-5-carbonitrile

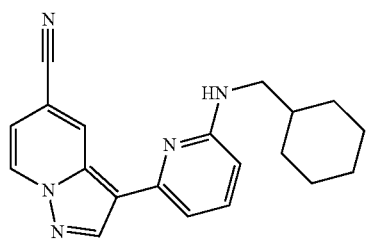 [SMILES: N#Cc1ccn2ncc(-c3cccc(NCC4CCCCC4)n3)c2c1]

A mixture of 3-(6-chloropyridin-2-yl)pyrazolo[1,5-a]pyridine-5-carbonitrile (Preparation 6, 30 mg, 0.12 mmol), cyclohexylmethanamine (46 µL, 0.35 mmol) and triethylamine (50 µL, 0.36 mmol) in dimethylsulfoxide (0.5 mL) was heated at 140° C. for 20 hours. The mixture was then cooled, water was added and the resultant precipitate was filtered and dried in vacuo. Purification of the solid by flash chromatography (dichloromethane to 150:1 dichloromethane/methanol) gave the title compound (13 mg, 33%) as a yellow foam.

LRMS (m/z): 332 (M+1)$^+$.

$^1$H-NMR δ (300 MHz, CDCl$_3$): 1.1 (m, 1H), 1.2-1.4 (m, 3H), 1.5-1.8 (m, 5H), 1.9 (m, 2H), 3.2 (m, 2H), 4.7 (bs, 1H), 6.3 (d, 1H), 6.9-7.0 (m, 2H), 7.5 (t, 1H), 8.4 (s, 1H), 8.5 (d, 1H), 9.1 (s, 1H).

Example 10

3-{6-[(2,2-Dimethylpropyl)amino]pyridin-2-yl}pyrazolo[1,5-a]pyridine-5-carbonitrile

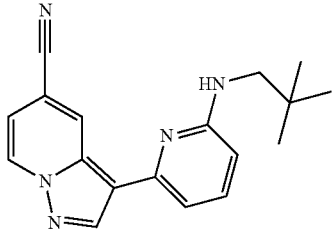 [SMILES: CC(C)(C)CNc1cccc(-c2cnn3ccc(C#N)cc23)n1]

An oven dried resealable Schlenk tube was charged with 3-(6-chloropyridin-2-yl)pyrazolo[1,5-a]pyridine-5-carbonitrile (Preparation 6, 30 mg, 0.12 mmol), (2,2-dimethylpropyl)amine (14 µL, 0.12 mmol), cesium carbonate (77 mg, 0.24 mmol), 1,1-binaphthalene-2,2'-diylbis(diphenylphosphine) (3 mg) and toluene (1.5 mL). The Schlenk tube was subjected to three cycles of evacuation-backfilling with argon and palladium (II) acetate (5 mg) was added. After three further cycles of evacuation-backfilling with argon, the Schlenk tube was capped and placed in an oil bath at 120° C. and stirred for 16 h. The mixture was then cooled and ethyl acetate was added. The organic layer was washed with water, dried (MgSO$_4$) and the solvents were evaporated. Purification of the residue by flash chromatography (dichloromethane to 150:1 dichloromethane/methanol) gave the title compound (13 mg, 34%) as a yellow solid.

LRMS (m/z): 306 (M+1)$^+$.

$^1$H-NMR δ (300 MHz, CDCl$_3$): 1.0 (s, 9H), 3.2 (d, 2H), 4.7 (bs, 1H), 6.3 (d, 1H), 6.9-7.0 (m, 2H), 7.5 (t, 1H), 8.4 (bs, 1H), 8.5 (d, 1H), 9.1 (bs, 1H).

Example 11

3-{6-[(3-Fluorobenzyl)amino]pyridin-2-yl}pyrazolo[1,5-a]pyridine-5-carbonitrile

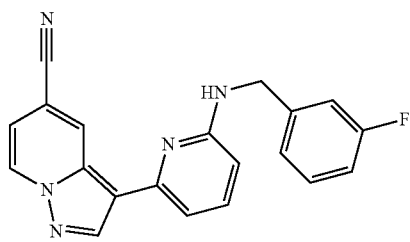 [SMILES: N#Cc1ccn2ncc(-c3cccc(NCc4cccc(F)c4)n3)c2c1]

Obtained as a yellow solid (57%) from 3-(6-chloropyridin-2-yl)pyrazolo[1,5-a]pyridine-5-carbonitrile (Preparation 6) and (3-fluorobenzyl)amine following the experimental procedure as described in Example 10 followed by purification by flash chromatography (dichloromethane to 250:1 dichloromethane/methanol).

LRMS (m/z): 344 (M+1)$^+$.

$^1$H-NMR δ (300 MHz, CDCl$_3$): 4.7 (bs, 2H), 5.1 (bs, 1H), 6.3 (d, 1H), 6.9 (d, 1H), 7.0 (t, 2H), 7.0-7.3 (m, 2H), 7.3-7.4 (m, 1H), 7.4-7.5 (m, 1H), 8.4 (s, 1H), 8.5 (d, 1H), 8.8 (bs, 1H).

Example 12

3-[6-(Benzylamino)pyridin-2-yl]pyrazolo[1,5-a]pyridine-5-carbonitrile

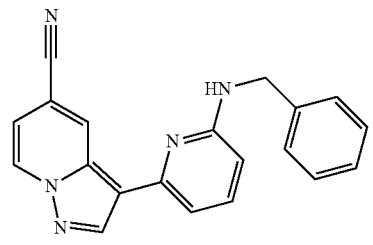 [SMILES: N#Cc1ccn2ncc(-c3cccc(NCc4ccccc4)n3)c2c1]

Obtained as a yellow solid (33%) from 3-(6-chloropyridin-2-yl)pyrazolo[1,5-a]pyridine-5-carbonitrile (Preparation 6) and benzylamine following the experimental procedure as described in Example 10 followed by purification by flash chromatography (100% dichloromethane to 300:1 dichloromethane/methanol).

LRMS (m/z): 326 (M+1)$^+$.

$^1$H-NMR δ (300 MHz, CDCl$_3$): 4.6 (d, 2H), 5.0 (bs, 1H), 6.3 (d, 1H), 6.9 (dd, 1H), 7.0 (d, 1H), 7.2-7.3 (m, 1H), 7.3-7.5 (m, 5H), 8.4 (s, 1H), 8.5 (d, 1H), 8.9 (bs, 1H).

Example 13

3-(6-{[(1S)-1-Phenylethyl]amino}pyridin-2-yl)pyrazolo[1,5-a]pyridine-5-carbonitrile

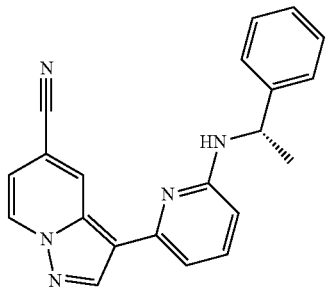 [SMILES: C[C@H](Nc1cccc(-c2cnn3ccc(C#N)cc23)n1)c1ccccc1]

Obtained as a yellow solid (39%) from 3-(6-chloropyridin-2-yl)pyrazolo[1,5-a]pyridine-5-carbonitrile (Preparation 6) and (S)-1-phenylethanamine following the experimental procedure as described in Example 10 followed by purification by flash chromatography (dichloromethane to 350:1 dichloromethane/methanol).

LRMS (m/z): 340 (M+1)$^+$.

$^1$H-NMR δ (300 MHz, CDCl$_3$): 1.7 (d, 3H), 4.9-5.0 (m, 1H), 5.0 (bs, 1H), 6.2 (d, 1H), 6.9 (dd, 1H), 7.0 (d, 1H), 7.2-7.3 (m, 2H), 7.3-7.5 (m, 4H), 8.4 (s, 1H), 8.5 (d, 1H), 8.9 (s, 1H).

Example 14

3-(4-{[(3R)-1-(Cyanoacetyl)piperidin-3-yl]amino}pyrimidin-2-yl)pyrazolo[1,5-a]pyridine-5-carbonitrile

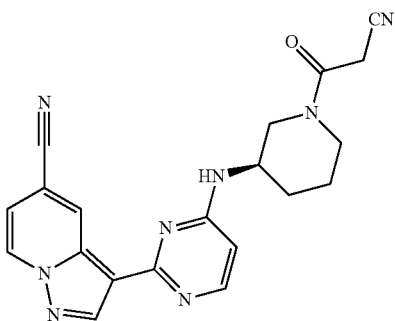 [SMILES: N#CCC(=O)N1CCC[C@@H](Nc2ccnc(-c3cnn4ccc(C#N)cc34)n2)C1]

3-[(2,5-Dioxopyrrolidin-1-yl)oxy]-3-oxopropanenitrile (prepared as described in BE875054(A1), 40 mg, 0.20 mmol) was added to a stirred solution of 3-{4-[(3R)-piperidin-3-ylamino]pyrimidin-2-yl}pyrazolo[1,5-a]pyridine-5-carbonitrile (Preparation 7b, 60 mg, 0.16 mmol) in ethanol (1.2 mL) and the mixture was stirred at ambient temperature for 20 hours. The solvent was then removed under reduced pressure and the residue was taken-up in a mixture of dichloromethane and 4% aqueous sodium hydrogen carbonate solution. The organic layer was separated, dried (MgSO$_4$) and the solvent evaporated in vacuo. The crude product was purified by flash chromatography (chloroform to 40:1 chloroform/methanol) to give the title compound (20 mg, 27%) as a solid.

LRMS (m/z): 388 (M+1)$^+$, 386 (M−1)$^−$.

$^1$H-NMR δ (300 MHz, CDCl$_3$, 2:1 mixture of rotamers): 1.7-1.9 (m, 4H), 2.0-2.1 (m, 1H), 2.2-2.3 (m, 1H), 2.9-3.0 (m, 1H), 3.3-3.4 (m, 1H), 3.5 (d, 1H), 3.5-3.6 (m, 1H), 4.1 (bs, 1H), 4.6 (d, 1H), 6.3 (d, 1H), 6.4 (d, 1H, minor rotamer), 7.0 (d, 1H), 7.1 (d, 1H, minor rotamer), 8.2 (d, 1H), 8.3 (d, 1H, minor rotamer), 8.5 (d, 1H), 8.6 (d, 1H, minor rotamer), 8.7 (s, 1H, minor rotamer), 8.8 (s, 1H), 9.0 (s, 1H).

Example 15

3-(4-{[(3R)-1-Acetylpiperidin-3-yl]amino}pyrimidin-2-yl)pyrazolo[1,5-a]pyridine-5-carbonitrile

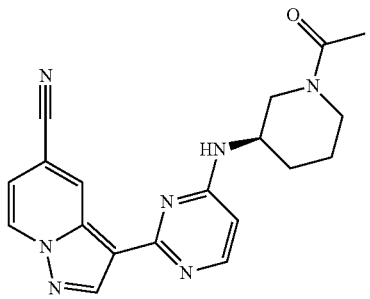 [SMILES: CC(=O)N1CCC[C@@H](Nc2ccnc(-c3cnn4ccc(C#N)cc34)n2)C1]

Triethylamine (44 μL, 0.32 mmol), acetic anhydride (8.2 μL, 0.09 mmol) and N,N-dimethylpyridin-4-amine (1.2 mg, 0.01 mmol) were added to a stirred solution of 3-{4-[(3R)-piperidin-3-ylamino]pyrimidin-2-yl}pyrazolo[1,5-a]pyridine-5-carbonitrile (Preparation 7b, 40 mg, 0.06 mmol) in dichloromethane (1.5 mL) and the mixture was stirred at ambient temperature for 20 hours before being partitioned between dichloromethane and 4% aqueous sodium hydrogen carbonate solution. The organic layer was separated, washed with water and brine, dried (MgSO$_4$) and the solvent was evaporated in vacuo. The crude product was purified by flash chromatography (100:1 to 20:1 chloroform/methanol) to give the title compound (10 mg, 44%) as a solid.

LRMS (m/z): 363 (M+1)$^+$, 361 (M−1)$^−$.

$^1$H-NMR δ (300 MHz, CDCl$_3$): 0.7-0.9 (m, 2H), 1.9 (d, 2H), 2.1 (d, 1H), 2.2 (s, 3H), 3.2-3.5 (m, 1H), 3.6 (bs, 1H), 3.8 (bs, 1H), 4.3-4.5 (m, 1H), 5.0 (bs, 1H), 6.2-6.3 (m, 1H), 7.0 (t, 1H), 8.3 (dd, 1H), 8.6 (t, 1H), 8.8 (d, 1H), 9.1 (d, 1H).

Example 16

3-(4-{[(3R)-1-(5-Cyanopyridin-2-yl)piperidin-3-yl]amino}pyrimidin-2-yl)pyrazolo[1,5-a]pyridine-5-carbonitrile

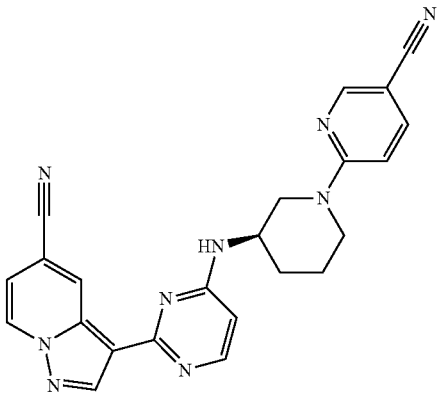 [SMILES: N#Cc1ccc(N2CCC[C@@H](Nc3ccnc(-c4cnn5ccc(C#N)cc45)n3)C2)nc1]

6-Chloronicotinonitrile (0.04 g, 0.29 mmol) and triethylamine (0.15 mL, 1.08 mmol) were added to a stirred solution of 3-{4-[(3R)-piperidin-3-ylamino]pyrimidin-2-yl}pyrazolo[1,5-a]pyridine-5-carbonitrile (Preparation 7b, 0.11 g, 0.24 mmol) in dichloromethane (3.3 mL) and the resulting mixture was stirred at 50° C. for 20 hours. The reaction mixture was then cooled to ambient temperature and dichloromethane and 4% aqueous sodium hydrogencarbonate solution were added. The organic layer was separated, washed with water and brine, dried (MgSO$_4$) and evaporated in vacuo. The crude product was purified by flash chromatography (200:1 to 60:1 chloroform/methanol) to give the title compound (0.07 g, 71%) as a pale yellow solid.

LRMS (m/z): 422 (M+1)$^+$, 420 (M−1)$^−$.

$^1$H-NMR δ (300 MHz, CDCl$_3$): 1.3-1.4 (m, 1H), 1.8 (m, 2H), 1.9-2.0 (m, 1H), 2.2-2.3 (m, 1H), 3.2-3.5 (m, 2H), 4.0-4.1 (m, 1H), 4.5-4.6 (m, 1H), 5.0 (bs, 1H), 6.3 (bs, 1H), 6.7 (d, 1H), 7.0 (dd, 1H), 7.6 (dd, 1H), 8.3 (d, 1H), 8.4 (bs, 1H), 8.6 (d, 1H), 8.8 (s, 1H), 9.0 (s, 1H).

Example 17

3-(4-{[(3R)-1-(3,3,3-Trifluoropropanoyl)piperidin-3-yl]amino}pyrimidin-2-yl) pyrazolo[1,5-a]pyridine-5-carbonitrile

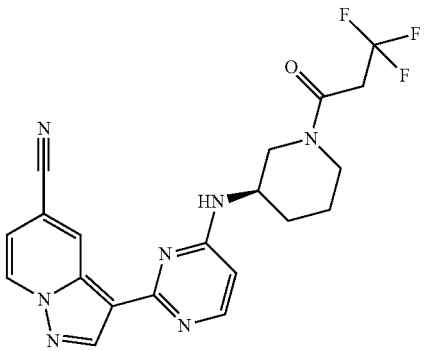 [SMILES: N#Cc1ccn2ncc(-c3nccc(N[C@@H]4CCCN(C(=O)CC(F)(F)F)C4)n3)c2c1]

3,3,3-Trifluoropropanoic acid (0.03 mL, 0.29 mmol), N-[(dimethylamino)(3H-[1,2,3]triazolo[4,5-b]pyridin-3-yloxy)methylene]-N-methylmethanaminium hexafluorophosphate (0.12 g, 0.30 mmol) and diisopropylethylamine (0.21 mL, 1.21 mmol) were added to a stirred solution of 3-{4-[(3R)-piperidin-3-ylamino]pyrimidin-2-yl}pyrazolo[1,5-a]pyridine-5-carbonitrile (Preparation 7b, 0.11 g, 0.24 mmol) in N,N'-dimethylformamide (3 mL) and the mixture was stirred at room temperature for 20 hours. The reaction mixture was then partitioned between dichloromethane and 4% aqueous sodium hydrogen carbonate solution. The organic layer was separated, washed with 4% aqueous sodium hydrogen carbonate solution, dried (MgSO$_4$) and the solvents were evaporated in vacuo. The crude product was purified by flash chromatography (200:1 to 10:1 chloroform/methanol) to give a residue that was repurified by flash chromatography (1:1 hexane/ethyl acetate to 100% ethyl acetate) to give the title compound (0.02 g, 19%) as a pale yellow solid.

LRMS (m/z): 430 (M+1)$^+$, 428 (M−1)$^−$.

$^1$H-NMR δ (300 MHz, CDCl$_3$): 1.9-2.0 (m, 1H), 3.0-3.2 (m, 2H), 3.3-3.5 (m, 4H), 3.6-3.8 (m, 1H), 3.9 (d, 1H), 4.1-4.3 (m, 1H), 4.5 (d, 1H), 5.0 (bs, 1H), 6.3 (dd, 1H), 6.9-7.0 (m, 1H), 8.2-8.3 (m, 1H), 8.6 (t, 1H), 8.7 (d, 1H), 9.1 (bs, 1H).

Example 18

3-{4-[[(3R)-1-(Cyanocarbonyl)piperidin-3-yl]methyl)amino]pyrimidin-2-yl}pyrazolo[1,5-a]pyridine-5-carbonitrile

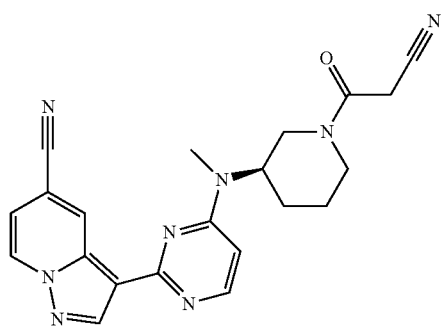 [SMILES: CN(c1ccnc(-c2cnn3ccc(C#N)cc23)n1)[C@@H]1CCCN(C(=O)CC#N)C1]

Obtained as a yellow solid (52%) from (R)-3-(4-(methyl(piperidin-3-yl)amino)pyrimidin-2-yl)pyrazolo[1,5-a]pyridine-5-carbonitrile (Preparation 8b) and 3-[(2,5-dioxopyrrolidin-1-yl)oxy]-3-oxopropanenitrile (prepared as described in BE875054(A1)) following the experimental procedure as described in Example 14 followed by purification by flash chromatography (dichloromethane to 9:1 dichloromethane/methanol).

LRMS (m/z): 401 (M+1)$^+$.

$^1$H-NMR δ (300 MHz, CDCl$_3$, 2:1 mixture of rotamers): 1.7-1.9 (m, 4H), 2.1-2.2 (m, 1H), 2.3-2.5 (m, 1H), 2.9-3.0 (m, 1H), 3.1 (s, 3H, minor rotamer), 3.2 (s, 3H, major rotamer), 3.3-3.4 (m, 1H), 3.5 (d, 1H), 3.6-3.7 (m, 1H), 4.2 (bs, 1H), 4.5 (d, 1H), 6.2 (d, 1H), 6.5 (d, 1H, minor rotamer), 7.1 (d, 1H), 7.2 (d, 1H, minor rotamer), 8.2 (d, 1H), 8.3 (d, 1H, minor rotamer), 8.5 (d, 1H), 8.7 (d, 1H, minor rotamer), 8.7 (s, 1H, minor rotamer), 8.8 (s, 1H), 9.0 (s, 1H).

Example 19

3-(4-((Trans)-4-Hydroxycyclohexylamino)pyrimidin-2-yl)pyrazolo[1,5-a]pyridine-5-carbonitrile

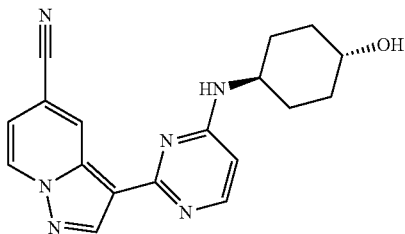 [SMILES: N#Cc1ccn2ncc(-c3nccc(N[C@H]4CC[C@H](O)CC4)n3)c2c1]

Trans-4-aminocyclohexanol (85 mg, 0.74 mmol) was added to a solution of 3-(4-(1H-benzo[d][1,2,3]triazol-1-yloxy)pyrimidin-2-yl)pyrazolo[1,5-a]pyridine-5-carbonitrile (byproduct of Preparation 7a, 105 mg, 0.30 mmol) in N,N'-dimethylformamide (3 mL) and the mixture was stirred at ambient temperature overnight. The solvent was then evaporated and the residue was partitioned between water and ethyl acetate. The organic layer was separated, washed with water and brine, dried (MgSO$_4$) and the solvent evaporated. The crude product was purified by flash chromatography (dichloromethane to 9:1 dichloromethane/methanol) to give the title compound (66 mg, 67%) as a yellow solid.

LRMS (m/z): 335 (M+1)$^+$.

$^1$H-NMR δ (400 MHz, DMSO-d$_6$): 0.4-0.6 (m, 3H), 1.0-1.1 (m, 3H), 1.2-1.3 (m, 2H), 2.3 (d, 1H), 2.7 (bs, 1H), 3.0 (bs, 1H), 5.5 (bs, 1H), 6.5 (d, 1H), 6.6 (d, 1H), 7.2 (bs, 1H), 7.9 (s, 1H), 8.1 (bs, 1H), 8.2 (d, 1H).

Example 20

N-(Cyclohexylmethyl)-2-pyrazolo[1,5-a]pyrazin-3-ylpyrimidin-4-amine

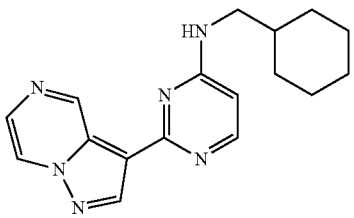 [SMILES: c1cn2ncc(-c3nccc(NCC4CCCCC4)n3)c2cn1]

Obtained as monoformate salt (16%) from 2-(pyrazolo[1,5-a]pyrazin-3-yl)pyrimidin-4-ol (Preparation 10b) and cyclohexylmethanamine following the experimental procedure as described in Preparation 7a followed by purification by reverse phase chromatography (C-18 silica from Waters, water/acetonitrile/methanol as eluents [0.1% v/v formic acid buffered] 5% to 50%).

LRMS (m/z): 309 (M+1)⁺.

¹H-NMR δ (300 MHz, CD₃OD): 0.8-1.0 (m, 1H), 1.0-1.2 (m, 2H), 1.2-1.4 (m, 4H), 1.7-1.8 (m, 4H), 1.9 (d, 2H), 6.4 (bs, 1H), 7.8-8.1 (m, 2H), 8.4-8.6 (m, 1H), 8.7 (bs, 2H), 10.0 (bs, 1H).

Example 21

(S)—N-(1-phenylethyl)-2-(pyrazolo[1,5-a]pyrazin-3-yl)pyrimidin-4-amine

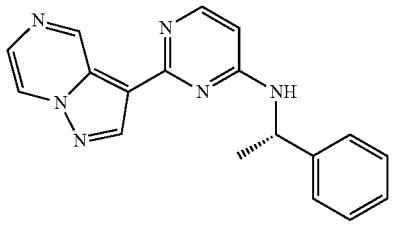 [SMILES: C[C@H](Nc1ccnc(-c2cnn3ccncc23)n1)c1ccccc1]

Obtained as a solid (38%) from 2-(pyrazolo[1,5-a]pyrazin-3-yl)pyrimidin-4-ol (Preparation 10b) and (S)-1-phenylethanamine following the experimental procedure as described in Preparation 7a followed by purification by flash chromatography (dichloromethane to 99:1 dichloromethane/methanol).

LRMS (m/z): 317 (M+1)⁺.

¹H-NMR δ (300 MHz, CD₃OD): 1.1-1.2 (m, 1H), 1.6 (d, 3H), 5.3 (bs, 1H), 7.1-7.2 (m, 1H), 7.3-7.4 (m, 2H), 7.4 (d, 2H), 7.9 (bs, 1H), 8.1 (d, 1H), 8.6 (d, 2H), 9.6 (bs, 1H).

Example 22

N-Benzyl-2-pyrazolo[1,5-a]pyrazin-3-ylpyrimidin-4-amine

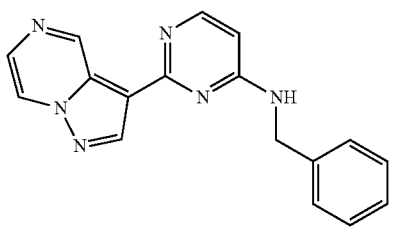 [SMILES: c1ccc(CNc2ccnc(-c3cnn4ccncc34)n2)cc1]

Obtained as monoformate salt (48%) from 2-(pyrazolo[1,5-a]pyrazin-3-yl)pyrimidin-4-ol (Preparation 10b) and benzylamine following the experimental procedure as described in Preparation 7a followed by purification by reverse phase chromatography (C-18 silica from Waters, water/acetonitrile/methanol as eluents [0.1% v/v formic acid buffered] 5% to 50%).

LRMS (m/z): 303 (M+1)⁺.

¹H-NMR δ (300 MHz, CD₃OD): 4.7 (s, 2H), 6.4 (bs, 1H), 7.2-7.3 (m, 1H), 7.3-7.5 (m, 4H), 8.0 (bs, 1H), 8.1 (bs, 1H), 8.5 (bs, 1H), 8.6 (bs, 2H), 9.7 (bs, 1H).

Example 23

N-(2,2-Dimethylpropyl)-2-pyrazolo[1,5-a]pyrazin-3-ylpyrimidin-4-amine

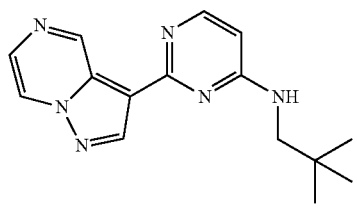 [SMILES: CC(C)(C)CNc1ccnc(-c2cnn3ccncc23)n1]

Obtained (43%) from 2-(pyrazolo[1,5-a]pyrazin-3-yl)pyrimidin-4-ol (Preparation 10b) and 2,2-dimethylpropan-1-amine following the experimental procedure as described in Preparation 7a followed by purification by flash chromatography (98:2 to 95:5 dichloromethane/methanol).

LRMS (m/z): 283 (M+1)⁺.

¹H-NMR δ (300 MHz, CDCl₃): 1.0 (s, 9H), 3.2 (bs, 2H), 5.1 (bs, 1H), 6.3 (d, 1H), 8.0 (d, 1H), 8.3 (d, 1H), 8.4 (d, 1H), 8.7-8.8 (m, 1H), 10.0 (bs, 1H).

Example 24

3-Oxo-3-{(3R)-3-[(2-pyrazolo[1,5-a]pyrazin-3-ylpyrimidin-4-yl)-amino]piperidin-1-yl}propanenitrile

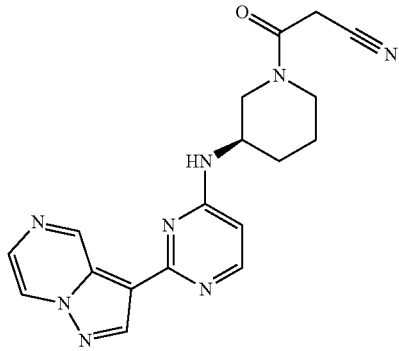 [SMILES: N#CCC(=O)N1CCC[C@@H](Nc2ccnc(-c3cnn4ccncc34)n2)C1]

Obtained as a solid (55%) from (R)—N-(piperidin-3-yl)-2-(pyrazolo[1,5-a]pyrazin-3-yl) pyrimidin-4-amine (Preparation 11b) and 3-[(2,5-dioxopyrrolidin-1-yl)oxy]-3-oxo propanenitrile (prepared as described in BE875054(A1)) following the experimental procedure as described in Example 14 followed by purification by flash chromatography (dichloromethane to 9:1 dichloromethane/methanol).

LRMS (m/z): 363 (M−1-1)⁺.

¹H-NMR δ (400 MHz, CDCl₃, 1:1 mixture of rotamers): 1.7-2.0 (m, 6H), 2.1-2.2 (m, 2H), 3.4 (s, 2H, rotamer 1), 3.6 (s, 2H, rotamer 2), 4.2-4.4 (m, 1H), 5.0 (bs, 1H), 6.3 (d, 1H, rotamer 1), 6.3 (d, 1H, rotamer 2), 8.0 (d, 1H, rotamer 1), 8.0 (d, 1H, rotamer 2), 8.3 (d, 1H, rotamer 1), 8.3 (d, 1H, rotamer 2), 8.4 (dd, 1H, rotamer 1), 8.5 (dd, 1H, rotamer 2), 8.7 (s, 1H, rotamer 1), 8.7 (s, 1H, rotamer 2), 10.0 (s, 1H).

Example 25

6-{(3R)-3-[(2-Pyrazolo[1,5-a]pyrazin-3-ylpyrimidin-4-yl)amino]piperidin-1-yl}nicotinonitrile

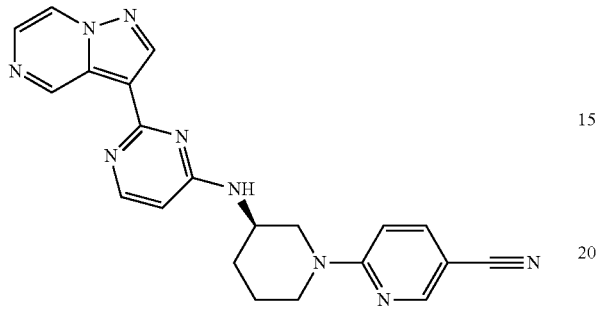

Obtained as a solid (23%) from (R)—N-(piperidin-3-yl)-2-(pyrazolo[1,5-a]pyrazin-3-yl)pyrimidin-4-amine (Preparation 11b) and 6-chloronicotinonitrile following the experimental procedure as described in Example 16 followed by purification by flash chromatography (dichloromethane to 85:15 dichloromethane/methanol).

LRMS (m/z): 398 (M+1)$^+$.

$^1$H-NMR δ (200 MHz, CDCl$_3$): 1.8 (m, 4H), 3.3-3.6 (m, 2H), 3.8-4.3 (m, 2H), 4.4 (m, 1H), 5.0 (bs, 1H), 6.3 (d, 1H), 6.7 (d, 1H), 7.6 (dd, 1H), 8.0 (d, 1H), 8.3 (d, 1H), 8.3-8.5 (m, 2H), 8.7 (s, 1H), 10.0 (s, 1H).

Example 26

2-Pyrazolo[1,5-a]pyrazin-3-yl-N-[(3R)-1-(3,3,3-trifluoropropanoyl)piperidin-3-yl]pyrimidin-4-amine

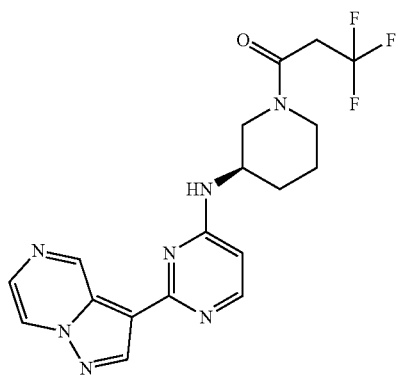 [SMILES: O=C(CC(F)(F)F)N1CCC[C@@H](Nc2ccnc(-c3cnn4ccncc34)n2)C1]

Obtained as a solid (12%) from (R)—N-(piperidin-3-yl)-2-(pyrazolo[1,5-a]pyrazin-3-yl) pyrimidin-4-amine (Preparation 11b) and 3,3,3-trifluoropropanoic acid following the experimental procedure as described in Example 17 followed by purification by flash chromatography (dichloromethane to 9:1 dichloromethane/methanol).

LRMS (m/z): 406 (M+1)$^+$.

$^1$H-NMR δ (400 MHz, CDCl$_3$, 4:3 mixture of rotamers): 1.7-1.8 (m, 1H), 1.8-2.0 (m, 2H), 2.0-2.2, (m, 2H), 2.6 (s, 2H, major rotamer), 2.7 (s, 2H, minor rotamer), 3.1-3.2 (m, 1H), 3.3-3.4 (m, 1H), 3.8-3.9 (m, 1H), 4.3 (bs, 1H), 4.9 (bs, 1H, minor rotamer), 5.0 (bs, 1H, major rotamer), 6.3 (d, 1H, minor rotamer), 6.3 (d, 1H, major rotamer), 8.0 (d, 1H), major rotamer), 8.0 (d, 1H, minor rotamer), 8.3 (d, 1H, major rotamer), 8.3 (d, 1H, minor rotamer), 8.4 (d, 1H, major rotamer), 8.4 (d, 1H, minor rotamer), 8.7 (s, 1H, minor rotamer), 8.7 (s, 1H, major rotamer), 10.0 (s, 1H).

Example 27

3-{(3R)-3-[Methyl(2-pyrazolo[1,5-a]pyrazin-3-ylpyrimidin-4-yl)amino]piperidin-1-yl}-3-oxopropanenitrile

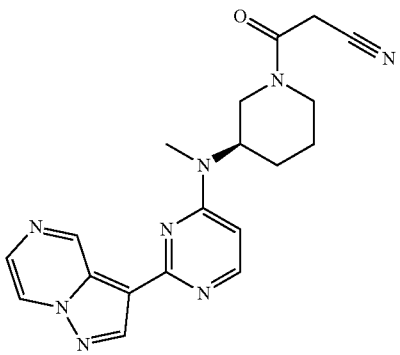 [SMILES: CN(c1ccnc(-c2cnn3ccncc23)n1)[C@@H]1CCCN(C(=O)CC#N)C1]

Obtained (76%) from N-methyl-N-[(3R)-piperidin-3-yl]-2-pyrazolo[1,5-a]pyrazin-3-yl) pyrimidin-4-amine (Preparation 12b) and 3-[(2,5-dioxopyrrolidin-1-yl)oxy]-3-oxopropane nitrile (prepared as described in BE875054(A1)) following the experimental procedure as described in Example 14.

LRMS (m/z): 377 (M+1)$^+$.

$^1$H-NMR δ (400 MHz, CDCl$_3$, 2:1 mixture of rotamers): 1.2-1.4 (m, 2H) 1.7-2.2 (m, 4H), 3.1 (s, 2H, major rotamer), 3.1 (s, 2H, minor rotamer), 3.1-3.3 (m, 1H) 3.5 (s, 3H, minor rotamer), 3.6 (s, 3H, major rotamer), 3.7-3.9 (m, 2H), 6.4 (d, 1H), 6.4 (d, 1H), 8.0 (d, 1H), 8.0 (d, 1H), 8.3 (d, 1H), 8.3 (d, 1H), 8.4 (dd, 1H), 8.4 (dd, 1H), 8.7 (s, 1H), 8.7 (s, 1H), 9.9 (s, 1H), 9.9 (s, 1H).

Example 28

3-{(3R)-3-[(5-Chloro-2-pyrazolo[1,5-a]pyrazin-3-ylpyrimidin-4-yl)amino]piperidin-1-yl}-3-oxopropanenitrile

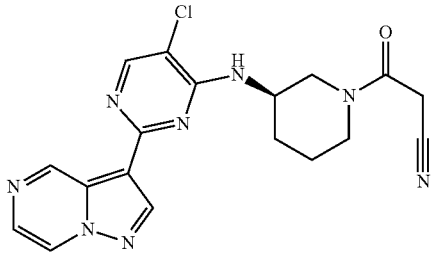 [SMILES: N#CCC(=O)N1CCC[C@@H](Nc2nc(-c3cnn4ccncc34)ncc2Cl)C1]

Obtained as a white solid (61%) from 5-chloro-N-(piperidin-3-yl)-2-(pyrazolo[1,5-a]pyrazin-3-yl)pyrimidin-4-amine (Preparation 15b) and 3-[(2,5-dioxopyrrolidin-1-yl)oxy]-3-oxopropanenitrile (prepared as described in BE875054(A1)) following the experimental procedure as described in Example 14 followed by purification by flash chromatography (dichloromethane to 9:1 dichloromethane/methanol).

LRMS (m/z): 397 (M+1)+.

$^1$H-NMR δ (300 MHz, CDCl$_3$): 1.7-2.0 (m, 2H), 2.2 (bs, 2H), 3.3-3.5 (m, 2H), 3.6 (s, 2H), 3.8 (bs, 1H), 4.4 (bs, 2H), 5.4 (bs, 1H), 8.0 (bs, 1H), 8.3 (s, 1H), 8.4 (bs, 1H), 8.8 (s, 1H), 9.9 (s, 1H).

Example 29

3-{(3R)-3-[(5-Fluoro-2-pyrazolo[1,5-a]pyrazin-3-ylpyrimidin-4-yl)amino]piperidin-1-yl}-3-oxopropanenitrile

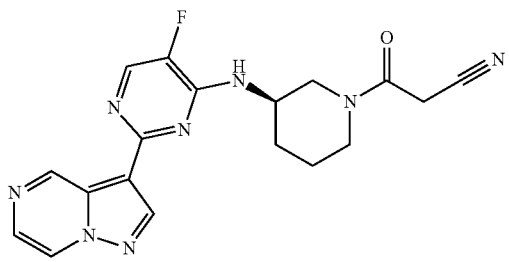 [SMILES: N#CCC(=O)N1CCC[C@@H](Nc2nc(-c3cnn4ccncc34)ncc2F)C1]

Obtained as a white solid (62%) from (R)-5-fluoro-N-(piperidin-3-yl)-2-(pyrazolo[1,5-a]pyrazin-3-yl)pyrimidin-4-amine (Preparation 18b) and 3-[(2,5-dioxopyrrolidin-1-yl)oxy]-3-oxopropanenitrile (prepared as described in BE875054(A1)) following the experimental procedure as described in Example 14 followed by purification by flash chromatography (dichloromethane to 8:2 dichloromethane/methanol).

LRMS (m/z): 381 (M+1)+.

$^1$H-NMR δ (400 MHz, CDCl$_3$, 1:1 mixture of rotamers): 1.7-2.0 (m, 4H), 2.1-2.25 (m, 1H), 3.3-3.4 (m, 1H), 3.4-3.6 (m, 1H), 3.6 (s, 2H), 3.8-3.9 (m, 1H), 4.3-4.4 (m, 1H), 5.1 (t, 1H), 8.0 (d, 1H, rotamer 2), 8.0 (d, 1H, rotamer 1), 8.1 (d, 1H, rotamer 2), 8.2 (d, 1H, rotamer 1), 8.4 (d, 1H, rotamer 2), 8.4 (d, 1H, rotamer 1), 8.6 (s, 1H, rotamer 2), 8.7 (s, 1H, rotamer 1), 9.9 (s, 1H).

Example 30

5-Fluoro-2-pyrazolo[1,5-a]pyrazin-3-yl-N-[(3R)-1-(3,3,3-trifluoropropanoyl) piperidin-3-yl]pyrimidin-4-amine

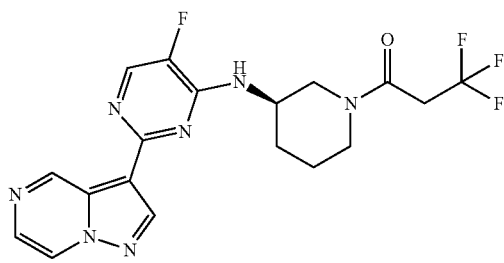 [SMILES: O=C(CC(F)(F)F)N1CCC[C@@H](Nc2nc(-c3cnn4ccncc34)ncc2F)C1]

Obtained as a white solid (42%) from (R)-5-fluoro-N-(piperidin-3-yl)-2-(pyrazolo[1,5-a]pyrazin-3-yl)pyrimidin-4-amine (Preparation 18b) and 3,3,3-trifluoropropanoic acid following the experimental procedure as described in Example 17 followed by purification by flash chromatography (dichloromethane to 92:8 dichloromethane/methanol).

LRMS (m/z): 424 (M+1)+.

$^1$H-NMR δ (400 MHz, CDCl$_3$, 1:1 mixture of rotamers): 1.7-1.8 (m, 2H), 1.8-2.0 (m, 4H), 2.1-2.2 (m, 1H), 3.3-3.4 (m, 1H, rotamer 1), 3.4-3.5 (m, 1H, rotamer 2), 3.6 (d, 1H, rotamer 1), 3.9 (d, 1H, rotamer 2), 4.2 (d, 1H, rotamer 1), 4.4 (bs, 1H, rotamer 2), 5.1 (d, 1H, rotamer 1), 5.2 (d, 1H, rotamer 2), 8.0 (d, 1H, rotamer 1), 8.0 (d, 1H, rotamer 2), 8.1 (d, 1H, rotamer 1), 8.2 (d, 1H, rotamer 2), 8.4 (d, 1H, rotamer 1), 8.4 (d, 1H, rotamer 2), 8.6 (s, 1H, rotamer 1), 8.7 (s, 1H, rotamer 2), 9.9 (s, 1H, rotamer 1), 9.9 (bs, 1H, rotamer 2).

Example 31

3-{(3R)-3-[(5-Methyl-2-pyrazolo[1,5-a]pyrazin-3-ylpyrimidin-4-yl)amino]piperidin-1-yl}-3-oxopropanenitrile

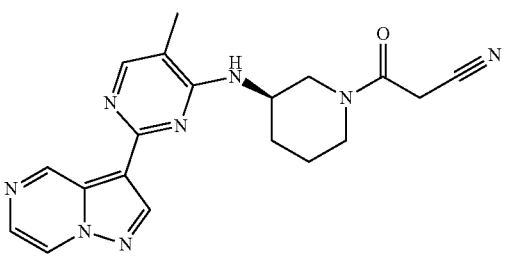 [SMILES: Cc1cnc(-c2cnn3ccncc23)nc1N[C@@H]1CCCN(C(=O)CC#N)C1]

Obtained as a white solid (45%) from 5-methyl-N-[(3R)-piperidin-3-yl]-2-pyrazolo[1,5-a]pyrazin-3-ylpyrimidin-4-amine (Preparation 21b) and 3-[(2,5-dioxopyrrolidin-1-yl)oxy]-3-oxopropanenitrile (prepared as described in BE875054(A1)) following the experimental procedure as described in Example 14 followed by purification by recrystallization from ethanol.

LRMS (m/z): 377 (M+1)+.

$^1$H-NMR δ (400 MHz, DMSO-d$_6$, 1:1 mixture of rotamers): 1.6-1.7 (m, 2H), 1.8 (bs, 2H), 2.1 (s, 3H), 2.1-2.2 (m, 1H, rotamer 2), 2.6-2.8 (m, 1H, rotamer 1), 3.0-3.2 (m, 1H), 3.4 (s, 2H), 3.7 (d, 1H, rotamer 2), 3.8 (d, 1H, rotamer 1), 3.9-4.2 (m, 1H, rotamer 2), 4.3 (bs, 1H, rotamer 1), 6.6 (d, 1H, rotamer 2), 6.7 (d, 1H, rotamer 1) 8.0 (bs, 1H, rotamer 2), 8.1 (bs, 1H, rotamer 1), 8.8 (s, 1H, rotamer 2), 8.8 (s, 1H, rotamer 1), 8.9 (bs, 1H), 9.8 (s, 1H, rotamer 2), 9.8 (s, 1H, rotamer 1).

Example 32

(S)—N-(1-(5-Fluoropyridin-2-yl)ethyl)-2-(pyrazolo[1,5-a]pyrazin-3-yl)pyrimidin-4-amine

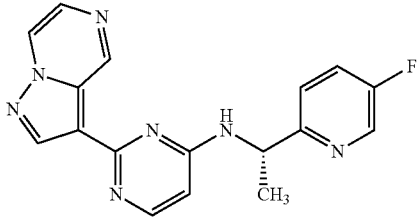 [SMILES: C[C@H](Nc1ccnc(-c2cnn3ccncc23)n1)c1ccc(F)cn1]

A solution of 3-(4-chloropyrimidin-2-yl)pyrazolo[1,5-a]pyrazine (Preparation 31, 170 mg, 0.61 mmol), (S)-1-(5-fluoropyridin-2-yl)ethanamine (85 mg, 0.61 mmol, prepared as described in WO2006/82392A1) and diisopropylethylamine (122 μL, 0.70 mmol) in N,N'-dimethylformamide (5 mL) was heated to 150° C. in a microwave oven for 75 min. The solvent was then removed under reduced pressure and the residue was partitioned between 4% aqueous sodium hydrogen carbonate solution and ethyl acetate. The organic phase was separated, washed with brine, dried (MgSO$_4$) and concentrated to give a crude which was purified by reverse phase chromatography (C-18 silica from Waters, water/acetonitrile/methanol as eluents [0.1% v/v formic acid buffered] 5% to 50%) to give the title compound (9 mg, 4%) as an oil. The corresponding fumarate salt was prepared by adding a solution of fumaric acid (3.1 mg, 0.027 mmol) in ethanol (0.5 mL) to a solution of the title compound (as free base, 9 mg, 0.027 mmol) in ethanol (2 mL) followed by evaporation of the solvent. The resulting solid was dried in an oven under vacuum to give 11 mg of the desired fumarate salt.

LRMS (m/z): 336 (M+1)$^+$ $^1$H NMR δ (400 MHz, CDCl$_3$, fumarate salt): 1.6 (d, 3H), 5.9-6.1 (m, 1H), 6.2-6.4 (m, 1H), 7.4 (dd, 2H), 8.0 (d, 1H), 8.2 (d, 1H), 8.4 (dd, 2H), 8.7 (s, 1H), 10.0 (s, 1H).

Example 33

N-((5-Fluoropyridin-2-yl)methyl)-2-(pyrazolo[1,5-a]pyrazin-3-yl)pyrimidin-4-amine

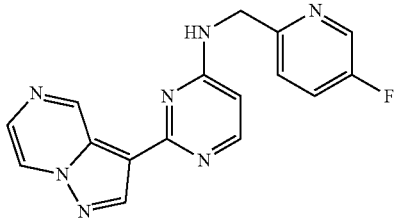 [SMILES: Fc1ccc(CNc2ccnc(-c3cnn4ccncc34)n2)nc1]

Obtained as a solid (5%) from 2-(pyrazolo[1,5-a]pyrazin-3-yl)pyrimidin-4-ol (Preparation 10b) and (5-fluoropyridin-2-1)methanamine following the experimental procedure as described in Preparation 7a followed by purification by reverse phase chromatography (C-18 silica from Waters©, water/acetonitrile/methanol as eluents [0.1% v/v formic acid buffered] 0% to 100%).

LRMS (m/z): 322 (M+1)$^+$, 320 (M−1)$^-$.

$^1$H NMR δ (400 MHz, CDCl$_3$): 4.7-5.0 (m, 2H), 6.3-6.4 (m, 1H), 7.4 (d, 2H), 8.0 (d, 1H), 8.3 (d, 1H), 8.4 (dd, 2H), 8.7 (s, 1H), 10.00 (d, 1H).

Example 34

5-Chloro-N-((5-fluoropyridin-2-yl)methyl)-2-(pyrazolo[1,5-a]pyrazin-3-yl)pyrimidin-4-amine

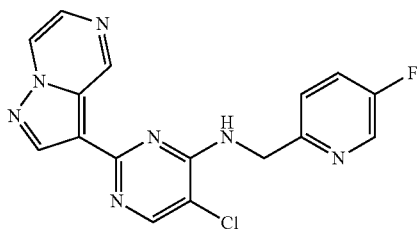 [SMILES: Fc1ccc(CNc2nc(-c3cnn4ccncc34)ncc2Cl)nc1]

A mixture of 3-(4,5-dichloropyrimidin-2-yl)pyrazolo[1,5-a]pyrazine (Preparation 32, 75 mg, 0.26 mmol), (5-fluoropyridin-2-yl)methanamine (33 mg, 0.26 mmol) and diisopropylethylamine (52 μL, 30 mmol) in tetrahydrofuran (3 mL) was heated to reflux for 72 h. The solvent was then evaporated under reduced pressure and the crude product was purified by reverse phase chromatography (C-18 silica from Waters©, water/acetonitrile/methanol as eluents [0.1% v/v formic acid buffered] 0% to 100%) to give the title compound (37 mg, 39%).

LRMS (m/z): 356 (M+1)$^+$ $^1$H NMR 15 (300 MHz, CDCl$_3$): 4.8-5.0 (m, 2H), 6.7 (bs, 1H), 7.4 (d, 2H), 8.0 (d, 1H), 8.3 (s, 1H), 8.4 (dd, 1H), 8.6 (s, 1H), 8.7 (s, 1H), 9.8 (s, 1H).

Example 35

2-(Pyrazolo[1,5-a]pyrazin-3-yl)-N$^4$-(tetrahydro-2H-pyran-4-yl)pyrimidine-4,5-diamine

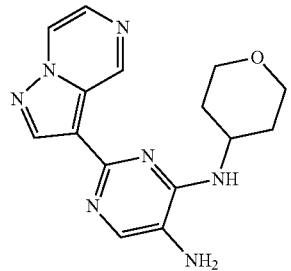 [SMILES: Nc1cnc(-c2cnn3ccncc23)nc1NC1CCOCC1]

10% Palladium on carbon (0.392 g, 0.37 mmol) was added to a suspension of 5-nitro-2-(pyrazolo[1,5-a]pyrazin-3-yl)-N-(tetrahydro-2H-pyran-4-yl)pyrimidin-4-amine (Preparation 25, 0.785 g, 2.31 mmol) in ethanol (50 mL) and the mixture was stirred under an hydrogen atmosphere at ambient temperature. After 4 hours, the mixture was filtered through Celite® and the filter cake was washed with ethanol. The combined filtrate and washings were evaporated to give the title compound (0.670 g, 94%) as a pale green solid.

LRMS (m/z): 312 (M+1)$^+$.

$^1$H NMR δ (300 MHz, DMSO-d$_6$): 1.6 (ddd, 2H), 2.1 (d, 2H), 3.5 (t, 2H), 4.0 (d, 2H), 4.2-4.3 (m, 1H), 5.0 (s, 2H), 6.4 (d, 1H), 7.7 (s, 1H), 7.9 (d, 1H), 8.5 (s, 1H), 8.8 (dd, 1H), 9.8 (d, 1H).

Example 36

N$^4$-(4,4-Difluorocyclohexyl)-2-(pyrazolo[1,5-a]pyrazin-3-yl)pyrimidine-4,5-diamine

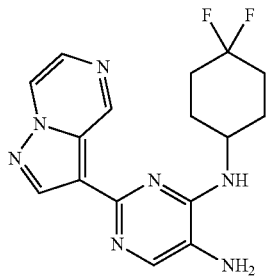 [SMILES: Nc1cnc(-c2cnn3ccncc23)nc1NC1CCC(F)(F)CC1]

Obtained as an off white solid (87%) from N-(4,4-difluorocyclohexyl)-5-nitro-2-(pyrazolo[1,5-a]pyrazin-3-yl)pyrimidin-4-amine (Preparation 26) following the experimental procedure as described in Example 35.

LRMS (m/z): 346 (M+1)+.

$^1$H NMR δ (300 MHz, DMSO-d$_6$): 1.7 (m, 2H), 2.0-2.2 (m, 6H), 4.3 (m, 1H), 5.0 (s, 2H), 6.4 (d, 1H), 7.7 (s, 1H), 8.0 (d, 1H), 8.6 (s, 1H), 8.8 (d, 1H), 9.8 (s, 1H).

Example 37

(S)-5-Chloro-N-(1-(5-fluoropyridin-2-yl)ethyl)-2-(pyrazolo[1,5-a]pyrazin-3-yl)pyrimidin-4-amine

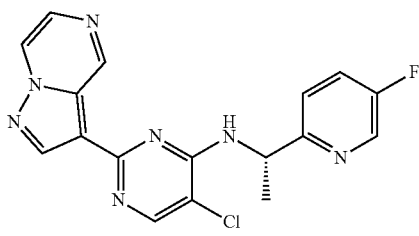 [SMILES: C[C@H](Nc1nc(-c2cnn3ccncc23)ncc1Cl)c1ccc(F)cn1]

Obtained as a solid (57%) from 3-(4,5-dichloropyrimidin-2-yl)pyrazolo[1,5-a]pyrazine (Preparation 32) and (S)-1-(5-fluoropyridin-2-yl)ethanamine (prepared as described in WO2006/82392) following the experimental procedure as described in Example 34.

LRMS (m/z): 370 (M+1)+

$^1$H NMR δ (300 MHz, CDCl$_3$): 1.7 (d, 3H), 5.4-5.6 (m, 1H), 6.6-6.8 (m, 1H), 7.3-7.5 (m, 2H), 7.9-8.1 (m, 1H), 8.3 (s, 1H), 8.3-8.5 (m, 1H), 8.5-8.6 (m, 1H), 8.7 (s, 1H), 9.9 (s, 1H).

Example 38

(R)-3-Oxo-3-(3-(6-(pyrazolo[1,5-a]pyrazin-3-yl)pyrazin-2-ylamino)piperidin-1-yl)propanenitrile

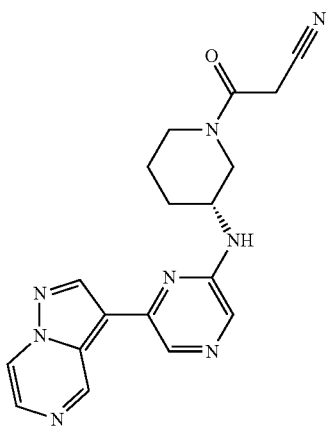 [SMILES: N#CCC(=O)N1CCC[C@@H](Nc2cncc(-c3cnn4ccncc34)n2)C1]

A solution of (R)—N-(piperidin-3-yl)-6-(pyrazolo[1,5-a]pyrazin-3-yl)pyrazin-2-amine (Preparation 30b, 0.23 g, 0.78 mmol), 3-[(2,5-dioxopyrrolidin-1-yl)oxy]-3-oxopropane nitrile (prepared as described in BE875054(A1), 0.17 g, 0.94 mmol)) and triethylamine (0.13 mL, 0.94 mmol) in methylene chloride (10 mL) was stirred overnight at ambient temperature. After evaporation of the solvent, the crude mixture was purified by flash chromatography (95:5 to 93:7 methylene chloride/methanol) to yield the title compound (0.158 g, 38%) as a pale yellow solid.

LRMS (m/z): 363 (M+1)+.

$^1$H-NMR δ (400 MHz, DMSO-d$_6$): 1.7 (m, 2H), 1.8 (m, 1H), 2.1 (m, 1H), 3.2 (m, 2H), 4.3-3.5 (m, 5H), 6.9 (s, 1H), 7.9 (s, 1H), 8.0 (d, 1H), 8.3 (s, 1H), 8.8 (m, 2H), 9.8 (s, 1H).

Example 39

(R)-3-oxo-3-(3-(6-(pyrazolo[1,5-a]pyridin-3-yl)pyrazin-2-ylamino)piperidin-1-yl)propanenitrile

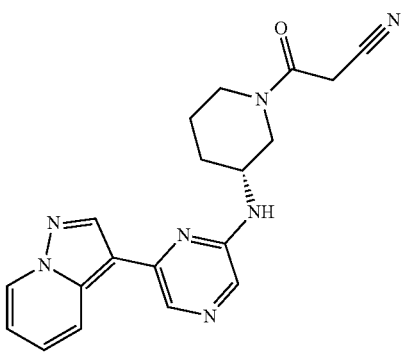 [SMILES: N#CCC(=O)N1CCC[C@@H](Nc2cncc(-c3cnn4ccccc34)n2)C1]

Obtained as a pale green solid (50%) from (R)—N-(piperidin-3-yl)-6-(pyrazolo[1,5-a]pyridin-3-yl)pyrazin-2-amine (Preparation 28b) and 3-[(2,5-dioxopyrrolidin-1-yl)oxy]-3-oxopropanenitrile (prepared as described in BE875054(A1) following the experimental procedure as described in Example 38 followed by purification by flash chromatography (95:5 methylene chloride/methanol).

LRMS (m/z): 362 (M+1)+.

$^1$H-NMR δ (400 MHz, DMSO-d$_6$): 1.6 (m, 2H), 1.8 (m, 1H), 2.1 (m, 1H), 3.2 (m, 1H), 4.4-3.6 (m, 5H), 4.5 (s, 1H), 6.9 (m, 1H), 7.0 (t, 1H), 7.4 (t, 1H), 7.8 (m, 1H), 8.3 (s, 1H), 8.4 (m, 1H), 8.6 (s, 1H), 8.7 (d, 1H).

Example 40

(R)-3-oxo-3-(3-(2-(pyrazolo[1,5-a]pyridin-3-yl)pyrimidin-4-ylamino)piperidin-1-yl)propanenitrile

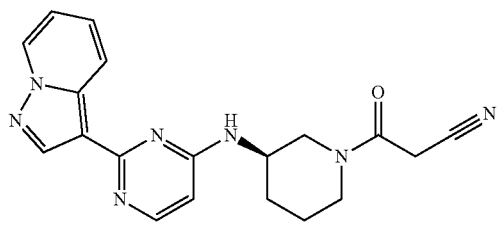 [SMILES: N#CCC(=O)N1CCC[C@@H](Nc2ccnc(-c3cnn4ccccc34)n2)C1]

Obtained as solid (41%) from ((R)—N-(piperidin-3-yl)-2-(pyrazolo[1,5-a]pyridin-3-yl) pyrimidin-4-amine (Preparation 34) and 3-[(2,5-dioxopyrrolidin-1-yl)oxy]-3-oxopropane nitrile (prepared as described in BE875054(A1) following the experimental procedure as described in Example 38 followed by purification by recristalization from acetonitrile.

LRMS (m/z): 362 (M+1)+.

¹H NMR δ (300 MHz, CDCl₃): 1.5-2.1 (m, 4H), 2.1 (d, 2H), 3.3-3.6 (m, 2H), 3.8 (d, 1H), 4.0-4.3 (m, 1H), 4.4-4.5 (m, 1H), 4.9-5.2 (m, 1H) 6.2 (t, 1H), 6.9 (d, 1H), 7.3 (t, 1H), 8.3 (d, 1H), 8.5 (d, 2H), 8.7 (d, 1H).

Example 41

(R)-3-(3-(5-Chloro-2-(pyrazolo[1,5-a]pyridin-3-yl)pyrimidin-4-ylamino)piperidin-1-yl)-3-oxopropanenitrile

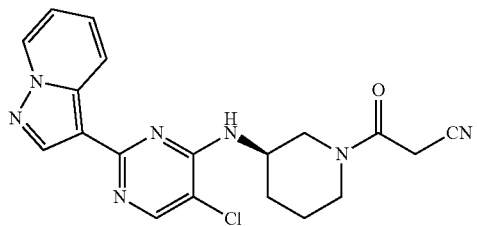 [SMILES: N#CCC(=O)N1CCC[C@@H](Nc2nc(-c3cnn4ccccc34)ncc2Cl)C1]

Obtained as a white solid (41%) from (R)-5-chloro-N-(piperidin-3-yl)-2-(pyrazolo[1,5-a]pyridin-3-yl)pyrimidin-4-amine (Preparation 37b) and 3-[(2,5-dioxopyrrolidin-1-yl)oxy]-3-oxopropanenitrile (prepared as described in BE875054(A1)) following the experimental procedure as described in Example 38 followed by purification by reverse phase chromatography (C-18 silica from Waters©, water/acetonitrile/methanol as eluents [0.1% v/v formic acid buffered] 0% to 100%).

LRMS (m/z): 396 (M+1)⁺

¹H NMR δ (300 MHz, DMSO-d₆): 1.5-1.9 (m, 3H), 2.0 (s, 1H), 2.7 (dd, 1H), 2.9-3.2 (m, 1H), 3.7 (dd, 1H), 3.9-4.2 (m, 2H), 4.3 (d, 1H), 4.7 (d, 1H), 7.0-7.2 (m, 2H), 7.5 (dd, 1H), 8.3 (d, 1H), 8.4 (d, 1H), 8.7 (d, 1H), 8.8 (t, 1H).

Example 42

(R)—N-(1-(4H-1,2,4-Triazol-3-yl)piperidin-3-yl)-2-(pyrazolo[1,5-a]pyridin-3-yl)pyrimidin-4-amine

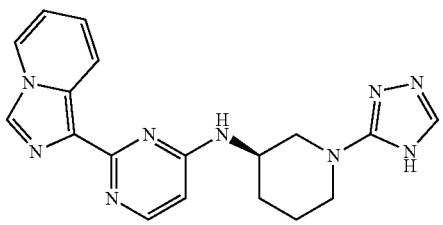 [SMILES: c1ccn2cnc(-c3nccc(N[C@@H]4CCCN(c5nnc[nH]5)C4)n3)c2c1]

A mixture of (R)—N-(piperidin-3-yl)-2-(pyrazolo[1,5-a]pyridin-3-yl)pyrimidin-4-amine (Preparation 34, 298 mg, 1.01 mmol) and 3-bromo-1H-1,2,4-triazole (75 mg, 0.51 mmol, prepared as described in *Journal of Medicinal Chemistry*, 2004, 47 (19), 4645-4648) was heated at 150° C. overnight. The crude mixture was purified by reverse phase chromatography (C-18 silica from Waters©, water/acetonitrile/methanol as eluents [0.1% v/v formic acid buffered] 0% to 100%) to give the title compound (96 mg, 52%) as a white solid.

LRMS (m/z): 362 (M+1)⁺.

¹H NMR δ (300 MHz, DMSO-d₆): 1.5 (d, 1H), 1.7 (ms, 1H), 1.8 (m, 1H), 2.0 (m, 1H), 2.8 (m, 1H), 3.0 (m, 1H), 3.4 (m, 1H), 3.7 (m, 1H), 4.2 (m, 2H), 6.3 (bs, 1H), 7.0 (t, 1H), 7.3 (m, 1H), 7.4 (m, 1H), 8.1 (m, 1H), 8.2 (s, 1H), 8.5 (m, 1H), 8.6 (s, 1H), 8.8 (d, 1H).

Example 43

N-[(3R)-1-(Aminoacetyl)piperidin-3-yl]-6-pyrazolo[1,5-a]pyridin-3-ylpyrazin-2-amine

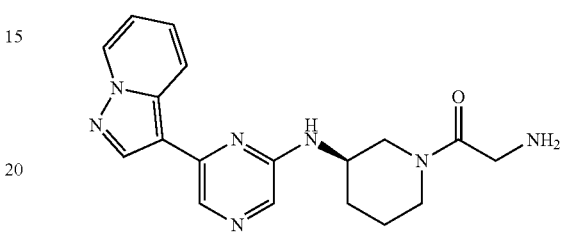

A solution of hydrochloric acid in dioxane (4M, 10 mL) was added to a solution of tert-butyl (2-oxo-2-{(3R)-3-[(6-pyrazolo[1,5-a]pyridin-3-ylpyrazin-2-yl)amino]piperidin-1-yl}ethyl)carbamate (Preparation 38, 88 mg, 0.23 mmol) in methanol (3 mL) and the resulting mixture was stirred at ambient temperature for one hour. The solvents were then evaporated to half of their volume and the yellow solid that precipitated was filtered, washed with diethyl ether and dried to give the title compound (76 mg, 95%).

LRMS (m/z): 352 (M+1)⁺.

Example 44

(R)-3-(3-(5-Fluoro-2-(pyrazolo[1,5-a]pyridin-3-yl)pyrimidin-4-ylamino)piperidin-1-yl)-3-oxopropanenitrile

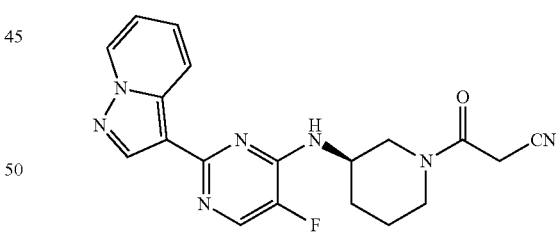

Obtained as a solid (68%) from 5-fluoro-N-[(3R)-piperidin-3-yl]-2-pyrazolo[1,5-a]pyridin-3-ylpyrimidin-4-amine (Preparation 40) and 3-[(2,5-dioxopyrrolidin-1-yl)oxy]-3-oxo propanenitrile (prepared as described in BE875054(A1)) following the experimental procedure as described in Example 38 followed by purification by flash chromatography (dichloromethane to 9:1 dichloromethane/methanol).

LRMS (m/z): 380 (M+1)⁺.

¹H NMR δ (400 MHz, DMSO-d₆): 1.5-1.7 (m, 1H), 1.8 (bs, 1H), 2.1 (m, 1H), 2.6-2.7 (m, 1H), 2.7-2.9 (m, 1H), 3.1 (td, 1H), 3.6 (bs, 1H), 3.8 (bs, 1H), 3.9-4.0 (m, 1H), 4.1 (q, 2H), 4.7 (d, 1H), 7.0 (t, 1H), 7.4-7.5 (m, 1H), 7.5-7.6 (m, 1H), 8.2 (d, 1H), 8.4 (d, 1H), 8.8 (t, 1H).

Example 45

3-((3s,4r)-4-Fluoro-3-(6-(pyrazolo[1,5-a]pyridin-3-yl)pyrazin-2-ylamino)piperidin-1-yl)-3-oxopropanenitrile

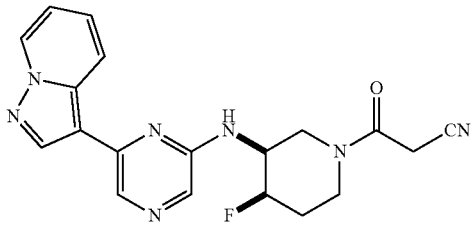

Obtained as a green solid (47%) from N-[(3s,4r)-4-fluoropiperidin-3-yl]-6-pyrazolo[1,5-a]pyridin-3-ylpyrazin-2-amine (Preparation 41) and 3-[(2,5-dioxopyrrolidin-1-yl)oxy]-3-oxopropanenitrile (prepared as described in BE875054(A1)) following the experimental procedure as described in Example 38 followed by purification by flash chromatography (dichloromethane to 93:7 dichloromethane/methanol).

LRMS (m/z): 381 (M+1)$^+$.

$^1$H NMR δ (400 MHz, CDCl$_3$, 1:1 mixture of rotamers): 1.9-2.3 (m, 2H), 2.9-3.8 (m, 5H), 4.3-5.2 (m, 4H), 6.9 (m, 1H), 7.4 (m, 1H), 7.8 (s, 1H, rotamer A), 7.9 (s, 1H, rotamer B), 8.2 (d, 1H, rotamer A), 8.3 (s, 1H, rotamer A), 8.3 (s, 1H, rotamer B), 8.4 (d, 1H, rotamer B), 8.4 (s, 1H), 8.5 (d, 1H, rotamer A), 8.6 (d, 1H, rotamer B).

Example 46

3-((3r,4r)-Methyl-3-(6-(pyrazolo[1,5-a]pyridin-3-yl)pyrazin-2-ylamino)piperidin-1-yl)-3-oxopropanenitrile

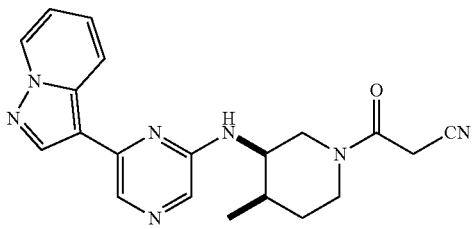

Example 47

(R)—N-(1-(4H-1,2,4-Triazol-3-yl)piperidin-3-yl)-6-(pyrazolo[1,5-a]pyridin-3-yl)pyrazin-2-amine

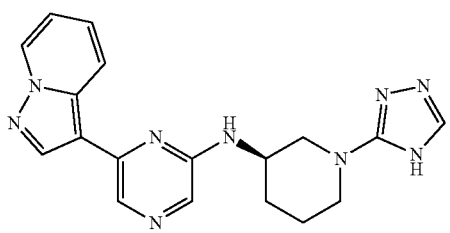 [SMILES: c1ccn2ncc(-c3cncc(N[C@@H]4CCCN(c5nnc[nH]5)C4)n3)c2c1]

Pharmacological Activity

In Vitro JAK Kinase Assays

Compounds were screened for their ability to inhibit JAK1, JAK2 and JAK3 using the assays as indicated below.

The catalytic domains of human JAK1 (aa 850-1154), JAK2 (aa 826-1132), JAK3 (aa 795-1124) and Tyk2 (aa 871-1187) were expressed as N-terminal GST-fusion proteins using a baculovirus expression system and were purchased from Carna Biosciences. The enzymatic activity was assayed using as substrate a biotinylated peptide, poly (GT)-Biotin (CisBio). The peptide concentration in the reactions was 60 nM for JAK1, 20 nM for JAK2, 140 nM for JAK3 and 50 nM for Tyk2. The degree of phosphorylation was detected by TR-FRET (time-resolved fluorescence energy transfer). IC$_{50}$s of compounds were measured for each kinase in a reaction mixture containing the enzyme, ATP and the peptide in 8 mM MOPS (pH 7.0), 10 mM MgCl$_2$, 0.05% β-mercaptoethanol, 0.45 mg/ml BSA. The ATP concentration in the reactions was 3 µM for JAK1, 0.2 µM for JAK2, 0.6 µM for JAK3 and 1.8 µM for Tyk2. The enzymatic reactions took place for 30 minutes at room temperature. Then, the reactions were stopped with 20 µL of quench detection buffer (50 mM HEPES, 0.5 M KF, EDTA 0.25 M, 0.1% (w/v) BSA, pH 7.5) containing 0.115 µg/mL of anti-phosphoTyr (PT66)-Cryptate (CisBio) and a variable concentration of SA-XL665 (CisBio) to keep the SA-B ratio constant. Incubate for 3 h and read on Victor 2V spectrofluorometer (PerkinElmer) set to read fluorescence resonance energy transfer.

Some of the acronyms used above have the following meaning:
AA: aminoacids
GST: glutathione-S-transferase
MOPS: 3-(N-morpholino)propane sulfonic acid
BSA: bovine serum albumin
ATP: adenosine tri-phosphate
EDTA: ethylenediaminetetraacetic acid
HEPES: 4-(2-hydroxyethyl)-1-piperazineethanesulfonic acid Table 1 depicts IC$_{50}$ values for certain exemplary compounds described in the invention. In Table 1, "A" represents an IC$_{50}$ value of less than 0.1 µM (100 nM), "B" represents an IC$_{50}$ value in the range of 0.1 µM (100 nM) to 1 µM, and C represents an IC$_{50}$ value higher than 1 µM.

TABLE 1

| Example No. | IC$_{50}$ JAK3 (µM) | IC$_{50}$ JAK2 (µM) | IC$_{50}$ JAK1 (µM) |
|---|---|---|---|
| 5 | A | A | B |
| 7 | B | A | C |
| 14 | A | A | B |
| 19 | A | A | B |
| 21 | A | A | A |
| 25 | A | A | B |
| 27 | A | A | B |
| 30 | A | A | B |
| 35 | B | A | B |
| 37 | A | A | A |

It can be seen from Table 1 that the compounds of formula (I) are potent inhibitors of JAK1, JAK2 and JAK3 kinases. Preferred heteroaryl imidazolone derivatives of the invention possess an IC$_{50}$ value for the inhibition of JAK1, JAK2 and JAK3 kinases (determined as defined above) of less than 1 µM, preferably less than 0.5 µM for each JAK kinase.

Combinations

The pyrazole derivatives defined herein may also be combined with other active compounds in the treatment of a pathological condition or disease susceptible to amelioration by inhibition of Janus Kinases.

The combinations of the invention can optionally comprise one or more additional active substances which are known to be useful in the treatment of myeloproliferative disorders (such as polycythemia vera, essential thrombocythemia or mielofibrosis), leukemia, lymphoid malignancies and solid tumors; bone marrow and organ transplant rejection; and immune-mediated diseases, more in particular wherein the pathological condition or disease is selected from rheumatoid arthritis, multiple sclerosis, inflammatory bowel disease, dry eye, uveitis, allergic conjunctivitis, allergic rhinitis, asthma, chronic obstructive pulmonary disease (COPD), atopic dermatitis and psoriasis, such as (a) Dyhydrofolate reductase inhibitors, such as Methotrexate or CH-1504; (b) DHODH inhibitors such as leflunomide, teriflunomide, or the compounds described in the International Patent Application Nos. WO2008/077639 and WO2009021696; (c) Immunomodulators such as Glatiramer acetate (Copaxone), Laquinimod or Imiquimod; (d) Inhibitors of DNA synthesis and repair, such as Mitoxantrone or Cladribine; (e) Anti-alpha 4 integrin antibodies, such as Natalizumab (Tysabri); (f) Alpha 4 integrin antagonists such as R-1295, TBC-4746, CDP-323, ELND-002, Firategrast or TMC-2003; (g) Corticoids and glucocorticoids such as prednisone or methylprednisolone, fluticasone, mometasone, or beta-metasone; (h) Fumaric acid esters, such as BG-12; (i) Anti-TNF alpha antibodies, such as Infliximab, Adalimumab, or Certolizumab pegol; (j) Soluble TNF alpha receptors such as Ethanercept; (k) Anti-CD20 monoclonal antibodies such as Rituximab, Ocrelizumab Ofatumumab or TRU-015; (l) Anti-CD52 such as alemtuzumab; (m) Anti-CD25 such as daclizumab; (n) Anti-CD88, such as eculizumab or pexilizumab; (o) Anti-IL12R/IL23R, such as ustekinumab; (p) Calcineurin inhibitors such as cyclosporine A or tacrolimus; (q) IMPDH inhibitors, such as mycophenolate mophetyl; (r) Cannabinoid receptor agonists such as Sativex; (s) Chemokine CCR1 antagonists such as MLN-3897 or PS-031291; (t) Chemokine CCR2 antagonists such as INCB-8696; (u) NF-kappaB activation inhibitors such as MLN-0415; (v) SIP receptor agonists such as fingolimod, BAF-312, ACT128800 or the compounds described in the International Patent Application Nos. PCT/EP2009/007348 and PCT/EP2009/008968; (w) S1P liase inhibitors such as LX2931; (x) Syk inhibitors, such as R-112; (y) PKC inhibitors, such as NVP-AEB071; (z) M3 antagonists such as tiotropium or aclidinium; (aa) Long-acting beta adrenergic agonists such as salmeterol, formoterol or indacaterol; (bb) Vitamin D derivatives like calcipotriol (Daivonex); (cc) Phosphodiesterase IV inhibitors such as roflumilast or GRC-4039; (dd) p38 Inhibitors such as ARRY-797; (ee) MEK inhibitors, such as ARRY-142886 or ARRY-438162; (ff) PI3Kδγ inhibitors; (gg) Interferons comprising Interferon beta 1a such as Avonex from Biogen Idec, CinnoVex from CinnaGen and Rebif from EMD Serono, and Interferon beta 1b such as Betaferon from Schering and Betaseron from Berlex; and (hh) Interferon alpha such as Sumiferon MP.

Typically, the additional active substance is not methotrexate. Preferably, the additional active substance is selected from (b) DHODH inhibitors such as leflunomide, teriflunomide, or the compounds described in the International Patent Application Nos. WO2008/077639 and WO2009021696; (c) Immunomodulators such as Glatiramer acetate (Copaxone), Laquinimod or Imiquimod; (e) Anti-alpha 4 integrin antibodies, such as Natalizumab (Tysabri); (f) Alpha 4 integrin antagonists such as R-1295, TBC-4746, CDP-323, ELND-002, Firategrast or TMC-2003; (g) Corticoids and glucocorticoids such as prednisone or methylprednisolone, fluticasone, mometasone, or beta-metasone; (h) Fumaric acid esters, such as BG-12; (i) Anti-TNF alpha antibodies, such as Infliximab, Adalimumab, or Certolizumab pegol; (j) Soluble TNF alpha receptors such as Ethanercept; (k) Anti-CD20 monoclonal antibodies such as Rituximab, Ocrelizumab Ofatumumab or TRU-015; (n) Anti-CD88, such as eculizumab or pexilizumab; (o) Anti-IL12R/IL23R, such as ustekinumab; (p) Calcineurin inhibitors such as cyclosporine A or tacrolimus; (q) IMPDH inhibitors, such as mycophenolate mophetyl; (r) Cannabinoid receptor agonists such as Sativex; (s) Chemokine CCR1 antagonists such as MLN-3897 or PS-031291; (t) Chemokine CCR2 antagonists such as INCB-8696; (u) NF-kappaB activation inhibitors such as MLN-0415; (v) S1P receptor agonists such as fingolimod, BAF-312, ACT128800 or the compounds described in the International Patent Application Nos. PCT/EP2009/007348 and PCT/EP2009/008968; (w) S1P liase inhibitors such as LX2931; (x) Syk inhibitors, such as R-112; (y) PKC inhibitors, such as NVP-AEB071; (z) M3 antagonists such as tiotropium or aclidinium; (aa) Long-acting beta adrenergic agonists such as salmeterol, formoterol or indacaterol; (bb) Vitamin D derivatives like calcipotriol (Daivonex); (cc) Phosphodiesterase IV inhibitors such as roflumilast or GRC-4039; (dd) p38 Inhibitors such as ARRY-797; (ee) ARRY-438162; (ff) PI3Kδγ inhibitors; (gg) Interferon beta 1a such as Avonex from Biogen Idec, CinnoVex from CinnaGen and Rebif from EMD Serono; and Interferon beta 1b such as Betaferon from Schering and Betaseron from Berlex.

More preferably, the additional active substance is selected from (b) DHODH inhibitors such as leflunomide, teriflunomide, or the compounds described in the International Patent Application Nos. WO2008/077639 and WO2009021696; (c) Immunomodulators such as Glatiramer acetate (Copaxone), Laquinimod or Imiquimod; (e) Anti-alpha 4 integrin antibodies, such as Natalizumab (Tysabri); (f) Alpha 4 integrin antagonists such as R-1295, TBC-4746, CDP-323, ELND-002, Firategrast or TMC-2003; (g) Corticoids and glucocorticoids such as prednisone or methylprednisolone, fluticasone, mometasone, or beta-metasone; (h) Fumaric acid esters, such as BG-12; (i) Anti-TNF alpha antibodies, such as Infliximab, Adalimumab, or Certolizumab pegol; (j) Soluble TNF alpha receptors such as Ethanercept; (k) Anti-CD20 monoclonal antibodies such as Rituximab, Ocrelizumab Ofatumumab or TRU-015; (n) Anti-CD88, such as eculizumab or pexilizumab; (o) Anti-IL12R/IL23R, such as ustekinumab; (p) Calcineurin inhibitors such as cyclosporine A or tacrolimus; (q) IMPDH inhibitors, such as mycophenolate mophetyl; (r) Cannabinoid receptor agonists such as Sativex; (s) Chemokine CCR1 antagonists such as MLN-3897 or PS-031291; (t) Chemokine CCR2 antagonists such as INCB-8696; (u) NF-kappaB activation inhibitors such as MLN-0415; (v) S1P receptor agonists such as fingolimod, BAF-312, ACT128800 or the compounds described in the International Patent Application Nos. PCT/EP2009/007348 and PCT/EP2009/008968; (w) SIP liase inhibitors such as LX2931; (x) Syk inhibitors, such as R-112; (y) PKC inhibitors, such as NVP-AEB071; (z) M3 antagonists such as tiotropium or aclidinium; (aa) Long-acting beta adrenergic agonists such as salmeterol, formoterol or indacaterol; (bb) Vitamin D derivatives like calcipotriol (Daivonex); (cc) Phosphodiesterase IV inhibitors such as roflumilast or GRC-4039; (dd) p38 Inhibitors such as ARRY-797; (ff) PI3Kδγ inhibitors; (gg) Interferon beta 1a such as Avonex from Biogen Idec, CinnoVex from CinnaGen and Rebif from EMD Serono; and Interferon beta 1b such as Betaferon from Schering and Betaseron from Berlex.

Specific examples of suitable corticoids and glucocorticoids that can be combined with the JAK inhibitors of the present invention are prednisolone, methylprednisolone, dexamethasone, dexamethasone cipecilate, naflocort, deflazacort, halopredone acetate, budesonide, beclomethasone dipropionate, hydrocortisone, triamcinolone acetonide, fluocinolone acetonide, fluocinonide, clocortolone pivalate, methylprednisolone aceponate, dexamethasone palmitoate, tipredane, hydrocortisone aceponate, prednicarbate, alclometasone dipropionate, halometasone, methylprednisolone suleptanate, mometasone furoate, rimexolone, prednisolone farnesylate, ciclesonide, butixocort propionate, RPR-106541, deprodone propionate, fluticasone propionate, fluticasone furoate, halobetasol propionate, loteprednol etabonate, betamethasone butyrate propionate, flunisolide, prednisone, dexamethasone sodium phosphate, triamcinolone, betamethasone 17-valerate, betamethasone, betamethasone dipropionate, hydrocortisone acetate, hydrocortisone sodium succinate, prednisolone sodium phosphate and hydrocortisone probutate.

Specific examples of suitable Syk kinase inhibitors that can be combined with the JAK inhibitors of the present invention are fosfamatinib (from Rigel), R-348 (from Rigel), R-343 (from Rigel), R-112 (from Rigel), piceatannol, 2-(2-Aminoethylamino)-4-[3-(trifluoromethyl)phenylamino]pyrimidine-5-carboxamide, R-091 (from Rigel), 6-[5-Fluoro-2-(3,4,5-trimethoxyphenylamino)pyrimidin-4-ylamino]-2,2-dimethyl-3,4-dihydro-2H-pyrido[3,2-b][1,4]oxazin-3-one benzenesulfonate (R-406 from Rigel), 1-(2,4,6-Trihydrayphenyl)-2-(4-methoxyphenyl)ethan-1-one, N-[4-[6-(Cyclobutylamino)-9H-purin-2-ylamino]phenyl]-N-methylacetamide (QAB-205 from Novartis), 2-[7-(3,4-Dimethoxyphenyl)imidazo[1,2-c]pyrimidin-5-ylamino]pyridine-3-carboxamide dihydrochloride (BAY-61-3606 from Bayer) and AVE-0950 (from Sanofi-Aventis).

Specific examples of suitable M3 antagonists (anticholinergics) that can be combined with the JAK inhibitors of the present invention are tiotropium salts, oxitropium salts, flutropium salts, ipratropium salts, glycopyrronium salts, trospium salts, revatropate, espatropate, 3-[2-Hydroxy-2,2-bis (2-thienyl)acetoxy]-1-(3-phenoxypropyl)-1-azoniabicyclo [2.2.2]octane salts (in particular aclidinium salts, more preferably aclidinium bromide), 1-(2-Phenylethyl)-3-(9H-xanthen-9-ylcarbonyloxy)-1-azoniabicyclo[2.2.2]octane salts, 2-oxo-1,2,3,4-tetrahydroquinazoline-3-carboxylic acid endo-8-methyl-8-azabicyclo[3.2.1]oct-3-yl ester salts (DAU-5884), 3-(4-Benzylpiperazin-1-yl)-1-cyclobutyl-1-hydroxy-1-phenylpropan-2-one (NPC-14695), N-[1-(6-Aminopyridin-2-ylmethyl)piperidin-4-yl]-2(R)-[3,3-difluoro-1(R)-cyclopentyl]-2-hydroxy-2-phenylacetamide (J-104135), 2(R)-Cyclopentyl-2-hydroxy-N-[1-[4(S)-methylhexyl]piperidin-4-yl]-2-phenylacetamide (J-106366), 2(R)-Cyclopentyl-2-hydroxy-N-[1-(4-methyl-3-pentenyl)-4-piperidinyl]-2-phenylacetamide (J-104129), 1-[4-(2-Aminoethyl) piperidin-1-yl]-2(R)-[3,3-difluorocyclopent-1(R)-yl]-2-hydroxy-2-phenylethan-1-one (Banyu-280634), N—[N-[2-[N-[1-(Cyclohexylmethyl)piperidin-3(R)-ylmethyl] carbamoyl]ethyl]carbamoylmethyl]-3,3,3-triphenylpropionamide (Banyu CPTP), 2(R)-Cyclopentyl-2-hydroxy-2-phenylacetic acid 4-(3-azabicyclo[3.1.0]hex-3-yl)-2-butynyl ester (Ranbaxy 364057), UCB-101333, Merck's OrM3,7-endo-(2-hydroxy-2,2-diphenylacetoxy)-9,9-dimethyl-3-oxa-9-azoniatricyclo[3.3.1.0(2,4)]nonane salts, 7-(2,2-diphenylpropionyloxy)-7,9,9-trimethyl-3-oxa-9-azoniatricyclo[3.3.1.0*2,4]nonane salts, 7-hydroxy-7,9,9-trimethyl-3-oxa-9-azoniatricyclo[3.3.1.0*2,4*]nonane 9-methyl-9H-fluorene-9-carboxylic acid ester salts, all of them optionally in the form of their racemates, their enantiomers, their diastereomers and mixtures thereof, and optionally in the form of their pharmacologically-compatible acid addition salts. Among the salts chlorides, bromides, iodides and methanesulphonates are preferred.

Specific examples of suitable long-acting beta adrenergic agonists (β2-agonists) that can be combined with the JAK inhibitors of the present invention are terbutaline sulphate, eformoterol fumarate, formoterol fumarate, bambuterol, procaterol hydrochloride, sibenadet hydrochloride, mabuterol hydrochloride, albuterol sulphate, salbutamol sulphate, salmeterol xinafoate, carmoterol hydrochloride, (R)-albuterol hydrochloride, Levalbuterol hydrochloride; Levosalbutamol hydrochloride; (−)-Salbutamol hydrochloride, (R,R)-Formoterol tartrate; Arformoterol tartrate, Bedoradrine sulphate, Indacaterol, Trantinterol hydrochloride, AZD-3199, GSK-159802; GSK-597901, GSK-678007, GSK-642444; GSK-961081; AR-C98955AA, Milveterol hydrochloride, BI-1744-CL, and compounds described in the international Patent Applications Nos. WO2007/124898, WO2006/122788A1, WO2008/046598 and WO2008095720.

Specific examples of suitable Phosphosdiesterase IV inhibitors that can be combined with the JAK inhibitors of the present invention are benafentrine dimaleate, etazolate, denbufylline, rolipram, cipamfylline, zardaverine, arofylline, filaminast, tipelukast, tofimilast, piclamilast, tolafentrine, mesopram, drotaverine hydrochloride, lirimilast, roflumilast, cilomilast, oglemilast, apremilast, tetomilast, filaminast, (R)-(+)-4-[2-(3-Cyclopentyloxy-4-methoxyphenyl)-2-phenylethyl]pyridine (CDP-840), N-(3,5-Dichloro-4-pyridinyl)-2-[1-(4-fluorobenzyl)-5-hydroxy-1H-indol-3-yl]-2-oxoacetamide (GSK-842470), 9-(2-Fluorobenzyl)-N6-methyl-2-(trifluoromethyl)adenine (NCS-613), N-(3,5-Dichloro-4-pyridinyl)-8-methoxyquinoline-5-carboxamide (D-4418), 3-[3-(Cyclopentyloxy)-4-methoxybenzyl]-6-(ethylamino)-8-isopropyl-3H-purine hydrochloride (V-11294A), 6-[3-(N,N-Dimethylcarbamoyl)phenylsulfonyl]-4-(3-methoxyphenylamino)-8-methylquinoline-3-carboxamide hydrochloride (GSK-256066), 4-[6,7-Diethoxy-2,3-bis(hydroxymethyl)naphthalen-1-yl]-1-(2-methoxyethyl) pyridin-2(1H)-one (T-440), (−)-trans-2-[3'-[3-(N-Cyclopropylcarbamoyl)-4-oxo-1,4-dihydro-1,8-naphthyridin-1-yl]-3-fluorobiphenyl-4-yl] cyclopropanecarboxylic acid (MK-0873), CDC-801, UK-500001, BLX-914, 2-carbomethoxy-4-cyano-4-(3-cyclopropylmethoxy-4-difluororomethoxyphenyl)cyclohexan1-one, cis [4-cyano-4-(3-cyclopropylmethoxy-4-difluoromethoxyphenyl)cyclohexan-1-ol, GRC-4039, CDC-801, 5(S)-[3-(Cyclopentyloxy)-4-methoxyphenyl]-3(S)-(3-methylbenzyl)piperidin-2-one (IPL-455903), ONO-6126 (Eur Respir J 2003, 22(Suppl. 45): Abst 2557) and the salts claimed in the International Patent Applications Nos. WO03/097613, WO2004/058729, WO 2005/049581, WO 2005/123693 and WO 2005/123692.

Examples of suitable PI3Kδγ inhibitors that can be combined with the JAK inhibitors of the present invention are 2-Methyl-2-[4-[3-methyl-2-oxo-8-(3-quinolinyl)-2,3-dihydro-1H-imidazo[4,5-c]quinolin-1-yl]phenyl]propanenitrile (BEZ-235 from Novartis), CAL-101 (from Calistoga Pharmaceuticals) and N-Ethyl-N'-[3-(3,4,5-trimethoxyphenylamino)pyrido[2,3-b]pyrazin-6-yl]thiourea (AEZS-126 from Aeterna Zentaris).

The compounds of formula (I) and the combinations described herein may be used in the treatment of myeloproliferative disorders, leukemia, lymphoid malignancies and solid tumors; bone marrow and organ transplant rejection; and immune-mediated diseases, wherein the use of a JAK inhibitor is expected to have a beneficial effect, for example rheumatoid arthritis, multiple sclerosis, inflammatory bowel disease (such as ulcerative colitis or Crohn's disease), dry eye, uveitis, allergic conjunctivitis, allergic rhinitis, asthma, chronic obstructive pulmonary disease (COPD), atopic dermatitis and psoriasis. The compounds of formula (I) and the combinations described herein may also be used in the treatment of inflammatory diseases.

In one aspect, the compounds of formula (I) and the combinations described herein may be used in the treatment of myeloproliferative disorders, leukemia, lymphoid malignancies and solid tumors. In this aspect, the treatment is effected by inhibition of Janus Kinases in the subject. In another aspect, the compounds of formula (I) and the combinations described herein may be used in the treatment of bone marrow and organ transplant rejection; immune-mediated diseases and inflammatory diseases, for example from bone marrow and organ transplant rejection; and immune-mediated diseases, e.g. bone marrow and organ transplant rejection.

The treatment of these diseases and conditions is typically effected by inhibiting Janus Kinases (JAK) in the subject. The compounds of formula (I) and the combinations described herein may be used in the inhibition of Janus Kinases (JAK).

The active compounds in the combination may be administered together in the same pharmaceutical composition or in different compositions intended for separate, simultaneous, concomitant or sequential administration by the same or a different route.

It is contemplated that all active agents would be administered at the same time, or very close in time. Alternatively, one or two active agents could be taken in the morning and the other (s) later in the day. Or in another scenario, one or two active agents could be taken twice daily and the other (s) once daily, either at the same time as one of the twice-a-day dosing occurred, or separately. Preferably at least two, and more preferably all, of the active agents would be taken together at the same time. Preferably, at least two, and more preferably all active agents would be administered as an admixture.

The invention is also directed to a combination product of the compounds described herein together with one or more other therapeutic agents for use in the treatment of a pathological condition or disease susceptible to amelioration by inhibition of Janus Kinases (JAK), in particular wherein the pathological condition or disease is selected from myeloproliferative disorders, leukemia, lymphoid malignancies and solid tumors; bone marrow and organ transplant rejection; immune-mediated diseases and inflammatory diseases, for example myeloproliferative disorders, leukemia, lymphoid malignancies and solid tumors; bone marrow and organ transplant rejection; and immune-mediated diseases. More particularly, the pathological condition or disease is selected from rheumatoid arthritis, multiple sclerosis, inflammatory bowel disease, dry eye, uveitis, allergic conjunctivitis, allergic rhinitis, asthma, chronic obstructive pulmonary disease (COPD), atopic dermatitis and psoriasis.

In one aspect, the combination product may be for the treatment of myeloproliferative disorders, leukemia, lymphoid malignancies and solid tumors. In this aspect, the treatment is effected by inhibition of Janus Kinases in the subject. In another aspect, the combination product may be used in the treatment of bone marrow and organ transplant rejection; immune-mediated diseases and inflammatory diseases, for example from bone marrow and organ transplant rejection; and immune-mediated diseases, e.g. bone marrow and organ transplant rejection.

The treatment of these diseases and conditions is typically effected by inhibiting Janus Kinases (JAK) in the subject. The combination product may be used in the inhibition of Janus Kinases (JAK).

The invention also encompasses the use of a combination of the compounds of the invention together with one or more other therapeutic agents for the manufacture of a formulation or medicament for treating these diseases.

The invention also provides a method of treatment of a pathological condition or disease susceptible to amelioration by inhibition of Janus Kinases (JAK), in particular wherein the pathological condition or disease is selected from myeloproliferative disorders, leukemia, lymphoid malignancies and solid tumors; bone marrow and organ transplant rejection; immune-mediated diseases and inflammatory diseases, for example myeloproliferative disorders, leukemia, lymphoid malignancies and solid tumors; bone marrow and organ transplant rejection; and immune-mediated diseases. More particularly, the pathological condition or disease is selected from rheumatoid arthritis, multiple sclerosis, inflammatory bowel disease, dry eye, uveitis, allergic conjunctivitis, allergic rhinitis, asthma, chronic obstructive pulmonary disease (COPD), atopic dermatitis and psoriasis; comprising administering a therapeutically effective amount of a combination of the compounds described herein together with one or more other therapeutic agents. In particular, the treatment is effected by inhibition of Janus Kinases in the subject.

The invention also provides a method of inhibiting Janus kinases in a subject in need thereof, which comprises administering to said subject a therapeutically effective amount of a combination of the compounds described herein together with one or more other therapeutic agents to a subject in need of such treatment.

The active compounds in the combinations of the invention may be administered by any suitable route, depending on the nature of the disorder to be treated, e.g. orally (as syrups, tablets, capsules, lozenges, controlled-release preparations, fast-dissolving preparations, etc); topically (as creams, ointments, lotions, nasal sprays or aerosols, etc); by injection (subcutaneous, intradermic, intramuscular, intravenous, etc.) or by inhalation (as a dry powder, a solution, a dispersion, etc).

The active compounds in the combination, i.e. the pyrazole derivatives of the invention, and the other optional active compounds may be administered together in the same pharmaceutical composition or in different compositions intended for separate, simultaneous, concomitant or sequential administration by the same or a different route.

One execution of the present invention consists of a kit of parts comprising a pyrazole derivative as described herein together with instructions for simultaneous, concurrent, separate or sequential use in combination with another active compound useful in the treatment of myeloproliferative disorders, leukemia, lymphoid malignancies and solid tumors; bone marrow and organ transplant rejection; immune-mediated diseases and inflammatory diseases, for example myeloproliferative disorders, leukemia, lymphoid malignancies and solid tumors; bone marrow and organ transplant rejection; and immune-mediated diseases, and more particularly, useful in the treatment of rheumatoid arthritis, multiple sclerosis, inflammatory bowel disease, dry eye, uveitis, allergic conjunctivitis, allergic rhinitis, asthma, chronic obstructive pulmonary disease (COPD), atopic dermatitis and psoriasis.

Another execution of the present invention consists of a package comprising a pyrazole derivative as described herein and another active compound useful in the treatment of myeloproliferative disorders, leukemia, lymphoid malignancies and solid tumors; bone marrow and organ transplant rejection; immune-mediated diseases and inflammatory diseases, for example myeloproliferative disorders, leukemia, lymphoid malignancies and solid tumors; bone marrow and organ transplant rejection; and immune-mediated diseases, and more particularly, useful in the treatment of rheumatoid arthritis, multiple sclerosis, inflammatory bowel disease, dry eye, uveitis, allergic conjunctivitis, allergic rhinitis, asthma, chronic obstructive pulmonary disease (COPD), atopic dermatitis and psoriasis.

Pharmaceutical Compositions

Pharmaceutical compositions according to the present invention comprise the compounds of the invention in association with a pharmaceutically acceptable diluent or carrier.

The invention further provides pharmaceutical compositions comprising the compounds of the invention in association with a pharmaceutically acceptable diluent or carrier together with one or more other therapeutic agents for use in the treatment of a pathological condition or disease susceptible to amelioration by inhibition of Janus Kinases (JAK), such as the ones previously described.

The invention is also directed to pharmaceutical compositions for use in the treatment of a pathological condition or disease susceptible to amelioration by inhibition of Janus Kinases (JAK), in particular wherein the pathological condition or disease is selected from myeloproliferative disorders, leukemia, lymphoid malignancies and solid tumors; bone marrow and organ transplant rejection; immune-mediated diseases and inflammatory diseases, for example myeloproliferative disorders, leukemia, lymphoid malignancies and solid tumors; bone marrow and organ transplant rejection; and immune-mediated diseases, and more particularly, wherein the pathological condition or disease is selected from rheumatoid arthritis, multiple sclerosis, inflammatory bowel disease, dry eye, uveitis, allergic conjunctivitis, allergic rhinitis, asthma, chronic obstructive pulmonary disease (COPD), atopic dermatitis and psoriasis. The invention also encompasses the use of a pharmaceutical composition of the invention for the manufacture of a medicament for treating these diseases.

In one aspect, the pharmaceutical composition may be for the treatment of myeloproliferative disorders, leukemia, lymphoid malignancies and solid tumors. In this aspect, the treatment is effected by inhibition of Janus Kinases in the subject. In another aspect, the pharmaceutical composition may be used in the treatment of bone marrow and organ transplant rejection; immune-mediated diseases and inflammatory diseases, for example from bone marrow and organ transplant rejection; and immune-mediated diseases, e.g. bone marrow and organ transplant rejection.

The treatment of these diseases and conditions is typically effected by inhibiting Janus Kinases (JAK) in the subject. The pharmaceutical composition may be used in the inhibition of Janus Kinases (JAK).

The invention also provides a method of treatment of a pathological condition or disease susceptible to amelioration by inhibition of Janus Kinases (JAK), in particular wherein the pathological condition or disease is selected from myeloproliferative disorders, leukemia, lymphoid malignancies and solid tumors; bone marrow and organ transplant rejection; immune-mediated diseases and inflammatory diseases, for example myeloproliferative disorders, leukemia, lymphoid malignancies and solid tumors; bone marrow and organ transplant rejection; and immune-mediated diseases, and more particularly, wherein the pathological condition or disease is selected from rheumatoid arthritis, multiple sclerosis, inflammatory bowel disease, dry eye, uveitis, allergic conjunctivitis, allergic rhinitis, asthma, chronic obstructive pulmonary disease (COPD), atopic dermatitis and psoriasis, comprising administering a therapeutically effective amount of a pharmaceutical composition as defined herein. In particular, the treatment is effected by inhibition of Janus Kinases in the subject.

The invention also provides a method of inhibiting Janus kinases in a subject in need thereof, which comprises administering to said subject a therapeutically effective amount of a pharmaceutical composition as defined herein to a subject in need of such treatment.

The present invention also provides pharmaceutical compositions which comprise, as an active ingredient, at least an pyrazole of formula (I) or a pharmaceutically acceptable salt thereof in association with a pharmaceutically acceptable excipient such as a carrier or diluent. The active ingredient may comprise 0.001% to 99% by weight, preferably 0.01% to 90% by weight, of the composition depending upon the nature of the formulation and whether further dilution is to be made prior to application. Preferably the compositions are made up in a form suitable for oral, inhalation, topical, nasal, rectal, percutaneous or injectable administration.

The pharmaceutically acceptable excipients which are admixed with the active compound or salts of such compound, to form the compositions of this invention are well-known per se and the actual excipients used depend inter alia on the intended method of administering the compositions.

Compositions for oral administration may take the form of tablets, retard tablets, sublingual tablets, capsules, inhalation aerosols, inhalation solutions, dry powder inhalation, or liquid preparations, such as mixtures, elixirs, syrups or suspensions, all containing the compound of the invention; such preparations may be made by methods well-known in the art.

The diluents which may be used in the preparation of the compositions include those liquid and solid diluents which are compatible with the active ingredient, together with colouring or flavouring agents, if desired. Tablets or capsules may conveniently contain between 0.01-3000 mg, more preferably 0.5-1000 mg of active ingredient or the equivalent amount of a pharmaceutically acceptable salt thereof.

The liquid composition adapted for oral use may be in the form of solutions or suspensions. The solutions may be aqueous solutions of a soluble salt or other derivative of the active compound in association with, for example, sucrose to form a syrup. The suspensions may comprise an insoluble active compound of the invention or a pharmaceutically acceptable salt thereof in association with water, together with a suspending agent or flavouring agent.

Compositions for parenteral injection may be prepared from soluble salts, which may or may not be freeze-dried and which may be dissolved in pyrogen free aqueous media or other appropriate parenteral injection fluid.

Compositions for topical administration may take the form of ointments, creams or lotions, all containing the compound of the invention; such preparations may be made by methods well-known in the art.

Effective doses are normally in the range of 0.01-3000 mg, more preferably 0.5-1000 mg of active ingredient or the equivalent amount of a pharmaceutically acceptable salt thereof per day. Daily dosage may be administered in one or more treatments, preferably from 1 to 4 treatments, per day.

The pharmaceutical compositions may conveniently be presented in unit dosage form and may be prepared by any of the methods well known in the art of pharmacy.

The pharmaceutical compositions of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A syrup formulation will generally consist of a suspension or solution of the compound or salt in a liquid carrier for example, ethanol, peanut oil, olive oil, glycerine or water with flavouring or colouring agent.

Where the composition is in the form of a tablet, any pharmaceutical carrier routinely used for preparing solid formulations may be used. Examples of such carriers include magnesium stearate, talc, gelatine, acacia, stearic acid, starch, lactose and sucrose.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent.

Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Where the composition is in the form of a capsule, any routine encapsulation is suitable, for example using the aforementioned carriers in a hard gelatine capsule. Where the composition is in the form of a soft gelatine capsule any pharmaceutical carrier routinely used for preparing dispersions or suspensions may be considered, for example aqueous gums, celluloses, silicates or oils, and are incorporated in a soft gelatine capsule.

Dry powder compositions for topical delivery to the lung by inhalation may, for example, be presented in capsules and cartridges of, for example, gelatine or blisters of, for example, laminated aluminium foil, for use in an inhaler or insufflator. Formulations generally contain a powder mix for inhalation of the compound of the invention and a suitable powder base (carrier substance) such as lactose or starch. Use of lactose is preferred. Each capsule or cartridge may generally contain between 2 µg and 150 µg of each therapeutically active ingredient. Alternatively, the active ingredient (s) may be presented without excipients.

Packaging of the formulation for inhalation may be carried out by using suitable inhaler devices such as Genuair® (formerly Novolizer® SD2FL) which is described in the following patent applications: WO97/000703, WO03/000325 and WO2006/008207.

Typical compositions for nasal delivery include those mentioned above for inhalation and further include non-pressurized compositions in the form of a solution or suspension in an inert vehicle such as water optionally in combination with conventional excipients such as buffers, anti-microbials, tonicity modifying agents and viscosity modifying agents which may be administered by nasal pump.

Typical dermal and transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer a single dose.

The amount of each active which is required to achieve a therapeutic effect will, of course, vary with the particular active, the route of administration, the subject under treatment, and the particular disorder or disease being treated.

The following preparations forms are cited as formulation examples:

Composition Example 1

50,000 capsules; each containing 100 mg of (S)—N-(1-Phenylethyl)-2-pyrazolo[1,5-a]pyrazin-3-ylpyrimidin-4-amine (active ingredient), were prepared according to the following formulation:

| | |
|---|---|
| Active ingredient | 5 Kg |
| Lactose monohydrate | 10 Kg |
| Colloidal silicon dioxide | 0.1 Kg |
| Corn starch | 1 Kg |
| Magnesium stearate | 0.2 Kg |

Procedure

The above ingredients were sieved through a 60 mesh sieve, and were loaded into a suitable mixer and filled into 50,000 gelatine capsules.

Composition Example 2

50,000 tablets, each containing 50 mg of N-Benzyl-2-pyrazolo[1,5-a]pyrimidin-3-ylpyrimidin-4-amine (active ingredient), are prepared from the following formulation:

| | |
|---|---|
| Active ingredient | 2.5 Kg |
| Microcrystalline cellulose | 1.95 Kg |
| Spray dried lactose | 9.95 Kg |
| Carboxymethyl starch | 0.4 Kg |
| Sodium stearyl fumarate | 0.1 Kg |
| Colloidal silicon dioxide | 0.1 Kg |

Procedure

All the powders are passed through a screen with an aperture of 0.6 mm, then mixed in a suitable mixer for 20 minutes and compressed into 300 mg tablets using 9 mm disc and flat bevelled punches.

Composition Example 3

50,000 tablets, each containing 50 mg of (S)—N-(1-Phenylethyl)-2-pyrazolo[1,5-a]pyrimidin-3-ylpyrimidin-4-amine (active ingredient), were prepared from the following formulation:

| | |
|---|---|
| Active ingredient | 2.5 Kg |
| Microcrystalline cellulose | 1.95 Kg |
| Spray dried lactose | 9.95 Kg |
| Carboxymethyl starch | 0.4 Kg |
| Sodium stearyl fumarate | 0.1 Kg |
| Colloidal silicon dioxide | 0.1 Kg |

Procedure

All the powders were passed through a screen with an aperture of 0.6 mm, then mixed in a suitable mixer for 20 minutes and compressed into 300 mg tablets using 9 mm disc and flat bevelled punches. The disintegration time of the tablets was about 3 minutes.

Modifications, which do not affect, alter, change or modify the essential aspects of the compounds, combinations or pharmaceutical compositions described, are included within the scope of the present invention.

The invention claimed is:
1. A compound of formula (I), or a pharmaceutically acceptable salt, or N-oxide, or stereoisomer thereof:

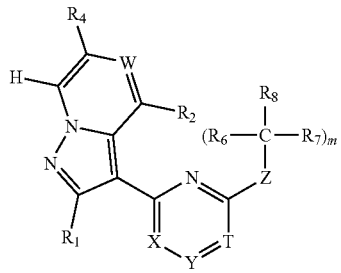

(I)

wherein T is —$CR_9$;
m is chosen from 0, 1, 2, or 3;
Z is chosen from an oxygen atom or $NR_5$;
W is —$CR_3$;
X and Y are independently chosen from a nitrogen atom or —$CR_9$, wherein one of X or Y is a nitrogen atom and the remaining X or Y group is —$CR_9$;
$R_1$, $R_2$, $R_3$, $R_4$ and $R_9$ are each independently chosen from a hydrogen atom, halogen atoms, cyano, linear or branched $C_1$-$C_6$ alkyl, $C_2$-$C_4$ alkenyl, $C_2$-$C_4$ alkynyl, $C_1$-$C_4$ haloalkyl, $C_1$-$C_4$ hydroxyalkyl, $C_3$-$C_{10}$ cycloalkyl, $C_3$-$C_{10}$ cycloalkenyl, monocyclic or polycyclic $C_5$-$C_{14}$ aryl, 5- to 14-membered heteroaryl containing at least one heteroatom chosen from O, S or N, 5- to 14-membered heterocyclyl containing at least one heteroatom chosen from O, S or N, bicyclyl containing a monocyclic $C_5$-$C_9$ aryl or heteroaryl bonded directly to a 5- to 9-membered cycloalkyl or heterocyclyl, wherein the heteroaryl or heterocyclyl contain at least one heteroatom chosen from O, S or N, an aza-bicycloalkyl comprising up to 12 carbon atoms, or aza-bicycloalkenyl comprising up to 12 carbon atoms,
wherein each of the alkenyl, alkynyl, haloalkyl, hydroxyalkyl, cycloalkyl, cycloalkenyl, aryl, heteroaryl, heterocyclyl, bicyclyl, aza-bicycloalkyl and aza-bicycloalkenyl is independently unsubstituted or substituted by at least one substituent chosen from Ra, and each of the alkyl groups is independently unsubstituted or substituted by at least one Rb;
or $R_1$, $R_2$, $R_3$, and $R_4$ are each independently chosen from a —$SR_{13}$, —$SOR_{13}$, —$S(O)_2R_{13}$, —$S(O)_2NR_{13}R_{14}$, —$NR_{13}S(O)_2R_{14}$, —$NR_{13}S(O)_2NR_{14}$, —$(CH_2)_nOR_{13}$, —$C(O)OR_{13}$, —$O$—$C(O)R_{13}$, —$C(O)$—$(CH_2)_n$—$R_{13}$, —$NR_{13}R_{14}$, —$C(O)$—$(CH_2)$—$NR_{13}R_{14}$, —$NR_{13}C(O)$—$(CH_2)_n$—$R_{14}$ or —$NR_{13}C(O)$—$(CH_2)_n$—$NR_{14}R_{15}$, wherein each n is independently chosen from 0, 1, or 2, and
$R_9$ is chosen from a —$SR_{13}$, —$SOR_{13}$, —$S(O)_2R_{13}$, —$S(O)_2NR_{13}R_{14}$, —$NR_{13}S(O)_2R_{14}$, —$NR_{13}S(O)_2NR_{14}$, —$(CH_2)_nOR_{13}$, —$C(O)OR_{13}$, —$O$—$C(O)R_{13}$, —$C(O)$—$(CH_2)_n$—$R_{13}$, —$C(O)$—$(CH_2)_n$—$NR_{13}R_{14}$, —$NR_{13}C(O)$—$(CH_2)_n$—$R_{14}$ or —$NR_{13}C(O)$—$(CH_2)_n$—$NR_{14}R_{15}$, wherein each n is independently chosen from 0, 1, or 2;
or when two adjacent —$CR_9$ groups are present, both adjacent —$CR_9$ and the carbon atoms to which they are bonded optionally form a $C_5$-$C_{12}$ aryl group or a 4- to 12-membered heteroaryl, cycloalkyl or heterocyclyl group, wherein the heteroaryl and heterocyclyl contain at least one heteroatom chosen from O, S or N, and wherein the aryl, heteroaryl, cycloalkyl and heterocyclyl are independently unsubstituted or substituted by at least one substituent chosen from halogen atoms, linear or branched $C_1$-$C_6$ alkyl, monocyclic or polycyclic $C_5$-$C_{14}$ aryl, 5- to 14-membered heteroaryl containing at least one heteroatom chosen from O, S or N, or 5- to 14-membered heterocyclyl containing at least one heteroatom chosen from O, S or N, wherein the alkyl, the aryl, the heteroaryl and the heterocyclyl substituents are independently unsubstituted or substituted by at least one substituent chosen from halogen atoms, hydroxyl, cyano, linear or branched $C_1$-$C_6$ alkyl or $C_1$-$C_4$ haloalkyl;
$R_5$ is chosen from a hydrogen atom, linear or branched $C_1$-$C_6$ alkyl unsubstituted or substituted by at least one substituent chosen from hydroxyl, cyano, $C_1$-$C_4$ haloalkyl, $C_1$-$C_4$ hydroxyalkyl, $C_3$-$C_{10}$ cycloalkyl, phenyl or 6-membered, saturated N-containing heterocyclyl ring, or $R_5$ is chosen from —$S(O)_2R_{10}$, —$S(O)_2NR_{10}R_{11}$, —$C(O)OR_{10}$, —$C(O)$—$(CH_2)_n$—$R_{10}$, or —$C(O)$—$(CH_2)_n$—$NR_{10}R_{11}$;
$R_6$ and $R_7$ are each independently chosen from a hydrogen atom or linear or branched $C_1$-$C_6$ alkyl independently unsubstituted or substituted by at least one substituent chosen from hydroxyl, cyano, $C_1$-$C_4$ haloalkyl, $C_1$-$C_4$ hydroxyalkyl, $C_1$-$C_4$ alkoxycarbonyl, $C_3$-$C_7$ cycloalkyl, phenyl or 6-membered, saturated N-containing heterocyclyl ring;
$R_8$ is chosen from a hydrogen atom, halogen atoms, cyano, linear or branched $C_1$-$C_6$ alkyl, $C_2$-$C_4$ alkenyl, $C_2$-$C_4$ alkynyl, $C_1$-$C_4$ haloalkyl, $C_1$-$C_4$ hydroxyalkyl, $C_3$-$C_{10}$ cycloalkyl, $C_3$-$C_{10}$ cycloalkenyl, monocyclic or polycyclic $C_5$-$C_{14}$ aryl, 5- to 14-membered heteroaryl containing at least one heteroatom chosen from O, S or N, 5- to 14-membered heterocyclyl containing at least one heteroatom chosen from O, S or N, bicyclyl containing a monocyclic $C_5$-$C_9$ aryl or heteroaryl bonded directly to a 5- to 9-membered cycloalkyl or heterocyclyl, wherein the heteroaryl or heterocyclyl contain at least one heteroatom chosen from O, S or N, an aza-bicycloalkyl comprising up to 12 carbon atoms, or aza-bicycloalkenyl comprising up to 12 carbon atoms,
wherein each of the alkenyl, alkynyl, haloalkyl, hydroxyalkyl, cycloalkyl, cycloalkenyl, aryl, heteroaryl, heterocyclyl, bicyclyl, aza-bicycloalkyl and aza-bicycloalkenyl is independently unsubstituted or substituted by at least one substituent chosen from Ra, —($C_1$-$C_4$ alkyl)-CN, or —($C_1$-$C_4$ alkyl)-C(O)NR'R" wherein R' and R" are the same or different and are independently chosen from hydrogen atoms or linear or branched $C_1$-$C_4$ alkyl; and each of the alkyl groups is independently unsubstituted or substituted by at least one Rb;
and when $R_8$ is a 5- to 7-membered heterocyclyl containing one nitrogen atom, the heterocyclyl is substituted by at least one substituent, and wherein the substitution is at least on the ring nitrogen of the heterocyclyl, with the proviso that the substituent on the ring nitrogen of the heterocyclyl is not tert-butoxycarbonyl;
or $R_8$ is chosen from —$SR_{13}$, —$SOR_{13}$, —$S(O)_2R_{13}$, —$S(O)_2NR_{13}R_{14}$, —$NR_{13}S(O)_2R_{14}$, —$NR_{13}S(O)_2NR_{14}$, —$(CH_2)_nOR_{13}$, —$C(O)OR_{13}$, —$O$—$C(O)R_{13}$, —$C(O)$—$(CH_2)_n$—$R_{13}$, —$NR_{13}R_{14}$, —$C(O)$—$(CH_2)_n$—$NR_{13}R_{14}$, —$NR_{13}C(O)$—$(CH_2)_n$—$R_{14}$, or —$NR_{13}C(O)$—$(CH_2)_n$—$NR_{14}R_{15}$, wherein each n is independently chosen from 0, 1, or 2,
or $R_8$ together with $R_5$ and the nitrogen atom to which $R_5$ is bonded form a 4- to 10-membered, saturated heterocyclyl group, wherein the heterocyclyl contains one or two nitrogen atoms, and is substituted by linear or branched $C_1$-$C_6$ alkyl, monocyclic or polycyclic $C_5$-$C_{14}$ aryl, 5- to 14-membered heteroaryl containing at least one heteroatom chosen from O, S or N, 5- to 14-membered heterocyclyl containing at least one heteroatom chosen from O, S or N, —$SO_2R_{10}$, —C(O)—$(CH_2)_n$—$R_{10}$, or —C(O)—$(CH_2)_n$—$NR_{10}R_{11}$, wherein each n is independently chosen from 0, 1, or 2, wherein each of the alkyl, aryl, heteroaryl and heterocyclyl is independently unsubstituted or substituted by at least one substituent chosen from halogen atoms, hydroxyl, cyano, linear or branched $C_1$-$C_6$ alkyl, or $C_1$-$C_4$ haloalkyl, and wherein each of the alkyl groups is independently unsubstituted or substituted by at least one substituent chosen from halogen atoms, hydroxyl, cyano or $C_1$-$C_4$ haloalkyl;

with the proviso that when m is zero, R is not —$SR_{13}$, —$SOR_{13}$, —$S(O)_2R_{13}$, —$S(O)_2NR_{13}R_{14}$, —$NR_{13}S(O)_2R_{14}$, —$NR_{13}S(O)_2NR_{14}$, —$(CH_2)_nOR_{13}$, —O—$C(O)R_{13}$, —$NR_{13}R_{14}$, —$NR_{13}C(O)$—$(CH_2)_n$—$R_{14}$, or —$NR_{13}C(O)$—$(CH_2)_n$—$NR_{14}R_{15}$;

wherein each Ra is independently chosen from halogen atoms, cyano, hydroxyl, linear or branched $C_1$-$C_6$ alkyl, $C_1$-$C_4$ haloalkyl, $C_1$-$C_4$ alkoxy, $C_1$-$C_4$ hydroxyalkyl, $C_3$-$C_7$ cycloalkyl or a $C_3$-$C_7$ cycloalkenyl unsubstituted or substituted by at least one Re, monocyclic or polycyclic $C_5$-$C_{14}$ aryl unsubstituted or substituted by at least one Re, 5- to 14-membered heteroaryl containing at least one heteroatom chosen from O, S or N unsubstituted or substituted by at least one Re, 5- to 14-membered heterocyclyl containing at least one heteroatom chosen from O, S or N unsubstituted or substituted by at least one substituent chosen from Re, —$SR_{10}$, —$SOR_{10}$, —$S(O)_2R_{10}$, —$S(O)_2NR_{10}R_{11}$, —$NR_{10}S(O)_2R_{11}$, —$NR_{10}S(O)_2NR_{11}$, —$(CH_2)_nOR_{10}$, —$C(O)OR_{10}$, —O—$C(O)R_{10}$ a —C(O)—$(CH_2)_n$—$R_{10}$, —$NR_{10}R_{11}$, —C(O)—$(CH_2)_n$—$NR_{10}R_{11}$, a —$NR_{10}C(O)$—$(CH_2)_n$—$R_{11}$ or —$NR_{10}C(O)$—$(CH_2)_n$—$NR_{11}R_{12}$, wherein each n is independently chosen from 0, 1, or 2;

each Rb is independently chosen from cyano, $C_1$-$C_4$ haloalkyl, $C_1$-$C_4$ alkoxy, $C_1$-$C_4$ hydroxyalkyl, $C_3$-$C_7$ cycloalkyl or a $C_3$-$C_7$ cycloalkenyl unsubstituted or substituted by at least one Re, monocyclic or polycyclic $C_5$-$C_{14}$ aryl unsubstituted or substituted by at least one Re, 5- to 14-membered heteroaryl containing at least one heteroatom chosen from O, S or N, unsubstituted or substituted by at least one Re, 5- to 14-membered heterocyclyl containing at least one heteroatom chosen from O, S or N, unsubstituted or substituted by at least one substituent chosen from Re, —$SR_{10}$, —$SOR_{10}$, —$S(O)_2R_{10}$, —$S(O)_2NR_{10}R_{11}$, —$NR_{10}S(O)_2R_{11}$, —$NR_{10}S(O)_2NR_{11}$, —$(CH_2)_nOR_{10}$, —$C(O)OR_{10}$, —O—$C(O)R_{10}$, —C(O)—$(CH_2)_n$—$R_{10}$, —$NR_{10}R_{11}$, —C(O)—$(CH_2)_n$—$NR_{10}R_1$, a —$NR_{10}C(O)$—$(CH_2)_n$—$R_{11}$, or —$NR_{10}C(O)$—$(CH_2)_n$—$NR_{11}R_{12}$, wherein each n is independently chosen from 0, 1 or 2;

$R_{10}$, $R_{11}$ and $R_{12}$ are each independently chosen from a hydrogen atom, cyano, linear or branched $C_1$-$C_6$ alkyl, $C_1$-$C_4$ haloalkyl, $C_1$-$C_4$ hydroxyalkyl, $C_1$-$C_4$ alkoxycarbonyl, $C_3$-$C_7$ cycloalkyl, phenyl, 5- to 6-membered monocyclic heteroaryl containing 1, 2, or 3 heteroatoms chosen from N, O or S, 5- to 6-membered, heterocyclyl containing 1, 2, or 3 nitrogen atoms, bicyclyl containing a monocyclic $C_5$-$C_6$ aryl or heteroaryl bonded directly to a 5- to 6-membered cycloalkyl or heterocyclyl, wherein the heteroaryl or heterocyclyl contains 1, 2, or 3 nitrogen atoms, and wherein each of the haloalkyl, hydroxyalkyl, alkoxycarbonyl, cycloalkyl, phenyl, heteroaryl, heterocyclyl and bicyclyl is independently unsubstituted or substituted by at least one Rc, and each of the alkyl groups is independently unsubstituted or substituted by at least one Rd;

each Rc is independently chosen from halogen atoms, hydroxyl, cyano, linear or branched $C_1$-$C_6$ alkyl, $C_1$-$C_4$ haloalkyl, $C_1$-$C_4$ alkoxy, $C_1$-$C_4$ hydroxyalkyl, $C_3$-$C_7$ cycloalkyl, phenyl, 5- to 6-membered monocyclic heteroaryl containing 1, 2, or 3 nitrogen atoms, 5- to 6-membered heterocyclyl containing 1, 2, or 3 nitrogen atoms, or $C_3$-$C_7$ heterocycloalkyl ketone containing 1, 2, or 3 nitrogen atoms, wherein each phenyl is independently unsubstituted or substituted by at least one halogen atom, and each of the heteroaryl, heterocyclyl and heterocycloalkyl ketone are independently unsubstituted or substituted by at least one linear or branched $C_1$-$C_3$ alkyl;

each Rd is independently chosen from cyano, $C_1$-$C_4$ haloalkyl, $C_1$-$C_4$ alkoxy, $C_1$-$C_4$ hydroxyalkyl, $C_3$-$C_7$ cycloalkyl, phenyl, 5- to 6-membered monocyclic heteroaryl containing 1, 2, or 3 nitrogen atoms, 5- to 6-membered heterocyclyl containing 1, 2, or 3 nitrogen atoms, or $C_3$-$C_7$ heterocycloalkyl ketone containing 1, 2, or 3 nitrogen atoms, wherein each phenyl is independently unsubstituted or substituted by at least one halogen atom, and each of the heteroaryl, heterocyclyl and heterocycloalkyl ketone are independently unsubstituted or substituted by at least one linear or branched $C_1$-$C_3$ alkyl;

each Re is independently chosen from halogen atoms, hydroxyl, cyano, linear or branched $C_1$-$C_6$ alkyl, or $C_1$-$C_4$ haloalkyl;

$R_{13}$, $R_{14}$, and $R_{15}$ are each independently chosen from a hydrogen atom, cyano, linear or branched $C_1$-$C_6$ alkyl, $C_1$-$C_4$ haloalkyl, $C_1$-$C_4$ hydroxyalkyl, $C_1$-$C_4$ alkoxycarbonyl, $C_3$-$C_7$ cycloalkyl, monocyclic or polycyclic $C_5$-$C_{14}$ aryl, 5- to 14-membered heteroaryl containing at least one heteroatom chosen from O, S or N, or 5- to 14-membered heterocyclyl containing at least one heteroatom chosen from O, S or N, wherein each of the haloalkyl, hydroxyalkyl, alkoxycarbonyl, cycloalkyl, aryl, heteroaryl and heterocyclyl is independently unsubstituted or substituted by at least one Ra, and each of the alkyl groups is independently unsubstituted or substituted by at least one Rb.

2. The compound according to claim 1, wherein:

$R_1$ is chosen from a hydrogen atom, halogen atoms, hydroxyl, cyano, linear or branched $C_1$-$C_6$ alkyl, $C_1$-$C_4$ haloalkyl, $C_1$-$C_4$ hydroxyalkyl, $C_3$-$C_{10}$ cycloalkyl, or $NR_{13}R_{14}$; wherein $R_{13}$ and $R_{14}$ are the same or different and each is independently chosen from a hydrogen atom, linear or branched $C_1$-$C_6$ alkyl, $C_1$-$C_4$ haloalkyl, or $C_1$-$C_4$ hydroxyalkyl;

$R_2$, $R_3$ and $R_4$ are the same or different and each is independently chosen from a hydrogen atom, halogen atoms, hydroxyl, cyano, linear or branched $C_1$-$C_6$ alkyl, $C_1$-$C_4$ haloalkyl, $C_1$-$C_4$ hydroxyalkyl, or $C_3$-$C_{10}$ cycloalkyl;

$R_5$ is chosen from a hydrogen atom, linear or branched $C_1$-$C_6$ alkyl unsubstituted or substituted by at least one substituent chosen from a hydroxyl, cyano, $C_1$-$C_4$ haloalkyl, $C_1$-$C_4$ hydroxyalkyl, $C_3$-$C_{10}$ cycloalkyl, phenyl, or 6-membered, saturated N-containing heterocyclyl ring;

$R_6$ and $R_7$ are the same or different and each is independently chosen from a hydrogen atom or linear or branched $C_1$-$C_6$ alkyl independently unsubstituted or substituted by at least one substituent chosen from $C_1$-$C_4$ haloalkyl or $C_1$-$C_4$ hydroxyalkyl;

$R_9$ is chosen from a hydrogen atom, halogen atoms, hydroxyl, cyano, linear or branched $C_1$-$C_6$ alkyl, $C_1$-$C_4$ haloalkyl, or $C_1$-$C_4$ hydroxyalkyl; wherein $R_{13}$ and $R_{14}$ are the same or different and each is independently chosen from a hydrogen atom, linear or branched $C_1$-$C_6$ alkyl, $C_1$-$C_4$ haloalkyl, or $C_1$-$C_4$ hydroxyalkyl;

$R_8$ is chosen from linear or branched $C_1$-$C_6$ alkyl, $C_1$-$C_4$ haloalkyl, $C_3$-$C_7$ cycloalkyl, phenyl, 5- to 6-membered monocyclic heteroaryl containing 1, 2, or 3 heteroatoms chosen from N, O or S, 5- to 7-membered heterocyclyl group containing 1, 2 or 3 heteroatoms chosen from N, O or S, or —(CH$_2$)$_n$OR$_{13}$ wherein n is chosen from 0 or 1 and $R_{13}$ is linear or branched $C_1$-$C_6$ alkyl or $C_1$-$C_4$ haloalkyl;

wherein each of the haloalkyl, cycloalkyl, phenyl, heteroaryl and heterocyclyl is independently unsubstituted or substituted by at least one Ra; and each of the alkyl groups is independently unsubstituted or substituted by at least one Rb;

each Ra is independently chosen from halogen atoms, cyano, hydroxyl, linear or branched $C_1$-$C_6$ alkyl, $C_1$-$C_4$ haloalkyl, $C_1$-$C_4$ alkoxy, $C_3$-$C_7$ cycloalkyl unsubstituted or substituted by at least one Re, phenyl unsubstituted or substituted by at least one Re, 5- to 6-membered monocyclic heteroaryl containing 1, 2, or 3 heteroatoms chosen from N, O or S, unsubstituted or substituted by one or more Re, or 6-membered, saturated N-containing heterocyclyl ring, unsubstituted or substituted by at least one substituent chosen from Re, —C(O)OR$_{10}$, or —C(O)—(CH$_2$)$_n$—R$_{10}$ wherein n is chosen from 0 or 1, each Rb is independently chosen from cyano, $C_1$-$C_4$ haloalkyl, a $C_1$-$C_4$ alkoxy, a $C_3$-$C_7$ cycloalkyl unsubstituted or substituted by at least one Re, phenyl unsubstituted or substituted by at least one Re, 5- to 6-membered monocyclic heteroaryl containing 1, 2, or 3 heteroatoms chosen from N, O or S, unsubstituted or substituted by at least one Re, 6-membered, saturated N-containing heterocyclyl ring, unsubstituted or substituted by at least one substituent chosen from Re, —C(O)OR$_{10}$, or —C(O)—(CH$_2$)$_n$—R$_{10}$ wherein n is chosen from 0 or 1;

each $R_{10}$ group in —C(O)OR$_{10}$ is independently chosen from a hydrogen atom, linear or branched $C_1$-$C_6$ alkyl, $C_1$-$C_4$ haloalkyl, $C_3$-$C_7$ cycloalkyl, phenyl, 5- to 6-membered monocyclic heteroaryl containing 1, 2, or 3 heteroatoms chosen from N, O or S, or 5- to 6-membered, saturated N-containing heterocyclyl ring; and each $R_{10}$ group in —C(O)—(CH$_2$)$_n$—R$_{10}$ is independently chosen from cyano, linear or branched $C_1$-$C_6$ alkyl, $C_1$-$C_4$ haloalkyl, $C_3$-$C_7$ cycloalkyl, phenyl, 5- to 6-membered monocyclic heteroaryl containing 1, 2, or 3 heteroatoms chosen from N, O or S, or 5- to 6-membered, saturated N-containing heterocyclyl ring;

wherein the cycloalkyl, phenyl, heteroaryl and heterocyclyl are independently unsubstituted or substituted by at least one substituent chosen from hydroxyl, cyano, linear or branched $C_1$-$C_5$ alkyl or $C_1$-$C_4$ haloalkyl.

3. The compound according to claim 2, wherein Z is NR$_5$.

4. The compound according to claim 2, wherein:
m is chosen from 0, 1, or 2;
Z is NR$_5$;
$R_1$ is chosen from a hydrogen atom or —NH$_2$;
$R_2$, $R_4$, $R_5$, $R_6$, and $R_7$ are each independently chosen from a hydrogen atom or linear or branched $C_1$-$C_3$ alkyl;

$R_3$ is chosen from a hydrogen atom, cyano, or linear or branched $C_1$-$C_3$ alkyl;

$R_8$ is chosen from linear or branched $C_1$-$C_6$ alkyl; $C_1$-$C_4$ haloalkyl; $C_3$-$C_7$ cycloalkyl unsubstituted or substituted by at least one substituent chosen from halogen atoms or hydroxyl; phenyl unsubstituted or substituted by at least one halogen atom; —(CH$_2$)$_n$—OR$_{13}$ wherein n is chosen from 0 or 1 and $R_{13}$ is a linear or branched $C_1$-$C_3$ alkyl; pyridyl unsubstituted or substituted by at least one substituent chosen from halogen atoms, hydroxyl, or cyano; tetrahydropyranyl, unsubstituted or substituted by at least one substituent chosen from halogen atoms or hydroxyl; piperidinyl unsubstituted or substituted by at least one substituent chosen from linear or branched $C_1$-$C_3$ alkyl or halogen atoms; or 1,2,4-triazolyl; and $R_9$ is chosen from a hydrogen atom, halogen atoms, or a linear or branched $C_1$-$C_3$ alkyl group.

5. The compound according to claim 4, wherein $R_8$ is chosen from a linear or branched $C_1$-$C_6$ alkyl; $C_1$-$C_4$ haloalkyl; $C_3$-$C_7$ cycloalkyl unsubstituted or substituted by at least one substituent chosen from halogen atoms or hydroxyl; phenyl unsubstituted or substituted by at least one halogen atom; —(CH$_2$)$_n$—OR$_{13}$ wherein n is chosen from 0 or 1 and $R_{13}$ is a linear or branched $C_1$-$C_3$ alkyl; pyridyl unsubstituted or substituted by at least one substituent chosen from halogen atoms, hydroxyl, or cyano; tetrahydropyranyl unsubstituted or substituted by at least one substituent chosen from halogen atoms or hydroxyl; piperidinyl substituted by at least one substituent, wherein the substitution is at least on the ring nitrogen of the piperidinyl and is chosen from linear or branched $C_1$-$C_3$ alkyl or halogen atoms; or 1,2,4-triazolyl.

6. The compound according to claim 1, wherein $R_8$ is chosen from a linear or branched $C_1$-$C_6$ alkyl, $C_1$-$C_4$ haloalkyl, $C_3$-$C_7$ cycloalkyl, phenyl, 5- to 6-membered monocyclic heteroaryl containing 1, 2, or 3 heteroatoms chosen from N, O or S, 5- to 7-membered heterocyclyl containing 1, 2, or 3 heteroatoms chosen from N, O or S, or —(CH$_2$)$_n$OR$_{13}$ wherein n is chosen from 0 or 1 and $R_{13}$ is chosen from linear or branched $C_1$-$C_6$ alkyl or $C_1$-$C_4$ haloalkyl;

wherein each of the haloalkyl, cycloalkyl, phenyl, heteroaryl and heterocyclyl is independently unsubstituted or substituted by at least one Ra; and each of the alkyl groups is independently unsubstituted or substituted by at least one Rb;

each Ra is independently chosen from halogen atoms, cyano, hydroxyl, linear or branched $C_1$-$C_6$ alkyl, $C_1$-$C_4$ haloalkyl, $C_1$-$C_4$ alkoxy, $C_3$-$C_7$ cycloalkyl unsubstituted or substituted by at least one Re, phenyl unsubstituted or substituted by at least one Re, 5- to 6-membered monocyclic heteroaryl containing 1, 2, or 3 heteroatoms chosen from N, O or S, unsubstituted or substituted by at least one Re, 6-membered, saturated N-containing heterocyclyl ring, unsubstituted or substituted by at least one substituent chosen from Re, —C(O)OR$_{10}$, or —C(O)—(CH$_2$)$_n$—R$_{10}$ wherein n is chosen from 0 or 1, each Rb is independently chosen from cyano, $C_1$-$C_4$ haloalkyl, $C_1$-$C_4$ alkoxy, $C_3$-$C_7$ cycloalkyl unsubstituted or substituted by at least one Re, phenyl unsubstituted or substituted by at least one Re, 5- to 6-membered monocyclic heteroaryl containing 1, 2, or 3 heteroatoms chosen from N, O or S, unsubstituted or substituted by at least one Re, 6-membered, saturated N-containing heterocyclyl ring, unsubstituted or substituted by at least one substituent chosen from Re, —C(O)OR$_{10}$, or —C(O)—(CH$_2$)$_n$—R$_{10}$ wherein n is chosen from 0 or 1;

each $R_{10}$ group in —C(O)OR$_{10}$ is independently chosen from a hydrogen atom, linear or branched $C_1$-$C_6$ alkyl, $C_1$-$C_4$ haloalkyl, $C_3$-$C_7$ cycloalkyl, phenyl, 5- to 6-membered monocyclic heteroaryl containing 1, 2, or 3 heteroatoms chosen from N, O or S, or 5- to 6-membered, saturated N-containing heterocyclyl ring; and each $R_{10}$ group in —C(O)—(CH$_2$)$_n$—$R_{10}$ is independently chosen from cyano, linear or branched $C_1$-$C_6$ alkyl, $C_1$-$C_4$ haloalkyl, $C_3$-$C_7$ cycloalkyl, phenyl, 5- to 6-membered monocyclic heteroaryl containing 1, 2, or 3 heteroatoms chosen from N, O or S, or 5- to 6-membered, saturated N-containing heterocyclyl ring; wherein the cycloalkyl, phenyl, heteroaryl and heterocyclyl are independently unsubstituted or substituted by at least one substituent chosen from hydroxyl, cyano, linear or branched $C_1$-$C_6$ alkyl or $C_1$-$C_4$ haloalkyl.

7. The compound according to claim 6, wherein Ra is chosen from a linear or branched $C_1$-$C_6$ alkyl, $C_1$-$C_4$ haloalkyl, $C_3$-$C_7$ cycloalkyl, phenyl, 5- to 7-membered heterocyclyl containing 1, 2, or 3 heteroatoms chosen from N, O or S, or —(CH$_2$)$_n$OR$_{13}$;

wherein each of the haloalkyl, cycloalkyl, phenyl, and heterocyclyl is unsubstituted or substituted by at least one Ra; and each of the alkyl groups is independently unsubstituted or substituted by at least one Rb;

each Ra is independently chosen from halogen atoms, cyano, hydroxyl, linear or branched $C_1$-$C_6$ alkyl, $C_1$-$C_4$ haloalkyl, 5- to 6-membered monocyclic heteroaryl containing 1, 2, or 3 heteroatoms chosen from N, O or S, unsubstituted or substituted by at least one substituent chosen from halogen atoms, hydroxyl, cyano, linear or branched $C_1$-$C_6$ alkyl or $C_1$-$C_4$ haloalkyl; and each Rb is independently chosen from cyano, $C_1$-$C_4$ haloalkyl, $C_1$-$C_4$ alkoxy, $C_3$-$C_7$ cycloalkyl unsubstituted or substituted by at least one substituent chosen from halogen atoms, hydroxyl, or cyano; phenyl unsubstituted or substituted by at least one substituent chosen from halogen atoms, hydroxyl group, cyano, or linear or branched $C_1$-$C_6$ alkyl.

8. The compound according to claim 1, wherein the compound is of formula (I-a):

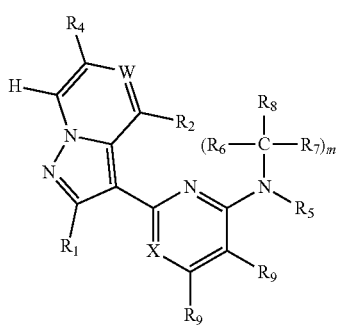

(I-a)

wherein
m is chosen from 0, 1, or 2;
X is a nitrogen atom;
$R_1$ is chosen from a hydrogen atom or —NH$_2$;
$R_3$ is chosen from a hydrogen atom, cyano, or linear or branched $C_1$-$C_3$ alkyl;
$R_2$, $R_4$, $R_5$, $R_6$ and $R_7$ are each independently chosen from a hydrogen atom or linear or branched $C_1$-$C_3$ alkyl;
$R_8$ is chosen from linear or branched $C_1$-$C_6$ alkyl; $C_1$-$C_4$ haloalkyl; $C_3$-$C_7$ cycloalkyl unsubstituted or substituted by at least one hydroxyl; phenyl unsubstituted or substituted by at least one halogen atom; —(CH$_2$)$_n$—OR$_{13}$ wherein n is chosen from 0 or 1 and $R_{13}$ is linear or branched $C_1$-$C_3$ alkyl; piperidinyl unsubstituted or substituted by at least one pyridyl, wherein the pyridyl is unsubstituted or substituted by at least one cyano; or —C(O)—(CH$_2$)$_n$—$R_{13}$, wherein n is chosen from 0 or 1 and $R_{13}$ is chosen from cyano, linear or branched $C_1$-$C_6$ alkyl, $C_1$-$C_4$ haloalkyl or $C_3$-$C_7$ cycloalkyl; and $R_9$ is chosen from a hydrogen atom, halogen atoms, or linear or branched $C_1$-$C_3$ alkyl.

9. The compound according to claim 8, wherein:
m is chosen from 0 or 1;
$R_1$, $R_2$ and $R_4$ are hydrogen atoms;
$R_3$ is chosen from a hydrogen atom or cyano;
$R_8$ is chosen from linear or branched $C_1$-$C_6$ alkyl; $C_1$-$C_4$ haloalkyl; $C_3$-$C_7$ cycloalkyl unsubstituted or substituted by at least one hydroxyl; phenyl unsubstituted or substituted by at least one halogen atom; —(CH$_2$)$_n$—OR$_{13}$ wherein n is chosen from 0 or 1 and $R_{13}$ is linear or branched $C_1$-$C_3$ alkyl; piperidinyl unsubstituted or substituted by at least one substituent chosen from pyridyl, wherein the pyridyl is unsubstituted or substituted by at least one cyano; or —C(O)—(CH$_2$)$_n$—$R_{13}$, wherein n is chosen from 0 or 1 and $R_{13}$ is chosen from cyano, linear or branched $C_1$-$C_3$ alkyl, or $C_1$-$C_4$ haloalkyl.

10. The compound according to claim 1, wherein Y is —CR$_9$.

11. The compound according to claim 1, wherein Z is NR$_5$.

12. The compound according to claim 1, wherein $R_1$ is chosen from a hydrogen atom, halogen atoms, cyano, linear or branched $C_1$-$C_6$ alkyl, $C_3$-$C_7$ cycloalkyl, or NR$_{13}$R$_{14}$, wherein $R_{13}$ and $R_{14}$ are the same or different and each is independently chosen from a hydrogen atom, linear or branched $C_1$-$C_6$ alkyl, or $C_1$-$C_4$ haloalkyl.

13. The compound according to claim ti, wherein $R_2$ is chosen from a hydrogen atom, halogen atoms, cyano, linear or branched $C_1$-$C_6$ alkyl, or $C_3$-$C_7$ cycloalkyl.

14. The compound according to claim 1, wherein $R_3$ is chosen from a hydrogen atom, halogen atoms, cyano, linear or branched $C_1$-$C_6$ alkyl, or $C_3$-$C_7$ cycloalkyl.

15. The compound according to claim 1, wherein $R_4$ is chosen from a hydrogen atom, halogen atoms, cyano, linear or branched $C_1$-$C_6$ alkyl, or $C_3$-$C_7$ cycloalkyl.

16. The compound according to claim 1, wherein $R_5$ is chosen from a hydrogen atom, linear or branched $C_1$-$C_4$ alkyl unsubstituted or substituted by at least one substituent chosen from hydroxyl, $C_1$-$C_4$ haloalkyl, $C_1$-$C_4$ hydroxyalkyl, or $C_3$-$C_7$ cycloalkyl.

17. The compound according to claim 1, wherein $R_6$ and $R_7$ are chosen from a hydrogen atom or linear or branched $C_1$-$C_6$ alkyl.

18. The compound according to claim 1, wherein $R_9$ is chosen from a hydrogen atom, halogen atoms, hydroxyl, cyano, or linear or branched $C_1$-$C_6$ alkyl.

19. The compound according to claim 1, wherein:
m is chosen from 0, 1, or 2;
Z is NR$_5$;
$R_1$ is chosen from a hydrogen atom or —NH$_2$;
$R_2$, $R_4$, $R_5$, $R_6$, and $R_7$ are each independently chosen from a hydrogen atom or linear or branched $C_1$-$C_3$ alkyl;
$R_3$ is chosen from a hydrogen atom, cyano, or linear or branched $C_1$-$C_3$ alkyl;
$R_8$ is chosen from linear or branched $C_1$-$C_6$ alkyl; $C_1$-$C_4$ haloalkyl; $C_3$-$C_7$ cycloalkyl unsubstituted or substituted by at least one hydroxyl; phenyl unsubstituted or substituted by at least one halogen atom; —(CH$_2$)$_n$—OR$_{13}$ wherein n is chosen from 0 or 1 and $R_{13}$ is a linear or branched $C_1$-$C_3$ alkyl; piperidinyl unsubstituted or substituted by at least one pyridyl, wherein the pyridyl is unsubstituted or substituted by at least one cyano; or —C(O)—(CH$_2$)$_n$—R$_{13}$, wherein n is chosen from 0 or 1 and R$_{13}$ is chosen from cyano, linear or branched $C_1$-$C_6$ alkyl, $C_1$-$C_4$ haloalkyl, or $C_3$-$C_7$ cycloalkyl; and R$_9$ is chosen from a hydrogen atom, halogen atoms, or linear or branched $C_1$-$C_3$ alkyl.

20. A pharmaceutical composition comprising the compound according to claim 1 and a pharmaceutically acceptable diluent or carrier.

21. A composition comprising:
(i) a compound according to claim 1; and
(ii) at least one other compound chosen from:
dihydrofolate reductase inhibitors;
dihydroorotate dehydrogenase inhibitors;
Immunomodulators;
Inhibitors of DNA synthesis and repair;
Anti-alpha 4 integrin antibodies;
Alpha 4 integrin antagonists;
Corticoids and glucocorticoids;
Fumaric acid esters;
Anti-tumor necrosis factor alpha antibodies;
Soluble tumor necrosis factor alpha receptors;
Anti-CD20 monoclonal antibodies;
Anti-CD52;
Anti-CD25;
Anti-CD88;
Anti-IL12R/IL23R;
Calcineurin inhibitors;
Inosine monophosphate dehydrogenase; inhibitors;
Cannabinoid receptor agonists;
Chemokine CCR1 antagonists;
Chemokine CCR2 antagonists;
NF-kappaB activation inhibitors;
Sphingosine-1-phosphate receptor agonists;
Sphingosine-1-phosphate ligase inhibitors;
Spleen tyrosine kinase inhibitors;
Protein kinase C inhibitors;
Muscarinic acetylcholine receptor M3 antagonist;
Long-acting beta adrenergic agonist;
Vitamin D derivatives;
Phosphosdiesterase IV inhibitors;
p38 mitogen-activated protein kinase inhibitors;
MEK inhibitors;
Phosphoinositide 3-kinase inhibitors;
Interferons comprising Interferon beta 1a and Interferon beta 1b; or
Interferon alpha.

22. A method of inhibiting Janus kinase activity in a subject comprising administering to a subject in need thereof an effective amount of the composition according to claim 21.

23. A method of inhibiting Janus kinase activity in a subject comprising administering to a subject in need thereof an effective amount of a compound according to claim 1.

24. The method according to claim 23, wherein the subject suffers from a pathological condition or disease chosen from the group consisting of a myeloproliferative disorder, a lymphoid malignancy, a solid tumor, a bone marrow transplant rejection, an organ transplant rejection, an immune-mediated disease, an inflammatory disease, and leukemia.

25. The method according to claim 24, wherein the subject suffers from a pathological condition or disease chosen from the group consisting of a myeloproliferative disorder, a lymphoid malignancy, a solid tumor, and leukemia.

26. The method according to claim 24, wherein the subject suffers from a pathological condition or disease chosen from the group consisting of a bone marrow transplant rejection, an organ transplant rejection, an immune-mediated disease, and an inflammatory disease.

27. The method according to claim 23, wherein the subject suffers from a pathological condition or disease chosen from the group consisting of rheumatoid arthritis, multiple sclerosis, inflammatory bowel disease, dry eye, uveitis, allergic conjunctivitis, allergic rhinitis, asthma, chronic obstructive pulmonary disease, atopic dermatitis, and psoriasis.

28. A compound chosen from:
3-(4-{[(1S)-1-Phenylethyl]amino}pyrimidin-2-yl)pyrazolo[1,5-a]pyridine-5-carbonitrile;
3-{4-[(Cyclohexylmethyl)amino]pyrimidin-2-yl}pyrazolo[1,5-a]pyridine-5-carbonitrile;
3-[4-(Benzylamino)pyrimidin-2-yl]pyrazolo[1,5-a]pyridine-5-carbonitrile;
3-{4-[(2,2-Dimethylpropyl)amino]pyrimidin-2-yl}pyrazolo[1,5-a]pyridine-5-carbonitrile;
3-(4-{[(1S)-2-Methoxy-1-methylethyl]amino}pyrimidin-2-yl)pyrazolo[1,5-a]pyridine-5-carbonitrile;
3-{4-[(Cyclopropylmethyl)amino]pyrimidin-2-yl}pyrazolo[1,5-a]pyridine-5-carbonitrile;
3-{4-[(2,2,2-Trifluoroethyl)amino]pyrimidin-2-yl}pyrazolo[1,5-a]pyridine-5-carbonitrile;
N-(1-Phenylethyl)-2-pyrazolo[1,5-a]pyridin-3-ylpyrimidin-4-amine;
3-(4-{[(3R)-1-(Cyanoacetyl)piperidin-3-yl]amino}pyrimidin-2-yl)pyrazolo[1,5-a]pyridine-5-carbonitrile;
3-(4-{[(3R)-1-Acetylpiperidin-3-yl]amino}pyrimidin-2-yl)pyrazolo[1,5-a]pyridine-5-carbonitrile;
3-(4-{[(3R)-1-(5-Cyanopyridin-2-yl)piperidin-3-yl]amino}pyrimidin-2-yl)pyrazolo[1,5-a]pyridine-5-carbonitrile;
3-(4-{[(3R)-1-(3,3,3-Trifluoropropanoyl)piperidin-3-yl]amino}pyrimidin-2-yl) pyrazolo[1,5-a]pyridine-5-carbonitrile;
3-{4-[[(3R)-1-(Cyanocarbonyl)piperidin-3-yl](methyl)amino]pyrimidin-2-yl}pyrazolo[1,5-a]pyridine-5-carbonitrile;
3-(4-((Trans)-4-Hydroxycyclohexylamino)pyrimidin-2-yl)pyrazolo[1,5-a]pyridine-5-carbonitrile;
(R)-3-oxo-3-(3-(2-(pyrazolo[1,5-a]pyridin-3-yl)pyrimidin-4-ylamino)piperidin-1-yl)propanenitrile;
3-(3-(5-fluoro-2-(pyrazolo[1,5-a]pyridin-3-yl)pyrimidin-4-ylamino)piperidin-1-yl)-3-oxopropanenitrile;
3-(3-(5-chloro-2-(pyrazolo[1,5-a]pyridin-3-yl)pyrimidin-4-ylamino)piperidin-1-yl)-3-oxopropanenitrile;
3-(4-fluoro-3-(6-(pyrazolo[1,5-a]pyridin-3-yl)pyrazin-2-ylamino)piperidin-1-yl)-3-oxopropanenitrile;
3-(4-methyl-3-(6-(pyrazolo[1,5-a]pyridin-3-yl)pyrazin-2-ylamino)piperidin-1-yl)-3-oxopropanenitrile;
N-(1-(4H-1,2,4-Triazol-3-yl)piperidin-3-yl)-6-(pyrazolo[1,5-a]pyridin-3-yl)pyrazin-2-amine;
N-(1-(4H-1,2,4-Triazol-3-yl)piperidin-3-yl)-2-(pyrazolo[1,5-a]pyridin-3-yl)pyrimidin-4-amine;
N-[(3R)-1-(Aminoacetyl)piperidin-3-yl]-6-pyrazolo[1,5-a]pyridin-3-ylpyrazin-2-amine;
(R)-3-oxo-3-(3-(6-(pyrazolo[1,5-a]pyridin-3-yl)pyrazin-2-ylamino)piperidin-1-yl)propanenitrile;
or a pharmaceutically acceptable salt, N-oxide, or stereoisomer thereof.

* * * * *